United States Patent
Ling et al.

(10) Patent No.: US 10,744,185 B2
(45) Date of Patent: Aug. 18, 2020

(54) METHODS OF USING VARIANTS OF FGF19 POLYPEPTIDES FOR THE TREATMENT OF PRURITUS

(71) Applicant: NGM Biopharmaceuticals, Inc., South San Francisco, CA (US)

(72) Inventors: Lei Ling, Foster City, CA (US); Jian Luo, Albany, CA (US); Hui Tian, Foster City, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 109 days.

(21) Appl. No.: 15/773,120

(22) PCT Filed: Nov. 8, 2016

(86) PCT No.: PCT/US2016/060944
§ 371 (c)(1),
(2) Date: May 2, 2018

(87) PCT Pub. No.: WO2017/083276
PCT Pub. Date: May 18, 2017

(65) Prior Publication Data
US 2018/0318390 A1    Nov. 8, 2018

Related U.S. Application Data

(60) Provisional application No. 62/252,939, filed on Nov. 9, 2015.

(51) Int. Cl.
| | | |
|---|---|---|
| *A61K 38/18* | (2006.01) | |
| *C07K 14/50* | (2006.01) | |
| *A61P 1/16* | (2006.01) | |
| *A61K 9/00* | (2006.01) | |
| *A61K 31/575* | (2006.01) | |

(52) U.S. Cl.
CPC .......... *A61K 38/1825* (2013.01); *A61P 1/16* (2018.01); *C07K 14/50* (2013.01); *A61K 9/0019* (2013.01); *A61K 31/575* (2013.01)

(58) Field of Classification Search
None
See application file for complete search history.

(56) References Cited

U.S. PATENT DOCUMENTS

| | | | |
|---|---|---|---|
| 6,635,468 B2 | 10/2003 | Ashkenazi | |
| 6,716,626 B1 | 4/2004 | Itoh | |
| 6,806,352 B2 | 10/2004 | Desnoyers | |
| 6,812,339 B1 | 11/2004 | Venter | |
| 6,987,121 B2 | 1/2006 | Kliewer | |
| 7,115,415 B2 | 10/2006 | Goddard | |
| 7,129,072 B1 | 10/2006 | Schlessinger | |
| 7,208,312 B1 | 4/2007 | Desnoyers | |
| 7,259,248 B2 | 8/2007 | Itoh | |
| 7,288,406 B2 | 10/2007 | Bogin | |
| 7,390,879 B2 | 6/2008 | Ashkenazi | |
| 7,459,540 B1 | 12/2008 | Thomason | |
| 7,491,697 B2 | 2/2009 | Beals | |
| 7,576,190 B2 | 8/2009 | Glaesner | |
| 7,582,607 B2 | 9/2009 | Frye | |
| 7,622,445 B2 | 11/2009 | Frye | |
| 7,655,627 B2 | 2/2010 | Frye | |
| 7,667,008 B2 | 2/2010 | Thomason | |
| 7,705,195 B2 | 4/2010 | French | |
| 7,723,297 B2 | 5/2010 | Itoh | |
| 7,947,866 B2 | 5/2011 | Sparks | |
| 8,012,931 B2 | 9/2011 | Cujec | |
| 8,034,770 B2 | 10/2011 | Belouski | |
| 8,188,040 B2 | 5/2012 | Belouski | |
| 8,324,160 B2 | 12/2012 | Li | |
| 8,361,963 B2 | 1/2013 | Belouski | |
| 8,383,365 B2 | 2/2013 | Cujec | |
| 8,410,051 B2 | 4/2013 | Belouski | |
| 8,420,088 B2 | 4/2013 | Glass | |
| 8,481,031 B2 | 7/2013 | Glass | |
| 8,535,912 B2 | 9/2013 | Sonoda | |
| 8,541,369 B2 | 9/2013 | Dickinson | |
| 8,580,936 B2 | 11/2013 | Williams | |

(Continued)

FOREIGN PATENT DOCUMENTS

| | | |
|---|---|---|
| CN | 101591653 A | 12/2009 |
| CN | 102656266 A | 9/2012 |

(Continued)

OTHER PUBLICATIONS

Bergasa, "Pruritus of Cholestasis", Chapter 6 in "Itch: Mechanisms and Treatment", CRC Press/Taylor & Francis, 2014, Carstens, Akiyama, ed.*
Aranha et al., "Bile acid levels are increased in the liver of patients with steatohepatitis," *Eur. J. Gastroenterol. Hepatol.*, 20(6):519-525 (2008).
Beenken et al, "The FGF family: biology, pathophysiology and therapy," *Nat. Rev. Drug Discov.*, 8:235-253 (2009).
Beuers et al., "Medical treatment of primary sclerosing cholangitis: a role for novel bile acids and other (post-) transcriptional modulators?," *Clin. Rev. Allergy Immunol.*, 36(1):52-61 (2009).

(Continued)

*Primary Examiner* — Christine J Saoud
(74) *Attorney, Agent, or Firm* — Jones Day

(57) ABSTRACT

Provided herein are variants of fibroblast growth factor 19 (FGF19) proteins and peptide sequences (and peptidomimetics) and fusions of FGF19 and/or fibroblast growth factor 21 (FGF21) proteins and peptide sequences (and peptidomimetics), and variants of fusions of FG-F19 and/or FGF21 proteins and peptide sequences (and peptidomimetics). In some embodiments, these variants and fusions modulate bile acid homeostasis, and are useful in treatment of bile acid related and associated disorders. In some embodiments, these variants and fusions have glucose lowering activity, and are useful in treatment of hyperglycemia and other disorders.

52 Claims, 11 Drawing Sheets
Specification includes a Sequence Listing.

(56) References Cited

U.S. PATENT DOCUMENTS

| Patent/Publication No. | Date | Inventor |
|---|---|---|
| 8,618,053 B2 | 12/2013 | Belouski |
| 8,642,546 B2 | 2/2014 | Belouski |
| 8,673,860 B2 | 3/2014 | Schellenberger |
| 8,741,841 B2 | 6/2014 | Darling |
| 8,795,985 B2 | 8/2014 | Belouski |
| 8,802,697 B2 | 8/2014 | Bifulco |
| 8,809,499 B2 | 8/2014 | Fan |
| 8,835,385 B2 | 9/2014 | Belouski |
| 8,883,726 B2 | 11/2014 | Dickinson |
| 8,889,426 B2 | 11/2014 | Mohammadi |
| 8,889,621 B2 | 11/2014 | Mohammadi |
| 8,927,492 B2 | 1/2015 | Darling |
| 8,932,589 B2 | 1/2015 | Glass |
| 8,951,966 B2 | 2/2015 | Ling |
| 8,962,557 B2 | 2/2015 | Blaber |
| 8,975,223 B2 | 3/2015 | Vignati |
| 8,993,727 B2 | 3/2015 | Walker |
| 8,999,929 B2 | 4/2015 | Mohammadi |
| 9,006,400 B2 | 4/2015 | Boettcher |
| 9,085,626 B2 | 7/2015 | Sonoda et al. |
| 9,089,525 B1 | 7/2015 | Ling |
| 9,273,107 B2 | 3/2016 | Ling |
| 9,290,557 B2 | 3/2016 | Ling |
| 9,474,785 B2 | 10/2016 | Mohammadi et al. |
| 9,475,856 B2 | 10/2016 | Mohammadi et al. |
| 9,550,820 B2 | 1/2017 | Mohammadi et al. |
| 9,580,483 B2 | 2/2017 | Ling |
| 9,670,260 B2 | 6/2017 | Ling |
| 9,751,924 B2 | 9/2017 | Ling |
| 9,789,160 B2 | 10/2017 | Wellstein |
| 9,878,008 B2 | 1/2018 | Ling |
| 9,878,009 B2 | 1/2018 | Ling |
| 9,889,177 B2 | 2/2018 | Ling |
| 9,889,178 B2 | 2/2018 | Ling |
| 9,895,416 B2 | 2/2018 | Ling |
| 9,925,242 B2 | 3/2018 | Ling |
| 9,926,356 B2 | 3/2018 | Mohammadi et al. |
| 9,963,494 B2 | 5/2018 | Ling |
| 9,974,833 B2 | 5/2018 | Ling |
| 10,174,090 B2 | 1/2019 | Mohammadi et al. |
| 10,369,199 B2 | 8/2019 | Ling |
| 10,398,758 B2 | 9/2019 | Ling et al. |
| 10,413,590 B2 | 9/2019 | Ling et al. |
| 10,434,144 B2 | 10/2019 | DePaoli et al. |
| 10,456,449 B2 | 10/2019 | Ling et al. |
| 10,517,929 B2 | 12/2019 | Lindhout et al. |
| 2002/0012961 A1 | 1/2002 | Botstein |
| 2002/0042367 A1 | 4/2002 | Stewart |
| 2002/0082205 A1 | 6/2002 | Itoh |
| 2002/0151496 A1 | 10/2002 | Bringmann |
| 2002/0155543 A1 | 10/2002 | Adams |
| 2003/0045489 A1 | 3/2003 | Murphy |
| 2003/0065140 A1 | 4/2003 | Vernet |
| 2003/0105302 A1 | 6/2003 | Itoh |
| 2003/0113718 A1 | 6/2003 | Ashkenazi |
| 2003/0119112 A1 | 6/2003 | Baker |
| 2003/0125521 A1 | 7/2003 | Baker |
| 2003/0166051 A1 | 9/2003 | Desnoyers |
| 2003/0170822 A1 | 9/2003 | Itoh |
| 2003/0180890 A1 | 9/2003 | Conklin |
| 2003/0185846 A1 | 10/2003 | Ashkenazi |
| 2003/0220246 A1 | 11/2003 | Conklin |
| 2004/0014658 A1 | 1/2004 | Bogin |
| 2004/0126852 A1 | 7/2004 | Stewart |
| 2004/0146908 A1 | 7/2004 | Adams |
| 2004/0185494 A1 | 9/2004 | Itoh |
| 2005/0026243 A1 | 2/2005 | Stewart |
| 2005/0026832 A1 | 2/2005 | Adams |
| 2005/0107475 A1 | 5/2005 | Jones |
| 2005/0153305 A1 | 7/2005 | Vernet |
| 2005/0181375 A1 | 8/2005 | Aziz |
| 2005/0196842 A1 | 9/2005 | Botstein |
| 2005/0250684 A1 | 11/2005 | Heuer |
| 2006/0160181 A1 | 7/2006 | Luethy |
| 2006/0172386 A1 | 8/2006 | Itoh |
| 2006/0246540 A1 | 11/2006 | Ashkenazi |
| 2006/0275794 A1 | 12/2006 | Carrino |
| 2006/0281679 A1 | 12/2006 | Itoh |
| 2007/0037165 A1 | 2/2007 | Venter |
| 2007/0042395 A1 | 2/2007 | Botstein |
| 2007/0077626 A1 | 4/2007 | Botstein |
| 2007/0238657 A1 | 10/2007 | Itoh |
| 2007/0253966 A1 | 11/2007 | Glaesner |
| 2008/0057076 A1 | 3/2008 | Bringmann |
| 2008/0124759 A1 | 5/2008 | Conklin |
| 2009/0081658 A1 | 3/2009 | Belouchi |
| 2009/0098603 A1 | 4/2009 | Botstein |
| 2009/0196876 A1 | 8/2009 | Sparks |
| 2009/0226459 A1 | 9/2009 | Powers |
| 2009/0312265 A1 | 12/2009 | Schmidtchen |
| 2010/0055730 A1 | 3/2010 | Usheva-Simidjiyska |
| 2010/0215657 A1 | 8/2010 | Glass |
| 2010/0239554 A1 | 9/2010 | Schellenberger |
| 2010/0240587 A1 | 9/2010 | Schlein |
| 2010/0323954 A1 | 12/2010 | Li |
| 2011/0015345 A1 | 1/2011 | Pinkstaff |
| 2011/0053787 A1 | 3/2011 | Brulliard |
| 2011/0104152 A1 | 5/2011 | Sonoda |
| 2011/0107439 A1 | 5/2011 | De Wit |
| 2011/0135657 A1 | 6/2011 | Hu |
| 2011/0150903 A1 | 6/2011 | Baurin |
| 2011/0195077 A1 | 8/2011 | Glass |
| 2011/0195895 A1 | 8/2011 | Walker |
| 2011/0207912 A1 | 8/2011 | Botstein |
| 2011/0268794 A1 | 11/2011 | Camilleri |
| 2011/0306129 A1 | 12/2011 | Nistor |
| 2011/0312881 A1 | 12/2011 | Silverman |
| 2012/0003216 A1 | 1/2012 | Belouski |
| 2012/0064544 A1 | 3/2012 | Econs |
| 2012/0157397 A1 | 6/2012 | Hazen |
| 2013/0004492 A1 | 1/2013 | Marshall |
| 2013/0023474 A1 | 1/2013 | Ling |
| 2013/0116171 A1 | 5/2013 | Jonker |
| 2013/0122004 A1 | 5/2013 | Glass |
| 2013/0143796 A1 | 6/2013 | Li |
| 2013/0172275 A1 | 7/2013 | Mohammadi |
| 2013/0183294 A1 | 7/2013 | Pai |
| 2013/0183319 A1 | 7/2013 | Bange |
| 2013/0184211 A1 | 7/2013 | Mohammadi |
| 2013/0231277 A1 | 9/2013 | Mohammadi |
| 2013/0324458 A1 | 12/2013 | Glass |
| 2013/0324701 A1 | 12/2013 | Williams |
| 2013/0331317 A1 | 12/2013 | Mohammadi |
| 2013/0331325 A1 | 12/2013 | Mohammadi |
| 2014/0094406 A1 | 4/2014 | Mohammadi |
| 2014/0148388 A1 | 5/2014 | Sonoda |
| 2014/0155316 A1 | 6/2014 | Mohammadi |
| 2014/0189893 A1 | 7/2014 | Li |
| 2014/0194353 A1 | 7/2014 | Ling |
| 2014/0243260 A1 | 8/2014 | Mohammadi |
| 2014/0243266 A1 | 8/2014 | Ling |
| 2015/0079065 A1 | 3/2015 | Wolf |
| 2015/0111821 A1 | 4/2015 | Suh |
| 2015/0132309 A1 | 5/2015 | Desnoyers |
| 2015/0284442 A1 | 10/2015 | Ling |
| 2015/0291677 A1 | 10/2015 | Ling |
| 2016/0045565 A1 | 2/2016 | Ling |
| 2016/0166642 A1 | 6/2016 | Ling |
| 2016/0168215 A1 | 6/2016 | Ling |
| 2016/0168216 A1 | 6/2016 | Ling |
| 2016/0168217 A1 | 6/2016 | Ling |
| 2016/0168218 A1 | 6/2016 | Ling |
| 2016/0168219 A1 | 6/2016 | Ling |
| 2016/0168220 A1 | 6/2016 | Ling |
| 2016/0168221 A1 | 6/2016 | Ling |
| 2016/0168222 A1 | 6/2016 | Ling |
| 2016/0200788 A1 | 7/2016 | Ling |
| 2016/0252497 A1 | 9/2016 | Ling |
| 2017/0173114 A1 | 6/2017 | Kahn et al. |
| 2017/0182122 A1 | 6/2017 | Ling |
| 2017/0182123 A1 | 6/2017 | Ling |
| 2017/0232067 A1 | 8/2017 | Lindhout |
| 2017/0327551 A1 | 11/2017 | Ling |
| 2018/0079806 A1 | 3/2018 | Sonoda |

(56) References Cited

U.S. PATENT DOCUMENTS

| | | |
|---|---|---|
| 2018/0100018 A1 | 4/2018 | Sonoda et al. |
| 2018/0110834 A1 | 4/2018 | DePaoli |
| 2018/0177846 A1 | 6/2018 | Ling |
| 2018/0186850 A1 | 7/2018 | Mohammadi et al. |
| 2018/0208677 A1 | 7/2018 | Desnoyers |
| 2018/0280479 A1 | 10/2018 | Choi et al. |
| 2018/0340028 A1 | 11/2018 | Rajan |
| 2018/0355007 A1 | 12/2018 | Ling |
| 2018/0362605 A1 | 12/2018 | Ling |
| 2018/0369331 A1 | 12/2018 | Fouillous-Meugnier et al. |
| 2019/0060403 A1 | 2/2019 | Ling |
| 2019/0175692 A1 | 6/2019 | Ling |
| 2019/0175693 A1 | 6/2019 | Ling |
| 2019/0175694 A1 | 6/2019 | Ling |
| 2019/0175695 A1 | 6/2019 | Ling |
| 2019/0175696 A1 | 6/2019 | Ling |
| 2019/0175697 A1 | 6/2019 | Ling |
| 2019/0177384 A1 | 6/2019 | Ling et al. |
| 2019/0194337 A1 | 6/2019 | Ling et al. |
| 2019/0307847 A1 | 10/2019 | Ling |

FOREIGN PATENT DOCUMENTS

| | | |
|---|---|---|
| CN | 103127503 A | 6/2013 |
| DE | 10100588 | 7/2002 |
| DE | 10100587 | 11/2002 |
| EA | 201001204 A1 | 2/2011 |
| EA | 015363 B1 | 6/2011 |
| EP | 2163626 | 3/2010 |
| JP | 2002112772 | 4/2002 |
| JP | 2009039117 | 2/2009 |
| JP | 2012530493 | 12/2012 |
| JP | 2013194049 | 9/2013 |
| NZ | 602702 | 3/2014 |
| WO | WO 2000/060085 | 10/2000 |
| WO | WO 2001/018209 | 3/2001 |
| WO | WO 2001/049740 | 7/2001 |
| WO | WO 2001/049849 | 7/2001 |
| WO | WO 2001/061007 | 8/2001 |
| WO | WO 2002/036732 | 5/2002 |
| WO | WO 2002/041911 | 5/2002 |
| WO | WO 2002/055693 | 7/2002 |
| WO | WO 2003/080803 | 10/2003 |
| WO | WO 2004/026228 | 4/2004 |
| WO | WO 2004/063355 | 7/2004 |
| WO | WO 2006/004076 | 1/2006 |
| WO | WO 2006/048291 | 5/2006 |
| WO | WO 2006/049854 | 5/2006 |
| WO | WO 2008/021196 | 2/2008 |
| WO | WO 2008/030273 | 3/2008 |
| WO | WO 2009/076478 | 6/2009 |
| WO | WO 2009/090553 | 7/2009 |
| WO | WO 2009/095372 | 8/2009 |
| WO | WO 2009/116861 | 9/2009 |
| WO | WO 2009/155381 | 12/2009 |
| WO | WO 2010/004204 | 1/2010 |
| WO | WO 2010/006214 | 1/2010 |
| WO | WO 2012/010553 | 1/2010 |
| WO | WO 2010/042747 | 4/2010 |
| WO | WO 2010/065439 | 6/2010 |
| WO | WO 2010/080976 | 7/2010 |
| WO | WO 2010/083051 | 7/2010 |
| WO | WO 2010/129600 | 11/2010 |
| WO | WO 2010/139741 | 12/2010 |
| WO | WO 2010/142665 | 12/2010 |
| WO | WO 2010/148142 | 12/2010 |
| WO | WO 2011/047267 | 4/2011 |
| WO | WO 2011/071783 | 6/2011 |
| WO | WO 2011/084808 | 7/2011 |
| WO | WO 2011/089203 | 7/2011 |
| WO | WO 2011/092234 | 8/2011 |
| WO | WO 2011/130417 | 10/2011 |
| WO | WO 2011/130729 | 10/2011 |
| WO | WO 2011/154349 | 12/2011 |
| WO | WO 2012/031603 | 3/2012 |
| WO | WO 2012/062078 | 5/2012 |
| WO | WO 2012/066075 | 5/2012 |
| WO | WO 2012/086809 | 6/2012 |
| WO | WO 2012/125812 | 9/2012 |
| WO | WO 2012/138919 | 10/2012 |
| WO | WO 2012/140650 | 10/2012 |
| WO | WO 2012/154263 | 11/2012 |
| WO | WO 2012/158704 | 11/2012 |
| WO | WO 2012/170438 | 12/2012 |
| WO | WO 2012/170704 | 12/2012 |
| WO | WO 2012/177481 | 12/2012 |
| WO | WO 2013/006486 | 1/2013 |
| WO | WO 2013/010780 | 1/2013 |
| WO | WO 2013/027191 | 2/2013 |
| WO | WO 2013/033452 | 3/2013 |
| WO | WO 2013/049234 | 4/2013 |
| WO | WO 2016/065106 | 4/2013 |
| WO | WO 2013/109856 | 7/2013 |
| WO | WO 2013/131091 | 9/2013 |
| WO | WO 2013/151671 | 10/2013 |
| WO | WO 2013/173158 | 11/2013 |
| WO | WO 2013/184958 | 12/2013 |
| WO | WO 2013/184960 | 12/2013 |
| WO | WO 2013/184962 | 12/2013 |
| WO | WO 2013/188182 | 12/2013 |
| WO | WO 2014/031420 | 2/2014 |
| WO | WO 2014/037373 | 3/2014 |
| WO | WO 2014/085365 | 6/2014 |
| WO | WO 2014/105939 | 7/2014 |
| WO | WO 2014/130659 | 8/2014 |
| WO | WO 2014/149699 | 9/2014 |
| WO | WO 2014/152089 | 9/2014 |
| WO | WO 2014/152090 | 9/2014 |
| WO | WO 2015/065897 | 5/2015 |
| WO | WO 2015/112886 | 7/2015 |
| WO | WO 2015/183890 | 12/2015 |
| WO | WO 2015/195509 | 12/2015 |
| WO | WO 2016/048995 | 3/2016 |
| WO | WO 2016/073855 | 5/2016 |
| WO | WO 2017/083276 | 5/2017 |
| WO | WO 2018/039557 | 3/2018 |
| WO | WO 2018/044778 | 3/2018 |
| WO | WO 2018/171557 | 9/2018 |
| WO | WO 2018/195390 | 10/2018 |
| WO | WO 2019/010314 | 1/2019 |

OTHER PUBLICATIONS

Bromberg et al., "Stat3 as an oncogene," *Cell*, 98:295-303 (1999).

Calvisi et al., "Ubiquitous activation of Ras and Jak/Stat pathways in human HCC," *Gastroenterol.*, 130:1117-1128 (2006).

Camilleri et al., "Measurement of Serum 7α-hydroxy-4-cholesten-3-one (or 7αC4), a Surrogate Test for Bile Acid Malabsorption in Health, Ileal Disease and Irritable Bowel Syndrome using Liquid Chromatography-Tandom Mass Spectrometry," *Neurogastroenterol Motil.*, 21(7):734-e43 (2009).

Chazouilleres, "Primary sclerosing cholangitis and bile acids," *Clinics and Research in Hepatology and Gastroenterology*, 36:S21-S25 (2012).

Chen et al., "Soluble FGFR4 extracellular domain inhibits FGF19-induced activation of FGFR4 signaling and prevents nonalcoholic fatty liver disease," *Biochem. Biophys. Res. Comm.*, 409:651-656 (2011).

Chen et al., "Sorafenib overcomes TRAIL resistance of hepatocellular carcinoma cells through the inhibition of STAT3," *Clin. Cancer Res.*, 16:5189-5199 (2010).

Claudel et al., "Role of Nuclear Receptors for Ble Acid Metabolism, Bile Secretion, Cholestasis, and Gallstone Disease," *Biochim. Biophys. Acta*, 1812:867-878 (2011).

Desnoyers et al., "Targeting FGF19 inhibits tumor growth in colon cancer xenograft and FGF19 transgenic hepatocellular carcinoma models," *Oncogene*, 27:85-97 (2008).

Dichenko et al., "Sat-374: Steroid 7 Alpha-Hydroxylases: Neurosteroids Activation and Cholesterol Catabolism," The Endocrine Society's 95th Annual Meeting and Expo, San Francisco, Abstract, Jun. 15-18, 2013.

(56) References Cited

OTHER PUBLICATIONS

Ďurovcová et al., "Plasma. Concentration of Fibroblast Growth Factors 21 and 19 in Patients with Cushing's Syndrome," *Physiol. Res.*, 59:415-422 (2010).
Foltz et al., "Treating Diabetes and Obesity with an FGF21-Mimetic Antibody Activating the βKlotho/FGFR1c Receptor Complex," *Sci. Transl. Med.*, 4:162ra153, pp. 1-10 (2012).
Foltz et al., "Supplementary Materials for: Treating Diabetes and Obesity with an FGF21-Mimetic Antibody Activating the βKlotho/FGFR1c Receptor Complex," *Sci. Transl. Med.*, 4:162ra153, pp. 1-13 (2012).
French et al., "Targeting FGFR4 Inhibits Hepatocellular Carcinoma in Preclinical Mouse Models," *PLoS One*, 7(5):e36713 (2012).
Ge et al., "Characterization of a FGF19 Variant with Altered Receptor Specificity Revealed a Central Role for FGFR1c in the Regulation of Glucose Metabolism," *PLoS One*, 7(3):e33603 (2012).
Harmer et al., "The Crystal Structure of Fibroblast Growth Factor (FGF) 19 Reveals Novel Features of the FGF Family and Offers a Structural Basis for Its Unusual Receptor Affinity," *Biochemistry*, 43:629-640 (2004).
Hasegawa, "The expansion of PROMININ-1-positive epithelial-mesenchymal cells within periportal fibrosis of rotavirusinduced biliary atresia," *Hepatol.*, 58:802A (2013).
He et al., "NF-κB and STAT3—key players in liver inflammation and cancer," *Cell Res.*, 21:159-168 (2011).
He et al., "Hepatocyte IKKbeta/NF-kappaB inhibits tumor promotion and progression by preventing oxidative stress-driven STAT3 activation," *Cancer Cell*, 17:286-297 (2010).
He et al., "Identification of liver cancer progenitors whose malignant progression depends on autocrine IL-6 signaling," *Cell*, 155:384-396 (2013).
Hofmann et al., "Chronic diarrhea due to excessive bile acid synthesis and not defective ileal transport: A new syndrome of defective FGF19 release," *Clin Gastroenterol Hepatol.*, 7(11):1151-1154 (2009).
Holt et al., "Definition of a novel growth factor-dependent signal cascade for the suppression of bile acid biosynthesis," *Genes Dev.*, 17:1581-1591 (2003).
Ikeda et al., "Leptin receptor somatic mutations are frequent in HCV-infected cirrhotic liver and associated with hepatocellular carcinoma," *Gastroenterol.*, 146:222-232 (2014).
Inagaki et al., "Fibroblast Growth Factor 15 Functions as an Enterohepatic Signal to Regulate Bile Acid Homeostasis," *Cell Metabolism*, 2:217-225 (2005).
Kakumu et al., "Interleukin 6 production by peripheral blood mononuclear cells in patients with chronic hepatitis B virus infection and primary biliary cirrhosis," *Gastroenterologia Japonica*, 28:18-24 (1993).
Karras et al., "STAT3 regulates the growth and immunoglobulin production of BCL(1) B cell lymphoma through control of cell cycle progression," *Cellular immunol.*, 202:124-135 (2000).
Kaushik et al., "Why is Trehalose an Exceptional Protein Stabilizer?," *J. Biol. Chem.*, 278(29):26458-26465 (2003).
Kenakin et al., "Signalling bias in new drug discovery: detection, quantification and therapeutic impact," *Nat. Rev. Drug Discov.*, 12:205-521 (2013).
Kir et al., "Roles of FGF19 in Liver Metabolism," *Cold Spring Harb. Symp. Quant. Biol.*, 76:139-144 (2011).
Kurosu et al., "Tissue-specific Expression fo βKlotho and Fibroblast Growth Factor (FGF) Receptor Isoforms Determines Metabolic Activity of FGF19 and FGF21," *J. Biol. Chem.*, 282(37):26687-26695 (2007).
Kurosu et al., "Supplemental Data for: Tissue-specific Expression fo βKlotho and Fibroblast Growth Factor (FGF) Receptor Isoforms Determines Metabolic Activity of FGF19 and FGF21," *J. Biol. Chem.*, (2007) (available at: http://www.jbc.org/content/suppl/2007/07/11/M704165200.DC1/Kurosu_Suppl_Data.pdf (last visited Jul. 23, 2014).
Lin et al., "The STAT3 inhibitor NSC 74859 is effective in hepatocellular cancers with disrupted TGF-beta signaling," *Oncogene*, 28:961-972 (2009).
Lin et al., "Adiponectin mediates the metabolic effects of FGF21 on glucose homeostasis and insulin sensitivity in mice," *Cell. Metab.*, 17:779-789 (2013).
Lindor, "Ursodeoxycholic acid for the treatment of primary biliary cirrhosis," *New Engl. J. Med.*, 11(357; 15) 1524-1529 (2007).
Ling et al., "Identification of Gut Factors that Mimic the Metabolic Benefits Seen After Gastric Bypass Surgery," American Diabetes Association, 72nd Scientific Sessions, Jun. 8-12, 2012, Philadelphia, PA, http://www.abstactsonline.com.
Ling et al., NGM Biopharmaceuticals, Identification of Gut Factors that Mimic the Metabolic Benefits of Gastric Bypass Surgery, p. 1, Jun. 8-12, 2012 Abstract.
Luo et al., "A nontumorigenic variant of FGF19 treats cholestatic liver diseases," *Sci. Transl. Med.*, 6: 247ra100 (2014).
Micanovic et al., "Different roles of N- and C-termini in the functional activity of FGF21," *J. Cell. Physiol.*, 219:227-234 (2009).
Miyata et al., "Involvement of Multiple Elements in FXR-mediated Transcriptional Activation of FGF19," *J. Steroid Biochm. Mol. Biol.*, 132:41-47 (2012).
Nguyen et al., "Purification of cholesterol 7 alpha-hydroxylase from human and rat liver and production of inhibiting polyclonal antibodies," *J. Biol. Chem.*, 265:4541-4546 (1990).
Nicholes et al., "A Mouse Model of Hepatocellular Carcinoma: Ectopic Expression of Fibroblast Growth Factor in Skeletal Muscle of Transgenic Mice," *Amer. J. Pathol.*, 160:2295-2307 (2002).
Ogawa et al., "BetaKlotho is Required for Metabolic Activity of Fibroblast Growth Factor 21," *Proc. Natl. Acad. Sci. USA*, 104:7432-7437 (2007).
Pai et al., "Antibody-Mediated Inhibition of Fibroblast Growth Factor 19 Results in Increased Bile Acids Synthesis and Ileal Malabsorption of Bile Acids in Cynomolgus Monkeys," *Toxicological Sciences*, 126(2):446-456 (2012).
Pattni et al., "Fibroblast Growth Factor 19 and 7α-Hydroxy-4-Cholesten-3-one in the Diagnosis of Patients With Possible Bile Acid Diarrhea," *Clinical and Translational Gastroenterology*, 26:312-324 (2012).
Potthoff et al., "Endocrine Fibroblast Growth Factors 15/19 and 21: From Feast to Famine," *Genes Dev.*, 26:312-324 (2012).
Pusl et al., "Intrahepatic cholestasis of pregnancy," *Orphanet J. Rare Diseases*, 2:26 (2007).
Rose et al., "Molecular Control of Systemic Bile Acid Homeostasis by the Liver Glucocorticoid Receptor," *Cell Metabolism*, 14:123-130 (2011).
Rossi et al., "P1313 Ngm282, a Novel Specific Inhibitor of Cyp7a1-Mediated Bile Acid Synthesis, is Safe and Well Tolerated with Predictable Pharmacokinetics in Healthy Human Subjects," *J. Hepatology*, 60(1):S533 (2014).
Ryan et al., "FXR is a Molecular Target for the Effects of Vertical Sleeve Gastroectomy," *Nature*, 509(7499):183-188 (2014); epub ahead of print Mar. 26, 2014.
Sawey et al., "Identification of a Therapeutic Strategy Targeting Amplified FGF19 in Liver Cancer by Oncogenomic Screening," *Cancer Cell*, 19(3):347-358 (2011).
Schaap et al., "High expression of the bile salt-homeostatic hormone fibroblast growth factor 19 in the liver of patients with extrahepatic cholestasis," *Hepatol.*, 49:1228-1235 (2009).
Schaap, "Role of Fibroblast Growth Factor 19 in the Control of Glucose Homeostasis," *Curr. Opin. Clin. Nutr. Metab. Care*, 15(4):386-391 (2012).
Tartaglia et al., "Identification and expression cloning of a leptin receptor, OB-R," *Cell*, 83:1263-1271 (1995).
Tokuriki et al., "Stability effects of mutations and protein evolvability," *Curr. Opin. Struct. Biol.*, 19(5):596-604 (2009).
Tomlinson et al., "Transgenic Mice Expressing Human Fibroblast Growth Factor-19 Display Increased Metabolic Rate and Decreased Adiposity," *Endocrinology*, 143(5):1741-1747 (2002).
Walters et al., "Managing bile acid diarrhoea," *Ther. Adv. Gastroenterol.*, 3(6):349-357 (2010).

(56) References Cited

OTHER PUBLICATIONS

Walters, "Bile acid diarrhoea and FGF19: new views on diagnosis, pathogenesis and therapy," *Nat. Rev. Gastroenterol. Hepatol.*, 11(7):426-434 (2014).
Walters, "A variant of FGF19 for treatment of disorders of cholestasis and bile acid metabolism," *Ann. Transl. Med.*, 3(S1): S7 (2015).
Wang et al., "Leptin in hepatocellular carcinoma," *World J. Gastroenterol.*, 16:5801-5809 (2010).
Wu et al., "C-terminal Tail of FGF19 Determines Its Specificity toward Klotho C-receptors," *J. Biol. Chem.*, 283(48):33304-33309 (2008).
Wu et al., "Role of FGF19 Induced FGFR4 Activation in the Regulation of Glucose Homeostasis," *Aging*, 1(12):1023-1027 (2009).
Wu et al., "Selective Activation of FGFR4 by an FGF19 Variant Does Not Improve Glucose Metabolism in ob/ob Mice," *Proc. Natl. Acad. Sci. USA*, 106(34):14379-14384 (2009).
Wu et al., "FGF19-induced Hepatocyte Proliferation is Mediated Through FGFR4 Activation," *J. Biol. Chem.*, 285(8):5165-5170 (2010).
Wu et al., "Separating Mitogenic and Metabolic Activities of Fibroblast Growth Factor 19 (FGF19)," *Proc. Natl. Acad. Sci. USA*, 107(32):14158-14163 (2010).
Wu et al., "Therapeutic Utilities of Fibroblast Growth Factor 19," *Expert Opin. Ther. Targets*, 15(11):1307-1316 (2011).
Wu et al., "FGF19 Regulates Cell Proliferation, Glucose and Bile Acid Metabolism via FGFR4-Dependent and Independent Pathways," *PLoS One*, 6(3):e17868 (2011).
Xie et al., "FGF-19, A Novel Fibroblast Growth Factor with Unique Specificity for FGFR4," *Cytokine*, 11(10):729-735 (1999).
Zhang et al., "Adenovirus-adeno-associated virus hybrid for large-scale recombinant adeno-associated virus production," *Hum. Gene Ther.*, 20:922-929 (2009).
Zhou et al., "Serum tumor markers for detection of hepatocellular carcinoma," *World J. Gastroenterol.*, 12(8):1175-1181 (2006).
Zhou et al., "Separating Tumorigenicity from Bile Acid Regulatory Activity for Endocrine Hormone FGF19," *Cancer Res.*, 74(12):3306-3316 (2014).
Zhou et al., "Engineered fibroblast growth factor 19 reduces liver injury and resolves sclerosing cholangitis in Mdr2-deficient mice," *Hepatology*, 63(3):914-929 (2016).
Angulo et al., "Liver Fibrosis, but No Other Histologic Features, Is Associated With Long-term Outcomes of Patients With Nonalcoholic Fatty Liver Disease," *Gastroenterology*, 149:389-397 (2015).
Camilleri et al., "Effect of increased bile acid synthesis or fecal excretion in irritable bowel syndrome-diarrhea," *Am. J. Gastroenterol.*, 109:1621-1630 (2014).
Depaoli et al., "NGM313, a novel activator of beta-Klotho/FGFR1c: A single dose significantly reduces steatosis (liver fat by MRI-PDFF), inflammation (ALT, AST) and fibrogenic activity (Pro-C3) in NAFLD subjects," Presentation at EASL International Liver Congress, Vienna, Austria, Apr. 12, 2019, 16 pages.
Depaoli et al., "NGM313, a novel activator of beta-Klotho/FGFR1c: A single dose significantly reduces steatosis (liver fat by MRI-PDFF), inflammation (ALT, AST) and fibrogenic activity (Pro-C3) in NAFLD subjects," Abstract 4579, EASL International Liver Congress, Vienna, Austria, Apr. 12, 2019, 3 pages.
Frankel et al., "Characterization of diphtheria fusion proteins targeted to the human interleukin-3 receptor," *Protein Eng.*, 13(8):575-581 (2000).
Galman et al., "Monitoring hepatic cholesterol 7α-hydroxylase activity by assay of the stable bile acid intermediate 7α-hydroxy-4-cholesten-3-one in peripheral blood," *J. Lipid Res.*, 44:859-866 (2003).
Harrison et al., "NGM282 Improves Liver Fibrosis and Histology in 12 Weeks in Patients With Nonalcoholic Steatohepatitis," *Hepatology*, 1-15 (2019).
Harrison et al., "NGM282 in NASH: 3 mg vs 6 mg QD (phase 2)," *Lancet*, 391:1174-1185 (2018).
Hirschfield et al., "Effect of NGM282, an FGF19 analogue, in primary sclerosing cholangitis: A multicenter, randomized, double-blind, placebo-controlled phase II trial," *J. Hepatology*, European Association for the Study of the Liver, pp. 1-12, 2018.
Hirschfield et al., "Serum Bile Acids Significantly Associate with the Fibrogenesis Biomarker Pro-C3: Analysis of a Randomized, Placebo-Controlled Trial of NGM282 in Patients with Primary Sclerosing Cholangitis (PSC)," NGM Biopharmaceuticals Inc. Poster, European Association for the Study of the Liver (EASL), International Liver Congress, Apr. 11, 2019.
Hirschfield et al., "A long term safety extension trial of the farnesoid X receptor (FXR) agonist obeticholic acid (OCA) and UDCA in primary biliary cirrhosis (PBC)," *Hepatol.*, 54(4):429A (2011).
Ilchenko, "Bile acids in norm and pathology," *Experimental and Clinical Gastroenterology*, 4:3-13 (2010). (English translation of abstract attached).
Islam et al., "Bile Acids: An Underrecognized and Underappreciated Cause of Chronic Diarrhea," *Pract. Gastroenterol.*, 110:32-44 (2012).
Kovar et al., "Regulation of Diurnal Variation of Cholesterol 7α-hydroxylase (CYP7A1) Activity in Healthy Subjects," *Physiol. Res.*, 59:233-238 (2010).
Kremer et al., "High serum autotaxin activity predisposes to sever pruritus during treatment with obeticholic acid in primary biliary cirrhosis," *J. Hepatol.*, 54:2, 1 page (2011).
Le et al., "Management of non-alcoholic fatty liver disease and steatohepatitis," *J. Clin. Exp. Hepatol.*, 2:156-173 (2012).
Ling et al., "NGM282 Promotes HDL Biogenesis and Transhepatic Cholesterol Efflux to Prevent Atherosclerosis in Mice," NGM Biopharmaceuticals Inc. Poster, European Association for the Study of the Liver (EASL), International Liver Congress, Apr. 11, 2019.
Mason et al., "Farnesoid-X receptor agonists: A new class of drugs for the treatment of PBC? An international study evaluating the addition of INT-747 to ursodeoxycholic acid," *J. Hepatol.*, 52:2, 1 page (2010).
Mayo et al., "Effect of NGM282, an FGF19 Analogue, on Pruritus in Patients with Primary Sclerosing Cholangitis: Analysis of a Phase 2, Multicenter, Randomized, Double-Blind, Placebo-Controlled Trial," NGM Biopharmaceuticals Inc. Poster, European Association for the Study of the Liver (EASL), International Liver Congress, Apr. 11, 2019.
Mudaliar et al., "Efficacy and safety of the farnesoid X receptor agonist obeticholic acid in patients with type 2 diabetes and non-alcoholic fatty liver disease," *Gastroenterology*, 145:574-582 (2013).
"NGM Bio Announces Results From Phase 2 Study of NGM282 in NASH Patients Demonstrating Clinically Significant Improvements in Liver Histology After 12 Weeks," PipielineReview.com, pp. 1-5 (Apr. 15, 2018). Retrieved from the Internet: https://pipelinereview.com/ . . . NASH-Patients-Demonstrating-Clinically-Significant-Improvements-In-Liver-Histology-After-12-Weeks.html, on Feb. 12, 2019.
Oduyebi et al., "Effects of NGM282, an FGF19 variant, on colonic transit and bowel function in functional constipation: a randomized phase 2 trial," *Am. J. Gastroenterol.*, 113:725-734 (2018).
Paredes et al., "NGM282 Maintains a Durable Off-Treatment Response on Hepatic Steatosis, Inflammation and Fibrogenesis in Patients with Biopsy- Confirmed Nonalcoholic Steatohepatitis: Results of a Multi-Center Phase 2 Dose-Finding Study," AASLD Abstracts, *Hepatology*, 68(1):1459A-1460A (2018).
Paredes et al., "NGM282 Maintains a Durable Off-Treatment Response on Hepatic Steatosis, Inflammation and Fibrogenesis in Patients with Biopsy-Confirmed Nonalcoholic Steatohepatitis: Results of a Multi-Center Phase 2 Dose-Finding Study," NGM Biopharmaceuticals Inc. Poster, American Association for the Study of Liver Diseases (AASLD), Liver Meeting, Nov. 12, 2018.
Sanyal et al., "Changes in Serum Bile Acids Correlate with 7alpha-Hydroxy-4-Cholesten-One and Fibrogenesis Biomarker Pro-C3 with NGM282 Therapy in Patients with Nonalcoholic Steatohepatitis," NGM Biopharmaceuticals, Inc. Poster, European Association for the Study of the Liver (EASL), International Liver Congress, Apr. 11, 2019.
"TaqMan SNP Genotyping Assays," Life Technologies Corporation (2012).

(56) References Cited

OTHER PUBLICATIONS

United States Securities and Exchange Commission, *Form S-1 Registration Statement: NGM Biopharmaceuticals, Inc.*, Sep. 28, 2018, pp. 1-282.

Vijayvargiya et al., "Diagnostic Methods for Bile Acid Malabsorption in Clinical Practice," *Clin. Gastroenterol. Hepatol.*, 11(10): 1232-1239 (2013).

Wong et al, "Pharmacogenetics of the effects of colesevelam on colonic transit in irritable bowel syndrome with diarrhea," *Dig. Dis. Sci.*, 57(5):1222-1226 (2012).

Zhou et al., "Non-cell-autonomous activation of IL-6/STAT3 signaling mediates FGF19-driven hepatocarcinogenesis," *Nat. Commun.*, 8:15433 (2017).

Zhou et al, "Therapeutic FGF19 promotes HDL biogenesis and transhepatic cholesterol efflux to prevent atherosclerosis," *J. Lipid Res.*, 60:550-565 (2019).

\* cited by examiner

FIG. 5

| Variants | Cyp7a1 IC50 (pM) | Relative Cyp7a1 Expression | HCC Score |
|---|---|---|---|
| Saline-treated | n/a | 100% | 0.00 |
| FGF19 | 2.3 | 4% | 1.00 |
| FGF21 | n/a | 35% | 0.00 |
| M1 | 1.1 | 10% | 0.04 |
| M2 | 0.9 | 2% | 0.00 |
| M5 | n/a | 100% | 0.00 |
| M32 | n/a | 100% | 0.00 |
| M69 | 8.6 | 0.5% | 0.00 |
| M70 | 4.8 | 0.2% | 0.00 |
| M75 | 34 | 12% | 0.00 |
| M76 | n/a | 17% | 0.00 |
| M85 | 3.6 | 16% | 0.00 |
| M90 | 859 | 100% | 1.00 |
| M96 | n/a | 100% | 1.00 |
| M98 | n/a | 100% | 1.00 |

METHODS OF USING VARIANTS OF FGF19 POLYPEPTIDES FOR THE TREATMENT OF PRURITUS

CROSS-REFERENCE TO RELATED APPLICATIONS

This application is a 371 national stage application of international application Serial No. PCT/US2016/060944 filed Nov. 8, 2016, which claims the benefit of priority to U.S. Ser. No. 62/252,939 filed Nov. 9, 2015, which is incorporated herein by reference in its entirety.

1. FIELD

Provided herein are variants of fibroblast growth factor 19 (FGF19) proteins and peptide sequences (and peptidomimetics) and fusions of FGF19 and/or fibroblast growth factor 21 (FGF21) proteins and peptide sequences (and peptidomimetics), and variants of fusions of FGF19 and/or FGF21 proteins and peptide sequences (and peptidomimetics). In some embodiments, these variants and fusions modulate bile acid homeostasis, and are useful in treatment of bile acid related and associated disorders. In some embodiments, these variants and fusions have glucose lowering activity, and are useful in treatment of hyperglycemia and other disorders.

2. SUMMARY

The invention is based, in part, on variants of FGF19 peptide sequences, fusions of FGF19 and/or FGF21 peptide sequences and variants of fusions (chimeras) of FGF19 and/or FGF21 peptide sequences having one or more activities. In one embodiment, the activity is glucose lowering activity. In another embodiment, the activity is bile acid homeostasis modulating activity. Such variants and fusions (chimeras) of FGF19 and/or FGF21 peptide sequences include sequences that do not substantially or significantly increase or induce hepatocellular carcinoma (HCC) formation or HCC tumorigenesis. Such variants and fusions (chimeras) of FGF19 and/or FGF21 peptide sequences further include sequences that do not induce a substantial elevation or increase in lipid profile.

In one embodiment, provide herein is a method of modulating bile acid homeostasis, comprising administering a chimeric peptide sequence provided herein. Also provided herein is a method of treating a bile acid-related disorder, comprising administering a chimeric peptide sequence provided herein. In another embodiment, provided herein is a method of treating a bile acid-associated disorder comprising administering a chimeric peptide sequence provided herein. In specific embodiments, an effective amount of the chimeric peptide sequence is administered.

In one embodiment, a chimeric peptide sequence comprises or consists of: a) an N-terminal region comprising at least seven amino acid residues, the N-terminal region having a first amino acid position and a last amino acid position, wherein the N-terminal region comprises DSSPL (SEQ ID NO:121) or DASPH (SEQ ID NO:122); and b) a C-terminal region comprising a portion of SEQ ID NO:99 (FGF19), the C-terminal region having a first amino acid position and a last amino acid position, wherein the C-terminal region comprises amino acid residues 16-29 of SEQ ID NO:99 (FGF19) (WGDPIRLRHLYTSG; SEQ ID NO:169), wherein the W residue corresponds to the first amino acid position of the C-terminal region.

In another embodiment, the treatment peptide, comprises: a) an N-terminal region comprising at least seven amino acid residues, the N-terminal region having a first amino acid position and a last amino acid position, wherein the N-terminal region comprises DSSPL (SEQ ID NO:121) or DASPH (SEQ ID NO:122); and b) a C-terminal region comprising a portion of SEQ ID NO:99 [FGF19], the C-terminal region having a first amino acid position and a last amino acid position, wherein the C-terminal region comprises (i) a first C-terminal region sequence comprising WGDPIRLRHLYTSG (amino acids 16 to 29 of SEQ ID NO:99 [FGF19]), wherein the W residue corresponds to the first amino acid position of the C-terminal region; and (ii) a second C-terminal region sequence comprising PHGLSSCFLRIRADGVVDCARGQSAHSLLEIKAVALRTVAIK-GVHSVRYLCMGADGKMQGL LQYSEEDCAFEEEIRP-DGYNVYRSEKHRLPVSLSSAKQRQLYKNRGFLPLS-HFLPMLPMVPE EPEDLRGHLESDMFSSPLETDSMDP-FGLVTGLEAVRSPSFEK (amino acid residues 30 to 194 of SEQ ID NO:99 [FGF19]).

In certain embodiments, the peptide (i) binds to fibroblast growth factor receptor 4 (FGFR4) with an affinity equal to or greater than FGF19 binding affinity for FGFR4; (ii) activates FGFR4 to an extent or amount equal to or greater than FGF19 activates FGFR4; (iii) has at least one of reduced hepatocellular carcinoma (HCC) formation; greater glucose lowering activity, less lipid increasing activity, less triglyceride activity, less cholesterol activity, less non-HDL activity or less HDL increasing activity, as compared to FGF19, or as compared to an FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19 (SEQ ID NO:99); and/or (iv) has less lean mass reducing activity as compared to FGF21.

In some embodiments, the second C-terminal region sequence of the treatment peptide comprises from 1 to 5 amino acid substitutions, deletions or insertions. In some embodiments, the treatment peptide is less than about 250 amino acids in length.

In one embodiment, the treatment peptide has an amino acid sequence comprising or consisting of MRDSS-PLVHYGWGDPIRLRHLYTSGPHGLSSCFLRIRADGV-VDCARGQSAHSLLEIKAVALR TVAIKGVHSVRYLC-MGADGKMQGLLQYSEEDCAFEEEIRPDGYNVYRS-EKHRLPVSLSSAK QRQLYKNRGFLPLSHFLPMLPM-VPEEPEDLRGHLESDMFSSPLETDSMDPF-GLVTGLEAVRS PSFEK (SEQ ID NO:70). In certain embodiments, the treatment peptide has an amino acid sequence comprising SEQ ID NO:70. In other embodiments, the treatment peptide has an amino acid sequence consisting of SEQ ID NO:70. In some embodiments, the treatment peptide is fused with an immunoglobulin Fc region.

In another embodiment, the treatment peptide has an amino acid sequence comprising or consisting of RDSS-PLVHYGWGDPIRLRHLYTSGPHGLSSCFLRIRADGV-VDCARGQSAHSLLEIKAVALRT VAIKGVHSVRYLCM-GADGKMQGLLQYSEEDCAFEEEIRPDGYNVYRSEK-HRLPVSLSSAKQ RQLYKNRGFLPLSHFLPMLPM-VPEEPEDLRGHLESDMFSSPLETDSMDPF-GLVTGLEAVRSP SFEK (SEQ ID NO:69). In certain embodiments, the treatment peptide has an amino acid sequence comprising SEQ ID NO:69. In other embodiments, the treatment peptide has an amino acid sequence consisting of SEQ ID NO:69. In some embodiments, the treatment peptide is fused with an immunoglobulin Fc region.

In another embodiment, a chimeric peptide sequence comprises or consists of: a) an N-terminal region comprising a portion of SEQ ID NO:100 (FGF21), the N-terminal region having a first amino acid position and a last amino acid position, wherein the N-terminal region comprises amino acid residues GQV, and wherein the V residue corresponds to the last amino acid position of the N-terminal region; and b) a C-terminal region comprising a portion of SEQ ID NO:99 (FGF19), the C-terminal region having a first amino acid position and a last amino acid position, wherein the C-terminal region comprises amino acid residues 21-29 of SEQ ID NO:99 (FGF19), RLRHLYTSG (SEQ ID NO:185), and wherein the R residue corresponds to the first position of the C-terminal region.

In a further embodiment, a chimeric peptide sequence comprises or consists of any of: a) an N-terminal region comprising a portion of SEQ ID NO:100 (FGF21), the N-terminal region having a first amino acid position and a last amino acid position, wherein the N-terminal region comprises at least 5 contiguous amino acids of SEQ ID NO:100 (FGF21) including the amino acid residues GQV, and wherein the V residue corresponds to the last amino acid position of the N-terminal region; and b) a C-terminal region comprising a portion of SEQ ID NO:99 (FGF19), the C-terminal region having a first amino acid position and a last amino acid position, wherein the C-terminal region comprises amino acid residues 21-29 of SEQ ID NO:99 (FGF19), RLRHLYTSG (SEQ ID NO:185), and wherein the R residue corresponds to the first position of the C-terminal region.

In an additional embodiment, a peptide sequence comprises or consists of any of: a) a FGF19 sequence variant having one or more amino acid substitutions, insertions or deletions compared to a reference or wild type FGF19; b) a FGF21 sequence variant having one or more amino acid substitutions, insertions or deletions compared to a reference or wild type FGF21; c) a portion of an FGF19 sequence fused to a portion of an FGF21 sequence; or d) a portion of an FGF19 sequence fused to a portion of an FGF21 sequence, wherein the FGF19 and/or FGF21 sequence portion(s) have one or more amino acid substitutions, insertions or deletions compared to a reference or wild type FGF19 and/or FGF21.

In particular aspects, the N-terminal region comprises at least 6 contiguous amino acids (or more, e.g., 7, 8, 9, 10, 11, 12, 13, 14, 15, 16, 17, 18, 19, 20, 20-25, 25-30, 30-40, 40-50, 50-75, 75-100 contiguous amino acids) of SEQ ID NO:100 (FGF21), including the amino acid residues GQ; or has an N-terminal region with at least 7 contiguous amino acids (or more, e.g., 8, 9, 10, 11, 12, 13, 14, 15, 16, 17, 18, 19, 20, 20-25, 25-30, 30-40, 40-50, 50-75, 75-100 contiguous amino acids) of SEQ ID NO:100 (FGF21), including the amino acid residues GQV.

In some embodiments, the peptide comprises i) a FGF19 sequence variant having one or more amino acid substitutions, insertions or deletions compared to a reference or wild type FGF19; ii) a FGF21 sequence variant having one or more amino acid substitutions, insertions or deletions compared to a reference or wild type FGF21; iii) a portion of a FGF19 sequence fused to a portion of a FGF21 sequence; or iv) a portion of a FGF19 sequence fused to a portion of a FGF21 sequence, wherein the FGF19 and/or FGF21 sequence portion(s) have one or more amino acid substitutions, insertions or deletions compared to a reference or wild type FGF19 and/or FGF21.

In still further embodiments, a peptide sequence or a chimeric peptide sequence comprises or consists of amino-terminal amino acids 1-16 of SEQ ID NO:100 (FGF21) fused to carboxy-terminal amino acids 21-194 of SEQ ID NO:99 (FGF19), or the peptide sequence has amino-terminal amino acids 1-147 of SEQ ID NO:99 (FGF19) fused to carboxy-terminal amino acids 147-181 of SEQ ID NO:100 (FGF21) (M41), or the peptide sequence has amino-terminal amino acids 1-20 of SEQ ID NO:99 (FGF19) fused to carboxy-terminal amino acids 17-181 of SEQ ID NO:100 (FGF21) (M44), or the peptide sequence has amino-terminal amino acids 1-146 of SEQ ID NO:100 (FGF21) fused to carboxy-terminal amino acids 148-194 of SEQ ID NO:99 (FGF19) (M45), or the peptide sequence has amino-terminal amino acids 1-20 of SEQ ID NO:99 (FGF19) fused to internal amino acids 17-146 of SEQ ID NO:100 (FGF21) or fused to carboxy-terminal amino acids 148-194 of SEQ ID NO:99 (FGF19) (M46).

In various further embodiments, a peptide sequence has at least one amino acid substitution to amino acid residues 125-129 of SEQ ID NO:99 (FGF19), EIRPD; at least one amino acid substitution to amino acid residues 126-128 of SEQ ID NO:99 (FGF19), IRP; or at least one amino acid substitution to amino acid residues 127-128 of SEQ ID NO:99 (FGF19), RP, or at least one amino acid substitution to amino acid residues 1-124 of SEQ ID NO:99 (FGF19) and/or to amino acid residues 130-194 of SEQ ID NO:99 (FGF19). More specifically, for example, a peptide sequence with a substitution to one of amino acid residues 127-128 of SEQ ID NO:99 (FGF19), RP, wherein at least one amino acid substitution is R127L or P128E. Said substitutions within a corresponding FGF19 sequence (e.g., EIRPD, IRP or RP) of a peptide variant provided herein is also contemplated. In certain embodiments, the peptide comprises both a R127L and P128E substitution to amino acid residues 127-128 of SEQ ID NO:99 (FGF19), RP, or the corresponding FGF19 sequence thereof in a variant peptide provided herein. In certain embodiments, the amino acid sequence of the peptide comprises at least one amino acid substitution in the Loop-8 region of FGF19, or the corresponding FGF19 sequence thereof in a variant peptide provided herein. In certain embodiments, the amino acid sequence of the peptide comprises one amino acid substitution to the EIRPD (amino acids 2-6 of SEQ ID NO:190) amino acid sequence in the Loop-8 region of FGF19. In some embodiments, the amino acid sequence of the peptide comprises two amino acid substitutions to the EIRPD (amino acids 2-6 of SEQ ID NO:190) amino acid sequence in the Loop-8 region of FGF19. In other embodiments, the amino acid sequence of the peptide comprises three amino acid substitutions to the EIRPD (amino acids 2-6 of SEQ ID NO:190) amino acid sequence in the Loop-8 region of FGF19. In certain embodiments, the amino acid sequence of the peptide comprises four amino acid substitutions to the EIRPD (amino acids 2-6 of SEQ ID NO:190) amino acid sequence in the Loop-8 region of FGF19. In some embodiments, the amino acid sequence of the peptide comprises five amino acid substitutions to the EIRPD (amino acids 2-6 of SEQ ID NO:190) amino acid sequence in the Loop-8 region of FGF19. In certain embodiments, the amino acid sequence of the peptide comprises one amino acid substitution to the IRP (amino acids 3-5 of SEQ ID NO:190) amino acid sequence in the Loop-8 region of FGF19. In some embodiments, the amino acid sequence of the peptide comprises two amino acid substitutions to the IRP (amino acids 3-5 of SEQ ID NO:190) amino acid sequence in the Loop-8 region of FGF19. In other embodiments, the amino acid sequence of the peptide comprises three amino acid substitutions to the IRP (amino acids 3-5 of SEQ ID NO:190) amino acid sequence in the Loop-8 region of FGF19. In certain embodiments, the amino acid sequence of the peptide comprises one amino acid substitution to the RP (amino acids 4-5 of SEQ ID NO:190) amino acid sequence in the Loop-8 region of FGF19. In some embodiments, the amino acid sequence of the peptide comprises two amino acid substitutions to the RP (amino acids 4-5 of SEQ ID NO:190) amino acid sequence in the Loop-8 region of FGF19. In certain embodiments, the amino acid substitution to the RP (amino acids 4-5 of SEQ ID NO:190) amino acid sequence in the Loop-8 region of FGF19 is an Arg (R) to Leu (L) substitution. In other embodiments, the substitution to the RP (amino acids 4-5 of SEQ ID NO:190) amino acid sequence in the Loop-8 region of FGF19 is a Pro (P) to Glu (E) substitution. In some embodiments, the substitutions to the RP (amino acids 4-5 of SEQ ID NO:190) amino acid sequence in the Loop-8 region of FGF19 is an Arg (R) to Leu (L) substitution and a Pro (P) to Glu (E) substitution. In specific embodiments, the foregoing substitution(s) in the Loop-8 region of FGF19 is in the corresponding FGF19 sequence thereof in a variant peptide provided herein. That is, said substitutions within a corresponding FGF19 sequence (e.g., EIRPD, IRP or RP) of a peptide variant provided herein is also contemplated.

Methods and uses provided herein can be practiced using a peptide or chimeric sequence, as set forth herein. For example, a sequence that comprises or consists of any peptide sequence set forth herein as M1 to M98, M101 to M160, or M200 to M207 or SEQ ID NOs:1 to 98, 101 to 135, 138 to 205 a peptide sequence that comprises or consists of any sequence set forth in Tables 1-11, or a peptide sequence that comprises or consists of any sequence set forth in the Sequence Listing herein.

In some embodiments, the peptide is a variant peptide designated M139. In some embodiments, the peptide comprises an amino acid sequence set forth in SEQ ID NO:193. In other embodiments, the peptide consists of an amino acid sequence set forth in SEQ ID NO:193. In some embodiments, the peptide is a variant peptide designated M140. In some embodiments, the peptide comprises an amino acid sequence set forth in SEQ ID NO:194. In other embodiments, the peptide consists of an amino acid sequence set forth in SEQ ID NO:194. In some embodiments, the peptide is a variant peptide designated M141. In some embodiments, the peptide comprises an amino acid sequence set forth in SEQ ID NO:195. In other embodiments, the peptide consists of an amino acid sequence set forth in SEQ ID NO:195. In some embodiments, the peptide is a variant peptide designated M160. In some embodiments, the peptide comprises an amino acid sequence set forth in SEQ ID NO:196. In other embodiments, the peptide consists of an amino acid sequence set forth in SEQ ID NO:196. In some embodiments, the peptide is a variant peptide designated M200. In some embodiments, the peptide comprises an amino acid sequence set forth in SEQ ID NO:197. In other embodiments, the peptide consists of an amino acid sequence set forth in SEQ ID NO:197. In some embodiments, the peptide is a variant peptide designated M201. In some embodiments, the peptide comprises an amino acid sequence set forth in SEQ ID NO:198. In other embodiments, the peptide consists of an amino acid sequence set forth in SEQ ID NO:198. In other embodiments, the peptide is a variant peptide designated M202. In some embodiments, the peptide comprises an amino acid sequence set forth in SEQ ID NO:199. In other embodiments, the peptide consists of an amino acid sequence set forth in SEQ ID NO:199. In certain embodiments, the peptide is a variant peptide designated M203. In some embodiments, the peptide comprises an amino acid sequence set forth in SEQ ID NO:200. In other embodiments, the peptide consists of an amino acid sequence set forth in SEQ ID NO:200. In some embodiments, the peptide is a variant peptide designated M204. In some embodiments, the peptide comprises an amino acid sequence set forth in SEQ ID NO:201. In other embodiments, the peptide consists of an amino acid sequence set forth in SEQ ID NO:201. In another embodiment, the peptide is a variant peptide designated M205. In some embodiments, the peptide comprises an amino acid sequence set forth in SEQ ID NO:202. In other embodiments, the peptide consists of an amino acid sequence set forth in SEQ ID NO:202. In other embodiments, the peptide is a variant peptide designated M206. In some embodiments, the peptide comprises an amino acid sequence set forth in SEQ ID NO:203. In other embodiments, the peptide consists of an amino acid sequence set forth in SEQ ID NO:203. In yet other embodiments, the peptide is a variant peptide designated M207. In some embodiments, the peptide comprises an amino acid sequence set forth in SEQ ID NO:204. In other embodiments, the peptide consists of an amino acid sequence set forth in SEQ ID NO:204.

In some embodiments, the N-terminal R residue is deleted. In other embodiments, the peptide comprises at least one (e.g., from 1 to 20, from 1 to 15, from 1 to 10 or from 1 to 5) amino acid substitution(s). In another embodiment, the peptide comprises at least one (e.g., from 1 to 20, from 1 to 15, from 1 to 10 or from 1 to 5) amino acid deletion(s). In other embodiments, the peptide comprises at least one (e.g., from 1 to 20, from 1 to 15, from 1 to 10 or from 1 to 5) amino acid insertion(s).

Methods and uses provided herein can be practiced using a peptide or chimeric sequence of any suitable length. In particular embodiments, the N-terminal or C-terminal region of the peptide or chimeric sequence is from about 20 to about 200 amino acid residues in length. In other particular aspects, a peptide or chimeric sequence has 1, 2, 3, 4, 5, 6, 7, 8, 9, 10, 11, 12, 13, 14, 15, 16, 17, 18, 19, 20 or more amino acid deletions from the amino terminus, the carboxy-terminus or internally. In further particular embodiments, a peptide or chimeric sequence has an N-terminal region, or a C-terminal region that comprises or consists of an amino acid sequence of about 5 to 10, 10 to 20, 20 to 30, 30 to 40, 40 to 50, 60 to 70, 70 to 80, 80 to 90, 90 to 100 or more amino acids. In additional more particular embodiments, a peptide or chimeric sequence has an FGF19 sequence portion, or an FGF21 sequence portion that comprises or consists of an amino acid sequence of about 5 to 10, 10 to 20, 20 to 30, 30 to 40, 40 to 50, 50 to 60, 60 to 70, 70 to 80, 80 to 90, 90 to 100 or more amino acids of FGF19 or FGF21.

In yet additional embodiments, a peptide sequence or a chimeric peptide sequence has a WGDPI (SEQ ID NO:170) sequence motif corresponding to the WGDPI sequence of amino acids 16-20 of SEQ ID NO:99 (FGF19); has a substituted, mutated or absent WGDPI (SEQ ID NO:170) sequence motif corresponding to FGF19 WGDPI (SEQ ID NO:170) sequence of amino acids 16-20 of FGF19; has a WGDPI (SEQ ID NO:170) sequence with one or more amino acids substituted, mutated or absent. In various other further aspects, the peptide sequence is distinct from an FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the FGF19 WGDPI (SEQ ID NO:170) sequence at amino acids 16-20.

In yet further embodiments, a peptide sequence or a chimeric peptide sequence has N-terminal region comprises amino acid residues VHYG (SEQ ID NO:101), wherein the N-terminal region comprises amino acid residues DASPHVHYG (SEQ ID NO:102), or the N-terminal region comprises amino acid residues DSSPLVHYG (SEQ ID NO:103). More particularly, in one aspect the G corresponds to the last position of the N-terminal region.

In various additional aspects, the N-terminal region comprises amino acid residues DSSPLLQ (SEQ ID NO:104), where the Q residue is the last amino acid position of the N-terminal region, or comprises amino acid residues DSSPLLQFGGQV (SEQ ID NO:105), where the V residue corresponds to the last position of the N-terminal region.

In certain embodiments, an N-terminal region comprises or consists of (or further comprises or consists of): RHPIP (SEQ ID NO:106), where R is the first amino acid position of the N-terminal region; or HPIP (SEQ ID NO:107), where H is the first amino acid position of the N-terminal region; or RPLAF (SEQ ID NO:108), where R is the first amino acid position of the N-terminal region; or PLAF (SEQ ID NO:109), where P is the first amino acid position of the N-terminal region; or R, where R is the first amino acid position of the N-terminal region.

In various other aspects, a peptide or chimeric sequence has: amino acid residues HPIP (SEQ ID NO:107), which are the first 4 amino acid residues of the N-terminal region. In various still further aspects, a peptide or chimeric sequence has: an R residue at the first position of the N-terminal region, or the first position of the N-terminal region is an M residue, or the first and second positions of the N-terminal region is an MR sequence, or the first and second positions of the N-terminal region is an RM sequence, or the first and second positions of the N-terminal region is an RD sequence, or the first and second positions of the N-terminal region is an DS sequence, or the first and second positions of the N-terminal region is an MD sequence, or the first and second positions of the N-terminal region is an MS sequence, or the first through third positions of the N-terminal region is an MDS sequence, or the first through third positions of the N-terminal region is an RDS sequence, or the first through third positions of the N-terminal region is an MSD sequence, or the first through third positions of the N-terminal region is an MSS sequence, or the first through third positions of the N-terminal region is an DSS sequence, or the first through fourth positions of the N-terminal region is an RDSS (SEQ ID NO:115), sequence, or the first through fourth positions of the N-terminal region is an MDSS (SEQ ID NO:116), sequence, or the first through fifth positions of the N-terminal region is an MRDSS (SEQ ID NO:117), sequence, or the first through fifth positions of the N-terminal region is an MSSPL (SEQ ID NO:113) sequence, or the first through sixth positions of the N-terminal region is an MDSSPL (SEQ ID NO:110) sequence, or the first through seventh positions of the N-terminal region is an MSDSSPL (SEQ ID NO:111) sequence.

In various other particular aspects, a peptide or chimeric sequence has at the N-terminal region first amino acid position an "M" residue, an "R" residue, a "S" residue, a "H" residue, a "P" residue, a "L" residue or an "D" residue. In various alternative particular aspects, a peptide or chimeric sequence peptide sequence does not have a "M" residue or an "R" residue at the first amino acid position of the N-terminal region.

In further various other aspects, a peptide or chimeric sequence has an N-terminal region with any one of the following sequences: MDSSPL (SEQ ID NO:110), MSDSSPL (SEQ ID NO:111), SDSSPL (SEQ ID NO:112), MSSPL (SEQ ID NO:113) or SSPL (SEQ ID NO:114).

In some embodiments, a peptide sequence or a chimeric peptide sequence has a residue at the last position of the C-terminal region that corresponds to about residue 194 of SEQ ID NO:99 (FGF19). In still other embodiments, a peptide sequence or a chimeric peptide sequence an addition of amino acid residues 30-194 of SEQ ID NO:99 (FGF19) at the C-terminus, resulting in a chimeric polypeptide having a residue at the last position of the C-terminal region that corresponds to about residue 194 of SEQ ID NO:99 (FGF19). In further other embodiments, a chimeric peptide sequence or peptide sequence comprises all or a portion of an FGF19 sequence (e.g., SEQ ID NO:99), positioned at the C-terminus of the peptide, or where the amino terminal "R" residue is deleted from the peptide.

In more particular embodiments, a chimeric peptide sequence or peptide sequence comprises or consists of any of M1 to M98, M101 to M160, or M200 to M207 variant peptide sequences, or a subsequence or fragment of any of the M1 to M98, M101 to M160, or M200 to M207 variant peptide sequences. Methods and uses provided herein can also be practiced using a peptide or chimeric sequence, as set forth herein. For example, a sequence that comprises or consists of any peptide sequence set forth herein as M1 to M98, M101 to M160, or M200 to M207 or SEQ ID NOs:1 to 98, 101 to 135, 138 to 205 a peptide sequence that comprises or consists of any sequence set forth in Tables 1-11 or a peptide sequence that comprises or consists of any sequence set forth in the Sequence Listing herein.

In various more particular aspects, a peptide sequence comprises or consists of any one of the following sequences:

```
                                          (SEQ ID NO: 3)
RPLAFSDAGPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEILEDGYNVYRSEKHRLPVSLSSAKQRQLYKNRGFLPLSHFLPMLPMV

PEEPEDLRGHLESDMFSSPLETDSMDPFGLVTGLEAVRSPSFEK (M3);

(SEQ ID NO: 194)
RPLAFSDAGPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEIREDGYNVYRSEKHRLPVSLSSAKQRQLYKNRGFLPLSHFLPMLPMV

PEEPEDLRGHLESDMFSSPLETDSMDPFGLVTGLEAVRSPSFEK (M140);

(SEQ ID NO: 196)
RPLAFSDAGPHVHYGWGDPIRQRHLYTSGPHGLSSCFLRIRADGVVDCAR

GQSAHSLLEIKAVALRTVAIKGVHSVRYLCMGADGKMQGLLQYSEEDCAF

EEEILEDGYNVYRSEKHRLPVSLSSAKQRQLYKNRGFLPLSHFLPMLPMV

PEEPEDLRGHLESDMFSSPLETDSMDPFGLVTGLEAVRSPSFEK
```

-continued (SEQ ID NO: 69)
RDSSPLVHYGWGDPIRLRHLYTSGPHGLSSCFLRIRADGVVDCARGQSAH
SLLEIKAVALRTVAIKGVHSVRYLCMGADGKMQGLLQYSEEDCAFEEEIR
PDGYNVYRSEKHRLPVSLSSAKQRQLYKNRGFLPLSHFLPMLPMVPEEPE
DLRGHLESDMFSSPLETDSMDPFGLVTGLEAVRSPSFEK (M69);

(SEQ ID NO: 52)
RDSSPLLQWGDPIRLRHLYTSGPHGLSSCFLRIRADGVVDCARGQSAHSL
LEIKAVALRTVAIKGVHSVRYLCMGADGKMQGLLQYSEEDCAFEEEIRPD
GYNVYRSEKHRLPVSLSSAKQRQLYKNRGFLPLSHFLPMLPMVPEEPEDL
RGHLESDMFSSPLETDSMDPFGLVTGLEAVRSPSFEK (M52);

(SEQ ID NO: 5)
RHPIPDSSPLLQFGGQVRLRHLYTSGPHGLSSCFLRIRADGVVDCARGQS
AHSLLEIKAVALRTVAIKGVHSVRYLCMGADGKMQGLLQYSEEDCAFEEE
IRPDGYNVYRSEKHRLPVSLSSAKQRQLYKNRGFLPLSHFLPMLPMVPEE
PEDLRGHLESDMFSSPLETDSMDPFGLVTGLEAVRSPSFEK (M5);

(SEQ ID NO: 160)
HPIPDSSPLLQFGGQVRLRHLYTSGPHGLSSCFLRIRADGVVDCARGQSA
HSLLEIKAVALRTVAIKGVHSVRYLCMGADGKMQGLLQYSEEDCAFEEEI
RPDGYNVYRSEKHRLPVSLSSAKQRQLYKNRGFLPLSHFLPMLPMVPEEP
EDLRGHLESDMFSSPLETDSMDPFGLVTGLEAVRSPSFEK (M5-R);

(SEQ ID NO: 71)
HPIPDSSPLLQFGGQVRQRYLYTDDAQQTEAHLEIREDGTVGGAADQSPE
SLLQLKALKPGVIQILGVKTSRFLCQRPDGALYGSLHFDPEACSFRELLL
EDGYNVYQSEAHSLPLHLPGNKSPHRDPAPRGPARFLPLPGLPPALPEPP
GILAPQPPDVGSSDPLSMVGPSQGRSPSYAS (M71);

(SEQ ID NO: 72)
HPIPDSSPLLQFGGQVRQRYLYTDDAQQTEAHLEIREDGTVGGAADQSPE
SLLQLKALKPGVIQILGVKTSRFLCQRPDGALYGSLHFDPEACSFRELLL
EDGYNVYQSEAHGLPLHLPGNKSPHRDPAPRGPARFLPLPGLPPAPPEPP
GILAPQPPDVGSSDPLSMVGPSQGRSPSYAS (M72);

(SEQ ID NO: 73)
HPIPDSSPLLQFGGQVRQRYLYTDDAQQTEAHLEIREDGTVGGAADQSPE
SLLQLKALKPGVIQILGVKTSRFLCQRPDGALYGSLHFDPEACSFRELLL
EDGYNVYQSEAHGLPLHLPGNKSPHRDPAPRGPARFLPLPGLPPALPEPP
GILAPQPPDVGSSDPLSMVVQDELQGVGGEGCHMHPENCKTLLTDIDRTH
TEKPVWDGITGE (M73);

(SEQ ID NO: 1 or 139)
RPLAFSDASPHVHYGWGDPIRLRHLYTSGPHGLSSCFLRIRADGVVDCAR
GQSAHSLLEIKAVALRTVAIKGVHSVRYLCMGADGKMQGLLQYSEEDCAF
EEEIRPDGYNVYRSEKHRLPVSLSSAKQRQLYKNRGFLPLSHFLPMLPMV
PEEPEDLRGHLESDMFSSPLETDSMDPFGLVTGLEAVRSPSFEK (M1);

(SEQ ID NO: 2 or 140)
RPLAFSDSSPLVHYGWGDPIRLRHLYTSGPHGLSSCFLRIRADGVVDCAR
GQSAHSLLEIKAVALRTVAIKGVHSVRYLCMGADGKMQGLLQYSEEDCAF
EEEIRPDGYNVYRSEKHRLPVSLSSAKQRQLYKNRGFLPLSHFLPMLPMV
PEEPEDLRGHLESDMFSSPLETDSMDPFGLVTGLEAVRSPSFEK (M2);

(SEQ ID NO: 48 or 6 or 148)
RDSSPLLQFGGQVRLRHLYTSGPHGLSSCFLRIRADGVVDCARGQSAHSL
LEIKAVALRTVAIKGVHSVRYLCMGADGKMQGLLQYSEEDCAFEEEIRPD
GYNVYRSEKHRLPVSLSSAKQRQLYKNRGFLPLSHFLPMLPMVPEEPEDL
RGHLESDMFSSPLETDSMDPFGLVTGLEAVRSPSFEK (M48);

(SEQ ID NO: 49 or 7 or 149)
RPLAFSDSSPLLQFGGQVRLRHLYTSGPHGLSSCFLRIRADGVVDCARGQ
SAHSLLEIKAVALRTVAIKGVHSVRYLCMGADGKMQGLLQYSEEDCAFEE
EIRPDGYNVYRSEKHRLPVSLSSAKQRQLYKNRGFLPLSHFLPMLPMVPE
EPEDLRGHLESDMFSSPLETDSMDPFGLVTGLEAVRSPSFEK (M49);

(SEQ ID NO: 50)
RHPIPDSSPLLQFGDQVRLRHLYTSGPHGLSSCFLRIRADGVVDCARGQS
AHSLLEIKAVALRTVAIKGVHSVRYLCMGADGKMQGLLQYSEEDCAFEEE
ILEDGYNVYRSEKHRLPVSLSSAKQRQLYKNRGFLPLSHFLPMLPMVPEE
PEDLRGHLESDMFSSPLETDSMDPFGLVTGLEAVRSPSFEK (M50);

(SEQ ID NO: 51 or 36 or 155)
RHPIPDSSPLLQFGGNVRLRHLYTSGPHGLSSCFLRIRADGVVDCARGQS
AHSLLEIKAVALRTVAIKGVHSVRYLCMGADGKMQGLLQYSEEDCAFEEE
IRPDGYNVYRSEKHRLPVSLSSAKQRQLYKNRGFLPLSHFLPMLPMVPEE
PEDLRGHLESDMFSSPLETDSMDPFGLVTGLEAVRSPSFEK (M51);

(SEQ ID NO: 192)
MDSSPLLQWGDPIRLRHLYTSGPHGLSSCFLRIRADGVVDCARGQSAHSL
LEIKAVALRTVAIKGVHSVRYLCMGADGKMQGLLQYSEEDCAFEEEIRPD
GYNVYRSEKHRLPVSLSSAKQRQLYKNRGFLPLSHFLPMLPMVPEEPEDL
RGHLESDMFSSPLETDSMDPFGLVTGLEAVRSPSFEK (M53);

(SEQ ID NO: 70)
MRDSSPLVHYGWGDPIRLRHLYTSGPHGLSSCFLRIRADGVVDCARGQSA
HSLLEIKAVALRTVAIKGVHSVRYLCMGADGKMQGLLQYSEEDCAFEEEI
RPDGYNVYRSEKHRLPVSLSSAKQRQLYKNRGFLPLSHFLPMLPMVPEEP
EDLRGHLESDMFSSPLETDSMDPFGLVTGLEAVRSPSFEK (M70);

(SEQ ID NO: 193)
RPLAFSDAGPHVHYGWGDPIRLRHLYTSGPHGLSSCFLRIRADGVVDCAR
GQSAHSLLEIKAVALRTVAIKGVHSVRYLCMGADGKMQGLLQYSEEDCAF
EEEILPDGYNVYRSEKHRLPVSLSSAKQRQLYKNRGFLPLSHFLPMLPMV
PEEPEDLRGHLESDMFSSPLETDSMDPFGLVTGLEAVRSPSFEK
(M139);
or (SEQ ID NO: 195)
RPLAFSDAGPHVHYGWGDPIRLRHLYTSGPHGLSSCFLRIRADGVVDCAR
GQSAHSLLEIKAVALRTVAIKGVHSVRYLCMGADGKMQGLLQYSEEDCAF

-continued

EEEILCDGYNVYRSEKHRLPVSLSSAKQRQLYKNRGFLPLSHFLPMLPMV

PEEPEDLRGHLESDMFSSPLETDSMDPFGLVTGLEAVRSPSFEK (M141);

or a subsequence or fragment of any of the foregoing peptide sequences. In certain embodiments of any of the foregoing peptide sequences, the R terminal residue (R residue at the N-terminus) is deleted.

In other embodiments, the peptide comprises or consists of:
RDSSPLVHYGWGDPIRLRELYTSGPHGLSSCFLRI-RADGVVDCARGOSAHSLLEIKAVALRT VAIKGVHS-VRYLCMGADGKMQGLLQYSEEDCAFEEEILEDGYN-VYRSEKHRLPVSLSSAKQ RQLYKNRGFLPLSH-FLPMLPMVPEEPEDLRGHLESDMFSSPLETDSMDPF-GLVTGLEAVRSP SFEK (M200) (SEQ ID NO:197); or a subsequence or fragment thereof. In one embodiment, the N-terminal R residue is deleted.

In some embodiments, the peptide comprises or consists of:
RPLAFSDSSPLVHYGWGDPIRLRELYTSGPHGLSSC-FLRIRADGVVDCARGQSAHSLLEIKAV ALRTVAIK-GVHSVRYLCMGADGKMQGLLQYSEEDCAFEEE-ILEDGYNVYRSEKHRLPVSLS SAKQRQLYKNR-GFLPLSHFLPMLPMVPEEPEDLRGHLESDMFSS-PLETDSMDPFGLVTGLEA VRSPSFEK (M201) (SEQ ID NO:198); or a subsequence or fragment thereof. In one embodiment, the N-terminal R residue is deleted.

In certain embodiments, the peptide comprises or consists of:
RPLAFSDASPHVHYGWGDPIRLRHLYTSGPHGLSSC-FLRIRADGVVDCARGOSAHSLLEIKA VALRTVAIK-GVHSVRYLCMGADGKMQGLLQYSEEDCAFEEE-ILEDGYNVYRSEKHRLPVSL SSAKQRQLYKN-RGFLPLSHFLPMLPMVPEEPEDLRGHLESDMFSS-PLETDSMDPFGLVTGLE AVRSPSFEK (M202) (SEQ ID NO:199); or a subsequence or fragment thereof. In one embodiment, the N-terminal R residue is deleted.

In other embodiments, the peptide comprises or consists of:
RDSSPLLQWGDPIRLRHLYTSGPHGLS SCFLRI-RADGVVDCARGQSAHSLLEIKAVALRTVAI KGVHS-VRYLCMGADGKMQGLLQYSEEDCAFEEEILEDGYN-VYRSEKEIRLPVSLSSAKQRQ LYKNRGFLPLSH-FLPMLPMVPEEPEDLRGHLESDMFSSPLETDSMDPF-GLVTGLEAVRSPSFE K (M203) (SEQ ID NO:200); or a subsequence or fragment thereof. In one embodiment, the N-terminal R residue is deleted.

In some embodiments, the peptide comprises or consists of:
RHPIPDSSPLLQFGDQVRLRHLYTSGPHGLSSCFLRI-RADGVVDCARGQSAHSLLEIKAVALR TVAIKGVHS-VRYLCMGADGKMQGLLQYSEEDCAFEEEILEDGYN-VYRSEKHRLPVSLSSAK QRQLYKNRGFLPLSHF-LPMLPMVPEEPEDLRGHLESDMFSSPLETDSMDPF-GLVTGLEAVRS PSFEK (M204) (SEQ ID NO:201); or a subsequence or fragment thereof. In one embodiment, the N-terminal R residue is deleted.

In certain embodiments, the peptide comprises or consists of:
RDSSPLLQFGGQVRLRHLYTSGPHGLSSCFLRI-RADGVVDCARGQSAHSLLEIKAVALRTVAI KGVHS-VRYLCMGADGKMQGLLQYSEEDCAFEEEILEDGYN-VYRSEKHRLPVSLSSAKQRQ LYKNRGFLPLSHF-LPMLPMVPEEPEDLRGHLESDMFSSPLETDSMDPF-GLVTGLEAVRSPSFE K (M205) (SEQ ID NO:202); or a subsequence or fragment thereof. In one embodiment, the N-terminal R residue is deleted.

In some embodiments, the peptide comprises or consists of:
RHPIPDSSPLLQFGGQVRLRHLYTSGPHGLSSCFLRI-RADGVVDCARGQSAHSLLEIKAVALR TVAIKGVHS-VRYLCMGADGKMQGLLQYSEEDCAFEEEILEDGYN-VYRSEKHRLPVSLSSAK QRQLYKNRGFLPLSHFLPMLPMVPEEPEDLRGHLES-DMFSSPLETDSMDPFGLVTGLEAVRS PSFEK (M206) (SEQ ID NO:203); or a subsequence or fragment thereof. In one embodiment, the N-terminal R residue is deleted.

In other embodiments, the peptide comprises or consists of:
MRDSSPLVHYGWGDPIRLRHLYTSGPHGLSSCFLRI-RADGVVDCARGQSAHSLLEIKAVALR TVAIKGVHS-VRYLCMGADGKMQGLLQYSEEDCAFEEEILEDGYN-VYRSEKHRLPVSLSSAK QRQLYKNRGFLPLPSHFLPMLPMVPEEPEDLRGHLES-DMFSSPLETDSMDPFGLVTGLEAVRS PSFEK (M207) (SEQ ID NO:204); or a subsequence or fragment thereof.

In some embodiments, the peptide is a variant peptide designated M139. In some embodiments, the peptide comprises an amino acid sequence set forth in SEQ ID NO:193. In other embodiments, the peptide consists of an amino acid sequence set forth in SEQ ID NO:193. In some embodiments, the peptide is a variant peptide designated M140. In some embodiments, the peptide comprises an amino acid sequence set forth in SEQ ID NO:194. In other embodiments, the peptide consists of an amino acid sequence set forth in SEQ ID NO:194. In some embodiments, the peptide is a variant peptide designated M141. In some embodiments, the peptide comprises an amino acid sequence set forth in SEQ ID NO:195. In other embodiments, the peptide consists of an amino acid sequence set forth in SEQ ID NO:195. In some embodiments, the peptide is a variant peptide designated M160. In some embodiments, the peptide comprises an amino acid sequence set forth in SEQ ID NO:196. In other embodiments, the peptide consists of an amino acid sequence set forth in SEQ ID NO:196. In some embodiments, the peptide is a variant peptide designated M200. In some embodiments, the peptide comprises an amino acid sequence set forth in SEQ ID NO:197. In other embodiments, the peptide consists of an amino acid sequence set forth in SEQ ID NO:197. In some embodiments, the peptide is a variant peptide designated M201. In some embodiments, the peptide comprises an amino acid sequence set forth in SEQ ID NO:198. In other embodiments, the peptide consists of an amino acid sequence set forth in SEQ ID NO:198. In other embodiments, the peptide is a variant peptide designated M202. In some embodiments, the peptide comprises an amino acid sequence set forth in SEQ ID NO:199. In other embodiments, the peptide consists of an amino acid sequence set forth in SEQ ID NO:199. In certain embodiments, the peptide is a variant peptide designated M203. In some embodiments, the peptide comprises an amino acid sequence set forth in SEQ ID NO:200. In other embodiments, the peptide consists of an amino acid sequence set forth in SEQ ID NO:200. In some embodiments, the peptide is a variant peptide designated M204. In some embodiments, the peptide comprises an amino acid sequence set forth in SEQ ID NO:201. In other embodiments, the peptide consists of an amino acid sequence set forth in SEQ ID NO:201. In another embodiment, the peptide is a variant peptide designated M205. In some embodiments, the peptide comprises an amino acid sequence set forth in SEQ ID NO:202. In other embodiments, the peptide consists of an amino acid sequence set forth in SEQ ID NO:202. In other embodiments, the peptide is a variant peptide designated M206. In some embodiments, the peptide comprises an amino acid sequence set forth in SEQ ID NO:203. In other embodiments, the peptide consists of an amino acid sequence set forth in SEQ ID NO:203. In yet other embodiments, the peptide is a variant peptide designated M207. In some embodiments, the peptide comprises an amino acid sequence set forth in SEQ ID NO:204. In other embodiments, the peptide consists of an amino acid sequence set forth in SEQ ID NO:204.

In various additional particular aspects, the N-terminus of the peptide sequence includes or consists of any of: HPIPDSSPLLQFGGQVRLRHLYTSG (M5-R) (amino acids 1-25 of SEQ ID NO:160); DSSPLLQFGGQVRLRHLYTSG (M6-R) (amino acids 2-22 of SEQ ID NO: 6); RPLAFSDSSPLLQFGGQVRLRHLYTSG (M7) (amino acids 1-27 of SEQ ID NO: 7); HPIPDSSPLLQWGDPIRLRHLYTSG (M8-R) (amino acids 2-26 of SEQ ID NO:8); HPIPDSSPLLQFGWGDPIRLRHLYTSG (M9-R) (amino acids 2-28 of SEQ ID NO:9); HPIPDSSPHVHYGWGDPIRLRHLYTSG (M10-R) (amino acids 2-28 of SEQ ID NO:10); RPLAFSDAGPLLQWGDPIRLRHLYTSG (M11) (amino acids 1-27 of SEQ ID NO:11); RPLAFSDAGPLLQFGWGDPIRLRHLYTSG (M12) (amino acids 1-29 of SEQ ID NO:12); RPLAFSDAGPLLQFGGQVRLRHLYTSG (M13) (amino acids 1-27 of SEQ ID NO:13); HPIPDSSPHVHYGGQVRLRHLYTSG (M14-R) (amino acids 2-26 of SEQ ID NO:14); RPLAFSDAGPHVHYGGQVRLRHLYTSG (M15) (amino acids 1-27 of SEQ ID NO:15); RPLAFSDAGPHVHWGDPIRLRHLYTSG (M16) (amino acids 1-27 of SEQ ID NO:16); RPLAFSDAGPHVGWGDPIRLRHLYTSG (M17) (amino acids 1-27 of SEQ ID NO:17); RPLAFSDAGPHYGWGDPIRLRHLYTSG (M18) (amino acids 1-27 of SEQ ID NO:18); RPLAFSDAGPVYGWGDPIRLRHLYTSG (M19) (amino acids 1-27 of SEQ ID NO:19); RPLAFSDAGPVHGWGDPIRLRHLYTSG (M20) (amino acids 1-27 of SEQ ID NO:20); RPLAFSDAGPVHYWGDPIRLRHLYTSG (M21) (amino acids 1-27 of SEQ ID NO:21); RPLAFSDAGPHVHGWGDPIRLRHLYTSG (M22) (amino acids 1-27 of SEQ ID NO:22); RPLAFSDAGPHHGWGDPIRLRHLYTSG (M23) (amino acids 1-27 of SEQ ID NO:23); RPLAFSDAGPHHYWGDPIRLRHLYTSG (M24) (amino acids 1-27 of SEQ ID NO:24); RPLAFSDAGPHVYWGDPIRLRHLYTSG (M25) (amino acids 1-27 of SEQ ID NO:25); RPLAFSDSSPLVHWGDPIRLRHLYTSG (M26) (amino acids 1-27 of SEQ ID NO:26); RPLAFSDSSPHVHWGDPIRLRHLYTSG (M27) (amino acids 1-27 of SEQ ID NO:27); RPLAFSDAGPHVWGDPIRLRHLYTSG (M28) (amino acids 1-26 of SEQ ID NO:28); RPLAFSDAGPHVHYWGDPIRLRHLYTSG (M29) (amino acids 1-28 of SEQ ID NO:29); RPLAFSDAGPHVHYAWGDPIRLRHLYTSG (M30) (amino acids 1-29 of SEQ ID NO:30); RHPIPDSSPLLQFGAQVRLRHLYTSG (M31) (amino acids 1-26 of SEQ ID NO:31); RHPIPDSSPLLQFGDQVRLRHLYTSG (M32) (amino acids 1-26 of SEQ ID NO:32); RHPIPDSSPLLQFGPQVRLRHLYTSG (M33) (amino acids 1-26 of SEQ ID NO:33); RHPIPDSSPLLQFGGAVRLRHLYTSG (M34) (amino acids 1-26 of SEQ ID NO:34); RHPIPDSSPLLQFGGEVRLRHLYTSG (M35) (amino acids 1-26 of SEQ ID NO:35); RHPIPDSSPLLQFGGNVRLRHLYTSG (M36) (amino acids 1-26 of SEQ ID NO:36); RHPIPDSSPLLQFGGQARLRHLYTSG (M37) (amino acids 1-26 of SEQ ID NO:37); RHPIPDSSPLLQFGGQIRLRHLYTSG (M38) (amino acids 1-26 of SEQ ID NO:38); RHPIPDSSPLLQFGGQTRLRHLYTSG (M39) (amino acids 1-26 of SEQ ID NO:39); RHPIPDSSPLLQFGWGQPVRLRHLYTSG (M40) (amino acids 1-28 of SEQ ID NO:40); DAGPHVHYGWGDPIRLRHLYTSG (M74-R) (amino acids 2-24 of SEQ ID NO:74); VHYGWGDPIRLRHLYTSG (M75-R) (amino acids 2-19 of SEQ ID NO:75); RLRHLYTSG (M77-R) (amino acids 2-10 of SEQ ID NO:77); RHPIPDSSPLLQFGWGDPIRLRHLYTSG (M9) (amino acids 1-28 of SEQ ID NO:9); RHPIPDSSPLLQWGDPIRLRHLYTSG (M8) (amino acids 1-26 of SEQ ID NO:8); RPLAFSDAGPLLQFGWGDPIRLRHLYTSG (M12) (amino acids 1-29 of SEQ ID NO:12); RHPIPDSSPHVHYGWGDPIRLRHLYTSG (M10) (amino acids 1-28 of SEQ ID NO:10); RPLAFSDAGPLLQFGGQVRLRHLYTSG (M13) (amino acids 1-27 of SEQ ID NO:13); RHPIPDSSPHVHYGGQVRLRHLYTSG (M14) (amino acids 1-26 of SEQ ID NO:14); RPLAFSDAGPHVHYGGDIRLRHLYTSG (M43) amino acids 1-27 of SEQ ID NO:43); or RDSSPLLQFGGQVRLRHLYTSG (M6) (amino acids 1-22 of SEQ ID NO:6). In certain embodiments, the peptide comprises or consists of any of: HPIPDSSPLLQFGGQVRLRHLYTSG (M5-R) (amino acids 1-25 of SEQ ID NO:160); DSSPLLQFGGQVRLRHLYTSG (M6-R) (amino acids 2-22 of SEQ ID NO:6); RPLAFSDSSPLLQFGGQVRLRHLYTSG (M7) (amino acids 1-27 of SEQ ID NO:7); HPIPDSSPLLQWGDPIRLRHLYTSG (M8-R) (amino acids 2-26 of SEQ ID NO:8); HPIPDSSPLLQFGWGDPIRLRHLYTSG (M9-R) (amino acids 2-28 of SEQ ID NO:9); HPIPDSSPHVHYGWGDPIRLRHLYTSG (M10-R) (amino acids 2-28 of SEQ ID NO:10); RPLAFSDAGPLLQWGDPIRLRHLYTSG (M11) (amino acids 1-27 of SEQ ID NO:11); RPLAFSDAGPLLQFGWGDPIRLRHLYTSG (M12) (amino acids 1-29 of SEQ ID NO:12); RPLAFSDAGPLLQFGGQVRLRHLYTSG (M13) (amino acids 1-27 of SEQ ID NO:13); HPIPDSSPHVHYGGQVRLRHLYTSG (M14-R) (amino acids 2-26 of SEQ ID NO:14); RPLAFSDAGPHVHYGGQVRLRHLYTSG (M15) (amino acids 1-27 of SEQ ID NO:15); RPLAFSDAGPHVHWGDPIRLRHLYTSG (M16) (amino acids 1-27 of SEQ ID NO:16); RPLAFSDAGPHVGWGDPIRLRHLYTSG (M17) (amino acids 1-27 of SEQ ID NO:17); RPLAFSDAGPHYGWGDPIRLRHLYTSG (M18) (amino acids 1-27 of SEQ ID NO:18); RPLAFSDAGPVYGWGDPIRLRHLYTSG (M19) (amino acids 1-27 of SEQ ID NO:19); RPLAFSDAGPVHGWGDPIRLRHLYTSG (M20) (amino acids 1-27 of SEQ ID NO:20); RPLAFSDAGPVHYWGDPIRLRHLYTSG (M21) (amino acids 1-27 of SEQ ID NO:21); RPLAFSDAGPHVHGWGDPIRLRHLYTSG (M22) (amino acids 1-27 of SEQ ID NO:22); RPLAFSDAGPHHGWGDPIRLRHLYTSG (M23) (amino acids 1-27 of SEQ ID NO:23); RPLAFSDAGPHVYWGDPIRLRHLYTSG (M24) (amino acids 1-27 of SEQ ID NO:24); RPLAFSDAGPHVYWGDPIRLRHLYTSG (M25) (amino acids 1-27 of SEQ ID NO:25); RPLAFSDSSPLVHWGDPIRLRHLYTSG (M26) (amino acids 1-27 of SEQ ID NO:26); RPLAFSDSSPHVHWGDPIRLRHLYTSG (M27) (amino acids 1-27 of SEQ ID NO:27); RPLAFSDAGPHVWGDPIRLRHLYTSG (M28) (amino acids 1-26 of SEQ ID NO:28); RPLAFSDAGPHVHYWGDPIRLRHLYTSG (M29) (amino acids 1-28 of SEQ ID NO:29); RPLAFSDAGPHVHYAWGDPIRLRHLYTSG (M30) (amino acids 1-29 of SEQ ID NO:30); RHPIPDSSPLLQFGAQVRLRHLYTSG (M31) (amino acids 1-26 of SEQ ID NO:31); RHPIPDSSPLLQFGDQVR- LRHLYTSG (M32) (amino acids 1-26 of SEQ ID NO:32); RHPIPDSSPLLQFGPQVRLRHLYTSG (M33) (amino acids 1-26 of SEQ ID NO:33); RHPIPDSSPLLQFGGAVRLRHLYTSG (M34) (amino acids 1-26 of SEQ ID NO:34); RHPIPDSSPLLQFGGEVRLRHLYTSG (M35) (amino acids 1-26 of SEQ ID NO:35); RHPIPDSSPLLQFGGNVRLRHLYTSG (M36) (amino acids 1-26 of SEQ ID NO:36); RHPIPDSSPLLQFGGQARLRHLYTSG (M37) (amino acids 1-26 of SEQ ID NO:37); RHPIPDSSPLLQFGGQIRLRHLYTSG (M38) (amino acids 1-26 of SEQ ID NO:38); RHPIPDSSPLLQFGGQTRLRHLYTSG (M39) (amino acids 1-26 of SEQ ID NO:39); RHPIPDSSPLLQFGWGQPVRLRHLYTSG (M40) (amino acids 1-28 of SEQ ID NO:40); DAGPHVHYGWGDPIRLRHLYTSG (M74-R) (amino acids 2-24 of SEQ ID NO:74); VHYGWGDPIRLRHLYTSG (M75-R) (amino acids 2-19 of SEQ ID NO:75); RLRHLYTSG (M77-R) (amino acids 2-10 of SEQ ID NO:77); RHPIPDSSPLLQFGWGDPIRLRHLYTSG (M9) (amino acids 1-28 of SEQ ID NO:9); RHPIPDSSPLLQWGDPIRLRHLYTSG (M8) (amino acids 1-26 of SEQ ID NO:8); RPLAFSDAGPLLQFGWGDPIRLRHLYTSG (M12) (amino acids 1-29 of SEQ ID NO:12); RHPIPDSSPHVHYGWGDPIRLRHLYTSG (M10) (amino acids 1-28 of SEQ ID NO:10); RPLAFSDAGPLLQFGGQVRLRHLYTSG (M13) (amino acids 1-27 of SEQ ID NO:13); RHPIPDSSPHVHYGGQVRLRHLYTSG (M14) (amino acids 1-26 of SEQ ID NO:14); RPLAFSDAGPHVHYGGDIRLRHLYTSG (M43) amino acids 1-27 of SEQ ID NO:43); or RDSSPLLQFGGQVRLRHLYTSG (M6) (amino acids 1-22 of SEQ ID NO:6). In some embodiments, the peptide comprises a C-terminal region comprising a portion of SEQ ID NO:99 (FGF19), the C-terminal region having a first amino acid position and a last amino acid position, wherein the C-terminal region comprises amino acid residues 16-29 of SEQ ID NO:99 (FGF19), WGDPIRLRHLYTSG (SEQ ID NO:169), wherein the W residue corresponds to the first amino acid position of the C-terminal region.

In various further particular aspects, a peptide sequence includes or consists of:

(SEQ ID NO: 160)
HPIPDSSPLLQFGGQVRLRHLYTSGPHGLSSCFLRIRADGVVDCARGQSA

HSLLEIKAVALRTVAIKGVHSVRYLCMGADGKMQGLLQYSEEDCAFEEEI

RPDGYNVYRSEKHRLPVSLSSAKQRQLYKNRGFLPLSHFLPMLPMVPEEP

EDLRGHLESDMFSSPLETDSMDPFGLVTGLEAVRSPSFEK;

(SEQ ID NO: 138 or 161)
DSSPLLQFGGQVRLRHLYTSGPHGLSSCFLRIRADGVVDCARGQSAHSLL

EIKAVALRTVAIKGVHSVRYLCMGADGKMQGLLQYSEEDCAFEEEIRPDG

YNVYRSEKHRLPVSLSSAKQRQLYKNRGFLPLSHFLPMLPMVPEEPEDLR

GHLESDMFSSPLETDSMDPFGLVTGLEAVRSPSFEK;

(SEQ ID NO: 1 or 139)
RPLAFSDASPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEIRPDGYNVYRSEKHRLPVSLSSAKQRQLYKNRGFLPLSHFLPMLPMV

PEEPEDLRGHLESDMFSSPLETDSMDPFGLVTGLEAVRSPSFEK;

(SEQ ID NO: 2 or 140)
RPLAFSDSSPLVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEIRPDGYNVYRSEKHRLPVSLSSAKQRQLYKNRGFLPLSHFLPMLPMV

PEEPEDLRGHLESDMFSSPLETDSMDPFGLVTGLEAVRSPSFEK;
or (SEQ ID NO: 141)
DSSPLVHYGWGDPIRLRHLYTSGPHGLSSCFLRIRADGVVDCARGQSAHS

LLEIKAVALRTVAIKGVHSVRYLCMGADGKMQGLLQYSEEDCAFEEEIRP

DGYNVYRSEKHRLPVSLSSAKQRQLYKNRGFLPLSHFLPMLPMVPEEPED

LRGHLESDMFSSPLETDSMDPFGLVTGLEAVRSPSFEK;

or a subsequence or fragment thereof of any of the foregoing peptide sequences. In certain embodiments of any of the foregoing peptide sequences, the R terminal residue is deleted.

In certain embodiments, a peptide sequence includes the addition of amino acid residues 30-194 of SEQ ID NO:99 (FGF19) at the C-terminus, resulting in a chimeric polypeptide. In some embodiments, a peptide sequence has at least one amino acid substitution to amino acid residues 125-129 of SEQ ID NO:99 (FGF19), EIRPD. In other embodiments, the peptide sequence has at least one amino acid substitution to amino acid residues 126-128 of SEQ ID NO:99 (FGF19), IRP. In other embodiments, the peptide sequence has at least one amino acid substitution to amino acid residues 127-128 of SEQ ID NO:99 (FGF19), RP. In other embodiments, the peptide sequence has at least one amino acid substitution to amino acid residues 1-124 of SEQ ID NO:99 (FGF19) and/or to amino acid residues 130-194 of SEQ ID NO:99 (FGF19). For example, in certain embodiments, a peptide sequence comprises substitution to one of amino acid residues 127-128 of SEQ ID NO:99 (FGF19), RP, wherein at least one amino acid substitution is R127L or P128E. Said substitutions within a corresponding FGF19 sequence (e.g., EIRPD, IRP or RP) of a peptide variant provided herein is also contemplated. In certain embodiments, the peptide comprises both a R127L and P128E substitution to amino acid residues 127-128 of SEQ ID NO:99 (FGF19), RP, or the corresponding FGF19 sequence thereof in a variant peptide provided herein. In certain embodiments, the amino acid sequence of the peptide comprises at least one amino acid substitution in the Loop-8 region of FGF19, or the corresponding FGF19 sequence thereof in a variant peptide provided herein. In certain embodiments, the amino acid sequence of the peptide comprises one amino acid substitution to the EIRPD (amino acids 2-6 of SEQ ID NO:190) amino acid sequence in the Loop-8 region of FGF19. In some embodiments, the amino acid sequence of the peptide comprises two amino acid substitutions to the EIRPD (amino acids 2-6 of SEQ ID NO:190) amino acid sequence in the Loop-8 region of FGF19. In other embodiments, the amino acid sequence of the peptide comprises three amino acid substitutions to the EIRPD (amino acids 2-6 of SEQ ID NO:190) amino acid sequence in the Loop-8 region of FGF19. In certain embodiments, the amino acid sequence of the peptide comprises four amino acid substitutions to the EIRPD (amino acids 2-6 of SEQ ID NO:190) amino acid sequence in the Loop-8 region of FGF19. In some embodiments, the amino acid sequence of the peptide comprises five amino acid substitutions to the EIRPD (amino acids 2-6 of SEQ ID NO:190) amino acid sequence in the Loop-8 region of FGF19. In certain embodiments, the amino acid sequence of the peptide comprises one amino acid substitution to the IRP (amino acids 3-5 of SEQ ID NO:190) amino acid sequence in the Loop-8 region of FGF19. In some embodiments, the amino acid sequence of the peptide comprises two amino acid substitutions to the IRP (amino acids 3-5 of SEQ ID NO:190) amino acid sequence in the Loop-8 region of FGF19. In other embodiments, the amino acid sequence of the peptide comprises three amino acid substitutions to the IRP (amino acids 3-5 of SEQ ID NO:190) amino acid sequence in the Loop-8 region of FGF19. In certain embodiments, the amino acid sequence of the peptide comprises one amino acid substitution to the RP (amino acids 4-5 of SEQ ID NO:190) amino acid sequence in the Loop-8 region of FGF19. In some embodiments, the amino acid sequence of the peptide comprises two amino acid substitutions to the RP (amino acids 4-5 of SEQ ID NO:190) amino acid sequence in the Loop-8 region of FGF19. In certain embodiments, the amino acid substitution to the RP (amino acids 4-5 of SEQ ID NO:190) amino acid sequence in the Loop-8 region of FGF19 is an Arg (R) to Leu (L) substitution. In other embodiments, the substitution to the RP (amino acids 4-5 of SEQ ID NO:190) amino acid sequence in the Loop-8 region of FGF19 is a Pro (P) to Glu (E) substitution. In some embodiments, the substitutions to the RP (amino acids 4-5 of SEQ ID NO:190) amino acid sequence in the Loop-8 region of FGF19 is an Arg (R) to Leu (L) substitution and a Pro (P) to Glu (E) substitution. In specific embodiments, the foregoing substitution(s) in the Loop-8 region of FGF19 is in the corresponding FGF19 sequence thereof in a variant peptide provided herein. That is, said substitutions within a corresponding FGF19 sequence (e.g., EIRPD, IRP or RP) of a peptide variant provided herein is also contemplated.

Methods and uses provided herein can be practiced using a peptide or chimeric sequence of any suitable length. In particular embodiments, the N-terminal or C-terminal region of the peptide or chimeric sequence is from about 20 to about 200 amino acid residues in length. In further particular embodiments, a chimeric peptide sequence or peptide sequence has at least one amino acid deletion. In other particular aspects, a peptide or chimeric sequence has 1, 2, 3, 4, 5, 6, 7, 8, 9, 10, 11, 12, 13, 14, 15, 16, 17, 18, 19, 20 or more amino acid deletions from the amino terminus, the carboxy-terminus or internally. In one embodiment, the amino acid substitution, or deletion is at any of amino acid positions 8-20 of FGF19 (AGPHVHYGWGDPI) (SEQ ID NO:187). In further particular embodiments, a peptide or chimeric sequence has an N-terminal region, or a C-terminal region that comprises or consists of an amino acid sequence of about 5 to 10, 10 to 20, 20 to 30, 30 to 40, 40 to 50, 60 to 70, 70 to 80, 80 to 90, 90 to 100 or more amino acids. In additional more particular embodiments, a peptide or chimeric sequence has an FGF19 sequence portion, or an FGF21 sequence portion that comprises or consists of an amino acid sequence of about 5 to 10, 10 to 20, 20 to 30, 30 to 40, 40 to 50, 50 to 60, 60 to 70, 70 to 80, 80 to 90, 90 to 100 or more amino acids of FGF19 or FGF21.

In various further embodiments, a peptide or chimeric sequence has an amino acid substitution, an addition, insertion or is a subsequence that has at least one amino acid deleted. Such amino acid substitutions, additions, insertions and deletions of a peptide sequence can be 1, 2, 3, 4, 5, 6, 7, 8, 9, 10 or more amino acid residues (10-20, 20-30, 30-40, 40-50, etc.), for example, at the N- or C-terminus, or internal. For example, a subsequence that has 1, 2, 3, 4, 5, 6, 7, 8, 9, 10, 11, 12, 13, 14, 15, 16, 17, 18, 19, 20 or more amino acid deletions from the amino terminus, the carboxy-terminus or internally. In a particular aspect, the amino acid substitution, or deletion is at any of amino acid positions 8-20 of FGF19 (AGPHVHYGWGDPI) (SEQ ID NO:187).

In various still more particular aspects, a peptide or chimeric sequence includes all or a portion of an FGF19 sequence set forth as: PHGLSSCFLRIRADGVVD-CARGQSAHSLLEIKAVALRTVAIKGVHSVRYLCM-GADGKMQGL LQYSEEDCAFEEEIRPDGYN-VYRSEKHRLPVSLSSAKQRQLYKNRGFLPLSHFLPM-LPMVPE EPEDLRGHLESDMFSSPLETDSMDPF-GLVTGLEAVRSPSFEK (SEQ ID NO:188) positioned at the C-terminus of the peptide, or the amino terminal "R" residue is deleted from the sequence.

In various embodiments, a peptide or chimeric sequence has a function or activity greater or less than a comparison sequence. In further particular embodiments, chimeric peptide sequences and peptide sequences have particular functions or activities. In one aspect, a chimeric peptide sequence or peptide sequence maintains or increases a fibroblast growth factor receptor 4 (FGFR4) mediated activity. In additional aspects, a chimeric peptide sequence or peptide sequence binds to FGFR4 or activates FGFR4, or does not detectably bind to FGFR4 or activate FGFR4, or binds to FGFR4 with an affinity less than, comparable to or greater than FGF19 binding affinity for FGFR4, or activates FGFR4 to an extent or amount less than, comparable to or greater than FGF19 activates FGFR4. In some embodiments, a chimeric peptide sequence or peptide sequence provided herein activates FGFR4 to an extent or amount less than the extent or amount that FGF19 activates FGFR4. In some embodiments, a chimeric peptide sequence or peptide sequence provided herein activates FGFR4 to an extent or amount comparable to the extent or amount that FGF19 activates FGFR4. In some embodiments, a chimeric peptide sequence or peptide sequence provided herein activates FGFR4 to an extent or amount greater than the extent or amount that FGF19 activates FGFR4.

In one embodiment, a chimeric peptide sequence or peptide sequence provided herein maintains an FGFR4 mediated activity. In one embodiment, a chimeric peptide sequence or peptide sequence provided herein increases an FGFR4 mediated activity. In some embodiments, a chimeric peptide sequence or peptide sequence provided herein binds to FGFR4 with an affinity less than FGF19 binding affinity for FGFR4. In some embodiments, a chimeric peptide sequence or peptide sequence provided herein binds to FGFR4 with an affinity comparable to FGF19 binding affinity for FGFR4. In some embodiments, a chimeric peptide sequence or peptide sequence provided herein binds to FGFR4 with an affinity greater than FGF19 binding affinity for FGFR4. In some embodiments, a chimeric peptide sequence or peptide sequence provided herein does not detectably bind to FGFR4.

In further aspects, a chimeric peptide sequence or peptide sequence has reduced HCC formation compared to FGF19, or an FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19; or has greater glucose lowering activity compared to FGF19, or an FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19; has less lipid increasing activity compared to FGF19, or an FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19; or has less triglyceride, cholesterol, non-HDL or HDL increasing activity compared to FGF19, or an FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19; or the peptide sequence has less lean mass reducing activity compared to FGF21. Such functions and activities can be ascertained in vitro or in vivo, for example, in a db/db mouse.

In one embodiment, a peptide or chimeric sequence has a function or activity greater or less than a comparison sequence. In some embodiments, the comparison sequence is FGF19. In another embodiment, the comparison sequence is FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19. In one embodiment, a peptide or chimeric peptide sequence provided herein has greater glucose lowering activity compared to a comparison sequence. In another embodiment, a peptide or chimeric peptide sequence provided herein has less lipid increasing activity compared to a comparison sequence. In other embodiment, a peptide or chimeric peptide sequence provided herein has lower or reduced lipid (e.g., triglyceride, cholesterol, non-HDL) activity compared to a comparison sequence. In other embodiments, a peptide or chimeric peptide sequence provided herein has more HDL increasing activity as compared to a comparison sequence. In other embodiment, a peptide or chimeric peptide sequence provided herein has less lean mass reducing activity compared to a comparison sequence or FGF21.

In further additional various embodiments, a peptide or chimeric sequence includes one or more L-amino acids, D-amino acids, non-naturally occurring amino acids, or amino acid mimetic, derivative or analogue. In still further various embodiments, a peptide or chimeric sequence has an N-terminal region, or a C-terminal region, or a FGF19 sequence portion, or an FGF21 sequence portion, joined by a linker or spacer.

In still additional embodiments, chimeric peptide sequences and peptide sequences isolated or purified, and/or chimeric peptide sequences and peptide sequences can be included in compositions. In one embodiment, a chimeric peptide sequence or peptide sequence is included in a pharmaceutical composition. Such compositions include combinations of inactive or other active ingredients. In one embodiment, a compositions, such as a pharmaceutical composition includes chimeric peptide sequence or peptide sequence and a glucose lowering agent.

In still additional embodiments, a chimeric peptide or peptide sequence is included in a pharmaceutical composition, which in turn can be used for practicing the methods and uses provided herein. Such compositions include combinations of inactive or other active ingredients. In one embodiment, a composition, such as a pharmaceutical composition includes chimeric peptide sequence or peptide sequence and a glucose lowering agent. In one embodiment, a composition, such as a pharmaceutical composition includes chimeric peptide sequence or peptide sequence and an agent that improves bile acid homeostasis.

In yet further embodiments, nucleic acid molecules encoding the chimeric peptide sequence or peptide sequence are provided. Such molecules can further include an expression control element in operable linkage that confers expression of the nucleic acid molecule encoding the peptide in vitro, in a cell or in vivo, or a vector comprising the nucleic acid molecule (e.g., a viral vector). Transformed and host cells that express the chimeric peptide sequences and peptide sequences are also provided.

Uses and methods of treatment that include administration or delivery of any chimeric peptide sequence or peptide sequence are also provided. In particular embodiments, a use or method of treatment of a subject includes administering a chimeric peptide or peptide sequence provided herein to a subject, such as a subject having, or at risk of having, a disease or disorder treatable by a peptide sequence provided herein, in an amount effective for treating the disease or disorder.

In one embodiment, provided herein is a method of preventing a disease or disorder in a subject having, or at risk of having, a disease or disorder preventable by a peptide sequence provided herein, comprising administering a pharmaceutical composition comprising a peptide provided herein to a subject in an amount effective for preventing the disease or disorder. In another embodiment, provided herein is a method of treating a disease or disorder in a subject having, or at risk of having, a disease or disorder treatable by a peptide sequence provided herein, comprising administering a pharmaceutical composition comprising a peptide provided herein to a subject in an amount effective for treating the disease or disorder. In yet another embodiment, provided herein is a method of managing a disease or disorder in a subject having, or at risk of having, a disease or disorder manageable by a peptide sequence provided herein, comprising administering a pharmaceutical composition comprising a peptide provided herein to a subject in an amount effective for managing the disease or disorder. In one embodiment, the disease or disorder is a bile acid-related disease or associated disorder.

Non-limiting exemplary bile acid-related or associated disorders preventable, treatable or manageable according to the methods and uses provided herein include: cholestasis, including, for example diseases of intrahepatic cholestasis (e.g., primary biliary cirrhosis (PBC), primary familial intrahepatic cholestasis (PFIC) (e.g., progressive PFIC), primary sclerosing choangitis (PSC), pregnancy intrahepatic cholestasis (PIC), neonatal cholestasis, and drug-induced cholestasis (e.g., estrogen)), and diseases of extrahepatic cholestasis (e.g., bile cut compression from tumor, bile duct blockade by gall stones); bile acid malabsorption and other disorders involving the distal small intestine, including ileal resection, inflammatory bowel diseases (e.g., Crohn's disease and ulcerative colitis), short bowel syndrome, disorders impairing absorption of bile acids not otherwise characterized (idiopathic)) leading to diarrhea (e.g., bile acid diarrhea (BAD)) and GI symptoms, and GI, liver, and/or biliary cancers (e.g., colon cancer and hepatocellular cancer); and/or bile acid synthesis abnormalities, such as those contributing to non-alcoholic steatohepatitis (NASH), cirrhosis and portal hypertension; e.g., in mammals, such as humans. Additional bile acid-related or associated disorders include metabolic syndrome; a lipid or glucose disorder; cholesterol or triglyceride metabolism; type 2 diabetes.

In one particular embodiment, the bile acid-related or associated disorder is bile acid malabsorption. In another particular embodiment, the bile acid-related or associated disorder is diarrhea. In another particular embodiment, the bile acid-related or associated disorder is bile acid diarrhea. In a still further particular embodiment, the bile acid-related or associated disorder is cholestasis. In one embodiment, the cholestasis is intrahepatic cholestasis. In another embodiment, the cholestasis is extrahepatic cholestasis. In another, further particular embodiment, the bile acid-related or associated disorder is an error in bile acid synthesis. In another further particular embodiment, the bile acid-related or associated disorder is primary biliary cirrhosis (PBC). In other particular embodiments, the bile acid-related or associated disorder is primary sclerosing cholangitis (PSC). In another embodiment, the bile acid-related or associated disorder is PFIC (e.g., progressive PFIC). In another embodiment, the bile acid-related or associated disorder is NASH. In another embodiment, the bile acid-related or associated disorder is a hyperglycemic condition. In a specific embodiment, the bile acid-related or associated disorder is type 2 diabetes.

In some embodiments, the pharmaceutical composition further comprises at least one additional agent effective in modulating bile acid homeostasis or treating a bile acid-related or associated disorder, wherein the additional agent is: a glucocorticoid; CDCA; UDCA; insulin, an insulin secretagogues, an insulin mimetic, a sulfonylurea and a meglitinide; a biguanide; an alpha-glucosidase inhibitors; a DPP-IV inhibitor, GLP-1, a GLP-1 agonists and a GLP-1 analog; a DPP-IV-resistant analogue; a PPAR gamma agonist, a dual-acting PPAR agonist, a pan-acting PPAR agonist; a PTP1B inhibitor; an SGLT inhibitor; an RXR agonist; a glycogen synthase kinase-3 inhibitor; an immune modulator; a beta-3 adrenergic receptor agonist; an 11beta-HSD1 inhibitor; amylin and an amylin analogue; a bile acid sequestrant; or an SGLT-2 inhibitor. In certain embodiments, the at least one additional agent effective in modulating PBC is UDCA, an FXR agonist, OCA, an ASBT inhibitor, an autoimmune agent, an anti-IL-12 agent, an anti-CD80 agent, an anti-CD20 agent, a CXCL10 neutralizing antibody, a ligand for CXCR3, a fibrate, fish oil, colchicine, methotrexate, azathioprine, cyclosporine, or an anti-retroviral therapy. In particular embodiments, the at least one additional agent effective in modulating PBC is UDCA, OCA, an ASBT inhibitor, an anti-IL-12 agent, an anti-CD20 agent, or a fibrate.

Non-limiting exemplary disorders or conditions preventable, treatable or manageable with the peptide formulations, methods and uses thereof provided herein, include metabolic diseases and disorders. Non-limiting examples of diseases and disorders include: metabolic syndrome; a lipid- or glucose-related disorder; cholesterol or triglyceride metabolism; type 2 diabetes; cholestasis, including, for example diseases of intrahepatic cholestasis (e.g., PBC, PFIC, PSC, PIC, neonatal cholestasis, and drug induced cholestasis (e.g., estrogen)), and diseases of extrahepatic cholestasis (e.g., bile cut compression from tumor, bile duct blockade by gall stones); bile acid malabsorption and other disorders involving the distal small intestine, including ileal resection, inflammatory bowel diseases (e.g., Crohn's disease and ulcerative colitis), disorders impairing absorption of bile acids not otherwise characterized (idiopathic)) leading to diarrhea (e.g., BAD) and GI symptoms, and GI, liver, and/or biliary cancers (e.g., colon cancer and hepatocellular cancer); and/or bile acid synthesis abnormalities, such as those contributing to NASH, cirrhosis and portal hypertension. For treatment, peptide provided herein can be administered to subjects in need of modulation of bile acid homeostasis or having a bile-acid related or associated disorder. Peptides provided herein may also be useful in other hyperglycemic-related disorders, including kidney damage (e.g., tubule damage or nephropathy), liver degeneration, eye damage (e.g., diabetic retinopathy or cataracts), and diabetic foot disorders; dyslipidemias and their sequelae such as, for example, atherosclerosis, coronary artery disease, cerebrovascular disorders and the like.

Other conditions which may be associated with metabolic syndrome, such as obesity and elevated body mass (including the co-morbid conditions thereof such as, but not limited to, nonalcoholic fatty liver disease (NAFLD), nonalcoholic steatohepatitis (NASH), and polycystic ovarian syndrome (PCOS)), and also include thromboses, hypercoagulable and prothrombotic states (arterial and venous), hypertension (including portal hypertension (defined as a hepatic venous pressure gradient (HVPG) greater than 5 mm Hg), cardiovascular disease, stroke and heart failure; disorders or conditions in which inflammatory reactions are involved, including atherosclerosis, chronic inflammatory bowel diseases (e.g., Crohn's disease and ulcerative colitis), asthma, lupus erythematosus, arthritis, or other inflammatory rheumatic disorders; Disorders of cell cycle or cell differentiation processes such as adipose cell tumors, lipomatous carcinomas including, for example, liposarcomas, solid tumors, and neoplasms; Neurodegenerative diseases and/or demyelinating disorders of the central and peripheral nervous systems and/or neurological diseases involving neuroinflammatory processes and/or other peripheral neuropathies, including Alzheimer's disease, multiple sclerosis, Parkinson's disease, progressive multifocal leukoencephalopathy and Guillian-Barre syndrome; Skin and dermatological disorders and/or disorders of wound healing processes, including erythemato-squamous dermatoses; and other disorders such as syndrome X, osteoarthritis, and acute respiratory distress syndrome.

In one embodiment, of the various methods provided herein, the subject is a human. In certain embodiments, the subject is a subject in need thereof.

In some embodiments, the chimeric peptide sequence or a peptide sequence described herein, either alone or in combination with at least one additional therapeutic agent or treatment modality, is assessed to ensure that it does not cause untoward adverse effects in the subject. In a particular aspect, the combination of a chimeric peptide sequence or a peptide sequence described herein and at least one additional therapeutic agent or treatment modality is assessed to ensure that it does not induce HCC in the subject. Such assessments may be performed before initiation of therapy (e.g., in a dose escalation study), during therapy, (e.g., by evaluating a marker correlating with HCC activity), or subsequent to termination of therapy (e.g., by performing a liver biopsy). In some aspects, the assessment is performed in a suitable test environment (e.g., a validated animal model). One of ordinary skill in the art is familiar with additional means for ensuring that the combination therapy described herein is suitable for the particular subject, or a subject population representative of the particular subject, taking into consideration all relevant factors including, for example, the severity of the subject's bile acid-related or associated disorder (e.g., PBC) and the other medications be taken by the subject.

In one embodiment, a method includes administering a chimeric peptide or peptide sequence provided herein to a subject, such as a subject having a hyperglycemic condition (e.g., diabetes, such as insulin-dependent (type I) diabetes, type II diabetes, or gestational diabetes), insulin resistance, hyperinsulinemia, glucose intolerance or metabolic syndrome, or is obese or has an undesirable body mass. In particular aspects of the methods and uses, a chimeric peptide sequence or peptide sequence is administered to a subject in an amount effective to improve glucose metabolism in the subject. In more particular aspects, a subject has a fasting plasma glucose level greater than 100 mg/dl or has a hemoglobin A1c (HbA1c) level above 6%, prior to administration. In further embodiments, a use or method of treatment of a subject is intended to or results in reduced glucose levels, increased insulin sensitivity, reduced insulin resistance, reduced glucagon, an improvement in glucose tolerance, or glucose metabolism or homeostasis, improved pancreatic function, or reduced triglyceride, cholesterol, IDL, LDL or VLDL levels, or a decrease in blood pressure, a decrease in intimal thickening of the blood vessel, or a decrease in body mass or weight gain.

In particular aspects of the invention methods and uses, a chimeric peptide sequence or peptide sequence is administered to a subject in an amount effective to improve or provide bile acid homeostasis. Non-limiting exemplary bile acid related or associated disorders treatable according to the invention methods and uses include: metabolic syndrome; a lipid- or glucose-related disorder; cholesterol or triglyceride metabolism; type 2 diabetes; cholestasis, including, for example diseases of intrahepatic cholestasis (e.g., PBC, PFIC, PSC, PIC, neonatal cholestasis, and drug induced cholestasis (e.g., estrogen)), and diseases of extrahepatic cholestasis (e.g., bile cut compression from tumor, bile duct blockade by gall stones); bile acid malabsorption and other disorders involving the distal small intestine, including ileal resection, inflammatory bowel diseases (e.g., Crohn's disease and ulcerative colitis), disorders impairing absorption of bile acids not otherwise characterized (idiopathic)) leading to diarrhea (e.g., BAD) and GI symptoms, and GI, liver, and/or biliary cancers (e.g., colon cancer and hepatocellular cancer); and/or bile acid synthesis abnormalities, such as those contributing to NASH, cirrhosis and portal hypertension. In one embodiment, the bile acid related or associated disorder is bile acid malabsorption. In another embodiment, the bile acid related or associated disorder is diarrhea. In another embodiment, the bile acid related or associated disorder is cholestasis (e.g., intrahepatic or extrahepatic cholestasis). In another embodiment, the bile acid related or associated disorder is primary billiary cirrhosis. In another embodiment, the bile acid related or associated disorder is primary sclerosing cholangitis. In another embodiment, the bile acid related or associated disorder is PFIC (e.g., progressive PFIC).

3. DESCRIPTION OF DRAWINGS

FIG. 1 shows cyp7a1 expression in db/db mice dosed intraperitoneally with the indicated concentrations of FGF19 and FGF21 (SEQ ID NOs:99 and 100).

FIG. 2A-2D show cyp7a1 expression in human primary hepatocytes following dosing of A) variant M1 (SEQ ID NO:1); B) variant M2 (SEQ ID NO:2); C) variant M5 (SEQ ID NO:5); and D) variant M32 (SEQ ID NO:32).

FIG. 3A-3D show cyp7a1 expression in human primary hepatocytes following dosing of A) variant M69 (SEQ ID NO:69); B) variant M75 (SEQ ID NO:75); C) variant M70 (SEQ ID NO:70); and D) variant M76 (SEQ ID NO:76).

FIG. 4A-4D show cyp7a1 expression in human primary hepatocytes following dosing of A) variant M85 (SEQ ID NO:85); B) variant M96 (SEQ ID NO:96); C) variant M90 (SEQ ID NO:90); and D) variant M98 (SEQ ID NO:98).

FIG. 5 is a table showing the cyp7a1 $IC_{50}$ (pM), relative cyp7a1 expression and HCC core of the indicated variants: M1, M2, M5, M32, M69, M70, M75, M76, M85, M90, M96 and M98.

4. DETAILED DESCRIPTION

Figure 1:
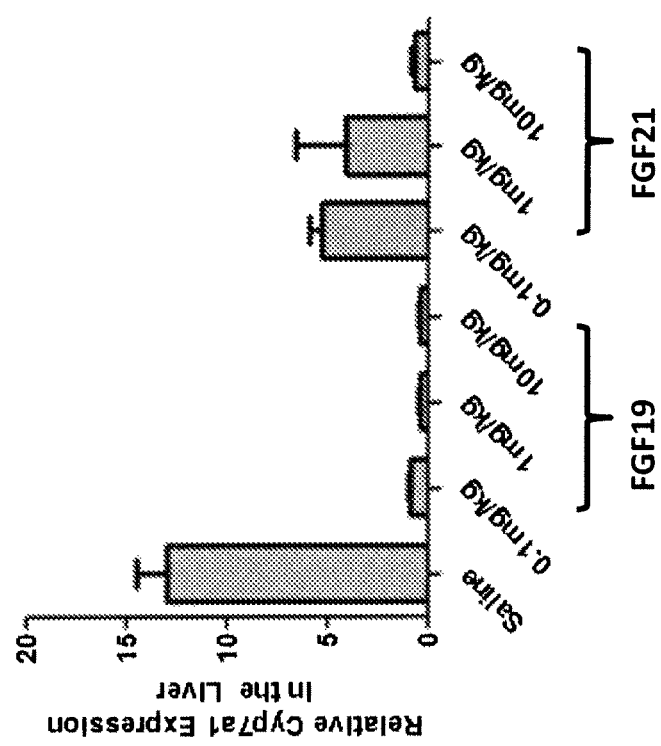

Before the present disclosure is further described, it is to be understood that the disclosure is not limited to the particular embodiments set forth herein, and it is also to be understood that the terminology used herein is for the purpose of describing particular embodiments only, and is not intended to be limiting.

4.1 Definitions

The terms "patient" or "subject" are used interchangeably to refer to a human or a non-human animal (e.g., a mammal).

The terms "treat", "treating", treatment" and the like refer to a course of action (such as administering a polypeptide or a pharmaceutical composition comprising a polypeptide) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (i.e., arresting the development or further development of the disease, disorder or condition or clinical symptoms association therewith) an active disease.

The term "in need of treatment" as used herein refers to a judgment made by a physician or other medical professional that a subject requires or will benefit from treatment.

The terms "prevent", "preventing", "prevention" and the like refer to a course of action (such as administering a polypeptide or a pharmaceutical composition comprising a polypeptide) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other medical professional that a subject requires or will benefit from preventative care.

The phrase "therapeutically effective amount" refers to the administration of an agent to a subject, either alone or as a part of a pharmaceutical composition and either in a single dose or as part of a series of doses, in an amount that is capable of having any detectable, positive effect on any symptom, aspect, or characteristics of a disease, disorder or condition when administered to a patient. The therapeutically effective amount can be ascertained by measuring relevant physiological effects. For example, in the case of a hyperglycemic condition, a lowering or reduction of blood glucose or an improvement in glucose tolerance test can be used to determine whether the amount of an agent is effective to treat the hyperglycemic condition. For example, a therapeutically effective amount is an amount sufficient to reduce or decrease any level (e.g., a baseline level) of fasting plasma glucose (FPG), wherein, for example, the amount is sufficient to reduce a FPG level greater than 200 mg/dl to less than 200 mg/dl, wherein the amount is sufficient to reduce a FPG level between 175 mg/dl and 200 mg/dl to less than the starting level, wherein the amount is sufficient to reduce a FPG level between 150 mg/dl and 175 mg/dl to less than the starting level, wherein the amount is sufficient to reduce a FPG level between 125 mg/dl and 150 mg/dl to less than the starting level, and so on (e.g., reducing FPG levels to less than 125 mg/dl, to less than 120 mg/dl, to less than 115 mg/dl, to less than 110 mg/dl, etc.). Moreover, in the case of HbA1c levels, the effective amount is an amount sufficient to reduce or decrease levels by more than about 10% to 9%, by more than about 9% to 8%, by more than about 8% to 7%, by more than about 7% to 6%, by more than about 6% to 5%, and so on. More particularly, a reduction or decrease of HbA1c levels by about 0.1%, 0.25%, 0.4%, 0.5%, 0.6%, 0.7%, 0.8%, 0.9%, 1%, 1.5%, 2%, 3%, 4%, 5%, 10%, 20%, 30%, 33%, 35%, 40%, 45%, 50%, or more is contemplated by the present disclosure. The therapeutically effective amount can be adjusted in connection with the dosing regimen and diagnostic analysis of the subject's condition and the like.

The phrase "in a sufficient amount to effect a change" means that there is a detectable difference between a level of an indicator measured before (e.g., a baseline level) and after administration of a particular therapy. Indicators include any objective parameter (e.g., level of glucose or insulin) or subjective parameter (e.g., a subject's feeling of well-being).

The phrase "glucose tolerance", as used herein, refers to the ability of a subject to control the level of plasma glucose and/or plasma insulin when glucose intake fluctuates. For example, glucose tolerance encompasses the subject's ability to reduce, within about 120 minutes, the level of plasma glucose back to a level determined before the intake of glucose.

Broadly speaking, the terms "diabetes" and "diabetic" refer to a progressive disease of carbohydrate metabolism involving inadequate production or utilization of insulin, frequently characterized by hyperglycemia and glycosuria. The terms "pre-diabetes" and "pre-diabetic" refer to a state wherein a subject does not have the characteristics, symptoms and the like typically observed in diabetes, but does have characteristics, symptoms and the like that, if left untreated, can progress to diabetes. The presence of these conditions can be determined using, for example, either the fasting plasma glucose (FPG) test or the oral glucose tolerance test (OGTT). Both usually require a subject to fast for at least 8 hours prior to initiating the test. In the FPG test, a subject's blood glucose is measured after the conclusion of the fasting; generally, the subject fasts overnight and the blood glucose is measured in the morning before the subject eats. A healthy subject would generally have a FPG concentration between about 90 and about 100 mg/dl, a subject with "pre-diabetes" would generally have a FPG concentration between about 100 and about 125 mg/dl, and a subject with "diabetes" would generally have a FPG level above about 126 mg/dl. In the OGTT, a subject's blood glucose is measured after fasting and again two hours after drinking a glucose-rich beverage. Two hours after consumption of the glucose-rich beverage, a healthy subject generally has a blood glucose concentration below about 140 mg/dl, a pre-diabetic subject generally has a blood glucose concentration about 140 to about 199 mg/dl, and a diabetic subject generally has a blood glucose concentration about 200 mg/dl or above. While the aforementioned glycemic values pertain to human subjects, normoglycemia, moderate hyperglycemia and overt hyperglycemia are scaled differently in murine subjects. A healthy murine subject after a four-hour fast would generally have a FPG concentration between about 100 and about 150 mg/dl, a murine subject with "pre-diabetes" would generally have a FPG concentration between about 175 and about 250 mg/dl and a murine subject with "diabetes" would generally have a FPG concentration above about 250 mg/dl.

The term "insulin resistance" as used herein refers to a condition where a normal amount of insulin is unable to produce a normal physiological or molecular response. In some cases, a hyper-physiological amount of insulin, either endogenously produced or exogenously administered, is able to overcome the insulin resistance, in whole or in part, and produce a biologic response.

The term "metabolic syndrome" refers to an associated cluster of traits that includes, but is not limited to, hyperinsulinemia, abnormal glucose tolerance, obesity, redistribution of fat to the abdominal or upper body compartment, hypertension, dysfibrinolysis, and dyslipidemia characterized by high triglycerides, low high density lipoprotein (HDL)-cholesterol, and high small dense low density lipoprotein (LDL) particles. Subjects having metabolic syndrome are at risk for development of type 2 diabetes and/or other disorders (e.g., atherosclerosis).

The phrase "glucose metabolism disorder" encompasses any disorder characterized by a clinical symptom or a combination of clinical symptoms that is associated with an elevated level of glucose and/or an elevated level of insulin in a subject relative to a healthy individual. Elevated levels of glucose and/or insulin can be manifested in the following diseases, disorders and conditions: hyperglycemia, type II diabetes, gestational diabetes, type I diabetes, insulin resistance, impaired glucose tolerance, hyperinsulinemia, impaired glucose metabolism, pre-diabetes, other metabolic disorders (such as metabolic syndrome, which is also referred to as syndrome X), and obesity, among others. The polypeptides of the present disclosure, and compositions thereof, can be used, for example, to achieve and/or maintain glucose homeostasis, e.g., to reduce glucose level in the bloodstream and/or to reduce insulin level to a range found in a healthy subject.

The term "hyperglycemia", as used herein, refers to a condition in which an elevated amount of glucose circulates in the blood plasma of a subject relative to a healthy individual. Hyperglycemia can be diagnosed using methods known in the art, including measurement of fasting blood glucose levels as described herein.

The term "hyperinsulinemia", as used herein, refers to a condition in which there are elevated levels of circulating insulin when, concomitantly, blood glucose levels are either elevated or normal. Hyperinsulinemia can be caused by insulin resistance which is associated with dyslipidemia, such as high triglycerides, high cholesterol, high low-density lipoprotein (LDL) and low high-density lipoprotein (HDL); high uric acids levels; polycystic ovary syndrome; type II diabetes and obesity. Hyperinsulinemia can be diagnosed as having a plasma insulin level higher than about 2 µU/mL.

As used herein, the phrase "body weight disorder" and similar terms refer to conditions associated with excessive body weight and/or enhanced appetite. Various parameters are used to determine whether a subject is overweight compared to a reference healthy individual, including the subject's age, height, sex and health status. For example, a subject can be considered overweight or obese by assessment of the subject's Body Mass Index (BMI), which is calculated by dividing a subject's weight in kilograms by the subject's height in meters squared. An adult having a BMI in the range of ~18.5 to ~24.9 $kg/m^2$ is considered to have a normal weight; an adult having a BMI between ~25 and ~29.9 $kg/m^2$ can be considered overweight (pre-obese); and an adult having a BMI of ~30 $kg/m^2$ or higher can be considered obese. Enhanced appetite frequently contributes to excessive body weight. There are several conditions associated with enhanced appetite, including, for example, night eating syndrome, which is characterized by morning anorexia and evening polyphagia often associated with insomnia, but which can be related to injury to the hypothalamus.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like. It will be appreciated that throughout this disclosure reference is made to amino acids according to the single letter or three letter codes.

As used herein, the term "variant" encompasses naturally-occurring variants (e.g., homologs and allelic variants) and non-naturally-occurring variants (e.g., muteins). Naturally-occurring variants include homologs, i.e., nucleic acids and polypeptides that differ in nucleotide or amino acid sequence, respectively, from one species to another. Naturally-occurring variants include allelic variants, i.e., nucleic acids and polypeptides that differ in nucleotide or amino acid sequence, respectively, from one individual to another within a species. Non-naturally-occurring variants include nucleic acids and polypeptides that comprise a change in nucleotide or amino acid sequence, respectively, where the change in sequence is artificially introduced, e.g., the change is generated in the laboratory or other facility by human intervention ("hand of man").

The term "native", in reference to FGF19, refers to biologically active, naturally-occurring FGF19, including biologically active, naturally-occurring FGF19 variants. The term includes the 194 amino acid human FGF19 mature sequence.

The terms "label", "labeling" and the like, when use in the context of a polypeptide or nucleic acid (or antibody, as appropriate) of the present disclosure are meant to refer broadly to any means useful in, for example, polypeptide purification, identification, isolation and synthesis. Labels are generally covalently bound to the polypeptide of interest and can be introduced in any manner known in the art, including attachment to a mature polypeptide (generally at the N- or C-terminus), incorporation during solid-phase peptide synthesis, or through recombinant means. Examples include, but are not limited to, fluorescence, biotinylation, and radioactive isotopes. Polypeptide and nucleic acid molecules can be labeled by both in vitro and in vivo methods. Labeling reagents and kits can be obtained from a number of commercial sources (e.g., Thermo Fischer Scientific, Rockford, Ill.; and Molecular Probes/Life Technologies; Grand Island, N.Y.).

The term "muteins" as used herein refers broadly to mutated recombinant proteins, i.e., a polypeptide comprising an artificially introduced change in amino acid sequence, e.g., a change in amino acid sequence generated in the laboratory or other facility by human intervention ("hand of man"). These proteins usually carry single or multiple amino acid substitutions and are frequently derived from cloned genes that have been subjected to site-directed or random mutagenesis, or from completely synthetic genes.

As used herein in reference to native human FGF19 or a FGF19 mutein, the terms "modified", "modification" and the like refer to one or more changes that enhance a desired property of human FGF19, a naturally-occurring FGF19 variant, or a FGF19 mutein, wherein the change(s) does not alter the primary amino acid sequence of the FGF19. Such desired properties include, for example, enhancing solubility, prolonging the circulation half-life, increasing the stability, reducing the clearance, altering the immunogenicity or allergenicity, improving aspects of manufacturability (e.g., cost and efficiency), and enabling the raising of particular antibodies (e.g., by introduction of unique epitopes) for use in detection assays. Changes to human FGF19, a naturally-occurring FGF19 variant, or a FGF19 mutein that can be carried out include, but are not limited to, pegylation (covalent attachment of one or more molecules of polyethylene glycol (PEG), or derivatives thereof); glycosylation (e.g., N-glycosylation), polysialylation and hesylation; albumin fusion; albumin binding through, for example, a conjugated fatty acid chain (acylation); Fc-fusion; and fusion with a PEG mimetic. Some particular embodiments entail modifications involving polyethylene glycol, other particular embodiments entail modifications involving albumin, and still other particular embodiments entail modifications involving glycosylation.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

The term "probe" refers to a fragment of DNA or RNA corresponding to a gene or sequence of interest, wherein the fragment has been labeled radioactively (e.g., by incorporating $^{32}P$ or $^{35}S$) or with some other detectable molecule, such as biotin, digoxygen or fluorescein. As stretches of DNA or RNA with complementary sequences will hybridize, a probe can be used, for example, to label viral plaques, bacterial colonies or bands on a gel that contain the gene of interest. A probe can be cloned DNA or it can be a synthetic DNA strand; the latter can be used to obtain a cDNA or genomic clone from an isolated protein by, for example, microsequencing a portion of the protein, deducing the nucleic acid sequence encoding the protein, synthesizing an oligonucleotide carrying that sequence, radiolabeling the sequence and using it as a probe to screen a cDNA library or a genomic library.

The term "heterologous" refers to two components that are defined by structures derived from different sources. For example, in the context of a polypeptide, a "heterologous" polypeptide can include operably linked amino acid sequences that are derived from different polypeptides. Similarly, in the context of a polynucleotide encoding a chimeric polypeptide, a "heterologous" polynucleotide can include operably linked nucleic acid sequences that can be derived from different genes. Exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which can be of different genetic origin than the promoter, the coding sequence or both). In the context of recombinant cells, "heterologous" can refer to the presence of a nucleic acid (or gene product, such as a polypeptide) that is of a different genetic origin than the host cell in which it is present.

The term "operably linked" refers to linkage between molecules to provide a desired function. For example, "operably linked" in the context of nucleic acids refers to a functional linkage between nucleic acid sequences. By way of example, a nucleic acid expression control sequence (such as a promoter, signal sequence, or array of transcription factor binding sites) can be operably linked to a second polynucleotide, wherein the expression control sequence affects transcription and/or translation of the second polynucleotide. In the context of a polypeptide, "operably linked" refers to a functional linkage between amino acid sequences (e.g., different domains) to provide for a described activity of the polypeptide.

As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

"Derived from", in the context of an amino acid sequence or polynucleotide sequence (e.g., an amino acid sequence "derived from" a FGF19 polypeptide), is meant to indicate that the polypeptide or nucleic acid has a sequence that is based on that of a reference polypeptide or nucleic acid (e.g., a naturally occurring FGF19 polypeptide or a FGF19-encoding nucleic acid), and is not meant to be limiting as to the source or method in which the protein or nucleic acid is made. By way of example, the term "derived from" includes homologues or variants of reference amino acid or DNA sequences.

In the context of a polypeptide, the term "isolated" refers to a polypeptide of interest that, if naturally occurring, is in an environment different from that in which it can naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates the polypeptide has been separated from an environment in which it was made by either synthetic or recombinant means.

"Enriched" means that a sample is non-naturally manipulated (e.g., by a scientist or a clinician) so that a polypeptide of interest is present in a) a greater concentration (e.g., at least 3-fold greater, at least 4-fold greater, at least 8-fold greater, at least 64-fold greater, or more) than the concentration of the polypeptide in the starting sample, such as a biological sample (e.g., a sample in which the polypeptide naturally occurs or in which it is present after administration), or b) a concentration greater than the environment in which the polypeptide was made (e.g., as in a bacterial cell).

"Substantially pure" indicates that a component (e.g., a polypeptide) makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "measuring" or "assaying" and grammatical variations thereof are used interchangeably herein and refer to either qualitative or quantitative determinations, or both qualitative and quantitative determinations. When the terms are used in reference to detection, any means of assessing the relative amount is contemplated, including the various methods set forth herein and known in the art. For example, gene expression can be assayed or measured by a Northern blot, Western blot, immunoprecipitation assay, or by measuring activity, function or amount of the expressed protein.

The terms "antibodies" (Abs) and "immunoglobulins" (Igs) refer to glycoproteins having the same structural characteristics. While antibodies exhibit binding specificity to a specific antigen, immunoglobulins include both antibodies and other antibody-like molecules which lack antigen specificity.

The term "monoclonal antibody" refers to an antibody obtained from a population of substantially homogeneous antibodies, that is, the individual antibodies comprising the population are identical except for possible naturally occurring mutations that can be present in minor amounts. Monoclonal antibodies are highly specific, being directed against a single antigenic site. In contrast to polyclonal antibody preparations, which can include different antibodies directed against different determinants (epitopes), each monoclonal antibody is directed against a single determinant on the antigen.

In the context of an antibody, the term "isolated" refers to an antibody that has been separated and/or recovered from contaminant components of its natural environment; such contaminant components include materials which might interfere with diagnostic or therapeutic uses for the antibody, and can include enzymes, hormones, and other proteinaceous or nonproteinaceous solutes.

As used herein, the term "FGF19-dependent" and similar terms, as used in the context of a disease, disorder or condition, refers to a disease, disorder or other condition that is caused all, or in part, by the expression of FGF19. In certain embodiments, the expression of FGF19 is amplified as compared to a control. In some embodiments, the expression of FGF19 is amplified 5%, 10%, 15%, 20%, 25%, 30%, 35%, 40%, 45%, 50%, 55%, 60%, 65%, 70%, 75%, 80%, 85%, 90%, 95% or more, or any numerical range thereof. In some embodiments, the amplified expression of FGF19 directly results in the disease, disorder or condition, or a symptom thereof. In other embodiments, the amplified expression of FGF19 indirectly results in the disease disorder or condition, or a symptom thereof.

4.2 Peptides

In certain embodiments, the pharmaceutical compositions, formulations and dosage forms provided herein comprise one or more peptides or peptide sequences provided herein. In certain embodiments, the pharmaceutical compositions, formulations and dosage forms provided herein comprise one or more variants of FGF19 peptide sequences, fusions of FGF19 and/or FGF21 peptide sequences and variants of fusions (chimeras) of FGF19 and/or FGF21 peptide sequences having one or more activities associated with the treatment and/or prevention of a bile acid-related or associated disorder (e.g., PBC), a metabolic disorder or a cancer or tumor. In certain embodiments, the activity is a glucose lowering activity. Such variants and fusions (chimeras) of FGF19 and/or FGF21 peptide sequences include sequences that do not substantially increase or induce HCC formation or HCC tumorigenesis and/or do not induce a substantial elevation or increase in lipid profile.

In one embodiment, a chimeric peptide sequence includes or consists of an N-terminal region having at least seven amino acid residues and the N-terminal region having a first amino acid position and a last amino acid position, where the N-terminal region has a DSSPL (SEQ ID NO:121) or DASPH (SEQ ID NO:122) sequence; and a C-terminal region having a portion of FGF19 and the C-terminal region having a first amino acid position and a last amino acid position, where the C-terminal region includes amino acid residues 16-29 of FGF19 (WGDPIRLRHLYTSG; SEQ ID NO:169) and the W residue corresponds to the first amino acid position of the C-terminal region. In particular embodiments, the variant is M70: MRDSSPLVHYGWGDPIRLRHLYTSGPHGLSSCFLRIRADGVVDCARGQSAHSLLEIKAV ALRTVAIKGVHSVRYLCMGADGKMQGLLQYSEEDCAFEEEIRPDGYNVYRSEKHRLPV SLSSAKQRQLYKNRGFLPLSHFLPMLPMVPEEPEDLRGHLESDMFSSPLETDS16MDPFG LVTGLEAVRSPSFEK (SEQ ID NO:70). In other particular embodiments, the variant is M69:

(SEQ ID NO: 69)
RDSSPLVHYGWGDPIRLRHLYTSGPHGLSSCFLRIRADGVVDCARGQSAH

SLLEIKAVALRTVAIKGVHSVRYLCMGADGKMQGLLQYSEEDCAFEEEIR

PDGYNVYRSEKHRLPVSLSSAKQRQLYKNRGFLPLSHFLPMLPMVPEEPE

DLRGHLESDMFSSPLETDS16MDPFGLVTGLEAVRSPSFEK.

In another embodiment, the treatment peptide, comprises: a) an N-terminal region comprising at least seven amino acid residues, the N-terminal region having a first amino acid position and a last amino acid position; and b) a C-terminal region comprising a portion of SEQ ID NO:99 [FGF19], the C-terminal region having a first amino acid position and a last amino acid position, wherein the C-terminal region comprises (i) a first C-terminal region sequence comprising WGDPIRLRHLYTSG (amino acids 16 to 29 of SEQ ID NO:99 [FGF19]), wherein the W residue corresponds to the first amino acid position of the C-terminal region; and (ii) a second C-terminal region sequence comprising PHGLSSCFLRIRADGVVDCARGQSAHSLLEIKAVALRTVAIK- GVHSVRYLCMGADGKMQGL LQYSEEDCAFEEEIRP- DGYNVYRSEKHRLPVSLSSAKQRQLYKNRGFLPLS- HFLPMLPMVPE EPEDLRGHLESDMFSSPLETDSMDP- FGLVTGLEAVRSPSFEK (amino acid residues 30 to 194 of SEQ ID NO:99 [FGF19]).

In another embodiment, the treatment peptide, comprises: a) an N-terminal region comprising at least seven amino acid residues, the N-terminal region having a first amino acid position and a last amino acid position, wherein the N-terminal region comprises DSSPL (SEQ ID NO:121) or DASPH (SEQ ID NO:122); and b) a C-terminal region comprising a portion of SEQ ID NO:99 [FGF19], the C-terminal region having a first amino acid position and a last amino acid position, wherein the C-terminal region comprises (i) a first C-terminal region sequence comprising WGDPIRLRHLYTSG (amino acids 16 to 29 of SEQ ID NO:99 [FGF19]), wherein the W residue corresponds to the first amino acid position of the C-terminal region; and (ii) a second C-terminal region sequence comprising PHGLSSCFLRIRADGVVDCARGQSAHSLLEIKAVALRTVAIK- GVHSVRYLCMGADGKMQGL LQYSEEDCAFEEEIRP- DGYNVYRSEKHRLPVSLSSAKQRQLYKNRGFLPLS- HFLPMLPMVPE EPEDLRGHLESDMFSSPLETDSMDP- FGLVTGLEAVRSPSFEK (amino acid residues 30 to 194 of SEQ ID NO:99 [FGF19]). In certain embodiments, the peptide (i) binds to FGFR4 with an affinity equal to or greater than FGF19 binding affinity for FGFR4; (ii) activates FGFR4 to an extent or amount equal to or greater than FGF19 activates FGFR4; (iii) has at least one of reduced HCC formation; greater glucose lowering activity, less lipid increasing activity, less triglyceride activity, less cholesterol activity, less non-HDL activity or less HDL increasing activity, as compared to FGF19, or as compared to an FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19 (SEQ ID NO:99); and/or (iv) has less lean mass reducing activity as compared to FGF21.

In certain embodiments, the second C-terminal region sequence comprises at least one amino acid substitution to the EIRPD (amino acids 2-6 of SEQ ID NO:190) sequence. In some embodiments, the at least one amino acid substitution is to the IRP sequence of the EIRPD (amino acids 2-6 of SEQ ID NO:190) sequence. In some embodiments, the at least one amino acid substitution is to the RP sequence of the EIRPD sequence (amino acids 2-6 of SEQ ID NO:190). In some embodiments, the at least one amino acid substitution is R to L substitution. In other embodiments, the at least one amino acid substitution is P to E substitution. In yet other embodiments, the at least one amino acid substitution is RP to LE substitution.

In some embodiments, the second C-terminal region sequence comprises from 2 to 5 amino acid substitutions, deletions or insertions. In other embodiments, the peptide is less than about 250 amino acids in length.

In one embodiment, the treatment peptide has an amino acid sequence comprising or consisting of MRDSSPLVHYGWGDPIRLRHLYTSGPHGLSSCFLRIRADGVVDCARGQSAHSLLEIKAVALR TVAIKGVHSVRYLCMGADGKMQGLLQYSEEDCAFEEEIRPDGYNVYRSEKHRLPVSLSSAK QRQLYKNRGFLPLSHFLPMLPMVPEEPEDLRGHLESDMFSSPLETDSMDPFGLVTGLEAVRS PSFEK (SEQ ID NO:70). In certain embodiments, the treatment peptide has an amino acid sequence comprising SEQ ID NO:70. In other embodiments, the treatment peptide has an amino acid sequence consisting of SEQ ID NO:70. In some embodiments, the treatment peptide is fused with an immunoglobulin Fc region.

In another embodiment, the treatment peptide has an amino acid sequence comprising or consisting of RDSSPLVHYGWGDPIRLRHLYTSGPHGLSSCFLRIRADGVVDCARGQSAHSLLEIKAVALRT VAIKGVHSVRYLCMGADGKMQGLLQYSEEDCAFEEEIRPDGYNVYRSEKHRLPVSLSSAKQ RQLYKNRGFLPLSHFLPMLPMVPEEPEDLRGHLESDMFSSPLETDSMDPFGLVTGLEAVRSP SFEK (SEQ ID NO:69). In certain embodiments, the treatment peptide has an amino acid sequence comprising SEQ ID NO:69. In other embodiments, the treatment peptide has an amino acid sequence consisting of SEQ ID NO:69. In some embodiments, the treatment peptide is fused with an immunoglobulin Fc region.

In another embodiment, the treatment peptide, comprises: a) an N-terminal region comprising at least seven amino acid residues, the N-terminal region having a first amino acid position and a last amino acid position; and b) a C-terminal region comprising a first amino acid position and a last amino acid position, wherein the C-terminal region comprises (i) a first C-terminal region sequence comprising WGDPIRQRHLYTSG (SEQ ID NO:169 with a L7Q substitution), wherein the W residue corresponds to the first amino acid position of the C-terminal region; and (ii) a second C-terminal region sequence comprising PHGLSSCFLRIRADGVVDCARGQSAHSLLEIKAVALRTVAIK-GVHSVRYLCMGADGKMQGL LQYSEEDCAFEEEIRPDGYNVYRSEKHRLPVSLSSAKQRQLYKNRGFLPLSHFLPMLPMVPE EPEDLRGHLESDMFSSPLETDSMDPFGLVTGLEAVRSPSFEK (SEQ ID NO:188).

In another embodiment, the treatment peptide, comprises: a) an N-terminal region comprising at least seven amino acid residues, the N-terminal region having a first amino acid position and a last amino acid position, wherein the N-terminal region comprises DSSPL (SEQ ID NO:121), DASPH (SEQ ID NO:122), or DAGPH (amino acids 7 to 11 of SEQ ID NO:99 [FGF19]); and b) a C-terminal region comprising a first amino acid position and a last amino acid position, wherein the C-terminal region comprises (i) a first C-terminal region sequence comprising WGDPIRQRHLYTSG (SEQ ID NO:169 with a L7Q substitution), wherein the W residue corresponds to the first amino acid position of the C-terminal region; and (ii) a second C-terminal region sequence comprising PHGLSSCFLRIRADGVVDCARGQ-SAHSLLEIKAVALRTVAIKGVHSVRYLCMGADGK-MQGL LQYSEEDCAFEEEIRPDGYNVYRSEKHR-LPVSLSSAKQRQLYKNRGFLPLSHFLPMLPMVPE EPEDLRGHLESDMFSSPLETDSMDPFGLVTGLEAVR-SPSFEK (SEQ ID NO:188). In some embodiments, the peptide (i) binds to FGFR4 with an affinity equal to or greater than FGF19 binding affinity for FGFR4; (ii) activates FGFR4 to an extent or amount equal to or greater than FGF19 activates FGFR4; (iii) has at least one of reduced hepatocellular carcinoma (HCC) formation; greater glucose lowering activity, less lipid increasing activity, less triglyceride activity, less cholesterol activity, less non-HDL activity or less HDL increasing activity, as compared to FGF19, or as compared to an FGF19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the FGF19 WGDPI (SEQ ID NO:170) sequence at amino acids 16-20; and/or (iv) has less lean mass reducing activity as compared to FGF21.

In certain embodiments, the second C-terminal region sequence comprises at least one amino acid substitution to the EIRPD (amino acids 2-6 of SEQ ID NO:190) sequence. In some embodiments, the at least one amino acid substitution is to the IRP sequence of the EIRPD (amino acids 2-6 of SEQ ID NO:190) sequence. In some embodiments, the at least one amino acid substitution is to the RP sequence of the EIRPD sequence (amino acids 2-6 of SEQ ID NO:190). In some embodiments, the at least one amino acid substitution is R to L substitution. In other embodiments, the at least one amino acid substitution is P to E substitution. In yet other embodiments, the at least one amino acid substitution is RP to LE substitution.

In some embodiments, the second C-terminal region sequence comprises from 2 to 5 amino acid substitutions, deletions or insertions. In other embodiments, the peptide is less than about 250 amino acids in length.

In another embodiment, a chimeric peptide sequence includes or consists of an N-terminal region having a portion of FGF21 and the N-terminal region having a first amino acid position and a last amino acid position, where the N-terminal region has a GQV sequence and the V residue corresponds to the last amino acid position of the N-terminal region; and a C-terminal region having a portion of FGF19 and the C-terminal region having a first amino acid position and a last amino acid position where the C-terminal region includes amino acid residues 21-29 of FGF19 (RLRH-LYTSG; SEQ ID NO: 185) and the R residue corresponds to the first position of the C-terminal region.

In particular aspects, modifications to the Loop-8 region of FGF19 are disclosed herein that possess favorable metabolic parameters without exhibiting substantial tumorigenicity. Herein, FGF19 residues 127-129 are defined as constituting the Loop-8 region, although in the literature the Loop-8 region is sometimes defined as including or consisting of other residues (e.g., residues 125-129). Certain combinations of R127L and P128E substitutions to the FGF19 framework had an unexpectedly positive effect on HCC formation. Even more surprisingly, a combination of R127L and P128E substitutions and a substitution of Gln (Q) for Leu (L) in the FGF19 core region had an even more significant effect on preventing HCC formation.

Accordingly, variants of FGF19 Loop-8 region are included since they can reduce or eliminate substantial, measurable or detectable HCC formation. Furthermore, the effect of reducing HCC formation may be enhanced by modifications to amino acid residues outside of the Loop-8 region (e.g., substitutions of amino acid residues in the core region, such as the region corresponding to amino acids 21-29 of SEQ ID NO:99). In some embodiments, the Loop-8 modified variant comprises a substitution in the FGF19 Loop-8 region corresponding to amino acids 127-129 of SEQ ID NO:99. In certain embodiments, the Loop-8 modified variant comprises a substitution in the FGF19 Loop-8 region corresponding to (i) a R127L substitution, (ii) a P128E substitution, or (iii) a R127L substitution and a P128E substitution.

In certain embodiments, the amino acid sequence of the peptide comprises at least one amino acid substitution in the Loop-8 region of FGF19, or the corresponding FGF19 sequence thereof in a variant peptide provided herein. In certain embodiments, the amino acid sequence of the peptide comprises one amino acid substitution to the EIRPD (amino acids 2-6 of SEQ ID NO:190) amino acid sequence in the Loop-8 region of FGF19. In some embodiments, the amino acid sequence of the peptide comprises two amino acid substitutions to the EIRPD (amino acids 2-6 of SEQ ID NO:190) amino acid sequence in the Loop-8 region of FGF19. In other embodiments, the amino acid sequence of the peptide comprises three amino acid substitutions to the EIRPD (amino acids 2-6 of SEQ ID NO:190) amino acid sequence in the Loop-8 region of FGF19. In certain embodiments, the amino acid sequence of the peptide comprises four amino acid substitutions to the EIRPD (amino acids 2-6 of SEQ ID NO:190) amino acid sequence in the Loop-8 region of FGF19. In some embodiments, the amino acid sequence of the peptide comprises five amino acid substitutions to the EIRPD (amino acids 2-6 of SEQ ID NO:190) amino acid sequence in the Loop-8 region of FGF19. In certain embodiments, the amino acid sequence of the peptide comprises one amino acid substitution to the IRP (amino acids 3-5 of SEQ ID NO:190) amino acid sequence in the Loop-8 region of FGF19. In some embodiments, the amino acid sequence of the peptide comprises two amino acid substitutions to the IRP (amino acids 3-5 of SEQ ID NO:190) amino acid sequence in the Loop-8 region of FGF19. In other embodiments, the amino acid sequence of the peptide comprises three amino acid substitutions to the IRP (amino acids 3-5 of SEQ ID NO:190) amino acid sequence in the Loop-8 region of FGF19. In certain embodiments, the amino acid sequence of the peptide comprises one amino acid substitution to the RP (amino acids 4-5 of SEQ ID NO:190) amino acid sequence in the Loop-8 region of FGF19. In some embodiments, the amino acid sequence of the peptide comprises two amino acid substitutions to the RP (amino acids 4-5 of SEQ ID NO:190) amino acid sequence in the Loop-8 region of FGF19. In certain embodiments, the amino acid substitution to the RP (amino acids 4-5 of SEQ ID NO:190) amino acid sequence in the Loop-8 region of FGF19 is an Arg (R) to Leu (L) substitution. In other embodiments, the substitution to the RP (amino acids 4-5 of SEQ ID NO:190) amino acid sequence in the Loop-8 region of FGF19 is a Pro (P) to Glu (E) substitution. In some embodiments, the substitutions to the RP (amino acids 4-5 of SEQ ID NO:190) amino acid sequence in the Loop-8 region of FGF19 is an Arg (R) to Leu (L) substitution and a Pro (P) to Glu (E) substitution. In specific embodiments, the foregoing substitution(s) in the Loop-8 region of FGF19 is in the corresponding FGF19 sequence thereof in a variant peptide provided herein. That is, said substitutions within a corresponding FGF19 sequence (e.g., EIRPD, IRP or RP) of a peptide variant provided herein is also contemplated.

In some embodiments, the FGF19 variant comprises or further comprises a substitution in the core region corresponding to amino acids 21-29 of SEQ ID NO:99. In certain embodiments, the FGF19 variant comprises or further comprises a substitution in the core region corresponding to a L22Q substitution.

In some embodiments, the Loop-8 modified variant is M70: MRDSSPLVHYGWGDPIRLRHLYTSGPHGLSSC-FLRIRADGVVDCARGQSAHSLLEIKAV ALRTVAIK-GVHSVRYLCMGADGKMQGLLQYSEEDCAFEEEI RPDGYNVYRSEKHRLPV SLSSAKQRQLYKNRGF-LPLSHFLPMLPMVPEEPEDLRGHLESDMFSSPLETD-S16MDPFG LVTGLEAVRSPSFEK (SEQ ID NO:70), comprising a substitution in the FGF19 Loop-8 region (underlined). In certain embodiments, the Loop-8 modified M70 variant comprises a substitution in the FGF19 Loop-8 region (RPD; underlined) corresponding to (i) an R to L substitution, (ii) a P to E substitution, or (iii) an R to L substitution and a P to E substitution (SEQ. ID NO:204). In certain embodiments, the Loop-8 modified M70 variant further comprises or further comprises a substitution in the FGF19 core region. In some embodiments, the Loop-8 modified M70 variant comprises a L18Q substitution (i.e., SEQ ID NO:70 with an L18Q substitution).

In some embodiments, the Loop-8 modified variant is M69: RDSSPLVHYGWGDPIRLRHLYTSGPHGLSSCFL-RIRADGVVDCARGQSAHSLLEIKAVA LRTVAIK-GVHSVRYLCMGADGKMQGLLQYSEEDCAFEEEI RPDGYNVYRSEKHRLPVS LSSAKQRQLYKNRGFL-PLSHFLPMLPMVPEEPEDLRGHLESDMFSSPLETDS-16MDPFGL VTGLEAVRSPSFEK (SEQ ID NO:69), comprising a substitution in the FGF19 Loop-8 region (underlined). In certain embodiments, the Loop-8 modified M69 variant comprises a substitution in the FGF19 Loop-8 region (RPD; underlined) corresponding to (i) an R to L substitution, (ii) a P to E substitution, or (iii) an R to L substitution and a P to E substitution. In certain embodiments, the Loop-8 modified M69 variant further comprises or further comprises a substitution in the FGF19 core region. In some embodiments, the Loop-8 modified M69 variant comprises a L17Q substitution (i.e., SEQ ID NO:69 with an L17Q substitution).

Other counterpart modifications in other variants provided herein are also contemplated. In certain embodiments, the amino acid sequence of the peptide comprises one amino acid substitution to the EIRPD (amino acids 2-6 of SEQ ID NO:190) amino acid sequence in the Loop-8 region of FGF19. In some embodiments, the amino acid sequence of the peptide comprises two amino acid substitutions to the EIRPD (amino acids 2-6 of SEQ ID NO:190) amino acid sequence in the Loop-8 region of FGF19. In other embodiments, the amino acid sequence of the peptide comprises three amino acid substitutions to the EIRPD (amino acids 2-6 of SEQ ID NO:190) amino acid sequence in the Loop-8 region of FGF19. In certain embodiments, the amino acid sequence of the peptide comprises four amino acid substitutions to the EIRPD (amino acids 2-6 of SEQ ID NO:190) amino acid sequence in the Loop-8 region of FGF19. In some embodiments, the amino acid sequence of the peptide comprises five amino acid substitutions to the EIRPD (amino acids 2-6 of SEQ ID NO:190) amino acid sequence in the Loop-8 region of FGF19. In certain embodiments, the amino acid sequence of the peptide comprises one amino acid substitution to the IRP (amino acids 3-5 of SEQ ID NO:190) amino acid sequence in the Loop-8 region of FGF19. In some embodiments, the amino acid sequence of the peptide comprises two amino acid substitutions to the IRP (amino acids 3-5 of SEQ ID NO:190) amino acid sequence in the Loop-8 region of FGF19. In other embodiments, the amino acid sequence of the peptide comprises three amino acid substitutions to the IRP (amino acids 3-5 of SEQ ID NO:190) amino acid sequence in the Loop-8 region of FGF19. In certain embodiments, the amino acid sequence of the peptide comprises one amino acid substitution to the RP (amino acids 4-5 of SEQ ID NO:190) amino acid sequence in the Loop-8 region of FGF19. In some embodiments, the amino acid sequence of the peptide comprises two amino acid substitutions to the RP (amino acids 4-5 of SEQ ID NO:190) amino acid sequence in the Loop-8 region of FGF19. In certain embodiments, the amino acid substitution to the RP (amino acids 4-5 of SEQ ID NO:190) amino acid sequence in the Loop-8 region of FGF19 is an Arg (R) to Leu (L) substitution. In other embodiments, the substitution to the RP (amino acids 4-5 of SEQ ID NO:190) amino acid sequence in the Loop-8 region of FGF19 is a Pro (P) to Glu (E) substitution. In some embodiments, the substitutions to the RP (amino acids 4-5 of SEQ ID NO:190) amino acid sequence in the Loop-8 region of FGF19 is an Arg (R) to Leu (L) substitution and a Pro (P) to Glu (E) substitution. In specific embodiments, the foregoing substitution(s) in the Loop-8 region of FGF19 is in the corresponding FGF19 sequence thereof in a variant peptide provided herein. That is, said substitutions within a corresponding FGF19 sequence (e.g., EIRPD, IRP or RP) of a peptide variant provided herein is also contemplated.

In further embodiments, a peptide sequence includes or consists of a FGF19 variant having one or more amino acid substitutions, insertions or deletions compared to a reference or wild type FGF19. In additional embodiments, a peptide sequence includes or consists of a FGF21 sequence variant having one or more amino acid substitutions, insertions or deletions compared to a reference or wild type FGF21. In yet additional embodiments, a peptide sequence includes or consists of a portion of a FGF19 sequence fused to a portion of a FGF21 sequence. In still additional embodiments, a peptide sequence includes or consists of a portion of a FGF19 sequence fused to a portion of a FGF21 sequence, where the FGF19 and/or FGF21 sequence portion(s) have one or more amino acid substitutions, insertions or deletions compared to a reference or wild type FGF19 and/or FGF21. Examples of such sequences are disclosed in PCT Pub. No. WO 2013/006486 and US Pub. No. 2013/0023474, as well as PCT Publ. No. WO 2014/085365, published Jun. 5, 2014. Tables 1-11 and the Sequence Listing also sets forth representative sequences that may be used in the methods provided herein.

In some embodiments, the treatment peptides provided herein include variants and fusions of FGF19 and/or FGF21 peptide sequences. In one embodiment, the treatment peptides include one or more variant or fusion FGF19 and/or FGF21 peptide. In other embodiments, the methods provided herein include contacting or administering to a subject one or more nucleic acid molecules encoding a variant or fusion FGF19 and/or FGF21 peptide sequence (for example, an expression control element in operable linkage with the nucleic acid encoding the peptide sequence, optionally including a vector), in an amount effective for treating a bile acid-related or associated disorder.

A representative reference or wild type FGF19 sequence is set forth as:

```
                                        (SEQ ID NO: 99)
RPLAFSDAGPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEIRPDGYNVYRSEKHRLPVSLSSAKQRQLYKNRGFLPLSHFLPMLPMV

PEEPEDLRGHLESDMFSSPLETDSMDPFGLVTGLEAVRSPSFEK.
```

A representative reference or wild type FGF21 sequence is set forth as: HPIPDSSPLLQFGGQVRQRYLYTD-DAQQTEAHLEIREDGTVGGAADQSPESLLQLKALK PGVIQILGVKTSRFLCQRPDGALYGSLHFD-PEACSFRELLLEDGYNVYQSEAHGLPLHLP GNK-SPHRDPAPRGPARFLPLPGLPPALPEPPGILAPQPPD-VGSSDPLSMVGPSQGRSPSYA S (SEQ ID NO:100). FGF21 allelic variants include, e.g., M70, M71 and M72.

The terms "peptide," "protein," and "polypeptide" sequence are used interchangeably herein to refer to two or more amino acids, or "residues," including chemical modifications and derivatives of amino acids, covalently linked by an amide bond or equivalent. The amino acids forming all or a part of a peptide may be from among the known 21 naturally occurring amino acids, which are referred to by both their single letter abbreviation or common three-letter abbreviation. In the peptide sequences provided herein, conventional amino acid residues have their conventional meaning. Thus, "Leu" is leucine, "Ile" is isoleucine, "Nle" is norleucine, and so on.

In various particular aspects, a peptide or chimeric sequence provided herein has at the N-terminal region first amino acid position an "M" residue, an "R" residue, a "S" residue, a "H" residue, a "P" residue, a "L" residue or an "D" residue. In various alternative particular aspects, a peptide or chimeric sequence peptide sequence does not have a "M" residue or an "R" residue at the first amino acid position of the N-terminal region.

Also provided herein are subsequences, variants and modified forms of the exemplified peptide sequences (including the FGF19 and FGF21 variants and subsequences listed in the Sequence Listing, or Tables 1-11), so long as the foregoing retains at least a detectable or measurable activity or function. Also, certain exemplified variant peptides, for example, those having all or a portion of FGF21 sequence at the amino-terminus, have an "R" residue positioned at the N-terminus, which can be omitted. Similarly, certain exemplified variant peptides, include an "M" residue positioned at the N-terminus, which can be appended to or further substituted for an omitted residue, such as an "R" residue. More particularly, in various embodiments peptide sequences at the N-terminus include any of: RDSS (SEQ ID NO:115), DSS, MDSS (SEQ ID NO:116) or MRDSS (SEQ ID NO:117). Furthermore, when a "M" residue is adjacent to a "S" residue, the "M" residue may be cleaved such that the "M" residue is deleted from the peptide sequence, whereas when the "M" residue is adjacent to a "D" residue, the "M" residue may not be cleaved. Thus, by way of example, in various embodiments peptide sequences include those with the following residues at the N-terminus: MDSSPL (SEQ ID NO:119), MSDSSPL (SEQ ID NO:120) (cleaved to SDSSPL (SEQ ID NO:112)) and MSSPL (SEQ ID NO:113) (cleaved to SSPL (SEQ ID NO:114)).

Exemplified herein are peptide sequences, distinct from reference FGF19 and FGF21 polypeptides set forth herein, that modulate bile acid homeostasis, hyperglycemic conditions, insulin resistance, hyperinsulinemia, glucose intolerance, metabolic syndrome, or related disorders, in vivo (e.g., Tables 1-11 and the Sequence Listing). Non-limiting particular examples are a peptide sequence with amino-terminal amino acids 1-16 of FGF21 fused to carboxy-terminal amino acids 21-194 of FGF19; a peptide sequence with amino-terminal amino acids 1-147 of FGF19 fused to carboxy-terminal amino acids 147-181 of FGF21; a peptide sequence with amino-terminal amino acids 1-20 of FGF19 fused to carboxy-terminal amino acids 17-181 of FGF21; a peptide sequence with amino-terminal amino acids 1-146 of FGF21 fused to carboxy-terminal amino acids 148-194 of FGF19; and a peptide sequence with amino-terminal amino acids 1-20 of FGF19 fused to internal amino acids 17-146 of FGF21 fused to carboxy-terminal amino acids 148-194 of FGF19.

Additional particular peptides sequences have a WGDPI (SEQ ID NO:170) sequence motif corresponding to the WGDPI sequence of amino acids 16-20 of FGF19 (SEQ ID NO:99), lack a WGDPI (SEQ ID NO:170) sequence motif corresponding to the WGDPI sequence of amino acids 16-20 of FGF19 (SEQ ID NO:99), or have a substituted (i.e., mutated) WGDPI (SEQ ID NO:170) sequence motif corresponding to FGF19 WGDPI sequence of amino acids 16-20 of FGF19 (SEQ ID NO:99).

Particular peptide sequences provided herein also include sequences distinct from FGF19 and FGF21 (e.g., as set forth herein), and FGF 19 variant sequences having any GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for FGF19 WGDPI (SEQ ID NO:170) sequence at amino acids 16-20. Accordingly, the wild-type FGF19 and FGF21 (e.g., as set forth herein as SEQ ID NOS:99 and 100, respectively) may be excluded sequences, and FGF19 having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19 may also be excluded. This exclusion, however, does not apply to where a sequence has, for example, 3 FGF21 residues fused to FGF19 having, for example, any of GQV, GQV, GDI, or GPI, or 2 FGF21 residues fused to any of WGPI (SEQ ID NO:171), WGDI (SEQ ID NO:173), GDPI (SEQ ID NO:174), WDPI (SEQ ID NO:181), WGDI (SEQ ID NO:182), or WGDP (SEQ ID NO:183).

Particular non-limiting examples of peptide sequences include or consist of all or a part of a sequence variant specified herein as M1-M98 (SEQ ID NOs:1-52, 192, and 54-98, respectively), M101 to M160, or M200 to M207. More particular non-limiting examples of peptide sequences include or consist of all or a part of a sequence set forth as: HPIPDSSPLLQFGGQVRLRHLYTSGPHGLSSCFLRI-RADGVVDCARGQSAHSLLEIKAVA LRTVAIKGVHS-VRYLCMGADGKMQGLLQYSEEDCAFEEEIRPDGYN-VYRSEKHRLPVS LSSAKQRQLYKNRGFLPLSHFLP-MLPMVPEEPEDLRGHLESDMFSSPLETDSMDPF-GLVT GLEAVRSPSFEK (M5-R) (SEQ ID NO:160) (FGF21 sequences can also include an "R" residue at the amino terminus); DSSPLLQFGGQVRLRHLYTSGPHGLSSCFLRIRADGV-VDCARGQSAHSLLEIKAVALRTV AIKGVHSVRYLC-MGADGKMQGLLQYSEEDCAFEEEIRPDGYN-VYRSEKHRLPVSLSSA KQRQLYKNRGFLPLSHFLP-MLPMVPEEPEDLRGHLESDMFSSPLETDSMDPF-GLVTGLE AVRSPSFEK (SEQ ID NO:138 and 161); RPLAFSDASPHVHYGWGDPIRLRHLYTSGPHGLSSC-FLRIRADGVVDCARGQSAHSLLEI KAVALRTVAIK-GVHSVRYLCMGADGKMQGLLQYSEEDCAFEEEIRP-DGYNVYRSEKH RLPVSLSSAKQRQLYKNRGFLPLS-HFLPMLPMVPEEPEDLRGHLESDMFSSPLETDSMDP FGLVTGLEAVRSPSFEK (M1) (SEQ ID NO:1 or 139); RPLAFSDSSPLVHYGWGDPIRLRHLYTSGPHGLSSC-FLRIRADGVVDCARGQSAHSLLEI KAVALRTVAIK-GVHSVRYLCMGADGKMQGLLQYSEEDCAFEEEIRP-DGYNVYRSEKH RLPVSLSSAKQRQLYKNRGFLP-LSHFLPMLPMVPEEPEDLRGHLESDMFSS-PLETDSMDP FGLVTGLEAVRSPSFEK (M2) (SEQ ID NO:2 or 140); DSSPLVHYGWGDPIRLRHLYTSGPHGLSSCFLRI-RADGVVDCARGQSAHSLLEIKAVAL RTVAIKGVHS-VRYLCMGADGKMQGLLQYSEEDCAFEEEIRPDGYN-VYRSEKHRLPVSL SSAKQRQLYKNRGFLPLSHFLP-MLPMVPEEPEDLRGHLESDMFSSPLETDSMDPF-GLVT GLEAVRSPSFEK (SEQ ID NO:141); RDSSPLVHYGWGDPIRLRHLYTSGPHGLSSCFLRI-RADGVVDCARGQSAHSLLEIKAVA LRTVAIKGVHS-VRYLCMGADGKMQGLLQYSEEDCAFEEEIRPDGYN-VYRSEKHRLPVS LSSAKQRQLYKNRGFLPLSHFLP-MLPMVPEEPEDLRGHLESDMFSSPLETDSMDPF-GLVT GLEAVRSPSFEK (M69) (SEQ ID NO:69); RDSSPLLQWGDPIRLRHLYTSGPHGLSSCFLRI-RADGVVDCARGQSAHSLLEIKAVALRT VAIKGVHS-VRYLCMGADGKMQGLLQYSEEDCAFEEEIRPDGYN-VYRSEKHRLPVSLSS AKQRQLYKNRGFLPLSHFLPM-LPMVPEEPEDLRGHLESDMFSSPLETDSMDPF-GLVTGL EAVRSPSFEK (M52) (SEQ ID NO:52); HPIPDSSPLLQFGGQVRLRHLYTSGPHGLSSCFLRI-RADGVVDCARGQSAHSLLEIKAVA LRTVAIKGVHS-VRYLCMGADGKMQGLLQYSEEDCAFEEEIRPDGYN-VYRSEKHRLPVS LSSAKQRQLYKNRGFLPLSHFLP-MLPMVPEEPEDLRGHLESDMFSSPLETDSMDPF-GLVT GLEAVRSPSFEK (M5-R) (SEQ ID NO:160); HPIPDSSPLLQFGGQVRQRYLYTDDAQQTEAHL-EIREDGTVGGAADQSPESLLQLKALK PGVIQILGVK-TSRFLCQRPDGALYGSLHFDPEACSFRELLLEDGYN-VYQSEAHSLPLHLP GNKSPHRDPAPRGPARFLPLP-GLPPALPEPPGILAPQPPDVGSSDPLSMVGPSQGR-SPSYA S (M71) (SEQ ID NO:71); HPIPDSSPLLQFGGQVRQRYLYTDDAQQTEAHL-EIREDGTVGGAADQSPESLLQLKALK PGVIQILGVK-TSRFLCQRPDGALYGSLHFDPEACSFRELLLEDGYN-VYQSEAHGLPLHLP GNKSPHRDPAPRGPARFLPLPGLPPAPPEPPGILAPQP-PDVGSSDPLSMVGPSQGRSPSYA S (M72) (SEQ ID NO:72); HPIPDSSPLLQFGGQVRQRYLYTDDAQQTEAHL-EIREDGTVGGAADQSPESLLQLKALK PGVIQILGVK-TSRFLCQRPDGALYGSLHFDPEACSFRELLLEDGYN- VYQSEAHGLPLHLP GNKSPHRDPAPRGPARFLPLPGLPPALPEPPGILAPQPPDVGSSDPLSMVVQDELQGVGG EGCHMHPENCKTLLTDIDRTHTEKPVWDGITGE (M73) (SEQ ID NO:73);
RPLAFSDAGPHVHYGWGDPIRLRHLYTSGPHGLSSCFLRIRADGVVDCARGQSAHSLLEI KAVALRTVAIKGVHSVRYLCMGADGKMQGLLQYSEEDCAFEEEILEDGYNVYRSEKHR LPVSLSSAKQRQLYKNRGFLPLSHFLPMLPMVPEEPEDLRGHLESDMFSSPLETDSMDPF GLVTGLEAVRSPSFEK (M3) (SEQ ID NO:3);
RDSSPLLQFGGQVRLRHLYTSGPHGLSSCFLRIRADGVVDCARGQSAHSLLEIKAVALRT VAIKGVHSVRYLCMGADGKMQGLLQYSEEDCAFEEEIRPDGYNVYRSEKHRLPVSLSS AKQRQLYKNRGFLPLSHFLPMLPMVPEEPEDLRGHLESDMFSSPLETDSMDPFGLVTGL EAVRSPSFEK (M48) (SEQ ID NO:48, 6 or 148);
RPLAFSDSSPLLQFGGQVRLRHLYTSGPHGLSSCFLRIRADGVVDCARGQSAHSLLEIKA VALRTVAIKGVHSVRYLCMGADGKMQGLLQYSEEDCAFEEEIRPDGYNVYRSEKHRLP VSLSSAKQRQLYKNRGFLPLSHFLPMLPMVPEEPEDLRGHLESDMFSSPLETDSMDPFGL VTGLEAVRSPSFEK (M49) (SEQ ID NO:49, 7 or 149);
RHPIPDSSPLLQFGDQVRLRHLYTSGPHGLSSCFLRIRADGVVDCARGQSAHSLLEIKAV ALRTVAIKGVHSVRYLCMGADGKMQGLLQYSEEDCAFEEEILEDGYNVYRSEKHRLPV SLSSAKQRQLYKNRGFLPLSHFLPMLPMVPEEPEDLRGHLESDMFSSPLETDSMDPFGLV TGLEAVRSPSFEK (M50) (SEQ ID NO:50);
RHPIPDSSPLLQFGGNVRLRHLYTSGPHGLSSCFLRIRADGVVDCARGQSAHSLLEIKAV ALRTVAIKGVHSVRYLCMGADGKMQGLLQYSEEDCAFEEEIRPDGYNVYRSEKHRLPV SLSSAKQRQLYKNRGFLPLSHFLPMLPMVPEEPEDLRGHLESDMFSSPLETDSMDPFGLV TGLEAVRSPSFEK (M51) (SEQ ID NO:51, 36 or 155);
MDSSPLLQWGDPIRLRHLYTSGPHGLSSCFLRIRADGVVDCARGQSAHSLLEIKAVALRT VAIKGVHSVRYLCMGADGKMQGLLQYSEEDCAFEEEIRPDGYNVYRSEKHRLPVSLSS AKQRQLYKNRGFLPLSHFLPMLPMVPEEPEDLRGHLESDMFSSPLETDSMDPFGLVTGL EAVRSPSFEK (M53) (SEQ ID NO:192);
MRDSSPLVHYGWGDPIRLRHLYTSGPHGLSSCFLRIRADGVVDCARGQSAHSLLEIKAV ALRTVAIKGVHSVRYLCMGADGKMQGLLQYSEEDCAFEEEIRPDGYNVYRSEKHRLPV SLSSAKQRQLYKNRGFLPLSHFLPMLPMVPEEPEDLRGHLESDMFSSPLETDSMDPFGLV TGLEAVRSPSFEK (M70) (SEQ ID NO:70);
RPLAFSDAGPHVHYGWGDPIRLRHLYTSGPHGLSSCFLRIRADGVVDCARGQSAHSLLEI KAVALRTVAIKGVHSVRYLCMGADGKMQGLLQYSEEDCAFEEEILPDGYNVYRSEKHR LPVSLSSAKQRQLYKNRGFLPLSHFLPMLPMVPEEPEDLRGHLESDMFSSPLETDSMDPF GLVTGLEAVRSPSFEK (M139) (SEQ ID NO:193);
RPLAFSDAGPHVHYGWGDPIRLRHLYTSGPHGLSSCFLRIRADGVVDCARGQSAHSLLEI KAVALRTVAIKGVHSVRYLCMGADGKMQGLLQYSEEDCAFEEEIREDGYNVYRSEKH RLPVSLSSAKQRQLYKNRGFLPLSHFLPMLPMVPEEPEDLRGHLESDMFSSPLETDSMDP FGLVTGLEAVRSPSFEK (M140) (SEQ ID NO:194);
RPLAFSDAGPHVHYGWGDPIRLRHLYTSGPHGLSSCFLRIRADGVVDCARGQSAHSLLEI KAVALRTVAIKGVHSVRYLCMGADGKMQGLLQYSEEDCAFEEEILCDGYNVYRSEKH RLPVSLSSAKQRQLYKNRGFLPLSHFLPMLPMVPEEPEDLRGHLESDMFSSPLETDSMDP FGLVTGLEAVRSPSFEK (M141) (SEQ ID NO:195); or
RPLAFSDAGPHVHYGWGDPIRQRHLYTSGPHGLSSCFLRIRADGVVDCARGQSAHSLLE IKAVALRTVAIKGVHSVRYLCMGADGKMQGLLQYSEEDCAFEEEILEDGYNVYRSEKH RLPVSLSSAKQRQLYKNRGFLPLSHFLPMLPMVPEEPEDLRGHLESDMFSSPLETDSMDP FGLVTGLEAVRSPSFEK (M160) (SEQ ID NO:196);

or a subsequence or fragment thereof any of the foregoing peptide sequences. In certain embodiments of any of the foregoing peptide sequences, the R terminal residue is deleted.

Additional particular non-limiting examples of peptide sequences, having at the N-terminus, a peptide sequence including or consisting of all or a part of any of:
HPIPDSSPLLQFGGQVRLRHLYTSG (M5-R) (amino acids 1-25 of SEQ ID NO:160);
DSSPLLQFGGQVRLRHLYTSG (M6) (M6-R) (amino acids 2-22 of SEQ ID NO:6);
RPLAFSDSSPLLQFGGQVRLRHLYTSG (M7) (amino acids 1-27 of SEQ ID NO:7);
HPIPDSSPLLQWGDPIRLRHLYTSG (M8-R) (amino acids 2-26 of SEQ ID NO:8);
HPIPDSSPLLQFGWGDPIRLRHLYTSG (M9-R) (amino acids 2-28 of SEQ ID NO:9);
HPIPDSSPHVHYGWGDPIRLRHLYTSG (M10-R) (amino acids 2-28 of SEQ ID NO:10);
RPLAFSDAGPLLQWGDPIRLRHLYTSG (M11) (amino acids 1-27 of SEQ ID NO:11);
RPLAFSDAGPLLQFGWGDPIRLRHLYTSG (M12) (amino acids 1-29 of SEQ ID NO:12);
RPLAFSDAGPLLQFGGQVRLRHLYTSG (M13) (amino acids 1-27 of SEQ ID NO:13);
HPIPDSSPHVHYGGQVRLRHLYTSG (M14-R) (amino acids 2-26 of SEQ ID NO:14);
RPLAFSDAGPHVHYGGQVRLRHLYTSG (M15) (amino acids 1-27 of SEQ ID NO:15);
RPLAFSDAGPHVHWGDPIRLRHLYTSG (M16) (amino acids 1-27 of SEQ ID NO:16);
RPLAFSDAGPHVGWGDPIRLRHLYTSG (M17) (amino acids 1-27 of SEQ ID NO:17);
RPLAFSDAGPHYGWGDPIRLRHLYTSG (M18) (amino acids 1-27 of SEQ ID NO:18);
RPLAFSDAGPVYGWGDPIRLRHLYTSG (M19) (amino acids 1-27 of SEQ ID NO:19);
RPLAFSDAGPVHGWGDPIRLRHLYTSG (M20) (amino acids 1-27 of SEQ ID NO:20);
RPLAFSDAGPVHYWGDPIRLRHLYTSG (M21) (amino acids 1-27 of SEQ ID NO:21);
RPLAFSDAGPHVHGWGDPIRLRHLYTSG (M22) (amino acids 1-27 of SEQ ID NO:22);
RPLAFSDAGPHHGWGDPIRLRHLYTSG (M23) (amino acids 1-27 of SEQ ID NO:23);
RPLAFSDAGPHHYWGDPIRLRHLYTSG (M24) (amino acids 1-27 of SEQ ID NO:24);
RPLAFSDAGPHVYWGDPIRLRHLYTSG (M25) (amino acids 1-27 of SEQ ID NO:25);
RPLAFSDSSPLVHWGDPIRLRHLYTSG (M26) (amino acids 1-27 of SEQ ID NO:26);
RPLAFSDSSPHVHWGDPIRLRHLYTSG (M27) (amino acids 1-27 of SEQ ID NO:27);

RPLAFSDAGPHVWGDPIRLRHLYTSG (M28) (amino acids 1-26 of SEQ ID NO:28);
RPLAFSDAGPHVHYWGDPIRLRHLYTSG (M29) (amino acids 1-28 of SEQ ID NO:29);
RPLAFSDAGPHVHYAWGDPIRLRHLYTSG (M30) (amino acids 1-29 of SEQ ID NO:30);
RHPIPDSSPLLQFGAQVRLRHLYTSG (M31) (amino acids 1-26 of SEQ ID NO:31);
RHPIPDSSPLLQFGDQVRLRHLYTSG (M32) (amino acids 1-26 of SEQ ID NO:32);
RHPIPDSSPLLQFGPQVRLRHLYTSG (M33) (amino acids 1-26 of SEQ ID NO:33);
RHPIPDSSPLLQFGGAVRLRHLYTSG (M34) (amino acids 1-26 of SEQ ID NO:34);
RHPIPDSSPLLQFGGEVRLRHLYTSG (M35) (amino acids 1-26 of SEQ ID NO:35);
RHPIPDSSPLLQFGGNVRLRHLYTSG (M36) (amino acids 1-26 of SEQ ID NO:36);
RHPIPDSSPLLQFGGQARLRHLYTSG (M37) (amino acids 1-26 of SEQ ID NO:37);
RHPIPDSSPLLQFGGQIRLRHLYTSG (M38) (amino acids 1-26 of SEQ ID NO:38);
RHPIPDSSPLLQFGGQTRLRHLYTSG (M39) (amino acids 1-26 of SEQ ID NO:39);
RHPIPDSSPLLQFGWGQPVRLRHLYTSG (M40) (amino acids 1-28 of SEQ ID NO:40);
DAGPHVHYGWGDPIRLRHLYTSG (M74-R) (amino acids 2-24 of SEQ ID NO:74);
VHYGWGDPIRLRHLYTSG (M75-R) (amino acids 2-19 of SEQ ID NO:75);
RLRHLYTSG (M77-R) (amino acids 2-10 of SEQ ID NO:77);
RHPIPDSSPLLQFGWGDPIRLRHLYTSG (M9) (amino acids 1-28 of SEQ ID NO:9);
RHPIPDSSPLLQWGDPIRLRHLYTSG (M8) (amino acids 1-26 of SEQ ID NO:8);
RPLAFSDAGPLLQFGWGDPIRLRHLYTSG (M12) (amino acids 1-29 of SEQ ID NO:12);
RHPIPDSSPHVHYGWGDPIRLRHLYTSG (M10) (amino acids 1-28 of SEQ ID NO:10);
RPLAFSDAGPLLQFGGQVRLRHLYTSG (M13) (amino acids 1-27 of SEQ ID NO:13);
RHPIPDSSPHVHYGGQVRLRHLYTSG (M14) (amino acids 1-26 of SEQ ID NO:14);
RPLAFSDAGPHVHYGGDIRLRHLYTSG (M43) amino acids 1-27 of SEQ ID NO:43); or
RDSSPLLQFGGQVRLRHLYTSG (M6) (amino acids 1-22 of SEQ ID NO:6);
and for any of the foregoing peptide sequences the amino terminal R residue may be deleted.

In certain embodiments, the peptide comprises or consists of any of:
HPIPDSSPLLQFGGQVRLRHLYTSG (M5-R) (amino acids 1-25 of SEQ ID NO:160);
DSSPLLQFGGQVRLRHLYTSG (M6-R) (amino acids 2-22 of SEQ ID NO:6);
RPLAFSDSSPLLQFGGQVRLRHLYTSG (M7) (amino acids 1-27 of SEQ ID NO:7);
HPIPDSSPLLQWGDPIRLRHLYTSG (M8-R) (amino acids 2-26 of SEQ ID NO:8);
HPIPDSSPLLQFGWGDPIRLRHLYTSG (M9-R) (amino acids 2-28 of SEQ ID NO:9);
HPIPDSSPHVHYGWGDPIRLRHLYTSG (M10-R) (amino acids 2-28 of SEQ ID NO:10);
RPLAFSDAGPLLQWGDPIRLRHLYTSG (M11) (amino acids 1-27 of SEQ ID NO:11);
RPLAFSDAGPLLQFGWGDPIRLRHLYTSG (M12) (amino acids 1-29 of SEQ ID NO:12);
RPLAFSDAGPLLQFGGQVRLRHLYTSG (M13) (amino acids 1-27 of SEQ ID NO:13);
HPIPDSSPHVHYGGQVRLRHLYTSG (M14-R) (amino acids 2-26 of SEQ ID NO:14);
RPLAFSDAGPHVHYGGQVRLRHLYTSG (M15) (amino acids 1-27 of SEQ ID NO:15);
RPLAFSDAGPHVHWGDPIRLRHLYTSG (M16) (amino acids 1-27 of SEQ ID NO:16);
RPLAFSDAGPHVGWGDPIRLRHLYTSG (M17) (amino acids 1-27 of SEQ ID NO:17);
RPLAFSDAGPHYGWGDPIRLRHLYTSG (M18) (amino acids 1-27 of SEQ ID NO:18);
RPLAFSDAGPVYGWGDPIRLRHLYTSG (M19) (amino acids 1-27 of SEQ ID NO:19);
RPLAFSDAGPVHGWGDPIRLRHLYTSG (M20) (amino acids 1-27 of SEQ ID NO:20);
RPLAFSDAGPHVYWGDPIRLRHLYTSG (M21) (amino acids 1-27 of SEQ ID NO:21);
RPLAFSDAGPHVHGWGDPIRLRHLYTSG (M22) (amino acids 1-27 of SEQ ID NO:22);
RPLAFSDAGPHHGWGDPIRLRHLYTSG (M23) (amino acids 1-27 of SEQ ID NO:23);
RPLAFSDAGPHHYWGDPIRLRHLYTSG (M24) (amino acids 1-27 of SEQ ID NO:24);
RPLAFSDAGPHVYWGDPIRLRHLYTSG (M25) (amino acids 1-27 of SEQ ID NO:25);
RPLAFSDSSPLVHWGDPIRLRHLYTSG (M26) (amino acids 1-27 of SEQ ID NO:26);
RPLAFSDSSPHVHWGDPIRLRHLYTSG (M27) (amino acids 1-27 of SEQ ID NO:27);
RPLAFSDAGPHVWGDPIRLRHLYTSG (M28) (amino acids 1-26 of SEQ ID NO:28);
RPLAFSDAGPHVHYWGDPIRLRHLYTSG (M29) (amino acids 1-28 of SEQ ID NO:29);
RPLAFSDAGPHVHYAWGDPIRLRHLYTSG (M30) (amino acids 1-29 of SEQ ID NO:30);
RHPIPDSSPLLQFGAQVRLRHLYTSG (M31) (amino acids 1-26 of SEQ ID NO:31);
RHPIPDSSPLLQFGDQVRLRHLYTSG (M32) (amino acids 1-26 of SEQ ID NO:32);
RHPIPDSSPLLQFGPQVRLRHLYTSG (M33) (amino acids 1-26 of SEQ ID NO:33);
RHPIPDSSPLLQFGGAVRLRHLYTSG (M34) (amino acids 1-26 of SEQ ID NO:34);
RHPIPDSSPLLQFGGEVRLRHLYTSG (M35) (amino acids 1-26 of SEQ ID NO:35);
RHPIPDSSPLLQFGGNVRLRHLYTSG (M36) (amino acids 1-26 of SEQ ID NO:36);
RHPIPDSSPLLQFGGQARLRHLYTSG (M37) (amino acids 1-26 of SEQ ID NO:37);
RHPIPDSSPLLQFGGQIRLRHLYTSG (M38) (amino acids 1-26 of SEQ ID NO:38);
RHPIPDSSPLLQFGGQTRLRHLYTSG (M39) (amino acids 1-26 of SEQ ID NO:39);
RHPIPDSSPLLQFGWGQPVRLRHLYTSG (M40) (amino acids 1-28 of SEQ ID NO:40);
DAGPHVHYGWGDPIRLRHLYTSG (M74-R) (amino acids 2-24 of SEQ ID NO:74);
VHYGWGDPIRLRHLYTSG (M75-R) (amino acids 2-19 of SEQ ID NO:75);
RLRHLYTSG (M77-R) (amino acids 2-10 of SEQ ID NO:77);
RHPIPDSSPLLQFGWGDPIRLRHLYTSG (M9) (amino acids 1-28 of SEQ ID NO:9);

RHPIPDSSPLLQWGDPIRLRHLYTSG (M8) (amino acids 1-26 of SEQ ID NO:8);
RPLAFSDAGPLLQFGWGDPIRLRHLYTSG (M12) (amino acids 1-29 of SEQ ID NO:12);
RHPIPDSSPHVHYGWGDPIRLRHLYTSG (M10) (amino acids 1-28 of SEQ ID NO:10);
RPLAFSDAGPLLQFGGQVRLRHLYTSG (M13) (amino acids 1-27 of SEQ ID NO:13);
RHPIPDSSPHVHYGGQVRLRHLYTSG (M14) (amino acids 1-26 of SEQ ID NO:14);
RPLAFSDAGPHVHYGGDIRLRHLYTSG (M43) amino acids 1-27 of SEQ ID NO:43); or
RDSSPLLQFGGQVRLRHLYTSG (M6) (amino acids 1-22 of SEQ ID NO:6). In some embodiments, the peptide comprise one of the foregoing sequences. In another embodiment, the peptide consists of one of the foregoing sequences. In some embodiments, the peptide comprises a C-terminal region comprising a portion of SEQ ID NO:99 (FGF19), the C-terminal region having a first amino acid position and a last amino acid position,
wherein the C-terminal region comprises amino acid residues 16-29 of SEQ ID NO:99 (FGF19), WGDPIRLRHLYTSG (SEQ ID NO:169), wherein the W residue corresponds to the first amino acid position of the C-terminal region.

In a specific embodiment, a peptide sequence comprises or consists of:
MRDSSPLVHYGWGDPIRLRHLYTSGPHGLSSCFLRIRADGVVDCARGQSAHSLLEIKAVALR TVAIKGVHSVRYLCMGADGKMQGLLQYSEEDCAFEEEIRPDGYNVYRSEKHRLPVSLSSAK QRQLYKNRGFLPLSHFLPMLPMVPEEPEDLRGHLESDMFSSPLETDSMDPFGLVTGLEAVRS PSFEK (M70) (SEQ ID NO:70), or a subsequence or fragment thereof.

In another embodiment, a peptide sequence comprises or consists of:
RDSSPLVHYGWGDPIRLRHLYTSGPHGLSSCFLRIRADGVVDCARGQSAHSLLEIKAVALRT VAIKGVHSVRYLCMGADGKMQGLLQYSEEDCAFEEEIRPDGYNVYRSEKHRLPVSLSSAKQ RQLYKNRGFLPLSHFLPMLPMVPEEPEDLRGHLESDMFSSPLETDSMDPFGLVTGLEAVRSP SFEK (M69) (SEQ ID NO:69), or a subsequence or fragment thereof.

In other embodiments, the peptide comprises or consists of:
RDSSPLVHYGWGDPIRLRHLYTSGPHGLSSCFLRIRADGVVDCARGQSAHSLLEIKAVALRT VAIKGVHSVRYLCMGADGKMQGLLQYSEEDCAFEEEILEDGYNVYRSEKHRLPVSLSSAKQ RQLYKNRGFLPLSHFLPMLPMVPEEPEDLRGHLESDMFSSPLETDSMDPFGLVTGLEAVRSP SFEK (M200) (SEQ ID NO:197); or a subsequence or fragment thereof. In one embodiment, the N-terminal R residue is deleted.

In some embodiments, the peptide comprises or consists of:
RPLAFSDSSPLVHYGWGDPIRLRHLYTSGPHGLSSCFLRIRADGVVDCARGQSAH SLLEIKAVALRTVAIK-GVHSVRYLCMGADGKMQGLLQYSEEDCAFEEE-ILEDGYNVYRSEK HRLPVSLSSAKQRQLYKNRGFLPLSHFLPMLPM-VPEEPEDLRGHLESDMFSSPLETDSMDPF GLVTGLEAVRSPSFEK (M201) (SEQ ID NO:198); or a subsequence or fragment thereof. In one embodiment, the N-terminal R residue is deleted.

In certain embodiments, the peptide comprises or consists of:
RPLAFSDASPHVHYGWGDPIRLRHLYTSGPHGLSS-CFLRIRADGVVDCARGQSA HSLLEIKAVALRTVAIK-GVHSVRYLCMGADGKMQGLLQYSEEDCAFEEE-ILEDGYNVYRSE KHRLPVSLSSAKQRQLYKNRGFLPLSHFLPMLPM-VPEEPEDLRGHLESDMFSSPLETDSMDP FGLVTGLEAVRSPSFEK (M202) (SEQ ID NO:199); or a subsequence or fragment thereof. In one embodiment, the N-terminal R residue is deleted.

In other embodiments, the peptide comprises or consists of:
RDSSPLLQWGDPIRLIZEILYTSGPHGLSSCFLRI-RADGVVDCARGQSAHSLLEIKA VALRTVAIKGVHS-VRYLCMGADGKMQGLLQYSEEDCAFEEEILEDGYN-VYRSEKHRLPVSL SSAKQRQLYKNRGFLPLSHFLPMLPMVPEEPEDL-RGHLESDMFSSPLETDSMDPFGLVTGLE AVRSPSFEK (M203) (SEQ ID NO:200); or a subsequence or fragment thereof. In one embodiment, the N-terminal R residue is deleted.

In some embodiments, the peptide comprises or consists of:
RHPIPDSSPLLQFGDQVRLRHLYTSGPHGLSSCFL-RIRADGVVDCARGQSAHSLLE IKAVALRTVAIK-GVHSVRYLCMGADGKMQGLLQYSEEDCAFEEE-ILEDGYNVYRSEKHRLP VSLSSAKQRQLYKNRGFLPLSHFLPMLPM-VPEEPEDLRGHLESDMFSSPLETDSMDPFGLVT GLEAVRSPSFEK (M204) (SEQ ID NO:201); or a subsequence or fragment thereof. In one embodiment, the N-terminal R residue is deleted.

In certain embodiments, the peptide comprises or consists of:
RDSSPLLQFGGQVRLRHLYTSGPHGLSSCFLRI-RADGVVDCARGQSAHSLLEIKA VALRTVAIKGVHS-VRYLCMGADGKMQGLLQYSEEDCAFEEEILEDGYN-VYRSEKHRLPVSL SSAKQRQLYKNRGFLPLSHFLPMLPMVPEEPEDL-RGHLESDMFSSPLETDSMDPFGLVTGLE AVRSPSFEK (M205) (SEQ ID NO:202); or a subsequence or fragment thereof. In one embodiment, the N-terminal R residue is deleted.

In some embodiments, the peptide comprises or consists of:
RHPIPDSSPLLQFGGQVRLRHLYTSGPHGLSSCFL-RIRADGVVDCARGQSAHSLLE IKAVALRTVAIK-GVHSVRYLCMGADGKMQGLLQYSEEDCAFEEE-ILEDGYNVYRSEKHRLP VSLSSAKQRQLYKNRGFLPLSHFLPMLPM-VPEEPEDLRGHLESDMFSSPLETDSMDPFGLVT GLEAVRSPSFEK (M206) (SEQ ID NO:203); or a subsequence or fragment thereof. In one embodiment, the N-terminal R residue is deleted.

In other embodiments, the peptide comprises or consists of:
MRDSSPLVHYGWGDPIRLRHLYTSGPHGLSSCFL-RIRADGVVDCARGQSAHSLL EIKAVALRTVAIK-GVHSVRYLCMGADGKMQGLLQYSEEDCAFEEE-ILEDGYNVYRSEKHRL PVSLSSAKQRQLYKNRGFLPLSHFLPMLPM-VPEEPEDLRGHLESDMFSSPLETDSMDPFGLV TGLEAVRSPSFEK (M207) (SEQ ID NO:204); or a subsequence or fragment thereof.

In some embodiments, the peptide is a variant peptide designated M139. In some embodiments, the peptide comprises an amino acid sequence set forth in SEQ ID NO:193. In other embodiments, the peptide consists of an amino acid sequence set forth in SEQ ID NO:193. In some embodiments, the peptide is a variant peptide designated M140. In some embodiments, the peptide comprises an amino acid sequence set forth in SEQ ID NO:194. In other embodiments, the peptide consists of an amino acid sequence set forth in SEQ ID NO:194. In some embodiments, the peptide is a variant peptide designated M141. In some embodiments, the peptide comprises an amino acid sequence set forth in SEQ ID NO:195. In other embodiments, the peptide consists of an amino acid sequence set forth in SEQ ID NO:195. In some embodiments, the peptide is a variant peptide designated M160. In some embodiments, the peptide comprises an amino acid sequence set forth in SEQ ID NO:196. In other embodiments, the peptide consists of an amino acid sequence set forth in SEQ ID NO:196. In some embodiments, the peptide is a variant peptide designated M200. In some embodiments, the peptide comprises an amino acid sequence set forth in SEQ ID NO:197. In other embodiments, the peptide consists of an amino acid sequence set forth in SEQ ID NO:197. In some embodiments, the peptide is a variant peptide designated M201. In some embodiments, the peptide comprises an amino acid sequence set forth in SEQ ID NO:198. In other embodiments, the peptide consists of an amino acid sequence set forth in SEQ ID NO:198. In other embodiments, the peptide is a variant peptide designated M202. In some embodiments, the peptide comprises an amino acid sequence set forth in SEQ ID NO:199. In other embodiments, the peptide consists of an amino acid sequence set forth in SEQ ID NO:199. In certain embodiments, the peptide is a variant peptide designated M203. In some embodiments, the peptide comprises an amino acid sequence set forth in SEQ ID NO:200. In other embodiments, the peptide consists of an amino acid sequence set forth in SEQ ID NO:200. In some embodiments, the peptide is a variant peptide designated M204. In some embodiments, the peptide comprises an amino acid sequence set forth in SEQ ID NO:201. In other embodiments, the peptide consists of an amino acid sequence set forth in SEQ ID NO:201. In another embodiment, the peptide is a variant peptide designated M205. In some embodiments, the peptide comprises an amino acid sequence set forth in SEQ ID NO:202. In other embodiments, the peptide consists of an amino acid sequence set forth in SEQ ID NO:202. In other embodiments, the peptide is a variant peptide designated M206. In some embodiments, the peptide comprises an amino acid sequence set forth in SEQ ID NO:203. In other embodiments, the peptide consists of an amino acid sequence set forth in SEQ ID NO:203. In yet other embodiments, the peptide is a variant peptide designated M207. In some embodiments, the peptide comprises an amino acid sequence set forth in SEQ ID NO:204. In other embodiments, the peptide consists of an amino acid sequence set forth in SEQ ID NO:204.

Peptide sequences provided herein additionally include those with reduced or absent induction or formation of HCC compared to FGF19, or a FGF 19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19. Peptide sequences provided herein also include those with greater glucose lowering activity compared to FGF19, or a FGF 19 variant sequence having any of GQV, GDI, WGPI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19. Peptide sequences provided herein moreover include those with less lipid (e.g., triglyceride, cholesterol, non-HDL or HDL) increasing activity compared to FGF19, or a FGF 19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19.

Typically, the number of amino acids or residues in a peptide sequence provided herein will total less than about 250 (e.g., amino acids or mimetics thereof). In various particular embodiments, the number of residues comprise from about 20 up to about 200 residues (e.g., amino acids or mimetics thereof). In additional embodiments, the number of residues comprise from about 50 up to about 200 residues (e.g., amino acids or mimetics thereof). In further embodiments, the number of residues comprise from about 100 up to about 195 residues (e.g., amino acids or mimetics thereof) in length.

Amino acids or residues can be linked by amide or by non-natural and non-amide chemical bonds including, for example, those formed with glutaraldehyde, N-hydroxysuccinimide esters, bifunctional maleimides, or N, N'-dicyclohexylcarbodiimide (DCC). Non-amide bonds include, for example, ketomethylene, aminomethylene, olefin, ether, thioether and the like (see, e.g., Spatola in *Chemistry and Biochemistry of Amino Acids, Peptides and Proteins*, Vol. 7, pp 267-357 (1983), "Peptide and Backbone Modifications," Marcel Decker, NY). Thus, when a peptide provided herein includes a portion of a FGF19 sequence and a portion of a FGF21 sequence, the two portions need not be joined to each other by an amide bond, but can be joined by any other chemical moiety or conjugated together via a linker moiety.

In some embodiments, the treatment peptides provided herein also include subsequences, variants and modified forms of the exemplified peptide sequences (including the FGF19 and FGF21 variants and subsequences listed in Tables 1-11 and Sequence Listing), so long as the foregoing retains at least a detectable or measurable activity or function. For example, certain exemplified variant peptides have FGF19 C-terminal sequence, PHGLSSCFLRIRADGVVD-CARGQSAHSLLEIKAVALRTVAIKGVHSVRYLCM-GADGKM QGLLQYSEEDCAFEEEIRPDGYN-VYRSEKHRLPVSLSSAKQRQLYKNRGFLPLSHFLPML PMVPEEPEDLRGHLESDMFSSPLETDSMDPF-GLVTGLEAVRSPSFEK (SEQ ID NO:188) at the C-terminal portion, e.g., following the "TSG" amino acid residues of the variant.

Also, certain exemplified variant peptides, for example, those having all or a portion of FGF21 sequence at the amino-terminus, have an "R" residue positioned at the N-terminus, which can be omitted. Similarly, certain exemplified variant peptides, include an "M" residue positioned at the N-terminus, which can be appended to or further substituted for an omitted residue, such as an "R" residue. More particularly, in various embodiments peptide sequences at the N-terminus include any of: RDSS (SEQ ID NO:115), DSS, MDSS (SEQ ID NO:116) or MRDSS (SEQ ID NO:117). Furthermore, in cells when a "M" residue is adjacent to a "S" residue, the "M" residue may be cleaved such that the "M" residue is deleted from the peptide sequence, whereas when the "M" residue is adjacent to a "D" residue, the "M" residue may not be cleaved. Thus, by way of example, in various embodiments peptide sequences include those with the following residues at the N-terminus: MDSSPL (SEQ ID NO:119), MSDSSPL (SEQ ID NO:120) (cleaved to SDSSPL (SEQ ID NO:112)) and MSSPL (SEQ ID NO:113) (cleaved to SSPL (SEQ ID NO:114)).

Accordingly, in some embodiments, the "peptide," "polypeptide," and "protein" sequences provided herein include subsequences, variants and modified forms of the FGF19 and FGF21 variants and subsequences listed in Tables 1-11 and Sequence Listing, and the FGF19/FGF21 fusions and chimeras listed in Tables 1-11 and Sequence Listing, so long as the subsequence, variant or modified form (e.g., fusion or chimera) retains at least a detectable activity or function, e.g., glucose lowering activity and/or modulation of bile acid homeostasis.

As used herein, the term "modify" and grammatical variations thereof, means that the composition deviates relative to a reference composition, such as a peptide sequence. Such modified peptide sequences, nucleic acids and other compositions may have greater or less activity or function, or have a distinct function or activity compared with a reference unmodified peptide sequence, nucleic acid, or other composition, or may have a property desirable in a protein formulated for therapy (e.g. serum half-life), to elicit antibody for use in a detection assay, and/or for protein purification. For example, a peptide sequence provided herein can be modified to increase serum half-life, to increase in vitro and/or in vivo stability of the protein, etc.

Particular examples of such subsequences, variants and modified forms of the peptide sequences exemplified herein (e.g., a peptide sequence listed in the Sequence Listing or Tables 1-11) include substitutions, deletions and/or insertions/additions of one or more amino acids, to or from the amino-terminus, the carboxy-terminus or internally. One example is a substitution of an amino acid residue for another amino acid residue within the peptide sequence. Another is a deletion of one or more amino acid residues from the peptide sequence, or an insertion or addition of one or more amino acid residues into the peptide sequence.

The number of residues substituted, deleted or inserted/added are one or more amino acids (e.g., 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250, or more) of a peptide sequence. Thus, a FGF19 or FGF21 sequence can have few or many amino acids substituted, deleted or inserted/added (e.g., 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250, or more). In addition, a FGF19 amino acid sequence can include or consist of an amino acid sequence of about 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250, or more amino acids from FGF21; or a FGF21 amino acid or sequence can include or consist of an amino acid sequence of about 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250, or more amino acids from FGF19.

Specific examples of substitutions include substituting a D residue for an L-residue. Accordingly, although residues are listed in the L-isomer configuration, D-amino acids at any particular or all positions of the peptide sequences provided herein are included, unless a D-isomer leads to a sequence that has no detectable or measurable function.

Additional specific examples are non-conservative and conservative substitutions. A "conservative substitution" is a replacement of one amino acid by a biologically, chemically or structurally similar residue. Biologically similar means that the substitution is compatible with a biological activity, e.g., activity that improves PBC and/or the manifestations thereof. Structurally similar means that the amino acids have side chains with similar length, such as alanine, glycine and serine, or having similar size, or the structure of a first, second or additional peptide sequence is maintained. Chemical similarity means that the residues have the same charge or are both hydrophilic and hydrophobic. Particular examples include the substitution of one hydrophobic residue, such as isoleucine, valine, leucine or methionine, for another, or the substitution of one polar residue for another, such as the substitution of arginine for lysine, glutamic for aspartic acids, or glutamine for asparagine, serine for threonine, etc. Routine assays can be used to determine whether a subsequence, variant or modified form has activity, e.g., activity that improves PBC and/or the manifestations thereof.

Particular examples of subsequences, variants and modified forms of the peptide sequences exemplified herein have 50%-60%, 60%-70%, 70%-75%, 75%-80%, 80%-85%, 85%-90%, 90%-95%, or 96%, 97%, 98%, or 99% identity to a reference peptide sequence. The term "identity" and "homology" and grammatical variations thereof mean that two or more referenced entities are the same. Thus, where two amino acid sequences are identical, they have the identical amino acid sequence. "Areas, regions or domains of identity" mean that a portion of two or more referenced entities are the same. Thus, where two amino acid sequences are identical or homologous over one or more sequence regions, they share identity in those regions.

The extent of identity between two sequences can be ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al., J. Mol. Biol. 215:403 (1990), publicly available through NCBI) has exemplary search parameters as follows: Mismatch-2; gap open 5; gap extension 2. For peptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., Proc. Natl. Acad. Sci. USA 85:2444 (1988); Pearson, Methods Mol Biol. 132:185 (2000); and Smith et al., J. Mol. Biol. 147:195 (1981)). Programs for quantitating protein structural similarity using Delaunay-based topological mapping have also been developed (Bostick et al., Biochem Biophys Res Commun. 304:320 (2003)).

In the peptide sequences, including subsequences, variants and modified forms of the peptide sequences exemplified herein, an "amino acid" or "residue" includes conventional alpha-amino acids as well as beta-amino acids; alpha, alpha disubstituted amino acids; and N-substituted amino acids, wherein at least one side chain is an amino acid side chain moiety as defined herein. An "amino acid" further includes N-alkyl alpha-amino acids, wherein the N-terminus amino group has a $C_1$ to $C_6$ linear or branched alkyl substituent. The term "amino acid" therefore includes stereoisomers and modifications of naturally occurring protein amino acids, non-protein amino acids, post-translationally modified amino acids (e.g., by glycosylation, phosphorylation, ester or amide cleavage, etc.), enzymatically modified or synthesized amino acids, derivatized amino acids, constructs or structures designed to mimic amino acids, amino acids with a side chain moiety modified, derivatized from naturally occurring moieties, or synthetic, or not naturally occurring, etc. Modified and unusual amino acids are included in the peptide sequences provided herein (see, for example, in *Synthetic Peptides: A User's Guide*; Hruby et al., Biochem. J. 268:249 (1990); and Toniolo C., Int. J. Peptide Protein Res. 35:287 (1990)).

In addition, protecting and modifying groups of amino acids are included. The term "amino acid side chain moiety" as used herein includes any side chain of any amino acid, as the term "amino acid" is defined herein. This therefore includes the side chain moiety in naturally occurring amino acids. It further includes side chain moieties in modified naturally occurring amino acids as set forth herein and known to one of skill in the art, such as side chain moieties in stereoisomers and modifications of naturally occurring protein amino acids, non-protein amino acids, post-translationally modified amino acids, enzymatically modified or synthesized amino acids, derivatized amino acids, constructs or structures designed to mimic amino acids, etc. For example, the side chain moiety of any amino acid disclosed herein or known to one of skill in the art is included within the definition.

A "derivative of an amino acid side chain moiety" is included within the definition of an amino acid side chain moiety. Non-limiting examples of derivatized amino acid side chain moieties include, for example: (a) adding one or more saturated or unsaturated carbon atoms to an existing alkyl, aryl, or aralkyl chain; (b) substituting a carbon in the side chain with another atom, such as oxygen or nitrogen; (c) adding a terminal group to a carbon atom of the side chain, including methyl (—$CH_3$), methoxy (—$OCH_3$), nitro (—$NO_2$), hydroxyl (—OH), or cyano (—C≡N); (d) for side chain moieties including a hydroxy, thiol or amino groups, adding a suitable hydroxy, thiol or amino protecting group; or (e) for side chain moieties including a ring structure, adding one or more ring substituents, including hydroxyl, halogen, alkyl, or aryl groups attached directly or through, e.g., an ether linkage. For amino groups, suitable protecting groups are known to the skilled artisan. Provided such derivatization provides a desired activity in the final peptide sequence (e.g., activity that improves PBC and/or the manifestations thereof).

An "amino acid side chain moiety" includes all such derivatization, and particular non-limiting examples include: gamma-amino butyric acid, 12-amino dodecanoic acid, alpha-aminoisobutyric acid, 6-amino hexanoic acid, 4-(aminomethyl)-cyclohexane carboxylic acid, 8-amino octanoic acid, biphenylalanine, Boc-t-butoxycarbonyl, benzyl, benzoyl, citrulline, diaminobutyric acid, pyrrollysine, diaminopropionic acid, 3,3-diphenylalanine, orthonine, citrulline, 1,3-dihydro-2H-isoindolecarboxylic acid, ethyl, Fmoc-fluorenylmethoxycarbonyl, heptanoyl ($CH_3$—($CH_2$)$_5$—C(=O)—), hexanoyl ($CH_3$—($CH_2$)$_4$—C(=O)—), homoarginine, homocysteine, homolysine, homophenylalanine, homoserine, methyl, methionine sulfoxide, methionine sulfone, norvaline (NVA), phenylglycine, propyl, isopropyl, sarcosine (SAR), tert-butylalanine, and benzyloxycarbonyl.

A single amino acid, including stereoisomers and modifications of naturally occurring protein amino acids, non-protein amino acids, post-translationally modified amino acids, enzymatically-synthesized amino acids, non-naturally occurring amino acids including derivatized amino acids, an alpha, alpha disubstituted amino acid derived from any of the foregoing (i.e., an alpha, alpha disubstituted amino acid, wherein at least one side chain is the same as that of the residue from which it is derived), a beta-amino acid derived from any of the foregoing (i.e., a beta-amino acid which, other than for the presence of a beta-carbon, is the same as the residue from which it is derived) etc., including all of the foregoing can be referred to herein as a "residue." Suitable substituents, in addition to the side chain moiety of the alpha-amino acid, include $C_1$ to $C_6$ linear or branched alkyl. Aib is an example of an alpha, alpha disubstituted amino acid. While alpha, alpha disubstituted amino acids can be referred to using conventional L- and D-isomeric references, it is to be understood that such references are for convenience, and that where the substituents at the alpha-position are different, such amino acid can interchangeably be referred to as an alpha, alpha disubstituted amino acid derived from the L- or D-isomer, as appropriate, of a residue with the designated amino acid side chain moiety. Thus (S)-2-Amino-2-methyl-hexanoic acid can be referred to as either an alpha, alpha disubstituted amino acid derived from L-Nle (norleucine) or as an alpha, alpha disubstituted amino acid derived from D-Ala. Similarly, Aib can be referred to as an alpha, alpha disubstituted amino acid derived from Ala. Whenever an alpha, alpha disubstituted amino acid is provided, it is to be understood as including all (R) and (S) configurations thereof.

An "N-substituted amino acid" includes any amino acid wherein an amino acid side chain moiety is covalently bonded to the backbone amino group, optionally where there are no substituents other than H in the alpha-carbon position. Sarcosine is an example of an N-substituted amino acid. By way of example, sarcosine can be referred to as an N-substituted amino acid derivative of Ala, in that the amino acid side chain moiety of sarcosine and Ala is the same, i.e., methyl.

In certain embodiments, covalent modifications of the peptide sequences, including subsequences, variants and modified forms of the peptide sequences exemplified herein are provided. An exemplary type of covalent modification includes reacting targeted amino acid residues with an organic derivatizing agent that is capable of reacting with selected side chains or the N- or C-terminal residues of the peptide. Derivatization with bifunctional agents is useful, for instance, for cross-linking peptide to a water-insoluble support matrix or surface for use in the method for purifying anti-peptide antibodies, and vice-versa. Commonly used cross linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the alpha-amino groups of lysine, arginine, and histidine side chains (T. E. Creighton, *Proteins: Structure and Molecular Properties*, W.H. Freeman & Co., San Francisco, pp. 79-86 (1983)), acetylation of the N-terminal amine, amidation of any C-terminal carboxyl group, etc.

Exemplified peptide sequences, and subsequences, variants and modified forms of the peptide sequences exemplified herein can also include alterations of the backbone for stability, derivatives, and peptidomimetics. The term "peptidomimetic" includes a molecule that is a mimic of a residue (referred to as a "mimetic"), including but not limited to piperazine core molecules, keto-piperazine core molecules and diazepine core molecules. Unless otherwise specified, an amino acid mimetic of a peptide sequence provided herein includes both a carboxyl group and amino group, and a group corresponding to an amino acid side chain, or in the case of a mimetic of Glycine, no side chain other than hydrogen.

By way of example, these would include compounds that mimic the sterics, surface charge distribution, polarity, etc. of a naturally occurring amino acid, but need not be an amino acid, which would impart stability in the biological system. For example, Proline may be substituted by other lactams or lactones of suitable size and substitution; Leucine may be substituted by an alkyl ketone, N-substituted amide, as well as variations in amino acid side chain length using alkyl, alkenyl or other substituents, others may be apparent to the skilled artisan. The essential element of making such substitutions is to provide a molecule of roughly the same size and charge and configuration as the residue used to design the molecule. Refinement of these modifications will be made by analyzing the compounds in a functional (e.g., glucose lowering) or other assay, and comparing the structure-activity relationship. Such methods are within the scope of the skilled artisan working in medicinal chemistry and drug development.

The term "bind," or "binding," when used in reference to a peptide sequence, means that the peptide sequence interacts at the molecular level. Specific and selective binding can be distinguished from non-specific binding using assays known in the art (e.g., competition binding, immunoprecipitation, ELISA, flow cytometry, Western blotting).

Peptides and peptidomimetics can be produced and isolated using methods known in the art. Peptides can be synthesized, in whole or in part, using chemical methods (see, e.g., Caruthers (1980). Nucleic Acids Res. Symp. Ser. 215; Horn (1980); and Banga, A. K., *Therapeutic Peptides and Proteins, Formulation, Processing and Delivery Systems* (1995) Technomic Publishing Co., Lancaster, Pa.). Peptide synthesis can be performed using various solid-phase techniques (see, e.g., Roberge Science 269:202 (1995); Merrifield, Methods Enzymol. 289:3 (1997)) and automated synthesis may be achieved, e.g., using the ABI 431A Peptide Synthesizer (Perkin Elmer) in accordance with the manufacturer's instructions. Peptides and peptide mimetics can also be synthesized using combinatorial methodologies. Synthetic residues and polypeptides incorporating mimetics can be synthesized using a variety of procedures and methodologies known in the art (see, e.g., *Organic Syntheses* Collective Volumes, Gilman, et al. (Eds) John Wiley & Sons, Inc., NY). Modified peptides can be produced by chemical modification methods (see, for example, Belousov, Nucleic Acids Res. 25:3440 (1997); Frenkel, Free Radic. Biol. Med. 19:373 (1995); and Blommers, Biochemistry 33:7886 (1994)). Peptide sequence variations, derivatives, substitutions and modifications can also be made using methods such as oligonucleotide-mediated (site-directed) mutagenesis, alanine scanning, and PCR-based mutagenesis. Site-directed mutagenesis (Carter et al., Nucl. Acids Res., 13:4331 (1986); Zoller et al., Nucl. Acids Res. 10:6487 (1987)), cassette mutagenesis (Wells et al., Gene 34:315 (1985)), restriction selection mutagenesis (Wells et al., Philos. Trans. R. Soc. London SerA 317:415 (1986)) and other techniques can be performed on cloned DNA to produce peptide sequences, variants, fusions and chimeras provided herein, and variations, derivatives, substitutions and modifications thereof.

A "synthesized" or "manufactured" peptide sequence is a peptide made by any method involving manipulation by the hand of man. Such methods include, but are not limited to, the aforementioned, such as chemical synthesis, recombinant DNA technology, biochemical or enzymatic fragmentation of larger molecules, and combinations of the foregoing.

Peptide sequences provided herein including subsequences, sequence variants and modified forms of the exemplified peptide sequences (e.g., sequences listed in the Sequence Listing or Tables 1-11), can also be modified to form a chimeric molecule. In certain embodiments, provided herein are peptide sequences that include a heterologous domain. Such domains can be added to the amino-terminus or at the carboxyl-terminus of the peptide sequence. Heterologous domains can also be positioned within the peptide sequence, and/or alternatively flanked by FGF19 and/or FGF21 derived amino acid sequences.

The term "peptide" also includes dimers or multimers (oligomers) of peptides. In certain embodiments, dimers or multimers (oligomers) of the exemplified peptide sequences are provided herein, as well as subsequences, variants and modified forms of the exemplified peptide sequences, including sequences listed in the Sequence Listing or Tables 1-11.

In certain embodiments, a peptide sequence provided herein comprises an amino acid sequence set forth in Table 1. In other embodiments, a peptide sequence provided herein consists of an amino acid sequence set forth in Table 1.

TABLE 1

| SEQ ID NO. | Amino Acid Sequence |
|---|---|
| 1. | RPLAFSDASPHVHYGWGDPIRLRHLYTSGPHGLSSCFLRIRADGVVDCARG QSAHSLLEIKAVALRTVAIKGVHSVRYLCMGADGKMQGLLQYSEEDCAFE EEIRPDGYNVYRSEKHRLPVSLSSAKQRQLYKNRGFLPLSHFLPMLPMVPE EPEDLRGHLESDMFSSPLETDSMDPFGLVTGLEAVRSPSFEK |
| 2. | RPLAFSDSSPLVHYGWGDPIRLRHLYTSGPHGLSSCFLRIRADGVVDCARG QSAHSLLEIKAVALRTVAIKGVHSVRYLCMGADGKMQGLLQYSEEDCAFE |

TABLE 1-continued

| SEQ ID NO. | Amino Acid Sequence |
|---|---|
| | EEIRPDGYNVYRSEKHRLPVSLSSAKQRQLYKNRGFLPLSHFLPMLPMVPE<br>EPEDLRGHLESDMFSSPLETDSMDPFGLVTGLEAVRSPSFEK |
| 3. | RPLAFSDAGPHVHYGWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEILEDGYNVYRSEKHRLPVSLSSAKQRQLYKNRGFLPLSHFLPMLPMVPE<br>EPEDLRGHLESDMFSSPLETDSMDPFGLVTGLEAVRSPSFEK |
| 4. | RPLAFSDAGPHVHYAWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAKQRQLYKNRGFLPLSHFLPMLPMVPE<br>EPEDLRGHLESDMFSSPLETDSMDPFGLVTGLEAVRSPSFEK |
| 5. | RHPIPDSSPLLQFGGQVRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 6. | RDSSPLLQFGGQVRLRHLYTSGPHGLSSCFLRIRADGVVDCARGQSAHSLL<br>EIKAVALRTVAIKGVHSVRYLCMGADGKMQGLLQYSEEDCAFEEEIRPDG<br>YNVYRSEKHRLPVSLSSAKQRQLYKNRGFLPLSHFLPMLPMVPEEPEDLRG<br>HLESDMFSSPLETDSMDPFGLVTGLEAVRSPSFEK |
| 7. | RPLAFSDSSPLLQFGGQVRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 8. | RHPIPDSSPLLQWGDPIRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 9. | RHPIPDSSPLLQFGWGDPIRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 10. | RHPIPDSSPHVHYGWGDPIRLRHLYTSGPHGLSSCFLRIRADGVVDCARGQ<br>SAHSLLEIKAVALRTVAIKGVHSVRYLCMGADGKMQGLLQYSEEDCAFEE<br>EIRPDGYNVYRSEKHRLPVSLSSAKQRQLYKNRGFLPLSHFLPMLPMVPEE<br>PEDLRGHLESDMFSSPLETDSMDPFGLVTGLEAVRSPSFEK |
| 11. | RPLAFSDAGPLLQWGDPIRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 12. | RPLAFSDAGPLLQFGWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAKQRQLYKNRGFLPLSHFLPMLPMVPE<br>EPEDLRGHLESDMFSSPLETDSMDPFGLVTGLEAVRSPSFEK |
| 13. | RPLAFSDAGPLLQFGGQVRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 14. | RHPIPDSSPHVHYGGQVRLRHLYTSGPHGLSSCFLRIRADGVVDCARGQSA<br>HSLLEIKAVALRTVAIKGVHSVRYLCMGADGKMQGLLQYSEEDCAFEEEI<br>RPDGYNVYRSEKHRLPVSLSSAKQRQLYKNRGFLPLSHFLPMLPMVPEEPE<br>DLRGHLESDMFSSPLETDSMDPFGLVTGLEAVRSPSFEK |
| 15. | RPLAFSDAGPHVHYGGQVRLRHLYTSGPHGLSSCFLRIRADGVVDCARGQ<br>SAHSLLEIKAVALRTVAIKGVHSVRYLCMGADGKMQGLLQYSEEDCAFEE<br>EIRPDGYNVYRSEKHRLPVSLSSAKQRQLYKNRGFLPLSHFLPMLPMVPEE<br>PEDLRGHLESDMFSSPLETDSMDPFGLVTGLEAVRSPSFEK |
| 16. | RPLAFSDAGPHVHWGDPIRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 17. | RPLAFSDAGPHVGWGDPIRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |

TABLE 1-continued

| SEQ ID NO. | Amino Acid Sequence |
|---|---|
| 18. | RPLAFSDAGPHYGWGDPIRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 19. | RPLAFSDAGPVYGWGDPIRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 20. | RPLAFSDAGPVHGWGDPIRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 21. | RPLAFSDAGPVHYWGDPIRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 22. | RPLAFSDAGPHVHGWGDPIRLRHLYTSGPHGLSSCFLRIRADGVVDCARGQ<br>SAHSLLEIKAVALRTVAIKGVHSVRYLCMGADGKMQGLLQYSEEDCAFEE<br>EIRPDGYNVYRSEKHRLPVSLSSAKQRQLYKNRGFLPLSHFLPMLPMVPEE<br>PEDLRGHLESDMFSSPLETDSMDPFGLVTGLEAVRSPSFEK |
| 23. | RPLAFSDAGPHHGWGDPIRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 24. | RPLAFSDAGPHHYWGDPIRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 25. | RPLAFSDAGPHVYGWGDPIRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 26. | RPLAFSDSSPLVHWGDPIRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 27. | RPLAFSDSSPHVHWGDPIRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 28. | RPLAFSDAGPHVWGDPIRLRHLYTSGPHGLSSCFLRIRADGVVDCARGQSA<br>HSLLEIKAVALRTVAIKGVHSVRYLCMGADGKMQGLLQYSEEDCAFEEEI<br>RPDGYNVYRSEKHRLPVSLSSAKQRQLYKNRGFLPLSHFLPMLPMVPEEPE<br>DLRGHLESDMFSSPLETDSMDPFGLVTGLEAVRSPSFEK |
| 29. | RPLAFSDAGPHVHYWGDPIRLRHLYTSGPHGLSSCFLRIRADGVVDCARGQ<br>SAHSLLEIKAVALRTVAIKGVHSVRYLCMGADGKMQGLLQYSEEDCAFEE<br>EIRPDGYNVYRSEKHRLPVSLSSAKQRQLYKNRGFLPLSHFLPMLPMVPEE<br>PEDLRGHLESDMFSSPLETDSMDPFGLVTGLEAVRSPSFEK |
| 30. | RPLAFSDAGPHVHYAWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAKQRQLYKNRGFLPLSHFLPMLPMVPE<br>EPEDLRGHLESDMFSSPLETDSMDPFGLVTGLEAVRSPSFEK |
| 31. | RHPIPDSSPLLQFGAQVRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 32. | RHPIPDSSPLLQFGDQVRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |

TABLE 1-continued

| SEQ ID NO. | Amino Acid Sequence |
|---|---|
| 33. | RHPIPDSSPLLQFGPQVRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 34. | RHPIPDSSPLLQFGGAVRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 35. | RHPIPDSSPLLQFGGEVRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 36. | RHPIPDSSPLLQFGGNVRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 37. | RHPIPDSSPLLQFGGQARLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 38. | RHPIPDSSPLLQFGGQIRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 39. | RHPIPDSSPLLQFGGQTRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 40. | RHPIPDSSPLLQFGWGQPVRLRHLYTSGPHGLSSCFLRIRADGVVDCARGQ<br>SAHSLLEIKAVALRTVAIKGVHSVRYLCMGADGKMQGLLQYSEEDCAFEE<br>EIRPDGYNVYRSEKHRLPVSLSSAKQRQLYKNRGFLPLSHFLPMLPMVPEE<br>PEDLRGHLESDMFSSPLETDSMDPFGLVTGLEAVRSPSFEK |
| 41. | RPLAFSDAGPHVHYGWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAKQRQLYKNRGFLPLSHFLPMLPEPPGI<br>LAPQPPDVGSSDPLSMVGPSQGRSPSYAS |
| 42. | HPIPDSSPLLQFGGQVRLRHLYTSGPHGLSSCFLRIRADGVVDCARGQSAHS<br>LLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPEPPGILAPQP<br>PDVGSSDPLSMVGPSQGRSPSYAS |
| 43. | RPLAFSDAGPHVHYGGDIRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 44. | RPLAFSDAGPHVHYGWGDPIRQRYLYTDDAQQTEAHLEIREDGTVGGAAD<br>QSPESLLQLKALKPGVIQILGVKTSRFLCQRPDGALYGSLHFDPEACSFREL<br>LLEDGYNVYQSEAHGLPLHLPGNKSPHRDPAPRGPARFLPLPGLPPALPEPP<br>GILAPQPPDVGSSDPLSMVGPSQGRSPSYAS |
| 45. | HPIPDSSPLLQFGGQVRQRYLYTDDAQQTEAHLEIREDGTVGGAADQSPES<br>LLQLKALKPGVIQILGVKTSRFLCQRPDGALYGSLHFDPEACSFRELLLEDG<br>YNVYQSEAHGLPLHLPGNKSPHRDPAPRGPARFLPLPGLPPALPMVPEEPE<br>DLRGHLESDMFSSPLETDSMDPFGLVTGLEAVRSPSFEK |
| 46. | RPLAFSDAGPHVHYGWGDPIRQRYLYTDDAQQTEAHLEIREDGTVGGAAD<br>QSPESLLQLKALKPGVIQILGVKTSRFLCQRPDGALYGSLHFDPEACSFREL<br>LLEDGYNVYQSEAHGLPLHLPGNKSPHRDPAPRGPARFLPLPGLPPALPEPP<br>GILAPQPPDVGSSDPLSMVGPSQGRSPSYASPMVPEEPEDLRGHLESDMFSS<br>PLETDSMDPFGLVTGLEAVRSPSFEK |
| 47. | HPIPDSSPLLQWGDPIRLRHLYTSGPHGLSSCFLRIRADGVVDCARGQSAHS<br>LLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |

TABLE 1-continued

| SEQ ID NO. | Amino Acid Sequence |
|---|---|
| 48. | RDSSPLLQFGGQVRLRHLYTSGPHGLSSCFLRIRADGVVDCARGQSAHSLL EIKAVALRTVAIKGVHSVRYLCMGADGKMQGLLQYSEEDCAFEEEIRPDG YNVYRSEKHRLPVSLSSAKQRQLYKNRGFLPLSHFLPMLPMVPEEPEDLRG HLESDMFSSPLETDSMDPFGLVTGLEAVRSPSFEK |
| 49. | RPLAFSDSSPLLQFGGQVRLRHLYTSGPHGLSSCFLRIRADGVVDCARGQS AHSLLEIKAVALRTVAIKGVHSVRYLCMGADGKMQGLLQYSEEDCAFEEE IRPDGYNVYRSEKHRLPVSLSSAKQRQLYKNRGFLPLSHFLPMLPMVPEEP EDLRGHLESDMFSSPLETDSMDPFGLVTGLEAVRSPSFEK |
| 50. | RHPIPDSSPLLQFGDQVRLRHLYTSGPHGLSSCFLRIRADGVVDCARGQSAH SLLEIKAVALRTVAIKGVHSVRYLCMGADGKMQGLLQYSEEDCAFEEEILE DGYNVYRSEKHRLPVSLSSAKQRQLYKNRGFLPLSHFLPMLPMVPEEPEDL RGHLESDMFSSPLETDSMDPFGLVTGLEAVRSPSFEK |
| 51. | RHPIPDSSPLLQFGGNVRLRHLYTSGPHGLSSCFLRIRADGVVDCARGQSAH SLLEIKAVALRTVAIKGVHSVRYLCMGADGKMQGLLQYSEEDCAFEEEIRP DGYNVYRSEKHRLPVSLSSAKQRQLYKNRGFLPLSHFLPMLPMVPEEPEDL RGHLESDMFSSPLETDSMDPFGLVTGLEAVRSPSFEK |
| 52. | RDSSPLLQWGDPIRLRHLYTSGPHGLSSCFLRIRADGVVDCARGQSAHSLL EIKAVALRTVAIKGVHSVRYLCMGADGKMQGLLQYSEEDCAFEEEIRPDG YNVYRSEKHRLPVSLSSAKQRQLYKNRGFLPLSHFLPMLPMVPEEPEDLRG HLESDMFSSPLETDSMDPFGLVTGLEAVRSPSFEK |
| 53. | MDSSPLVHYGWGDPIRLRHLYTSGPHGLSSCFLRIRADGVVDCARGQSAHS LLEIKAVALRTVAIKGVHSVRYLCMGADGKMQGLLQYSEEDCAFEEEIRP DGYNVYRSEKHRLPVSLSSAKQRQLYKNRGFLPLSHFLPMLPMVPEEPEDL RGHLESDMFSSPLETDSMDPFGLVTGLEAVRSPSFEK |
| 54. | RPLAFSDAGPLLQWGDPIRLRHLYTSGPHGLSSCFLRIRADGVVDCARGQS AHSLLEIKAVALRTVAIKGVHSVRYLCMGADGKMQGLLQYSEEDCAFEEE IRPDGYNVYRSEKHRLPVSLSSAKQRQLYKNRGFLPLSHFLPMLPMVPEEP EDLRGHLESDMFSSPLETDSMDPFGLVTGLEAVRSPSFEK |
| 55. | RPLAFSDAGPHYGWGDPIRLRHLYTSGPHGLSSCFLRIRADGVVDCARGQS AHSLLEIKAVALRTVAIKGVHSVRYLCMGADGKMQGLLQYSEEDCAFEEE IRPDGYNVYRSEKHRLPVSLSSAKQRQLYKNRGFLPLSHFLPMLPMVPEEP EDLRGHLESDMFSSPLETDSMDPFGLVTGLEAVRSPSFEK |
| 56. | RPLAFSDAGPVYGWGDPIRLRHLYTSGPHGLSSCFLRIRADGVVDCARGQS AHSLLEIKAVALRTVAIKGVHSVRYLCMGADGKMQGLLQYSEEDCAFEEE IRPDGYNVYRSEKHRLPVSLSSAKQRQLYKNRGFLPLSHFLPMLPMVPEEP EDLRGHLESDMFSSPLETDSMDPFGLVTGLEAVRSPSFEK |
| 57. | RPLAFSDAGPVHGWGDPIRLRHLYTSGPHGLSSCFLRIRADGVVDCARGQS AHSLLEIKAVALRTVAIKGVHSVRYLCMGADGKMQGLLQYSEEDCAFEEE IRPDGYNVYRSEKHRLPVSLSSAKQRQLYKNRGFLPLSHFLPMLPMVPEEP EDLRGHLESDMFSSPLETDSMDPFGLVTGLEAVRSPSFEK |
| 58. | RPLAFSDAGPVHYWGDPIRLRHLYTSGPHGLSSCFLRIRADGVVDCARGQS AHSLLEIKAVALRTVAIKGVHSVRYLCMGADGKMQGLLQYSEEDCAFEEE IRPDGYNVYRSEKHRLPVSLSSAKQRQLYKNRGFLPLSHFLPMLPMVPEEP EDLRGHLESDMFSSPLETDSMDPFGLVTGLEAVRSPSFEK |
| 59. | RPLAFSDAGPHHGWGDPIRLRHLYTSGPHGLSSCFLRIRADGVVDCARGQS AHSLLEIKAVALRTVAIKGVHSVRYLCMGADGKMQGLLQYSEEDCAFEEE IRPDGYNVYRSEKHRLPVSLSSAKQRQLYKNRGFLPLSHFLPMLPMVPEEP EDLRGHLESDMFSSPLETDSMDPFGLVTGLEAVRSPSFEK |
| 60. | RPLAFSDAGPHHYWGDPIRLRHLYTSGPHGLSSCFLRIRADGVVDCARGQS AHSLLEIKAVALRTVAIKGVHSVRYLCMGADGKMQGLLQYSEEDCAFEEE IRPDGYNVYRSEKHRLPVSLSSAKQRQLYKNRGFLPLSHFLPMLPMVPEEP EDLRGHLESDMFSSPLETDSMDPFGLVTGLEAVRSPSFEK |
| 61. | RPLAFSDAGPHVGWGDPIRLRHLYTSGPHGLSSCFLRIRADGVVDCARGQS AHSLLEIKAVALRTVAIKGVHSVRYLCMGADGKMQGLLQYSEEDCAFEEE IRPDGYNVYRSEKHRLPVSLSSAKQRQLYKNRGFLPLSHFLPMLPMVPEEP EDLRGHLESDMFSSPLETDSMDPFGLVTGLEAVRSPSFEK |
| 62. | RPLAFSDAGPHVYWGDPIRLRHLYTSGPHGLSSCFLRIRADGVVDCARGQS AHSLLEIKAVALRTVAIKGVHSVRYLCMGADGKMQGLLQYSEEDCAFEEE IRPDGYNVYRSEKHRLPVSLSSAKQRQLYKNRGFLPLSHFLPMLPMVPEEP EDLRGHLESDMFSSPLETDSMDPFGLVTGLEAVRSPSFEK |
| 63. | RPLAFSDAGPHVHWGDPIRLRHLYTSGPHGLSSCFLRIRADGVVDCARGQS AHSLLEIKAVALRTVAIKGVHSVRYLCMGADGKMQGLLQYSEEDCAFEEE |

TABLE 1-continued

| SEQ ID NO. | Amino Acid Sequence |
|---|---|
|  | IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 64. | RPLAFSDSSPLVHWGDPIRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 65. | RPLAFSDSSPHVHWGDPIRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 66. | RPLAFSDAGPHLQWGDPIRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 67. | RPLAFSDAGPHVWGDPIRLRHLYTSGPHGLSSCFLRIRADGVVDCARGQSA<br>HSLLEIKAVALRTVAIKGVHSVRYLCMGADGKMQGLLQYSEEDCAFEEEI<br>RPDGYNVYRSEKHRLPVSLSSAKQRQLYKNRGFLPLSHFLPMLPMVPEEPE<br>DLRGHLESDMFSSPLETDSMDPFGLVTGLEAVRSPSFEK |
| 68. | RPLAFSDAGPHVHYGDPIRLRHLYTSGPHGLSSCFLRIRADGVVDCARGQ<br>SAHSLLEIKAVALRTVAIKGVHSVRYLCMGADGKMQGLLQYSEEDCAFEE<br>EIRPDGYNVYRSEKHRLPVSLSSAKQRQLYKNRGFLPLSHFLPMLPMVPEE<br>PEDLRGHLESDMFSSPLETDSMDPFGLVTGLEAVRSPSFEK |
| 69. | RDSSPLVHYGWGDPIRLRHLYTSGPHGLSSCFLRIRADGVVDCARGQSAHS<br>LLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 70. | MRDSSPLVHYGWGDPIRLRHLYTSGPHGLSSCFLRIRADGVVDCARGQSA<br>HSLLEIKAVALRTVAIKGVHSVRYLCMGADGKMQGLLQYSEEDCAFEEEI<br>RPDGYNVYRSEKHRLPVSLSSAKQRQLYKNRGFLPLSHFLPMLPMVPEEPE<br>DLRGHLESDMFSSPLETDSMDPFGLVTGLEAVRSPSFEK |
| 71. | HPIPDSSPLLQFGGQVRQRYLYTDDAQQTEAHLEIREDGTVGGAADQSPES<br>LLQLKALKPGVIQILGVKTSRFLCQRPDGALYGSLHFDPEACSFRELLLEDG<br>YNVYQSEAHSLPLHLPGNKSPHRDPAPRGPARFLPLPGLPPALPEPPGILAP<br>QPPDVGSSDPLSMVGPSQGRSPSYAS |
| 72. | HPIPDSSPLLQFGGQVRQRYLYTDDAQQTEAHLEIREDGTVGGAADQSPES<br>LLQLKALKPGVIQILGVKTSRFLCQRPDGALYGSLHFDPEACSFRELLLEDG<br>YNVYQSEAHGLPLHLPGNKSPHRDPAPRGPARFLPLPGLPPAPPEPPGILAP<br>QPPDVGSSDPLSMVGPSQGRSPSYAS |
| 73. | HPIPDSSPLLQFGGQVRQRYLYTDDAQQTEAHLEIREDGTVGGAADQSPES<br>LLQLKALKPGVIQILGVKTSRFLCQRPDGALYGSLHFDPEACSFRELLLEDG<br>YNVYQSEAHGLPLHLPGNKSPHRDPAPRGPARFLPLPGLPPALPEPPGILAP<br>QPPDVGSSDPLSMVVQDELQGVGGEGCHMHPENCKTLLTDIDRTHTEKPV<br>WDGITGE |
| 74. | RDAGPHVHYGWGDPIRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 75. | RVHYGWGDPIRLRHLYTSGPHGLSSCFLRIRADGVVDCARGQSAHSLLEIK<br>AVALRTVAIKGVHSVRYLCMGADGKMQGLLQYSEEDCAFEEEIRPDGYN<br>VYRSEKHRLPVSLSSAKQRQLYKNRGFLPLSHFLPMLPMVPEEPEDLRGHL<br>ESDMFSSPLETDSMDPFGLVTGLEAVRSPSFEK |
| 76. | RGDPIRLRHLYTSGPHGLSSCFLRIRADGVVDCARGQSAHSLLEIKAVALRT<br>VAIKGVHSVRYLCMGADGKMQGLLQYSEEDCAFEEEIRPDGYNVYRSEKH<br>RLPVSLSSAKQRQLYKNRGFLPLSHFLPMLPMVPEEPEDLRGHLESDMFSSP<br>LETDSMDPFGLVTGLEAVRSPSFEK |
| 77. | RRLRHLYTSGPHGLSSCFLRIRADGVVDCARGQSAHSLLEIKAVALRTVAI<br>KGVHSVRYLCMGADGKMQGLLQYSEEDCAFEEEIRPDGYNVYRSEKHRL<br>PVSLSSAKQRQLYKNRGFLPLSHFLPMLPMVPEEPEDLRGHLESDMFSSPLE<br>TDSMDPFGLVTGLEAVRSPSFEK |
| 78. | RAGPHVHYGWGDPIRLRHLYTSGPHGLSSCFLRIRADGVVDCARGQSAHS<br>LLEIKAVALRTVAIKGVHSVRYLCMGADGKMQGLLQYSEEDCAFEEEIRP |

TABLE 1-continued

| SEQ ID NO. | Amino Acid Sequence |
|---|---|
| | DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 79. | RGPHVHYGWGDPIRLRHLYTSGPHGLSSCFLRIRADGVVDCARGQSAHSLL<br>EIKAVALRTVAIKGVHSVRYLCMGADGKMQGLLQYSEEDCAFEEEIRPDG<br>YNVYRSEKHRLPVSLSSAKQRQLYKNRGFLPLSHFLPMLPMVPEEPEDLRG<br>HLESDMFSSPLETDSMDPFGLVTGLEAVRSPSFEK |
| 80. | RPHVHYGWGDPIRLRHLYTSGPHGLSSCFLRIRADGVVDCARGQSAHSLLE<br>IKAVALRTVAIKGVHSVRYLCMGADGKMQGLLQYSEEDCAFEEEIRPDGY<br>NVYRSEKHRLPVSLSSAKQRQLYKNRGFLPLSHFLPMLPMVPEEPEDLRGH<br>LESDMFSSPLETDSMDPFGLVTGLEAVRSPSFEK |
| 81. | RHVHYGWGDPIRLRHLYTSGPHGLSSCFLRIRADGVVDCARGQSAHSLLEI<br>KAVALRTVAIKGVHSVRYLCMGADGKMQGLLQYSEEDCAFEEEIRPDGY<br>NVYRSEKHRLPVSLSSAKQRQLYKNRGFLPLSHFLPMLPMVPEEPEDLRGH<br>LESDMFSSPLETDSMDPFGLVTGLEAVRSPSFEK |
| 82. | RPLAFSAAGPHVHYGWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAKQRQLYKNRGFLPLSHFLPMLPMVPE<br>EPEDLRGHLESDMFSSPLETDSMDPFGLVTGLEAVRSPSFEK |
| 83. | RPLAFSDAAPHVHYGWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAKQRQLYKNRGFLPLSHFLPMLPMVPE<br>EPEDLRGHLESDMFSSPLETDSMDPFGLVTGLEAVRSPSFEK |
| 84. | RPLAFSDAGAHVHYGWGDPIRLRHLYTSGPHGLSSCFLRIRADGVVDCAR<br>GQSAHSLLEIKAVALRTVAIKGVHSVRYLCMGADGKMQGLLQYSEEDCAF<br>EEEIRPDGYNVYRSEKHRLPVSLSSAKQRQLYKNRGFLPLSHFLPMLPMVP<br>EEPEDLRGHLESDMFSSPLETDSMDPFGLVTGLEAVRSPSFEK |
| 85. | RPLAFSDAGPHVHYGAGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAKQRQLYKNRGFLPLSHFLPMLPMVPE<br>EPEDLRGHLESDMFSSPLETDSMDPFGLVTGLEAVRSPSFEK |
| 86. | RPLAFSDAGPHVHYGWGAPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAKQRQLYKNRGFLPLSHFLPMLPMVPE<br>EPEDLRGHLESDMFSSPLETDSMDPFGLVTGLEAVRSPSFEK |
| 87. | RPLAFSDAGPHVHYGWGDAICARGQSAHSLLEIKAVALRTVAIKGVHSVR<br>YLCMGADGKMQGLLQYSEEDCAFEEEIRPDGYNVYRSEKHRLPVSLSSAK<br>QRQLYKNRGFLPLSHFLPMLPMVPEEPEDLRGHLESDMFSSPLETDSMDPF<br>GLVTGLEAVRSPSFEK |
| 88. | RPLAFSDAGPHVHYGWGDPIRLRHLYTSGPAGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAKQRQLYKNRGFLPLAHFLPMLPMVPE<br>EPEDLRGHLESDMFSSPLETDSMDPFGLVTGLEAVRSPSFEK |
| 89. | RPLAFSDAGPHVHYGWGDPIRLRHLYTSGPAGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAKQRQLYKNRGFLPLSAFLPMLPMVPE<br>EPEDLRGHLESDMFSSPLETDSMDPFGLVTGLEAVRSPSFEK |
| 90. | RPLAFSDAGPHVHYGWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAAQAQLYKNRGFLPLSHFLPMLPMVPE<br>EPEDLRGHLESDMFSSPLETDSMDPFGLVTGLEAVRSPSFEK |
| 91. | RPLAFSDAGPHVHYGWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAAQRQLYKNRGFLPLAHFLPMLPMVPE<br>EPEDLRGHLESDMFSSPLETDSMDPFGLVTGLEAVRSPSFEK |
| 92. | RPLAFSDAGPHVHYGWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAAQRQLYKNRGFLPLSAFLPMLPMVPE<br>EPEDLRGHLESDMFSSPLETDSMDPFGLVTGLEAVRSPSFEK |
| 93. | RPLAFSDAGPHVHYGWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAKQAQLYKNRGFLPLAHFLPMLPMVPE<br>EPEDLRGHLESDMFSSPLETDSMDPFGLVTGLEAVRSPSFEK |

TABLE 1-continued

| SEQ ID NO. | Amino Acid Sequence |
|---|---|
| 94. | RPLAFSDAGPHVHYGWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAKQRQLYKNRGFLPLAAFLPMLPMVPE<br>EPEDLRGHLESDMFSSPLETDSMDPFGLVTGLEAVRSPSFEK |
| 95. | RPLAFSDAGPHVHYGWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAAQRQLYKNRGFLPLSAFLPMLPMVPE<br>EPEDLRGHLESDMFSSPLETDSMDPFGLVTGLEAVRSPSFEK |
| 96. | RPLAFSDAGPHVHYGWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAAQAQLYKNRGFLPLAHFLPMLPMVPE<br>EPEDLRGHLESDMFSSPLETDSMDPFGLVTGLEAVRSPSFEK |
| 97. | RPLAFSDAGPHVHYGWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAAQAQLYKNRGFLPLSAFLPMLPMVPE<br>EPEDLRGHLESDMFSSPLETDSMDPFGLVTGLEAVRSPSFEK |
| 98. | RPLAFSDAGPHVHYGWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAAQAQLYKNRGFLPLAAFLPMLPMVPE<br>EPEDLRGHLESDMFSSPLETDSMDPFGLVTGLEAVRSPSFEK |
| 138. | DSSPLLQFGGQVRLRHLYTSGPHGLSSCFLRIRADGVVDCARGQSAHSLLEI<br>KAVALRTVAIKGVHSVRYLCMGADGKMQGLLQYSEEDCAFEEEIRPDGY<br>NVYRSEKHRLPVSLSSAKQRQLYKNRGFLPLSHFLPMLPMVPEEPEDLRGH<br>LESDMFSSPLETDSMDPFGLVTGLEAVRSPSFEK |
| 139. | RPLAFSDASPHVHYGWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAKQRQLYKNRGFLPLSHFLPMLPMVPE<br>EPEDLRGHLESDMFSSPLETDSMDPFGLVTGLEAVRSPSFEK |
| 140. | RPLAFSDSSPLVHYGWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAKQRQLYKNRGFLPLSHFLPMLPMVPE<br>EPEDLRGHLESDMFSSPLETDSMDPFGLVTGLEAVRSPSFEK |
| 141. | DSSPLVHYGWGDPIRLRHLYTSGPHGLSSCFLRIRADGVVDCARGQSAHSL<br>LEIKAVALRTVAIKGVHSVRYLCMGADGKMQGLLQYSEEDCAFEEEIRPD<br>GYNVYRSEKHRLPVSLSSAKQRQLYKNRGFLPLSHFLPMLPMVPEEPEDLR<br>GHLESDMFSSPLETDSMDPFGLVTGLEAVRSPSFEK |
| 142. | RHPIPDSSPLLQFGWGDPIRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 143. | RHPIPDSSPLLQWGDPIRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 144. | RPLAFSDAGPLLQFGWGDPIRLRHLYTSGPHGLSSCFLRIRADGVVDCARG<br>QSAHSLLEIKAVALRTVAIKGVHSVRYLCMGADGKMQGLLQYSEEDCAFE<br>EEIRPDGYNVYRSEKHRLPVSLSSAKQRQLYKNRGFLPLSHFLPMLPMVPE<br>EPEDLRGHLESDMFSSPLETDSMDPFGLVTGLEAVRSPSFEK |
| 145. | RHPIPDSSPHVHYGWGDPIRLRHLYTSGPHGLSSCFLRIRADGVVDCARGQ<br>SAHSLLEIKAVALRTVAIKGVHSVRYLCMGADGKMQGLLQYSEEDCAFEE<br>EIRPDGYNVYRSEKHRLPVSLSSAKQRQLYKNRGFLPLSHFLPMLPMVPEE<br>PEDLRGHLESDMFSSPLETDSMDPFGLVTGLEAVRSPSFEK |
| 146. | RPLAFSDAGPLLQFGGQVRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 147. | RHPIPDSSPHVHYGGQVRLRHLYTSGPHGLSSCFLRIRADGVVDCARGQSA<br>HSLLEIKAVALRTVAIKGVHSVRYLCMGADGKMQGLLQYSEEDCAFEEEI<br>RPDGYNVYRSEKHRLPVSLSSAKQRQLYKNRGFLPLSHFLPMLPMVPEEPE<br>DLRGHLESDMFSSPLETDSMDPFGLVTGLEAVRSPSFEK |

TABLE 1-continued

| SEQ ID NO. | Amino Acid Sequence |
|---|---|
| 148. | RDSSPLLQFGGQVRLRHLYTSGPHGLSSCFLRIRADGVVDCARGQSAHSLL<br>EIKAVALRTVAIKGVHSVRYLCMGADGKMQGLLQYSEEDCAFEEEIRPDG<br>YNVYRSEKHRLPVSLSSAKQRQLYKNRGFLPLSHFLPMLPMVPEEPEDLRG<br>HLESDMFSSPLETDSMDPFGLVTGLEAVRSPSFEK |
| 149. | RPLAFSDSSPLLQFGGQVRLRHLYTSGPHGLSSCFLRIRADGVVDCARGQS<br>AHSLLEIKAVALRTVAIKGVHSVRYLCMGADGKMQGLLQYSEEDCAFEEE<br>IRPDGYNVYRSEKHRLPVSLSSAKQRQLYKNRGFLPLSHFLPMLPMVPEEP<br>EDLRGHLESDMFSSPLETDSMDPFGLVTGLEAVRSPSFEK |
| 150. | RHPIPDSSPLLQFGAQVRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 151. | RHPIPDSSPLLQFGDQVRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 152. | RHPIPDSSPLLQFGPQVRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 153. | RHPIPDSSPLLQFGGAVRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 154. | RHPIPDSSPLLQFGGEVRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 155. | RHPIPDSSPLLQFGGNVRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 156. | RHPIPDSSPLLQFGGQARLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 157. | RHPIPDSSPLLQFGGQIRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 158. | RHPIPDSSPLLQFGGQTRLRHLYTSGPHGLSSCFLRIRADGVVDCARGQSAH<br>SLLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 159. | RHPIPDSSPLLQFGWGQPVRLRHLYTSGPHGLSSCFLRIRADGVVDCARGQ<br>SAHSLLEIKAVALRTVAIKGVHSVRYLCMGADGKMQGLLQYSEEDCAFEE<br>EIRPDGYNVYRSEKHRLPVSLSSAKQRQLYKNRGFLPLSHFLPMLPMVPEE<br>PEDLRGHLESDMFSSPLETDSMDPFGLVTGLEAVRSPSFEK |
| 160. | HPIPDSSPLLQFGGQVRLRHLYTSGPHGLSSCFLRIRADGVVDCARGQSAHS<br>LLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 161. | DSSPLLQFGGQVRLRHLYTSGPHGLSSCFLRIRADGVVDCARGQSAHSLLEI<br>KAVALRTVAIKGVHSVRYLCMGADGKMQGLLQYSEEDCAFEEEIRPDGY<br>NVYRSEKHRLPVSLSSAKQRQLYKNRGFLPLSHFLPMLPMVPEEPEDLRGH<br>LESDMFSSPLETDSMDPFGLVTGLEAVRSPSFEK |
| 162. | HPIPDSSPLLQWGDPIRLRHLYTSGPHGLSSCFLRIRADGVVDCARGQSAHS<br>LLEIKAVALRTVAIKGVHSVRYLCMGADGKMQGLLQYSEEDCAFEEEIRP<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |

TABLE 1-continued

| SEQ ID NO. | Amino Acid Sequence |
|---|---|
| 163. | HPIPDSSPLLQFGWGDPIRLRHLYTSGPHGLSSCFLRIRADGVVDCARGQSA
HSLLEIKAVALRTVAIKGVHSVRYLCMGADGKMQGLLQYSEEDCAFEEEI
RPDGYNVYRSEKHRLPVSLSSAKQRQLYKNRGFLPLSHFLPMLPMVPEEPE
DLRGHLESDMFSSPLETDSMDPFGLVTGLEAVRSPSFEK |
| 164. | HPIPDSSPHVHYGWGDPIRLRHLYTSGPHGLSSCFLRIRADGVVDCARGQS
AHSLLEIKAVALRTVAIKGVHSVRYLCMGADGKMQGLLQYSEEDCAFEEE
IRPDGYNVYRSEKHRLPVSLSSAKQRQLYKNRGFLPLSHFLPMLPMVPEEP
EDLRGHLESDMFSSPLETDSMDPFGLVTGLEAVRSPSFEK |
| 165. | HPIPDSSPHVHYGGQVRLRHLYTSGPHGLSSCFLRIRADGVVDCARGQSAH
SLLEIKAVALRTVAIKGVHSVRYLCMGADGKMQGLLQYSEEDCAFEEEIRP
DGYNVYRSEKHRLPVSLSSAKQRQLYKNRGFLPLSHFLPMLPMVPEEPEDL
RGHLESDMFSSPLETDSMDPFGLVTGLEAVRSPSFEK |
| 166. | DAGPHVHYGWGDPIRLRHLYTSGPHGLSSCFLRIRADGVVDCARGQSAHS
LLEIKAVALRTVAIKGVHSVRYLCMGADGKMQGLLQYSEEDCAFEEEIRP
DGYNVYRSEKHRLPVSLSSAKQRQLYKNRGFLPLSHFLPMLPMVPEEPEDL
RGHLESDMFSSPLETDSMDPFGLVTGLEAVRSPSFEK |
| 167. | VHYGWGDPIRLRHLYTSGPHGLSSCFLRIRADGVVDCARGQSAHSLLEIKA
VALRTVAIKGVHSVRYLCMGADGKMQGLLQYSEEDCAFEEEIRPDGYNV
YRSEKHRLPVSLSSAKQRQLYKNRGFLPLSHFLPMLPMVPEEPEDLRGHLE
SDMFSSPLETDSMDPFGLVTGLEAVRSPSFEK |
| 168. | RLRHLYTSGPHGLSSCFLRIRADGVVDCARGQSAHSLLEIKAVALRTVAIK
GVHSVRYLCMGADGKMQGLLQYSEEDCAFEEEIRPDGYNVYRSEKHRLP
VSLSSAKQRQLYKNRGFLPLSHFLPMLPMVPEEPEDLRGHLESDMFSSPLET
DSMDPFGLVTGLEAVRSPSFEK |
| 188. | PHGLSSCFLRIRADGVVDCARGQSAHSLLEIKAVALRTVAIKGVHSVRYLC
MGADGKMQGLLQYSEEDCAFEEEIRPDGYNVYRSEKHRLPVSLSSAKQRQ
LYKNRGFLPLSHFLPMLPMVPEEPEDLRGHLESDMFSSPLETDSMDPFGLV
TGLEAVRSPSFEK |
| 192. | MDSSPLLQWGDPIRLRHLYTSGPHGLSSCFLRIRADGVVDCARGQSAHSLL
EIKAVALRTVAIKGVHSVRYLCMGADGKMQGLLQYSEEDCAFEEEIRPDG
YNVYRSEKHRLPVSLSSAKQRQLYKNRGFLPLSHFLPMLPMVPEEPEDLRG
HLESDMFSSPLETDSMDPFGLVTGLEAVRSPSFEK |
| 193. | RPLAFSDAGPHVHYGWGDPIRLRHLYTSGPHGLSSCFLRIRADGVVDCARG
QSAHSLLEIKAVALRTVAIKGVHSVRYLCMGADGKMQGLLQYSEEDCAFE
EEILPDGYNVYRSEKHRLPVSLSSAKQRQLYKNRGFLPLSHFLPMLPMVPE
EPEDLRGHLESDMFSSPLETDSMDPFGLVTGLEAVRSPSFEK |
| 194. | RPLAFSDAGPHVHYGWGDPIRLRHLYTSGPHGLSSCFLRIRADGVVDCARG
QSAHSLLEIKAVALRTVAIKGVHSVRYLCMGADGKMQGLLQYSEEDCAFE
EEIREDGYNVYRSEKHRLPVSLSSAKQRQLYKNRGFLPLSHFLPMLPMVPE
EPEDLRGHLESDMFSSPLETDSMDPFGLVTGLEAVRSPSFEK |
| 195. | RPLAFSDAGPHVHYGWGDPIRLRHLYTSGPHGLSSCFLRIRADGVVDCARG
QSAHSLLEIKAVALRTVAIKGVHSVRYLCMGADGKMQGLLQYSEEDCAFE
EEILCDGYNVYRSEKHRLPVSLSSAKQRQLYKNRGFLPLSHFLPMLPMVPE
EPEDLRGHLESDMFSSPLETDSMDPFGLVTGLEAVRSPSFEK |
| 196. | RPLAFSDAGPHVHYGWGDPIRQRHLYTSGPHGLSSCFLRIRADGVVDCAR
GQSAHSLLEIKAVALRTVAIKGVHSVRYLCMGADGKMQGLLQYSEEDCAF
EEEILEDGYNVYRSEKHRLPVSLSSAKQRQLYKNRGFLPLSHFLPMLPMVP
EEPEDLRGHLESDMFSSPLETDSMDPFGLVTGLEAVRSPSFEK |
| 197. | RDSSPLVHYGWGDPIRLRHLYTSGPHGLSSCFLRIRADGVVDCARGQSAHS
LLEIKAVALRTVAIKGVHSVRYLCMGADGKMQGLLQYSEEDCAFEEEILE
DGYNVYRSEKHRLPVSLSSAKQRQLYKNRGFLPLSHFLPMLPMVPEEPEDL
RGHLESDMFSSPLETDSMDPFGLVTGLEAVRSPSFEK |
| 198. | RPLAFSDSSPLVHYGWGDPIRLRHLYTSGPHGLSSCFLRIRADGVVDCARG
QSAHSLLEIKAVALRTVAIKGVHSVRYLCMGADGKMQGLLQYSEEDCAFE
EEILEDGYNVYRSEKHRLPVSLSSAKQRQLYKNRGFLPLSHFLPMLPMVPE
EPEDLRGHLESDMFSSPLETDSMDPFGLVTGLEAVRSPSFEK |
| 199. | RPLAFSDASPHVHYGWGDPIRLRHLYTSGPHGLSSCFLRIRADGVVDCARG
QSAHSLLEIKAVALRTVAIKGVHSVRYLCMGADGKMQGLLQYSEEDCAFE
EEILEDGYNVYRSEKHRLPVSLSSAKQRQLYKNRGFLPLSHFLPMLPMVPE
EPEDLRGHLESDMFSSPLETDSMDPFGLVTGLEAVRSPSFEK |
| 200. | RDSSPLLQWGDPIRLRHLYTSGPHGLSSCFLRIRADGVVDCARGQSAHSLL
EIKAVALRTVAIKGVHSVRYLCMGADGKMQGLLQYSEEDCAFEEEILEDG |

TABLE 1-continued

| SEQ ID NO. | Amino Acid Sequence |
|---|---|
| | YNVYRSEKHRLPVSLSSAKQRQLYKNRGFLPLSHFLPMLPMVPEEPEDLRG<br>HLESDMFSSPLETDSMDPFGLVTGLEAVRSPSFEK |
| 201. | RHPIPDSSPLLQFGDQVRLRHLYTSGPHGLSSCFLRIRADGVVDCARGQSAH<br>SLLEIKAVALRTVAIKGVHSVRYLCMGADGKMQGLLQYSEEDCAFEEEILE<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 202. | RDSSPLLQFGGQVRLRHLYTSGPHGLSSCFLRIRADGVVDCARGQSAHSLL<br>EIKAVALRTVAIKGVHSVRYLCMGADGKMQGLLQYSEEDCAFEEEILEDG<br>YNVYRSEKHRLPVSLSSAKQRQLYKNRGFLPLSHFLPMLPMVPEEPEDLRG<br>HLESDMFSSPLETDSMDPFGLVTGLEAVRSPSFEK |
| 203. | RHPIPDSSPLLQFGGQVRLRHLYTSGPHGLSSCFLRIRADGVVDCARGQSAH<br>SLLEIKAVALRTVAIKGVHSVRYLCMGADGKMQGLLQYSEEDCAFEEEILE<br>DGYNVYRSEKHRLPVSLSSAKQRQLYKNRGFLPLSHFLPMLPMVPEEPEDL<br>RGHLESDMFSSPLETDSMDPFGLVTGLEAVRSPSFEK |
| 204. | MRDSSPLVHYGWGDPIRLRHLYTSGPHGLSSCFLRIRADGVVDCARGQSA<br>HSLLEIKAVALRTVAIKGVHSVRYLCMGADGKMQGLLQYSEEDCAFEEEIL<br>EDGYNVYRSEKHRLPVSLSSAKQRQLYKNRGFLPLSHFLPMLPMVPEEPED<br>LRGHLESDMFSSPLETDSMDPFGLVTGLEAVRSPSFEK |

In one embodiment, the peptide sequence comprises an amino acid sequence set forth in SEQ ID NO:1. In another embodiment, the peptide sequence comprises an amino acid sequence set forth in SEQ ID NO:2. In other embodiments, the peptide sequence comprises an amino acid sequence set forth in SEQ ID NO:3. In one embodiment, the peptide sequence comprises an amino acid sequence set forth in SEQ ID NO:4. In another embodiment, the peptide sequence comprises an amino acid sequence set forth in SEQ ID NO:5. In other embodiments, the peptide sequence comprises an amino acid sequence set forth in SEQ ID NO:6. In one embodiment, the peptide sequence comprises an amino acid sequence set forth in SEQ ID NO:7. In another embodiment, the peptide sequence comprises an amino acid sequence set forth in SEQ ID NO:8. In other embodiments, the peptide sequence comprises an amino acid sequence set forth in SEQ ID NO:9. In one embodiment, the peptide sequence comprises an amino acid sequence set forth in SEQ ID NO:10. In another embodiment, the peptide sequence comprises an amino acid sequence set forth in SEQ ID NO:11. In other embodiments, the peptide sequence comprises an amino acid sequence set forth in SEQ ID NO:12. In one embodiment, the peptide sequence comprises an amino acid sequence set forth in SEQ ID NO:13. In another embodiment, the peptide sequence comprises an amino acid sequence set forth in SEQ ID NO:14. In other embodiments, the peptide sequence comprises an amino acid sequence set forth in SEQ ID NO:15. In one embodiment, the peptide sequence comprises an amino acid sequence set forth in SEQ ID NO:16. In another embodiment, the peptide sequence comprises an amino acid sequence set forth in SEQ ID NO:17. In other embodiments, the peptide sequence comprises an amino acid sequence set forth in SEQ ID NO:18. In one embodiment, the peptide sequence comprises an amino acid sequence set forth in SEQ ID NO:19. In another embodiment, the peptide sequence comprises an amino acid sequence set forth in SEQ ID NO:20. In other embodiments, the peptide sequence comprises an amino acid sequence set forth in SEQ ID NO:21. In one embodiment, the peptide sequence comprises an amino acid sequence set forth in SEQ ID NO:22. In another embodiment, the peptide sequence comprises an amino acid sequence set forth in SEQ ID NO:23. In other embodiments, the peptide sequence comprises an amino acid sequence set forth in SEQ ID NO:24. In one embodiment, the peptide sequence comprises an amino acid sequence set forth in SEQ ID NO:25. In another embodiment, the peptide sequence comprises an amino acid sequence set forth in SEQ ID NO:26. In other embodiments, the peptide sequence comprises an amino acid sequence set forth in SEQ ID NO:27. In one embodiment, the peptide sequence comprises an amino acid sequence set forth in SEQ ID NO:28. In another embodiment, the peptide sequence comprises an amino acid sequence set forth in SEQ ID NO:29. In other embodiments, the peptide sequence comprises an amino acid sequence set forth in SEQ ID NO:30. In one embodiment, the peptide sequence comprises an amino acid sequence set forth in SEQ ID NO:31. In another embodiment, the peptide sequence comprises an amino acid sequence set forth in SEQ ID NO:32. In other embodiments, the peptide sequence comprises an amino acid sequence set forth in SEQ ID NO:33. In one embodiment, the peptide sequence comprises an amino acid sequence set forth in SEQ ID NO:34. In another embodiment, the peptide sequence comprises an amino acid sequence set forth in SEQ ID NO:35. In other embodiments, the peptide sequence comprises an amino acid sequence set forth in SEQ ID NO:36. In one embodiment, the peptide sequence comprises an amino acid sequence set forth in SEQ ID NO:37. In another embodiment, the peptide sequence comprises an amino acid sequence set forth in SEQ ID NO:38. In other embodiments, the peptide sequence comprises an amino acid sequence set forth in SEQ ID NO:39. In one embodiment, the peptide sequence comprises an amino acid sequence set forth in SEQ ID NO:40. In another embodiment, the peptide sequence comprises an amino acid sequence set forth in SEQ ID NO:41. In other embodiments, the peptide sequence comprises an amino acid sequence set forth in SEQ ID NO:42. In one embodiment, the peptide sequence comprises an amino acid sequence set forth in SEQ ID NO:43. In another embodiment, the peptide sequence comprises an amino acid sequence set forth in SEQ ID NO:44. In other embodiments, the peptide sequence comprises an amino acid sequence set forth in SEQ ID NO:45. In one embodiment, the peptide sequence comprises an amino acid sequence set forth in SEQ ID NO:46. In another embodiment, the peptide sequence comprises an amino acid sequence set forth in SEQ ID NO:47. In other embodiments, the peptide sequence comprises an amino acid sequence set forth in SEQ ID NO:48. In one embodiment, the peptide sequence comprises an amino acid sequence set forth in SEQ ID NO:49. In another embodiment, the peptide sequence comprises an amino acid sequence set forth in SEQ ID NO:50. In other embodiments, the peptide sequence comprises an amino acid sequence set forth in SEQ ID NO:51. In one embodiment, the peptide sequence comprises an amino acid sequence set forth in SEQ ID NO:52. In another embodiment, the peptide sequence comprises an amino acid sequence set forth in SEQ ID NO:53. In other embodiments, the peptide sequence comprises an amino acid sequence set forth in SEQ ID NO:54. In one embodiment, the peptide sequence comprises an amino acid sequence set forth in SEQ ID NO:55. In another embodiment, the peptide sequence comprises an amino acid sequence set forth in SEQ ID NO:56. In other embodiments, the peptide sequence comprises an amino acid sequence set forth in SEQ ID NO:57. In one embodiment, the peptide sequence comprises an amino acid sequence set forth in SEQ ID NO:58. In another embodiment, the peptide sequence comprises an amino acid sequence set forth in SEQ ID NO:59. In other embodiments, the peptide sequence comprises an amino acid sequence set forth in SEQ ID NO:60. In one embodiment, the peptide sequence comprises an amino acid sequence set forth in SEQ ID NO:61. In another embodiment, the peptide sequence comprises an amino acid sequence set forth in SEQ ID NO:62. In other embodiments, the peptide sequence comprises an amino acid sequence set forth in SEQ ID NO:63. In one embodiment, the peptide sequence comprises an amino acid sequence set forth in SEQ ID NO:64. In another embodiment, the peptide sequence comprises an amino acid sequence set forth in SEQ ID NO:65. In other embodiments, the peptide sequence comprises an amino acid sequence set forth in SEQ ID NO:66. In one embodiment, the peptide sequence comprises an amino acid sequence set forth in SEQ ID NO:67. In another embodiment, the peptide sequence comprises an amino acid sequence set forth in SEQ ID NO:68. In other embodiments, the peptide sequence comprises an amino acid sequence set forth in SEQ ID NO:69. In one embodiment, the peptide sequence comprises an amino acid sequence set forth in SEQ ID NO:70. In another embodiment, the peptide sequence comprises an amino acid sequence set forth in SEQ ID NO:71. In other embodiments, the peptide sequence comprises an amino acid sequence set forth in SEQ ID NO:72. In one embodiment, the peptide sequence comprises an amino acid sequence set forth in SEQ ID NO:73. In another embodiment, the peptide sequence comprises an amino acid sequence set forth in SEQ ID NO:74. In other embodiments, the peptide sequence comprises an amino acid sequence set forth in SEQ ID NO:75. In one embodiment, the peptide sequence comprises an amino acid sequence set forth in SEQ ID NO:76. In another embodiment, the peptide sequence comprises an amino acid sequence set forth in SEQ ID NO:77. In other embodiments, the peptide sequence comprises an amino acid sequence set forth in SEQ ID NO:78. In one embodiment, the peptide sequence comprises an amino acid sequence set forth in SEQ ID NO:79. In another embodiment, the peptide sequence comprises an amino acid sequence set forth in SEQ ID NO:80. In other embodiments, the peptide sequence comprises an amino acid sequence set forth in SEQ ID NO:81. In one embodiment, the peptide sequence comprises an amino acid sequence set forth in SEQ ID NO:82. In another embodiment, the peptide sequence comprises an amino acid sequence set forth in SEQ ID NO:83. In other embodiments, the peptide sequence comprises an amino acid sequence set forth in SEQ ID NO:84. In one embodiment, the peptide sequence comprises an amino acid sequence set forth in SEQ ID NO:85. In another embodiment, the peptide sequence comprises an amino acid sequence set forth in SEQ ID NO:86. In other embodiments, the peptide sequence comprises an amino acid sequence set forth in SEQ ID NO:87. In one embodiment, the peptide sequence comprises an amino acid sequence set forth in SEQ ID NO:88. In another embodiment, the peptide sequence comprises an amino acid sequence set forth in SEQ ID NO:89. In other embodiments, the peptide sequence comprises an amino acid sequence set forth in SEQ ID NO:90. In one embodiment, the peptide sequence comprises an amino acid sequence set forth in SEQ ID NO:91. In another embodiment, the peptide sequence comprises an amino acid sequence set forth in SEQ ID NO:92. In other embodiments, the peptide sequence comprises an amino acid sequence set forth in SEQ ID NO:93. In one embodiment, the peptide sequence comprises an amino acid sequence set forth in SEQ ID NO:94. In another embodiment, the peptide sequence comprises an amino acid sequence set forth in SEQ ID NO:95. In other embodiments, the peptide sequence comprises an amino acid sequence set forth in SEQ ID NO:96. In one embodiment, the peptide sequence comprises an amino acid sequence set forth in SEQ ID NO:97. In another embodiment, the peptide sequence comprises an amino acid sequence set forth in SEQ ID NO:98. In other embodiments, the peptide sequence comprises an amino acid sequence set forth in SEQ ID NO:138. In one embodiment, the peptide sequence comprises an amino acid sequence set forth in SEQ ID NO:139. In another embodiment, the peptide sequence comprises an amino acid sequence set forth in SEQ ID NO:140. In other embodiments, the peptide sequence comprises an amino acid sequence set forth in SEQ ID NO:141. In one embodiment, the peptide sequence comprises an amino acid sequence set forth in SEQ ID NO:142. In another embodiment, the peptide sequence comprises an amino acid sequence set forth in SEQ ID NO:143. In other embodiments, the peptide sequence comprises an amino acid sequence set forth in SEQ ID NO:144. In one embodiment, the peptide sequence comprises an amino acid sequence set forth in SEQ ID NO:145. In another embodiment, the peptide sequence comprises an amino acid sequence set forth in SEQ ID NO:146. In other embodiments, the peptide sequence comprises an amino acid sequence set forth in SEQ ID NO:147. In one embodiment, the peptide sequence comprises an amino acid sequence set forth in SEQ ID NO:148. In another embodiment, the peptide sequence comprises an amino acid sequence set forth in SEQ ID NO:149. In other embodiments, the peptide sequence comprises an amino acid sequence set forth in SEQ ID NO:150. In one embodiment, the peptide sequence comprises an amino acid sequence set forth in SEQ ID NO:151. In another embodiment, the peptide sequence comprises an amino acid sequence set forth in SEQ ID NO:152. In other embodiments, the peptide sequence comprises an amino acid sequence set forth in SEQ ID NO:153. In one embodiment, the peptide sequence comprises an amino acid sequence set forth in SEQ ID NO:154. In another embodiment, the peptide sequence comprises an amino acid sequence set forth in SEQ ID NO:155. In other embodiments, the peptide sequence comprises an amino acid sequence set forth in SEQ ID NO:156. In one embodiment, the peptide sequence comprises an amino acid sequence set forth in SEQ ID NO:157. In another embodiment, the peptide sequence comprises an amino acid sequence set forth in SEQ ID NO:158. In other embodiments, the peptide sequence comprises an amino acid sequence set forth in SEQ ID NO:159. In one embodiment, the peptide sequence comprises an amino acid sequence set forth in SEQ ID NO:160. In another embodiment, the peptide sequence comprises an amino acid sequence set forth in SEQ ID NO:161. In other embodiments, the peptide sequence comprises an amino acid sequence set forth in SEQ ID NO:162. In one embodiment, the peptide sequence comprises an amino acid sequence set forth in SEQ ID NO:163. In another embodiment, the peptide sequence comprises an amino acid sequence set forth in SEQ ID NO:164. In other embodiments, the peptide sequence comprises an amino acid sequence set forth in SEQ ID NO:165. In one embodiment, the peptide sequence comprises an amino acid sequence set forth in SEQ ID NO:166. In another embodiment, the peptide sequence comprises an amino acid sequence set forth in SEQ ID NO:167. In other embodiments, the peptide sequence comprises an amino acid sequence set forth in SEQ ID NO:168. In another embodiment, the peptide sequence comprises an amino acid sequence set forth in SEQ ID NO:192. In other embodiments, the peptide sequence comprises an amino acid sequence set forth in SEQ ID NO:193. In one embodiment, the peptide sequence comprises an amino acid sequence set forth in SEQ ID NO:194. In another embodiment, the peptide sequence comprises an amino acid sequence set forth in SEQ ID NO:195. In other embodiments, the peptide sequence comprises an amino acid sequence set forth in SEQ ID NO:196. In one embodiment, the peptide sequence comprises an amino acid sequence set forth in SEQ ID NO:197. In another embodiment, the peptide sequence comprises an amino acid sequence set forth in SEQ ID NO:198. In other embodiments, the peptide sequence comprises an amino acid sequence set forth in SEQ ID NO:199. In one embodiment, the peptide sequence comprises an amino acid sequence set forth in SEQ ID NO:200. In another embodiment, the peptide sequence comprises an amino acid sequence set forth in SEQ ID NO:201. In other embodiments, the peptide sequence comprises an amino acid sequence set forth in SEQ ID NO:202. In one embodiment, the peptide sequence comprises an amino acid sequence set forth in SEQ ID NO:203. In another embodiment, the peptide sequence comprises an amino acid sequence set forth in SEQ ID NO:204. In certain embodiments of the various peptide sequences provided herein, the R residue at the N-terminus is deleted.

In yet other embodiments, the peptide sequence consists of an amino acid sequence set forth in SEQ ID NO:1. In another embodiment, the peptide sequence consists of an amino acid sequence set forth in SEQ ID NO:2. In other embodiments, the peptide sequence consists of an amino acid sequence set forth in SEQ ID NO:3. In one embodiment, the peptide sequence consists of an amino acid sequence set forth in SEQ ID NO:4. In another embodiment, the peptide sequence consists of an amino acid sequence set forth in SEQ ID NO:5. In other embodiments, the peptide sequence consists of an amino acid sequence set forth in SEQ ID NO:6. In one embodiment, the peptide sequence consists of an amino acid sequence set forth in SEQ ID NO:7. In another embodiment, the peptide sequence consists of an amino acid sequence set forth in SEQ ID NO:8. In other embodiments, the peptide sequence consists of an amino acid sequence set forth in SEQ ID NO:9. In one embodiment, the peptide sequence consists of an amino acid sequence set forth in SEQ ID NO:10. In another embodiment, the peptide sequence consists of an amino acid sequence set forth in SEQ ID NO:11. In other embodiments, the peptide sequence consists of an amino acid sequence set forth in SEQ ID NO:12. In one embodiment, the peptide sequence consists of an amino acid sequence set forth in SEQ ID NO:13. In another embodiment, the peptide sequence consists of an amino acid sequence set forth in SEQ ID NO:14. In other embodiments, the peptide sequence consists of an amino acid sequence set forth in SEQ ID NO:15. In one embodiment, the peptide sequence consists of an amino acid sequence set forth in SEQ ID NO:16. In another embodiment, the peptide sequence consists of an amino acid sequence set forth in SEQ ID NO:17. In other embodiments, the peptide sequence consists of an amino acid sequence set forth in SEQ ID NO:18. In one embodiment, the peptide sequence consists of an amino acid sequence set forth in SEQ ID NO:19. In another embodiment, the peptide sequence consists of an amino acid sequence set forth in SEQ ID NO:20. In other embodiments, the peptide sequence consists of an amino acid sequence set forth in SEQ ID NO:21. In one embodiment, the peptide sequence consists of an amino acid sequence set forth in SEQ ID NO:22. In another embodiment, the peptide sequence consists of an amino acid sequence set forth in SEQ ID NO:23. In other embodiments, the peptide sequence consists of an amino acid sequence set forth in SEQ ID NO:24. In one embodiment, the peptide sequence consists of an amino acid sequence set forth in SEQ ID NO:25. In another embodiment, the peptide sequence consists of an amino acid sequence set forth in SEQ ID NO:26. In other embodiments, the peptide sequence consists of an amino acid sequence set forth in SEQ ID NO:27. In one embodiment, the peptide sequence consists of an amino acid sequence set forth in SEQ ID NO:28. In another embodiment, the peptide sequence consists of an amino acid sequence set forth in SEQ ID NO:29. In other embodiments, the peptide sequence consists of an amino acid sequence set forth in SEQ ID NO:30. In one embodiment, the peptide sequence consists of an amino acid sequence set forth in SEQ ID NO:31. In another embodiment, the peptide sequence consists of an amino acid sequence set forth in SEQ ID NO:32. In other embodiments, the peptide sequence consists of an amino acid sequence set forth in SEQ ID NO:33. In one embodiment, the peptide sequence consists of an amino acid sequence set forth in SEQ ID NO:34. In another embodiment, the peptide sequence consists of an amino acid sequence set forth in SEQ ID NO:35. In other embodiments, the peptide sequence consists of an amino acid sequence set forth in SEQ ID NO:36. In one embodiment, the peptide sequence consists of an amino acid sequence set forth in SEQ ID NO:37. In another embodiment, the peptide sequence consists of an amino acid sequence set forth in SEQ ID NO:38. In other embodiments, the peptide sequence consists of an amino acid sequence set forth in SEQ ID NO:39. In one embodiment, the peptide sequence consists of an amino acid sequence set forth in SEQ ID NO:40. In another embodiment, the peptide sequence consists of an amino acid sequence set forth in SEQ ID NO:41. In other embodiments, the peptide sequence consists of an amino acid sequence set forth in SEQ ID NO:42. In one embodiment, the peptide sequence consists of an amino acid sequence set forth in SEQ ID NO:43. In another embodiment, the peptide sequence consists of an amino acid sequence set forth in SEQ ID NO:44. In other embodiments, the peptide sequence consists of an amino acid sequence set forth in SEQ ID NO:45. In one embodiment, the peptide sequence consists of an amino acid sequence set forth in SEQ ID NO:46. In another embodiment, the peptide sequence consists of an amino acid sequence set forth in SEQ ID NO:47. In other embodiments, the peptide sequence consists of an amino acid sequence set forth in SEQ ID NO:48. In one embodiment, the peptide sequence consists of an amino acid sequence set forth in SEQ ID NO:49. In another embodiment, the peptide sequence consists of an amino acid sequence set forth in SEQ ID NO:50. In other embodiments, the peptide sequence consists of an amino acid sequence set forth in SEQ ID NO:51. In one embodiment, the peptide sequence consists of an amino acid sequence set forth in SEQ ID NO:52. In another embodiment, the peptide sequence consists of an amino acid sequence set forth in SEQ ID NO:53. In other embodiments, the peptide sequence consists of an amino acid sequence set forth in SEQ ID NO:54. In one embodiment, the peptide sequence consists of an amino acid sequence set forth in SEQ ID NO:55. In another embodiment, the peptide sequence consists of an amino acid sequence set forth in SEQ ID NO:56. In other embodiments, the peptide sequence consists of an amino acid sequence set forth in SEQ ID NO:57. In one embodiment, the peptide sequence consists of an amino acid sequence set forth in SEQ ID NO:58. In another embodiment, the peptide sequence consists of an amino acid sequence set forth in SEQ ID NO:59. In other embodiments, the peptide sequence consists of an amino acid sequence set forth in SEQ ID NO:60. In one embodiment, the peptide sequence consists of an amino acid sequence set forth in SEQ ID NO:61. In another embodiment, the peptide sequence consists of an amino acid sequence set forth in SEQ ID NO:62. In other embodiments, the peptide sequence consists of an amino acid sequence set forth in SEQ ID NO:63. In one embodiment, the peptide sequence consists of an amino acid sequence set forth in SEQ ID NO:64. In another embodiment, the peptide sequence consists of an amino acid sequence set forth in SEQ ID NO:65. In other embodiments, the peptide sequence consists of an amino acid sequence set forth in SEQ ID NO:66. In one embodiment, the peptide sequence consists of an amino acid sequence set forth in SEQ ID NO:67. In another embodiment, the peptide sequence consists of an amino acid sequence set forth in SEQ ID NO:68. In other embodiments, the peptide sequence consists of an amino acid sequence set forth in SEQ ID NO:69. In one embodiment, the peptide sequence consists of an amino acid sequence set forth in SEQ ID NO:70. In another embodiment, the peptide sequence consists of an amino acid sequence set forth in SEQ ID NO:71. In other embodiments, the peptide sequence consists of an amino acid sequence set forth in SEQ ID NO:72. In one embodiment, the peptide sequence consists of an amino acid sequence set forth in SEQ ID NO:73. In another embodiment, the peptide sequence consists of an amino acid sequence set forth in SEQ ID NO:74. In other embodiments, the peptide sequence consists of an amino acid sequence set forth in SEQ ID NO:75. In one embodiment, the peptide sequence consists of an amino acid sequence set forth in SEQ ID NO:76. In another embodiment, the peptide sequence consists of an amino acid sequence set forth in SEQ ID NO:77. In other embodiments, the peptide sequence consists of an amino acid sequence set forth in SEQ ID NO:78. In one embodiment, the peptide sequence consists of an amino acid sequence set forth in SEQ ID NO:79. In another embodiment, the peptide sequence consists of an amino acid sequence set forth in SEQ ID NO:80. In other embodiments, the peptide sequence consists of an amino acid sequence set forth in SEQ ID NO:81. In one embodiment, the peptide sequence consists of an amino acid sequence set forth in SEQ ID NO:82. In another embodiment, the peptide sequence consists of an amino acid sequence set forth in SEQ ID NO:83. In other embodiments, the peptide sequence consists of an amino acid sequence set forth in SEQ ID NO:84. In one embodiment, the peptide sequence consists of an amino acid sequence set forth in SEQ ID NO:85. In another embodiment, the peptide sequence consists of an amino acid sequence set forth in SEQ ID NO:86. In other embodiments, the peptide sequence consists of an amino acid sequence set forth in SEQ ID NO:87. In one embodiment, the peptide sequence consists of an amino acid sequence set forth in SEQ ID NO:88. In another embodiment, the peptide sequence consists of an amino acid sequence set forth in SEQ ID NO:89. In other embodiments, the peptide sequence consists of an amino acid sequence set forth in SEQ ID NO:90. In one embodiment, the peptide sequence consists of an amino acid sequence set forth in SEQ ID NO:91. In another embodiment, the peptide sequence consists of an amino acid sequence set forth in SEQ ID NO:92. In other embodiments, the peptide sequence consists of an amino acid sequence set forth in SEQ ID NO:93. In one embodiment, the peptide sequence consists of an amino acid sequence set forth in SEQ ID NO:94. In another embodiment, the peptide sequence consists of an amino acid sequence set forth in SEQ ID NO:95. In other embodiments, the peptide sequence consists of an amino acid sequence set forth in SEQ ID NO:96. In one embodiment, the peptide sequence consists of an amino acid sequence set forth in SEQ ID NO:97. In another embodiment, the peptide sequence consists of an amino acid sequence set forth in SEQ ID NO:98. In other embodiments, the peptide sequence consists of an amino acid sequence set forth in SEQ ID NO:138. In one embodiment, the peptide sequence consists of an amino acid sequence set forth in SEQ ID NO:139. In another embodiment, the peptide sequence consists of an amino acid sequence set forth in SEQ ID NO:140. In other embodiments, the peptide sequence consists of an amino acid sequence set forth in SEQ ID NO:141. In one embodiment, the peptide sequence consists of an amino acid sequence set forth in SEQ ID NO:142. In another embodiment, the peptide sequence consists of an amino acid sequence set forth in SEQ ID NO:143. In other embodiments, the peptide sequence consists of an amino acid sequence set forth in SEQ ID NO:144. In one embodiment, the peptide sequence consists of an amino acid sequence set forth in SEQ ID NO:145. In another embodiment, the peptide sequence consists of an amino acid sequence set forth in SEQ ID NO:146. In other embodiments, the peptide sequence consists of an amino acid sequence set forth in SEQ ID NO:147. In one embodiment, the peptide sequence consists of an amino acid sequence set forth in SEQ ID NO:148. In another embodiment, the peptide sequence consists of an amino acid sequence set forth in SEQ ID NO:149. In other embodiments, the peptide sequence consists of an amino acid sequence set forth in SEQ ID NO:150. In one embodiment, the peptide sequence consists of an amino acid sequence set forth in SEQ ID NO:151. In another embodiment, the peptide sequence consists of an amino acid sequence set forth in SEQ ID NO:152. In other embodiments, the peptide sequence consists of an amino acid sequence set forth in SEQ ID NO:153. In one embodiment, the peptide sequence consists of an amino acid sequence set forth in SEQ ID NO:154. In another embodiment, the peptide sequence consists of an amino acid sequence set forth in SEQ ID NO:155. In other embodiments, the peptide sequence consists of an amino acid sequence set forth in SEQ ID NO:156. In one embodiment, the peptide sequence consists of an amino acid sequence set forth in SEQ ID NO:157. In another embodiment, the peptide sequence consists of an amino acid sequence set forth in SEQ ID NO:158. In other embodiments, the peptide sequence consists of an amino acid sequence set forth in SEQ ID NO:159. In one embodiment, the peptide sequence consists of an amino acid sequence set forth in SEQ ID NO:160. In another embodiment, the peptide sequence consists of an amino acid sequence set forth in SEQ ID NO:161. In other embodiments, the peptide sequence consists of an amino acid sequence set forth in SEQ ID NO:162. In one embodiment, the peptide sequence consists of an amino acid sequence set forth in SEQ ID NO:163. In another embodiment, the peptide sequence consists of an amino acid sequence set forth in SEQ ID NO:164. In other embodiments, the peptide sequence consists of an amino acid sequence set forth in SEQ ID NO:165. In one embodiment, the peptide sequence consists of an amino acid sequence set forth in SEQ ID NO:166. In another embodiment, the peptide sequence consists of an amino acid sequence set forth in SEQ ID NO:167. In other embodiments, the peptide sequence consists of an amino acid sequence set forth in SEQ ID NO:168. In another embodiment, the peptide sequence consists of an amino acid sequence set forth in SEQ ID NO:192. In other embodiments, the peptide sequence consists of an amino acid sequence set forth in SEQ ID NO:193. In one embodiment, the peptide sequence consists of an amino acid sequence set forth in SEQ ID NO:194. In another embodiment, the peptide sequence consists of an amino acid sequence set forth in SEQ ID NO:195. In other embodiments, the peptide sequence consists of an amino acid sequence set forth in SEQ ID NO:196. In one embodiment, the peptide sequence consists of an amino acid sequence set forth in SEQ ID NO:197. In another embodiment, the peptide sequence consists of an amino acid sequence set forth in SEQ ID NO:198. In other embodiments, the peptide sequence consists of an amino acid sequence set forth in SEQ ID NO:199. In one embodiment, the peptide sequence consists of an amino acid sequence set forth in SEQ ID NO:200. In another embodiment, the peptide sequence consists of an amino acid sequence set forth in SEQ ID NO:201. In other embodiments, the peptide sequence consists of an amino acid sequence set forth in SEQ ID NO:202. In one embodiment, the peptide sequence consists of an amino acid sequence set forth in SEQ ID NO:203. In another embodiment, the peptide sequence consists of an amino acid sequence set forth in SEQ ID NO:204. In certain embodiments of the various peptide sequences provided herein, the R residue at the N-terminus is deleted.

4.3 Particular Modifications to Enhance Peptide Function

It is frequently beneficial, and sometimes imperative, to improve one of more physical properties of the treatment modalities disclosed herein and/or the manner in which they are administered. Improvements of physical properties include, for example, modulating immunogenicity; methods of increasing solubility, bioavailability, serum half-life, and/or therapeutic half-life; and/or modulating biological activity. Certain modifications may also be useful to, for example, raise of antibodies for use in detection assays (e.g., epitope tags) and to provide for ease of protein purification. Such improvements must generally be imparted without adversely impacting the bioactivity of the treatment modality and/or increasing its immunogenicity.

Pegylation of is one particular modification contemplated herein, while other modifications include, but are not limited to, glycosylation (N- and O-linked); polysialylation; albumin fusion molecules comprising serum albumin (e.g., human serum albumin (HSA), cyno serum albumin, or bovine serum albumin (BSA)); albumin binding through, for example a conjugated fatty acid chain (acylation); and Fc-fusion proteins.

4.3.1 Pegylation

The clinical effectiveness of protein therapeutics is often limited by short plasma half-life and susceptibility to protease degradation. Studies of various therapeutic proteins (e.g., filgrastim) have shown that such difficulties may be overcome by, for example, conjugating or linking the protein to any of a variety of nonproteinaceous polymers, e.g., polyethylene glycol (PEG), polypropylene glycol, or polyoxyalkylenes. This is frequently effected by a linking moiety covalently bound to both the protein and the nonproteinaceous polymer, e.g., a PEG. Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity. In addition to the beneficial effects of pegylation on pharmacokinetic parameters, pegylation itself may enhance activity.

PEGs suitable for conjugation to a polypeptide sequence are generally soluble in water at room temperature, and have the general formula $R(O-CH_2-CH_2)_nO-R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. A molecular weight of the PEG used in embodiments provided herein is not restricted to any particular range, and examples are set forth elsewhere herein; by way of example, certain embodiments have molecular weights between 500 Da and 20 kDa, while other embodiments have molecular weights between 4 kDa and 10 kDa.

In other embodiments, provided herein are compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. Cation exchange chromatography may be used to separate conjugates, and a fraction is then identified which contains the conjugate having, for example, the desired number of PEGs attached, purified free from unmodified protein sequences and from conjugates having other numbers of PEGs attached.

Pegylation most frequently occurs at the alpha amino group at the N-terminus of the polypeptide, the epsilon amino group on the side chain of lysine residues, and the imidazole group on the side chain of histidine residues.

Since most recombinant polypeptides possess a single alpha and a number of epsilon amino and imidazole groups, numerous positional isomers can be generated depending on the linker chemistry.

General pegylation strategies known in the art can be applied herein. PEG may be bound to a polypeptide provided herein via a terminal reactive group (a "spacer" or "linker") which mediates a bond between the free amino or carboxyl groups of one or more of the polypeptide sequences and polyethylene glycol. The PEG having the spacer which may be bound to the free amino group includes N-hydroxysuccinylimide polyethylene glycol which may be prepared by activating succinic acid ester of polyethylene glycol with N-hydroxysuccinylimide. Another activated polyethylene glycol which may be bound to a free amino group is 2,4-bis(O-methoxypolyethyleneglycol)-6-chloro-s-triazine, which may be prepared by reacting polyethylene glycol monomethyl ether with cyanuric chloride. The activated polyethylene glycol which is bound to the free carboxyl group includes polyoxyethylenediamine.

Conjugation of one or more of the polypeptide sequences provided herein to PEG having a spacer may be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions may be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGs attached. Various means known in the art may be used to terminate the reaction. In some embodiments, the reaction is terminated by acidifying the reaction mixture and freezing at, e.g., −20° C. Pegylation of various molecules is discussed in, for example, U.S. Pat. Nos. 5,252,714; 5,643,575; 5,919,455; 5,932,462; and 5,985,263.

In some embodiments, also provided herein are uses of PEG mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., XTEN technology; Amunix; Mountain View, Calif.). This obviates the need for an additional conjugation step during the manufacturing process. Moreover, established molecular biology techniques enable control of the side chain composition of the polypeptide chains, allowing optimization of immunogenicity and manufacturing properties.

4.3.2 Glycosylation

As used herein, "glycosylation" is meant to broadly refer to the enzymatic process by which glycans are attached to proteins, lipids or other organic molecules. The use of the term "glycosylation" herein is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present.

Glycosylation can dramatically affect the physical properties (e.g., solubility) of polypeptides and can also be important in protein stability, secretion, and subcellular localization. Glycosylated polypeptides may also exhibit enhanced stability or may improve one or more pharmacokinetic properties, such as half-life. In addition, solubility improvements can, for example, enable the generation of formulations more suitable for pharmaceutical administration than formulations comprising the non-glycosylated polypeptide.

Addition of glycosylation sites can be accomplished by altering the amino acid sequence. The alteration to the polypeptide may be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type may be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein. A particular embodiment comprises the generation and use of N-glycosylation variants.

The polypeptide sequences provided herein may optionally be altered through changes at the nucleic acid level, particularly by mutating the nucleic acid encoding the polypeptide at preselected bases such that codons are generated that will translate into the desired amino acids.

Various cell lines can be used to produce proteins that are glycosylated. One non-limiting example is Dihydrofolate reductase (DHFR)—deficient Chinese Hamster Ovary (CHO) cells, which are a commonly used host cell for the production of recombinant glycoproteins. These cells do not express the enzyme beta-galactoside alpha-2,6-sialyltransferase and therefore do not add sialic acid in the alpha-2,6 linkage to N-linked oligosaccharides of glycoproteins produced in these cells.

4.3.3 Polysialylation

In certain embodiments, also provided herein is the use of polysialylation, the conjugation of polypeptides to the naturally occurring, biodegradable α-(2→8) linked polysialic acid ("PSA") in order to improve the polypeptides' stability and in vivo pharmacokinetics.

Albumin Fusion:

Additional suitable components and molecules for conjugation include albumins such as human serum albumin (HSA), cyno serum albumin, and bovine serum albumin (BSA).

In some embodiments, albumin is conjugated to a drug molecule (e.g., a polypeptide described herein) at the carboxyl terminus, the amino terminus, both the carboxyl and amino termini, and internally (see, e.g., U.S. Pat. Nos. 5,876,969 and 7,056,701).

In the HSA-drug molecule conjugates embodiments provided herein, various forms of albumin may be used, such as albumin secretion pre-sequences and variants thereof, fragments and variants thereof, and HSA variants. Such forms generally possess one or more desired albumin activities. In additional embodiments, fusion proteins are provided herein comprising a polypeptide drug molecule fused directly or indirectly to albumin, an albumin fragment, an albumin variant, etc., wherein the fusion protein has a higher plasma stability than the unfused drug molecule and/or the fusion protein retains the therapeutic activity of the unfused drug molecule. In some embodiments, the indirect fusion is effected by a linker, such as a peptide linker or modified version thereof.

As alluded to above, fusion of albumin to one or more polypeptides provided herein can, for example, be achieved by genetic manipulation, such that the nucleic acid coding for HSA, or a fragment thereof, is joined to the nucleic acid coding for the one or more polypeptide sequences.

4.3.4 Alternative Albumin Binding Strategies

Several albumin—binding strategies have been developed as alternatives to direct fusion and may be used with the agents described herein. By way of example, in certain embodiments, provided herein is albumin binding through a conjugated fatty acid chain (acylation) and fusion proteins which comprise an albumin binding domain (ABD) polypeptide sequence and the sequence of one or more of the polypeptides described herein.

Fusion of albumin to a peptide sequence can, for example, be achieved by genetic manipulation, such that the DNA coding for HSA (human serum albumin), or a fragment thereof, is joined to the DNA coding for a peptide sequence. Thereafter, a suitable host can be transformed or transfected with the fused nucleotide sequence in the form of, for example, a suitable plasmid, so as to express a fusion polypeptide. The expression may be effected in vitro from, for example, prokaryotic or eukaryotic cells, or in vivo from, for example, a transgenic organism. In some embodiments, the expression of the fusion protein is performed in mammalian cell lines, for example, CHO cell lines.

Further means for genetically fusing target proteins or peptides to albumin include a technology known as Albufuse® (Novozymes Biopharma A/S; Denmark), and the conjugated therapeutic peptide sequences frequently become much more effective with better uptake in the body. The technology has been utilized commercially to produce Albuferon® (Human Genome Sciences), a combination of albumin and interferon α-2B used to treat hepatitis C infection.

Another embodiment entails the use of one or more human domain antibodies (dAb). dAbs are the smallest functional binding units of human antibodies (IgGs) and have favorable stability and solubility characteristics. The technology entails a dAb(s) conjugated to HSA (thereby forming a "AlbudAb"; see, e.g., EP1517921B, WO2005/118642 and WO2006/051288) and a molecule of interest (e.g., a peptide sequence provided herein). AlbudAbs are often smaller and easier to manufacture in microbial expression systems, such as bacteria or yeast, than current technologies used for extending the serum half-life of peptides. As HSA has a half-life of about three weeks, the resulting conjugated molecule improves the half-life. Use of the dAb technology may also enhance the efficacy of the molecule of interest.

4.3.5 Conjugation with Other Molecules

Additional suitable components and molecules for conjugation include, for example, thyroglobulin; tetanus toxoid; Diphtheria toxoid; polyamino acids such as poly(D-lysine: D-glutamic acid); VP6 polypeptides of rotaviruses; influenza virus hemagglutinin, influenza virus nucleoprotein; Keyhole Limpet Hemocyanin (KLH); and hepatitis B virus core protein and surface antigen; or any combination of the foregoing.

Thus, in certain embodiments, conjugation of one or more additional components or molecules at the N- and/or C-terminus of a polypeptide sequence, such as another polypeptide (e.g., a polypeptide having an amino acid sequence heterologous to the subject polypeptide), or a carrier molecule is also contemplated. Thus, an exemplary polypeptide sequence can be provided as a conjugate with another component or molecule.

A polypeptide may also be conjugated to large, slowly metabolized macromolecules such as proteins; polysaccharides, such as sepharose, agarose, cellulose, or cellulose beads; polymeric amino acids such as polyglutamic acid, or polylysine; amino acid copolymers; inactivated virus particles; inactivated bacterial toxins such as toxoid from diphtheria, tetanus, cholera, or leukotoxin molecules; inactivated bacteria; and dendritic cells. Such conjugated forms, if desired, can be used to produce antibodies against a polypeptide provided herein.

4.3.6 Fc-Fusion Molecules

In certain embodiments, the amino- or carboxyl-terminus of a polypeptide sequence provided herein is fused with an immunoglobulin Fc region to form a fusion conjugate (or fusion molecule). In a specific embodiment, the immunoglobuling Fc region is a human Fc region. Fusion conjugates have been shown to increase the systemic half-life of biopharmaceuticals, and thus the biopharmaceutical product may require less frequent administration. In certain embodiments, the half-life is increased as compared to the same polypeptide that is not fused to an immunoglobuling Fc region.

Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

Well-known and validated Fc-fusion drugs consist of two copies of a biopharmaceutical linked to the Fc region of an antibody to improve pharmacokinetics, solubility, and production efficiency. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

In some embodiments, provided herein is a fusion of M70 to a human antibody Fc fragment. In some embodiments, provided herein is a fusion of M69 to a human antibody Fc fragment. Such fusions can be useful in the treatment of bile acid related disorders and other metabolic disorders provided herein. In some embodiments, the Fc-fusion of M70 has a longer half-life. In specific embodiments, the longer half-life of the Fc-fusion of M70 is as compared to M70 that is not an Fc-fusion. In some embodiments, the Fc-fusion of M69 has a longer half-life. In specific embodiments, the longer half life of the Fc-fusion of M69 is as compared to M69 that is not an Fc-fusion. Such a long half-life makes these fusions suitable for once weekly, or less frequent dosing.

In some embodiments, the Fc-fusion comprises a linker. Exemplary flexible linkers include glycine polymers $(G)_n$, glycine-serine polymers, glycine-alanine polymers, alanine-serine polymers, and other flexible linkers. In certain embodiments, the linker is $(G)_4S$. In some embodiments, the linker is $((G)_4S)_n$, where n is an integer of at least one. In some embodiments, the linker is $((G)_4S)_2$. Glycine and glycine-serine polymers are relatively unstructured, and therefore may serve as a neutral tether between components.

In some embodiments, the glycine-serine polymer is $(GS)_n$, where n is an integer of at least one. In some embodiments, the glycine-serine polymer is $GSGGS_n$ (SEQ ID NO:129), where n is an integer of at least one. In some embodiments, the glycine-serine polymer is $GGGS_n$ (SEQ ID NO:130), where n is an integer of at least one. In certain embodiments, the linker comprises an additional G residue at the N' terminus of SEQ ID NO:130. In one embodiment, the linker is GGSG (SEQ ID NO:131). In one embodiment, the linker is GGSGG (SEQ ID NO:132). In one embodiment, the linker is GSGSG (SEQ ID NO:133). In one embodiment, the linker is GSGGG (SEQ ID NO:134). In one embodiment, the linker is GGGSG (SEQ ID NO:189). In one embodiment, the linker is GSSSG (SEQ ID NO:135).

4.3.7 Purification

Additional suitable components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

Purification methods such as cation exchange chromatography may be used to separate conjugates by charge difference, which effectively separates conjugates into their various molecular weights. For example, the cation exchange column can be loaded and then washed with ~20 mM sodium acetate, pH~4, and then eluted with a linear (0 M to 0.5 M) NaCl gradient buffered at a pH from 3 to 5.5, such as at pH~4.5. The content of the fractions obtained by cation exchange chromatography may be identified by molecular weight using conventional methods, for example, mass spectroscopy, SDS-PAGE, or other known methods for separating molecular entities by molecular weight. A fraction is then identified which contains the conjugate having the desired number of PEGs attached, purified free from unmodified protein sequences and from conjugates having other numbers of PEGs attached.

4.3.8 Other Modifications

In certain embodiments, also provided herein is the use of other modifications, currently known or developed in the future, to improve one or more properties. Examples include hesylation, various aspects of which are described in, for example, U.S. Patent Appln. Nos. 2007/0134197 and 2006/0258607, and fusion molecules comprising SUMO as a fusion tag (LifeSensors, Inc.; Malvern, Pa.).

In still other embodiments, a peptide sequence provided herein is linked to a chemical agent (e.g., an immunotoxin or chemotherapeutic agent), including, but are not limited to, a cytotoxic agent, including taxol, cytochalasin B, gramicidin D, mitomycin, etoposide, tenoposide, vincristine, vinblastine, colchicin, doxorubicin, daunorubicin, and analogs or homologs thereof. Other chemical agents include, for example, antimetabolites (e.g., methotrexate, 6-mercaptopurine, 6-thioguanine, cytarabine, 5-fluorouracil decarbazine); alkylating agents (e.g., mechlorethamine, carmustine and lomustine, cyclothosphamide, busulfan, dibromomannitol, streptozotocin, mitomycin C, and cisplatin); antibiotics (e.g., bleomycin); and anti-mitotic agents (e.g., vincristine and vinblastine). Cytotoxins can be conjugated to a peptide provided herein using linker technology known in the art and described herein.

Further suitable components and molecules for conjugation include those suitable for detection in an assay. Particular non-limiting examples include detectable labels, such as a radioisotope (e.g., $^{125}I$, $^{35}S$, $^{32}P$; $^{33}P$), an enzyme which generates a detectable product (e.g., luciferase, β-galactosidase, horse radish peroxidase and alkaline phosphatase), a fluorescent protein, a chromogenic protein, dye (e.g., fluorescein isothiocyanate); fluorescence emitting metals (e.g., $^{152}Eu$); chemiluminescent compounds (e.g., luminol and acridinium salts); bioluminescent compounds (e.g., luciferin); and fluorescent proteins. Indirect labels include labeled or detectable antibodies that bind to a peptide sequence, where the antibody may be detected.

In certain embodiments, a peptide sequence provided herein is conjugated to a radioactive isotope to generate a cytotoxic radiopharmaceutical (radioimmunoconjugates) useful as a diagnostic or therapeutic agent. Examples of such radioactive isotopes include, but are not limited to, iodine$^{131}$, indium$^{111}$, yttrium$^{90}$ and lutetium$^{177}$. Methods for preparing radioimmunoconjugates are known to the skilled artisan. Examples of radioimmunoconjugates that are commercially available include ibritumomab, tiuxetan, and tositumomab.

4.3.9 Linkers

Linkers and their use have been described above. Any of the foregoing components and molecules used to modify the polypeptide sequences provided herein may optionally be conjugated via a linker. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids.

Exemplary flexible linkers include glycine polymers $(G)_n$, glycine-serine polymers (for example, $(GS)_n$, $GSGGS_n$ (SEQ ID NO:129) and $GGGS_n$ (SEQ ID NO:130), where n is an integer of at least one), glycine-alanine polymers, alanine-serine polymers, and other flexible linkers. Glycine and glycine-serine polymers are relatively unstructured, and therefore may serve as a neutral tether between components. Exemplary flexible linkers include, but are not limited to GGSG (SEQ ID NO:131), GGSGG (SEQ ID NO:132), GSGSG (SEQ ID NO:133), GSGGG (SEQ ID NO:134), GGGSG (SEQ ID NO:189), and GSSSG (SEQ ID NO:135). In certain embodiments, the linker is $(G)_4S$. In some embodiments, the linker is $((G)_4S)_n$, where n is an integer of at least one. In some embodiments, the linker is $((G)_4S)_2$. In some embodiments, the glycine-serine polymer is $(GS)_n$, where n is an integer of at least one. In some embodiments, the glycine-serine polymer is $GSGGS_n$ (SEQ ID NO:129), where n is an integer of at least one. In some embodiments, the glycine-serine polymer is $GGGS_n$ (SEQ ID NO:130), where n is an integer of at least one. In certain embodiments, the linker comprises an additional G residue at the N' terminus of SEQ ID NO:130. In one embodiment, the linker is GGSG (SEQ ID NO:131). In one embodiment, the linker is GGSGG (SEQ ID NO:132). In one embodiment, the linker is GSGSG (SEQ ID NO:133). In one embodiment, the linker is GSGGG (SEQ ID NO:134). In one embodiment, the linker is GGGSG (SEQ ID NO:189). In one embodiment, the linker is GSSSG (SEQ ID NO:135).

Peptide sequences provided herein, including the FGF19 and FGF21 variants and subsequences and the FGF19/FGF21 fusions and chimeras listed in Tables 1-11 and Sequence Listing, as well as subsequences, sequence variants and modified forms of the sequences listed in Tables 1-11 and Sequence Listing have one or more activities as set forth herein. One example of an activity is modulating bile acid homeostasis. Another example of an activity is reduced stimulation or formation of HCC, for example, as compared to FGF19. An additional example of an activity is lower or reduced lipid (e.g., triglyceride, cholesterol, non-HDL) or HDL increasing activity, for example, as compared to FGF21. A further example of an activity is a lower or reduced lean muscle mass reducing activity, for example, as compared to FGF21. Yet another example of an activity is binding to FGFR4, or activating FGFR4, for example, peptide sequences that bind to FGFR4 with an affinity comparable to or greater than FGF19 binding affinity for FGFR4; and peptide sequences that activate FGFR4 to an extent or amount comparable to or greater than FGF19 activates FGFR4. Still further examples of activities include treating a bile acid-related or associated disorder. Activities such as, for example, modulation of bile acid homeostasis, glucose lowering activity, analysis of a bile acid-related or associated disorder, HCC formation or tumorigenesis, lipid increasing activity, or lean mass reducing activity can be ascertained in an animal, such as a db/db mouse. Measurement of binding to FGFR4 or activation of FGFR4 can be ascertained by assays disclosed herein or known to the skilled artisan.

Various methodologies can be used in the screening and diagnosis of HCC and are well known to the skilled artisan. Indicators for HCC include detection of a tumor maker such as elevated alpha-fetoprotein (AFP) or des-gamma carboxy-prothrombin (DCP) levels. A number of different scanning and imaging techniques are also helpful, including ultrasound, CT scans and Mill. In certain embodiments, evaluation of whether a peptide (e.g., a candidate peptide) exhibits evidence of inducing HCC may be determined in vivo by, for example, quantifying HCC nodule formation in an animal model, such as db/db mice, administered a peptide, compared to HCC nodule formation by wild type FGF19. Macroscopically, liver cancer may be nodular, where the tumor nodules (which are round-to-oval, grey or green, well circumscribed but not encapsulated) appear as either one large mass or multiple smaller masses. Alternatively, HCC may be present as an infiltrative tumor which is diffuse and poorly circumscribed and frequently infiltrates the portal veins. Pathological assessment of hepatic tissue samples is generally performed after the results of one or more of the aforementioned techniques indicate the likely presence of HCC. Thus, methods provided herein may further include assessing a hepatic tissue sample from an in vivo animal model (e.g., a db/db mouse) useful in HCC studies in order to determine whether a peptide sequence exhibits evidence of inducing HCC. By microscopic assessment, a pathologist can determine whether one of the four general architectural and cytological types (patterns) of HCC are present (i.e., fibrolamellar, pseudoglandular (adenoid), pleomorphic (giant cell) and clear cell).

More particularly, peptide sequences provided herein, including the FGF19 and FGF21 variants and subsequences and the FGF19/FGF21 fusions and chimeras listed in Tables 1-11 and Sequence Listing, as well as subsequences, variants and modified forms of the sequences listed in Tables 1-11 and Sequence Listing include those with the following activities: peptide sequences modulating bile acid homeostasis or treating a bile acid-related or associated disorder while having reduced HCC formation compared to FGF19, or a FGF 19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19; peptide sequences having greater bile acid modulating activity compared to FGF19, or FGF 19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19; peptide sequences having less lipid increasing activity (e.g., less triglyceride, cholesterol, non-HDL) or more HDL increasing activity compared to FGF19, or a FGF 19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19; and peptide sequences having less lean mass reducing activity as compared to FGF21.

More particularly, peptide sequences provided herein, including the FGF19 and FGF21 variants and subsequences and the FGF19/FGF21 fusions and chimeras listed in Tables 1-11 and Sequence Listing, as well as subsequences, variants and modified forms of the sequences listed in Tables 1-11 and the Sequence Listing include those with the following activities: peptide sequences that modulate bile acid homeostasis; peptide sequences that treat a bile acid-related or associated disorder, peptide sequences that bind to FGFR4, or activate FGFR4, such as peptide sequences that bind to FGFR4 with an affinity comparable to or greater than FGF19 binding affinity for FGFR4; peptide sequences that activate FGFR4 to an extent or amount comparable to or greater than FGF19 activates FGFR4; peptide sequences that downregulate or reduce aldo-keto reductase gene expression, for example, compared to FGF19; and peptide sequences that up-regulate or increase solute carrier family 1, member 2 (Slc1a2) gene expression as compared to FGF21.

As disclosed herein, variants include various N-terminal modifications and/or truncations of FGF19, including variants in which there has been a substitution of one or several N-terminal FGF19 amino acids with amino acids from FGF21. Such variants include variants having glucose lowering activity, as well as a favorable lipid profile and are not measurably or detectably tumorigenic.

4.4 Dosing and Administration

Peptide sequences provided herein including subsequences, sequence variants and modified forms of the exemplified peptide sequences (e.g., sequences listed in the Sequence Listing or Tables 1-11), may be formulated in a unit dose or unit dosage form. In a particular embodiment, a peptide sequence is in an amount effective to treat a subject in need of treatment, e.g., due to abnormal or aberrant bile acid homeostasis, such as metabolic syndrome; a lipid- or glucose-related disorder; cholesterol or triglyceride metabolism; type 2 diabetes; cholestasis, including, for example diseases of intrahepatic cholestasis (e.g., PBC, PFIC, PSC, PIC, neonatal cholestasis, and drug induced cholestasis (e.g., estrogen)), and diseases of extrahepatic cholestasis (e.g., bile cut compression from tumor, bile duct blockade by gall stones); bile acid malabsorption and other disorders involving the distal small intestine, including ileal resection, inflammatory bowel diseases (e.g., Crohn's disease and ulcerative colitis), disorders impairing absorption of bile acids not otherwise characterized (idiopathic)) leading to diarrhea (e.g., BAD) and GI symptoms, and GI, liver, and/or biliary cancers (e.g., colon cancer and hepatocellular cancer); and/or bile acid synthesis abnormalities, such as those contributing to NASH, cirrhosis and portal hypertension. Exemplary unit doses range from about 25-250, 250-500, 500-1000, 1000-2500 or 2500-5000, 5000-25,000, 25,000-50,000 ng; from about 25-250, 250-500, 500-1000, 1000-2500 or 2500-5000, 5000-25,000, 25,000-50,000 µg; and from about 25-250, 250-500, 500-1000, 1000-2500 or 2500-5000, 5000-25,000, 25,000-50,000 mg.

Peptide sequences provided herein including subsequences, sequence variants and modified forms of the exemplified peptide sequences (e.g., sequences listed in the Sequence Listing or Tables 1-11) can be administered to provide the intended effect as a single dose or multiple dosages, for example, in an effective or sufficient amount. Exemplary doses range from about 25-250, 250-500, 500-1000, 1000-2500 or 2500-5000, 5000-25,000, 25,000-50,000 pg/kg; from about 50-500, 500-5000, 5000-25,000 or 25,000-50,000 ng/kg; and from about 25-250, 250-500, 500-1000, 1000-2500 or 2500-5000, 5000-25,000, 25,000-50,000 µg/kg. Single or multiple doses can be administered, for example, multiple times per day, on consecutive days, alternating days, weekly or intermittently (e.g., twice per week, once every 1, 2, 3, 4, 5, 6, 7 or 8 weeks, or once every 2, 3, 4, 5 or 6 months).

Peptide sequences provided herein including subsequences, variants and modified forms of the exemplified peptide sequences (e.g., sequences listed in the Sequence Listing or Tables 1-11) can be administered and methods may be practiced via systemic, regional or local administration, by any route. For example, a peptide sequence can be administered parenterally (e.g., subcutaneously, intravenously, intramuscularly, or intraperitoneally), orally (e.g., ingestion, buccal, or sublingual), inhalation, intradermally, intracavity, intracranially, transdermally (topical), transmucosally or rectally. Peptide sequences provided herein including subsequences, variants and modified forms of the exemplified peptide sequences (e.g., sequences listed in the Sequence Listing or Tables 1-11) and methods provided herein including pharmaceutical compositions can be administered via a (micro)encapsulated delivery system or packaged into an implant for administration.

A particular non-limiting example of parenteral (e.g., subcutaneous) administration entails the use of Intarcia's subcutaneous delivery system (Intarcia Therapeutics, Inc.; Hayward, Calif.). The system comprises a miniature osmotic pump that delivers a consistent amount of a therapeutic agent over a desired period of time. In addition to maintaining drug levels within an appropriate therapeutic range, the system can be used with formulations that maintain the stability of proteinaceous therapeutic agents at human body temperature for extended periods of time.

Another non-limiting example of parenteral administration entails the use of DUROS®-type implantable osmotic pumps (from, e.g., DURECT Corp.). The DUROS® system can be used for therapies requiring systemic or site-specific administration of a drug. To deliver drugs systemically, the DUROS® system is placed just under the skin, for example in the upper arm, in an outpatient procedure that is completed in just a few minutes using local anesthetic. To deliver a drug to a specific site, miniaturized catheter technology can be used. The catheter can be attached to the DUROS® system to direct the flow of a drug to the target organ, tissue or synthetic medical structure, such as a graft. Site-specific delivery enables a therapeutic concentration of a drug to be administered to the desired target without exposing the entire body to a similar concentration. The precision, size and performance of the DUROS® system will allow for continuous site-specific delivery to a variety of precise locations within the body.

Yet another non-limiting example of parenteral administration entails the use of an on-body delivery system (e.g., the Neulasta® Delivery Kit by Amgen). This on-body delivery system includes an on-body injector, which is a small, lightweight, injection system applied on the same day as a doctor visit (such as the day of chemotherapy). It is designed to deliver a dose of the therapeutic agent the next day, or in the near future of the doctor visit, so that the patient does not need to return to the doctor's office to receive the injection.

Various methods of controlled release is also contemplated herein. Encapsulation of therapeutic molecules within polymer particles is a well-established method for achieving controlled release and can be used in methods provided herein. Also, by taking advantage of the adsorption of protein therapeutics to poly(lactic-co-glycolic acid) (PLGA) nanoparticles, controlled release can also be achieved without encapsulation. In particular, extended-release for protein therapeutics cam be applied with and without encapsulation in PLGA nanoparticles embedded within a hydrogel. The release profile tunable by modifying nanoparticle concentration, nanoparticle size, or environmental pH. Pakulska et al., *Science Advances* 2(5): e1600519 (2016)

4.5 Methods of Preventing, Treating and Managing Diseases and Disorders

In one embodiment, provided herein is a method of preventing a disease or disorder in a subject having, or at risk of having, a disease or disorder preventable by a peptide sequence provided herein, comprising administering a pharmaceutical composition comprising a peptide provided herein to a subject in an amount effective for preventing the disease or disorder. In another embodiment, provided herein is a method of treating a disease or disorder in a subject having, or at risk of having, a disease or disorder treatable by a peptide sequence provided herein, comprising administering a pharmaceutical composition comprising a peptide provided herein to a subject in an amount effective for treating the disease or disorder. In yet another embodiment, provided herein is a method of managing a disease or disorder in a subject having, or at risk of having, a disease or disorder manageable by a peptide sequence provided herein, comprising administering a pharmaceutical composition comprising a peptide provided herein to a subject in an amount effective for managing the disease or disorder. In one embodiment, the disease or disorder is a bile acid-related disease or associated disorder. In another embodiment, the disease or disorder is a metabolic disease or disorder. In other embodiments, the disease or disorder is a cancer or tumor.

Administration of various FGF19 and/FGF21 variants and fusion peptide sequences to mice successfully modulated bile acid homeostasis and hyperglycemia (data not shown). Furthermore, in contrast to FGF19, certain peptide sequences did not stimulate or induce HCC formation or tumorigenesis in mice (data not shown). Thus, administration of peptides provided herein, including subsequences, variants and modified forms of the exemplified peptide sequences (including the FGF19 and FGF21 variants and subsequences listed in Tables 1-11 and the Sequence Listing, and the FGF19/FGF21 fusions and chimeras listed in Tables 1-11 and the Sequence Listing), into an animal, either by direct or indirect in vivo or by ex vivo methods (e.g., administering the variant or fusion peptide, a nucleic acid encoding the variant or fusion peptide, or a transformed cell or gene therapy vector expressing the variant or fusion peptide), can be used to treat various disorders, such as bile-acid related or associated disorders, and metabolic disorders, such as disorders related to high sugar levels, hyperglycemic conditions, insulin resistance, hyperinsulinemia, glucose intolerance, metabolic syndrome, or related disorders, as set forth herein, 4.5.1 Methods of Preventing, Treating and Managing Bile Acid-Related or Associated Disorders As used herein, the phrases "bile acid-related disorder," "bile acid-related or associated disorder," and the like, when used in reference to a condition of a subject, means a disruption of bile acid homeostasis, which may manifest itself as, for example, an acute, transient or chronic abnormal level of a bile acid or one or more bile acids. The condition can be caused by inhibition, reduction or a delay in bile acid synthesis, metabolism or absorption such that the subject exhibits a bile acid level not typically found in normal subjects.

Also provided herein are in vitro, ex vivo and in vivo (e.g., on or in a subject) methods and uses. Such methods and uses can be practiced with any of the peptide sequences set forth herein. In various embodiments, the methods include administering a peptide sequence, such as a FGF19 or FGF21 variant, fusion or chimera disclosed herein (e.g., in the Sequence Listing or Tables 1-11), or a subsequence, a variant or modified form of a FGF19 or FGF21 variant, fusion or chimera disclosed herein (e.g., the Sequence Listing or Tables 1-11), to a subject in an amount effective for treating a bile acid-related or associated disorder.

In certain embodiments, the peptide is administered in combination with an additional therapeutic agent(s) and/or treatment modalities (e.g., an agent useful in the treatment and/or prevention of PBC). The additional therapeutic agent(s) can be administered before, with, or following administration of the peptides described herein.

Also provided herein are methods of preventing (e.g., in subjects predisposed to having a particular disorder(s)), delaying, slowing or inhibiting progression of, the onset of, or treating (e.g., ameliorating) a bile acid-related or associated disorder relative to an appropriate matched subject of comparable age, gender, race, etc.). Thus, in various embodiments, a method provided herein for, for example, modulating bile acid homeostasis or treating a bile acid-related or associated disorder includes contacting or administering one or more peptides provided herein (e.g., a variant or fusion of FGF19 and/or FGF21 as set forth in the Sequence Listing or Tables 1-11) in an amount effective to modulate bile acid homeostasis or treat a bile acid-related or associated disorder. In certain embodiments the method further comprises contacting or administering at least one additional therapeutic agent or treatment modality that is useful in the treatment or prevention of a bile acid-related or associated disorder (e.g., PBC).

The term "subject" refers to an animal. Typically, the animal is a mammal that would benefit from treatment with a peptide sequence provided herein. Particular examples include primates (e.g., humans), dogs, cats, horses, cows, pigs, and sheep.

Subjects include those having a disorder, e.g., a bile acid-related or associated disorder, such as cholestasis, including, for example diseases of intrahepatic cholestasis (e.g., PBC, PFIC, PSC, PIC, neonatal cholestasis, and drug induced cholestasis (e.g., estrogen)), and diseases of extrahepatic cholestasis (e.g., bile cut compression from tumor, bile duct blockade by gall stones); bile acid malabsorption and other disorders involving the distal small intestine, including ileal resection, inflammatory bowel diseases (e.g., Crohn's disease and ulcerative colitis), short bowel syndrome, disorders impairing absorption of bile acids not otherwise characterized (idiopathic)) leading to diarrhea (e.g., BAD) and GI symptoms, and GI, liver, and/or biliary cancers (e.g., colon cancer and hepatocellular cancer); and/or bile acid synthesis abnormalities, such as those contributing to NASH, cirrhosis and portal hypertension; or subjects that do not have a disorder but may be at risk of developing the disorder.

Non-limiting exemplary bile acid-related or associated disorders preventable, treatable or manageable according to the methods and uses provided herein include: cholestasis, including, for example diseases of intrahepatic cholestasis (e.g., primary biliary cirrhosis (PBC), primary familial intrahepatic cholestasis (PFIC) (e.g., progressive PFIC), primary sclerosing choangitis (PSC), pregnancy intrahepatic cholestasis (PIC), neonatal cholestasis, and drug-induced cholestasis (e.g., estrogen)), and diseases of extrahepatic cholestasis (e.g., bile cut compression from tumor, bile duct blockade by gall stones); bile acid malabsorption and other disorders involving the distal small intestine, including ileal resection, inflammatory bowel diseases (e.g., Crohn's disease and ulcerative colitis), short bowel syndrome, disorders impairing absorption of bile acids not otherwise characterized (idiopathic)) leading to diarrhea (e.g., bile acid diarrhea (BAD)) and GI symptoms, and GI, liver, and/or biliary cancers (e.g., colon cancer and hepatocellular cancer); and/or bile acid synthesis abnormalities, such as those contributing to non-alcoholic steatohepatitis (NASH), cirrhosis and portal hypertension; e.g., in mammals, such as humans. Additional bile acid-related or associated disorders include metabolic syndrome; a lipid or glucose disorder; cholesterol or triglyceride metabolism; type 2 diabetes. In one particular embodiment, the bile acid-related or associated disorder is bile acid malabsorption. In another particular embodiment, the bile acid-related or associated disorder is diarrhea. In a still further particular embodiment, the bile acid-related or associated disorder is cholestasis (e.g., intrahepatic or extrahepatic cholestasis). In another further particular embodiment, the bile acid-related or associated disorder is primary biliary cirrhosis (PBC). In other particular embodiments, the bile acid-related or associated disorder is primary sclerosing cholangitis. In another embodiment, the bile acid-related or associated disorder is PFIC (e.g., progressive PFIC). In another embodiment, the bile acid-related or associated disorder is NASH. In another embodiment, the bile acid-related or associated disorder is a hyperglycemic condition. In a specific embodiment, the bile acid-related or associated disorder is type 2 diabetes.

In some embodiments, the methods provided herein comprises administration of at least one additional agent effective in modulating bile acid homeostasis or treating a bile acid-related or associated disorder, wherein the additional agent is: a glucocorticoid; CDCA; UDCA; insulin, an insulin secretagogues, an insulin mimetic, a sulfonylurea and a meglitinide; a biguanide; an alpha-glucosidase inhibitors; a DPP-IV inhibitor, GLP-1, a GLP-1 agonists and a GLP-1 analog; a DPP-IV-resistant analogue; a PPAR gamma agonist, a dual-acting PPAR agonist, a pan-acting PPAR agonist; a PTP1B inhibitor; an SGLT inhibitor; an RXR agonist; a glycogen synthase kinase-3 inhibitor; an immune modulator; a beta-3 adrenergic receptor agonist; an 11beta-HSD1 inhibitor; amylin and an amylin analogue; a bile acid sequestrant; or an SGLT-2 inhibitor. In certain embodiments, the at least one additional agent effective in modulating PBC is UDCA, an FXR agonist, OCA, an ASBT inhibitor, an autoimmune agent, an anti-IL-12 agent, an anti-CD80 agent, an anti-CD20 agent, a CXCL10 neutralizing antibody, a ligand for CXCR3, a fibrate, fish oil, colchicine, methotrexate, azathioprine, cyclosporine, or an anti-retroviral therapy. In particular embodiments, the at least one additional agent effective in modulating PBC is UDCA, OCA, an ASBT inhibitor, an anti-IL-12 agent, an anti-CD20 agent, or a fibrate.

Additional bile acid-related or associated disorders that may be treated or prevented with the peptide sequences provided herein include metabolic syndrome, a lipid or glucose disorder, cholesterol or triglyceride metabolism, diabetes (e.g., type 2 diabetes), other hyperglycemic-related disorders, including kidney damage (e.g., tubule damage or nephropathy), liver degeneration, eye damage (e.g., diabetic retinopathy or cataracts), and diabetic foot disorders, and dyslipidemias and their sequelae such as, for example, atherosclerosis, coronary artery disease, cerebrovascular disorders and the like.

Other conditions which may be associated with metabolic syndrome, such as obesity and elevated body mass (including the co-morbid conditions thereof such as, but not limited to, nonalcoholic fatty liver disease (NAFLD), nonalcoholic steatohepatitis (NASH), and polycystic ovarian syndrome (PCOS)), and also include thromboses, hypercoagulable and prothrombotic states (arterial and venous), hypertension (including portal hypertension (defined as a hepatic venous pressure gradient (HVPG) greater than 5 mm Hg), cardiovascular disease, stroke and heart failure; Disorders or conditions in which inflammatory reactions are involved, including atherosclerosis, chronic inflammatory bowel diseases (e.g., Crohn's disease and ulcerative colitis), asthma, lupus erythematosus, arthritis, or other inflammatory rheumatic disorders; Disorders of cell cycle or cell differentiation processes such as adipose cell tumors, lipomatous carcinomas including, for example, liposarcomas, solid tumors, and neoplasms; Neurodegenerative diseases and/or demyelinating disorders of the central and peripheral nervous systems and/or neurological diseases involving neuroinflammatory processes and/or other peripheral neuropathies, including Alzheimer's disease, multiple sclerosis, Parkinson's disease, progressive multifocal leukoencephalopathy and Guillian-Barre syndrome; Skin and dermatological disorders and/or disorders of wound healing processes, including erythemato-squamous dermatoses; and Other Disorders such as syndrome X, osteoarthritis, and acute respiratory distress syndrome.

Treatment of a bile acid-related or associated disorder (e.g., NASH) may have the benefit of alleviating or abolishing a disorder secondary thereto. By way of example, a subject suffering from NASH may also have depression or anxiety due to NASH; thus, treating the subject's NASH may also indirectly treat the depression or anxiety. The use of the therapies disclosed herein to target such secondary disorders is also contemplated in certain embodiments.

In particular embodiments, the subject has or is at risk of having PBC. In other particular embodiments, the subject has or is at risk of having NASH.

Subjects at risk of developing a bile acid-related or associated disorder (such as the disorders described above) include, for example, those who may have a family history or genetic predisposition toward such disorder, as well those whose diet may contribute to development of such disorders.

As disclosed herein, treatment methods include contacting or administering a peptide as set forth herein (e.g., a variant or fusion of FGF19 and/or FGF21 provided herein, for example, as set forth in the Sequence Listing or Tables 1-11) in an amount effective to achieve a desired outcome or result in a subject. A treatment that results in a desired outcome or result includes decreasing, reducing or preventing the severity or frequency of one or more symptoms of the condition in the subject, e.g., an improvement in the subject's condition or a "beneficial effect" or "therapeutic effect." Therefore, treatment can decrease or reduce or prevent the severity or frequency of one or more symptoms of the disorder, stabilize or inhibit progression or worsening of the disorder, and in some instances, reverse the disorder, transiently (e.g., for 1-6, 6-12, or 12-24 hours), for medium term (e.g., 1-6, 6-12, 12-24 or 24-48 days) or long term (e.g., for 1-6, 6-12, 12-24, 24-48 weeks, or greater than 24-48 weeks). Thus, in the case of a bile acid-related or associated disorder, treatment can lower or reduce one or more symptoms or effects of the bile acid-related or associated disorders described above.

In certain embodiments, the various methods provided herein further include contacting or administering one or more additional agents or therapeutic modalities useful in the treatment or prevention of a bile acid-related or associated disorder, such as those agents or therapeutic modalities described herein, in an amount effective to achieve a desired outcome or result in a subject.

An "effective amount" or a "sufficient amount" for use and/or for treating a subject refers to an amount that provides, in single or multiple doses, alone, or in combination with one or more other agents, treatments, protocols, or therapeutic regimens, a detectable response of any duration of time (transient, medium or long term), a desired outcome in or an objective or subjective benefit to a subject of any measurable or detectable degree or for any duration of time (e.g., for hours, days, months, years, in remission or cured). Such amounts typically are effective to ameliorate a disorder, or one, multiple or all adverse symptoms, consequences or complications of the disorder, to a measurable extent, although reducing or inhibiting a progression or worsening of the disorder, is considered a satisfactory outcome.

As used herein, the term "ameliorate" means an improvement in the subject's disorder, a reduction in the severity of the disorder, or an inhibition of progression or worsening of the disorder (e.g., stabilizing the disorder). In the case of a bile acid-related or associated disorder such as those described above, including cholestasis (e.g., PBC), disorders impairing absorption of bile acids leading to diarrhea (e.g., BAD) and bile acid synthesis abnormalities (e.g., NASH), an improvement can be a lowering or a reduction in one or more symptoms or effects of the disorder.

A therapeutic benefit or improvement therefore need not be complete ablation of any one, most or all symptoms, complications, consequences or underlying causes associated with the disorder or disease. Thus, a satisfactory endpoint is achieved when there is a transient, medium or long term, incremental improvement in a subject's condition, or a partial reduction in the occurrence, frequency, severity, progression, or duration, or inhibition or reversal, of one or more associated adverse symptoms or complications or consequences or underlying causes, worsening or progression (e.g., stabilizing one or more symptoms or complications of the condition, disorder or disease), of the disorder or disease, over a duration of time (hours, days, weeks, months, etc.).

Thus, in the case of a disorder treatable by a peptide sequence provided herein, either alone or in combination with an additional agent, the amount of the peptide (and optionally the additional agent) sufficient to ameliorate a disorder will depend on the type, severity and extent, or duration of the disorder, the therapeutic effect or outcome desired, and can be readily ascertained by the skilled artisan. Appropriate amounts will also depend upon the individual subject (e.g., the bioavailability within the subject, gender, age, etc.). For example, a transient, or partial, restoration of normal bile acid homeostasis in a subject can reduce the dosage amount or frequency of the peptides and agents described herein in order to treat the bile acid-related or associated disorders described previously even though complete freedom from treatment has not resulted. An effective amount can be ascertained, for example, by measuring one or more relevant physiological effects.

Methods and uses provided herein for treating a subject are applicable for prophylaxis to prevent or reduce the likelihood of a disorder in a subject, such as a bile acid-related or associated disorder. Accordingly, methods and uses provided herein for treating a subject having, or at risk of developing, a bile acid-related or associated disorder can be practiced prior to, substantially contemporaneously with, or following administration or application of another agent useful for the treatment or prevention of a bile acid-related or associated disorder, and/or can be supplemented with other forms of therapy. Supplementary therapies include other glucose lowering treatments, such as insulin, an insulin sensitivity enhancer and other drug treatments, a change in diet (low sugar, fats, etc.), weight loss surgery-(reducing stomach volume by gastric bypass, gastrectomy), gastric banding, gastric balloon, gastric sleeve, etc. For example, a method or use provided herein for treating a hyperglycemic or insulin resistance disorder can be used in combination with drugs or other pharmaceutical compositions that lower glucose or increase insulin sensitivity in a subject.

In one embodiment, a method or use includes contacting or administering to a subject one or more variant or fusion FGF19 and/or FGF21 peptide sequences in an amount effective for preventing a bile-acid related or associated disorder. In one embodiment, a method or use includes contacting or administering to a subject one or more variant or fusion FGF19 and/or FGF21 peptide sequences in an amount effective for treating a bile-acid related or associated disorder. In one embodiment, a method or use includes contacting or administering to a subject one or more variant or fusion FGF19 and/or FGF21 peptide sequences in an amount effective for managing a bile-acid related or associated disorder.

4.5.1.1 PBC and Therapy with Agents Effective in the Treatment or Prevention Thereof Primary biliary cirrhosis (PBC), the most common cholestatic liver disease, is a progressive hepatic disease that primarily results from autoimmune destruction of the bile ducts that transport bile acids out of the liver. As the disease progresses, persistent toxic build-up of bile acids causes progressive liver damage marked by chronic inflammation and fibrosis. Because patients with PBC have an increased risk of HCC, therapy with the variants of FGF19 peptide sequences, fusions of FGF19 and/or FGF21 peptide sequences and variants of fusions (chimeras) of FGF19 and/or FGF21 peptide sequences described herein is of particular import, as such sequences do not induce, or do not substantially increase, HCC formation or HCC tumorigenesis.

Although patients with PBC are often asymptomatic at the time of initial diagnosis, most present, or subsequently develop, one or more of the following: pruritus; fatigue; jaundice; xanthoma; disorders associated with an extrahepatic autoimmune disorder (e.g., Sjögren's Syndrome and rheumatoid arthritis); and complications that result from cirrhosis or portal hypertension (e.g., ascites, esophageal varices and hepatic encephalopathy).

While a definitive cause of PBC has not been identified, most research suggests that it is an autoimmune disorder. There appears to be a genetic predisposition, and genetic studies have indicated that part of the IL-12 signaling cascade, including IL-12A and I-12RB2 polymorphisms, is important in the etiology of the disease.

There is no definitive means of diagnosing PBC; rather, assessment of a number of factors is generally required. Moreover, diagnosis of PBC requires that other conditions with similar symptoms (e.g., autoimmune hepatitis and primary sclerosing cholangitis) be ruled out; by way of example, abdominal ultrasound or CT scan is usually performed to rule out blockage of the bile ducts.

Diagnostic blood tests include deranged liver function tests (gamma-glutamyl transferase and alkaline phosphatase) and the presence of particular antibodies (antimitochondrial antibody (AMA) an antinuclear antibody (ANA)). Antinuclear antibodies are believed to be prognostic indicators of PBC. When other tests and procedures are indicative of PBC, a liver biopsy is frequently performed to confirm disease. Endoscopic retrograde cholangiopancreatography (ERCP), an endoscopic evaluation of the bile duct, may also be employed to confirm disease.

PBC is classified into four stages marking the progression of disease. Stage 1 (Portal Stage) is characterized by portal inflammation and mild bile duct damage; Stage 2 (Periportal Stage) is characterized by enlarged triads, periportal fibrosis or inflammation; Stage 3 (Septal Stage) is characterized by active and/or passive fibrous septa; and Stage 4 (Biliary Cirrhosis) is characterized by the presence of hepatic nodules. Liver biopsy is required to determine the stage of disease.

Serum bilirubin is an indicator of PBC progression and prognosis. Patients with a serum bilirubin level of 2-6 mg/dL have a mean survival time of 4.1 years, patients with a serum bilirubin level of 6-10 mg/dL have a mean survival time of 2.1 years, and patients with a serum bilirubin level above 10 mg/dL have a mean survival time of 1.4 years. Liver transplantation is an option in advanced cases of PBC, although the recurrence rate may be as high as 18% at 5 years, and up to 30% at 10 years.

Although disease progression may be slowed, pharmaceutical intervention with currently used therapies is neither curative nor effective in all patient populations. In order to improve the therapeutic outcome of pharmacological therapy, one aspect pertains to the use of one or more current therapies in combination with variants of FGF19 peptide sequences, fusions of FGF19 and/or FGF21 peptide sequences and variants of fusions (chimeras) of FGF19 and/or FGF21 peptide sequences having one or more activities associated with the treatment and/or prevention of PBC and associated diseases, disorders and conditions. The most commonly used and/or promising agents for combination therapy are set forth hereafter, although it is to be understood that these agents are illustrative, and not exclusionary.

PBC treatment most frequently involves the bile acid ursodeoxycholic acid (Urosdiol, UDCA). UDCA therapy is helpful in reducing the cholestasis and improving the liver function tests in PBC patients; however, it does not demonstrably improve symptoms and has a questionable impact on prognosis. UDCA has been shown to reduce mortality, adverse events and the need for transplantation in PBC. Although UDCA is considered the first-line therapy, approximately one-third of patients may be non-responsive and remain at risk of progressive liver disease and are candidates for alternative or additive therapy.

There are several alternative and adjuvant therapies, some of which are currently in clinical development, that can be used in combination with variants of FGF19 peptide sequences, fusions of FGF19 and/or FGF21 peptide sequences and variants of fusions (chimeras) of FGF19 and/or FGF21 peptide sequences provided herein having one or more activities associated with the treatment and/or prevention of PBC and associated diseases, disorders and conditions.

Farnesoid-X-receptor agonists represent a promising class of agents that may be used in combination therapy. One of the primary functions of agonists of FXR, a nuclear receptor expressed at high levels in the liver and intestine, is the suppression of cholesterol 7a hydroxylase-1 (CYP7A1), the rate-limiting enzyme in the synthesis of bile acids from cholesterol. Obeticholic acid (OCA; Intercept Pharmaceuticals, NY) is a bile acid analog and FXR agonist derived from the primary human bile acid chenodeoxycholic acid, or CDCA. OCA is currently being evaluated for patients having an inadequate therapeutic response to ursodiol or who are unable to tolerate ursodiol.

Inhibitors of the apical sodium-dependent bile acid transporter (ASBT) represent another class of agents that may be used in combination with the variants of FGF19 peptide sequences, fusions of FGF19 and/or FGF21 peptide sequences and variants of fusions (chimeras) of FGF19 and/or FGF21 peptide sequences described herein for the treatment and/or prevention of PBC and associated diseases. ASBT, a member of the sodium/bile-salt co-transport family coded by gene SLC10A2, is currently thought to be the primary mechanism for bile acid reabsorption in the intestine. Examples of ABST inhibitors include LUM001 and SC-435, both of which are being developed by Lumena Pharmaceuticals (San Diego, Calif.).

Bile acid sequestrants also find use in the treatment of PBC. Cholestyramine and colestipol are the best known bile acid sequestrants. However, their use is sometimes limited because they are only available in powder form and are not tolerated by many patients, often because of the poor texture and taste of the resin powder. The bile acid sequestrant colesevelam is available in tablet form and is often better tolerated. All bile acid sequestrants are capable of binding other compounds, including the fat-soluble vitamins A, D, E and K, and deficiencies of these vitamins many necessitate supplementation. Importantly, the PBC patient population inherently has poor lipid-dependent absorption of vitamins A, D, E and K, and thus patients taking bile acid sequestrants are at particular risk for deficiency of those vitamins.

Agents associated with immune and inflammatory function are candidates for combination therapy with the variants of FGF19 peptide sequences, fusions of FGF19 and/or FGF21 peptide sequences and variants of fusions (chimeras) of FGF19 and/or FGF21 peptide sequences having one or more activities associated with the treatment and/or prevention of PBC and associated diseases, disorders and conditions.

The interleukin IL-12 is linked with autoimmunity. Data indicate that the IL-12 signaling pathway plays a key role in the effector mechanisms that lead to biliary destruction. Targeting the p40 subunit of IL-12 has also been shown to ameliorate experimental immune-mediated cholangiopathy. Thus, anti-IL-12 agents (e.g., monoclonal Ab inhibitors) provide a promising treatment. Furthermore, because polymorphisms in CD80 have been identified as conferring an increased susceptibility to PBC, blockade of co-stimulation between T cells and antigen-presenting cells through CD80 by use of an anti-CD80 agent could represent an important therapeutic approach for the treatment of PBC. In addition, improvement in IgM titre and an increase in intrahepatic regulatory T-cell number using the anti-CD20 antibody rituximab (RITUXAN) have shown promise.

The immune-mediated destruction of small-sized bile ducts in PBC is predominantly cell-mediated, characterized by Th1 cells, CD8+ T cells, NK cells and NKT cells which express CXCR3. Therefore, neutralizing antibodies to CXCL10, a ligand for CXCR3, may offer the possibility to interfere with one of the key inflammatory processes and contribute to immune-mediated biliary destruction in PBC. Similarly, blockade of co-stimulatory signals between T cells expressing CD28 and antigen-presenting cells expressing CD80 (e.g. cholangiocytes, antibody-secreting B cells) might represent an important approach for the treatment of autoimmune diseases.

The variants of FGF19 peptide sequences, fusions of FGF19 and/or FGF21 peptide sequences and variants of fusions (chimeras) of FGF19 and/or FGF21 peptide sequences described herein can be used alone or in combination with other agents for the treatment and/or prevention of those bile acid-related or associated disorders referenced herein that have an immune and/or inflammatory component, including, but not limited to, PBC and associated diseases, disorders and conditions. Examples of such other agents include, for example, non-steroidal anti-inflammatory drugs (NSAID); steroids; cytokine suppressive anti-inflammatory drug(s) (CSAIDs); antibodies to, or antagonists of, other human cytokines or growth factors (e.g., IL-2, IL-6, or PDGF); TNF antagonists (e.g., agents such as REMICADE, p75TNFRIgG (ENBREL) or p55TNFR1gG (LENERCEPT)); interferon-β1a (AVONEX); interferon-β1b (BETASERON); and immune checkpoint inhibitors, including PD1 (associated agents include the antibodies nivolumab and lambrolizumab), PDL1, BTLA, CTLA4 (associated agents include the fully humanized CTLA4 monoclonal antibody ipilimumab (YERVOY), TIM3, LAGS, and A2aR.

Fibrates have been shown to improve various aspects of PBC, including liver function tests, both as monotherapy and in combination with UDCA non-responders. In certain embodiments, a fibrate is a member selected from the group of bezafibrate (BEZALIP), ciprofibrate (MODALIM), gemfibrozil (LOPID), clofibrate, and fenofibrate (TRICOR). Fish oil has exhibited similar benefits.

In PBC patients demonstrating certain characteristics of hepatitis on biopsy, corticosteroids such as budesonide may improve liver histology and biochemistry, particularly when used in combination with UDCA. Colchicine has been shown to improve liver function tests (e.g., AST and ALP) and represents another alternative treatment for PBC.

Though not an exhaustive list, other drugs that have shown promise include methotrexate as an immunomodulatory treatment, azathioprine, cyclosporine, and certain agents used in anti-retroviral therapy (e.g., combivir).

Various treatments exist for the sequelae associated with PBC. For example, itching can be relieved by the bile acid sequestrant cholestyramine, or alternatively naltrexone and rifampicin. The fatigue associated with PBC may effectively be treated with modafinil (Provigil; Teva (formerly Cephalon)) without damaging the liver. As patients with PBC have increased risk of developing osteoporosis and esophageal varices compared to the general population (and others with liver disease), screening and treatment of these complications is an important part of the management of PBC. Variants of FGF19 peptide sequences, fusions of FGF19 and/or FGF21 peptide sequences and variants of fusions (chimeras) of FGF19 and/or FGF21 peptide sequences having one or more activities associated with the treatment and/or prevention of PBC and associated diseases, disorders and conditions, as provided herein, either alone or in combination with other agents, offer novel, promising alternatives to the management of such sequelae.

4.5.1.2 NASH and NAFLD and Therapy with Agents Effective in the Treatment or Prevention Thereof Non-alcoholic steatohepatitis (NASH), considered part of a spectrum of non-alcoholic fatty liver diseases (NAFLD), causes inflammation and accumulation of fat and fibrous tissue in the liver. Although the exact cause of NASH is unknown, risk factors include central obesity, type-2 diabetes mellitus, insulin resistance (IR) and dyslipidemia; combinations of the foregoing are frequently described as the metabolic syndrome. In addition, certain drugs have been linked to NASH, including tamoxifen, amiodarone and steroids (e.g., prednisone and hydrocortisone). Non-alcoholic fatty liver disease is the most common cause of chronic liver disease in the United States, and the estimated prevalence of NAFLD is 20-30% and for NASH it is estimated at 3.5-5%. (See, e.g., Abrams, G. A., et al., Hepatology, 2004. 40(2):475-83; Moreira, R. K., Arch Pathol Lab Med, 2007. 131(11):1728-34).

NASH frequently presents with no overt symptoms, complicating its diagnosis. Liver function tests generally begin the diagnostic process, with levels of AST (aspartate aminotransferase) and ALT (alanine aminotransferase) elevated in about 90% percent of individuals with NASH. Other blood tests are often used for ruling out other causes of liver disease, such as hepatitis. Imaging tests (e.g., ultrasound, CT scan, or MRI) may reveal fat accumulation in the liver but frequently cannot differentiate NASH from other causes of liver disease that have a similar appearance. A liver biopsy is required to confirm NASH.

The prognosis for individuals suffering from NASH is difficult to predict, although features in the liver biopsy can be helpful. The most serious complication of NASH is cirrhosis, which occurs when the liver becomes severely scarred. It has been reported that between 8 and 26 percent of individuals with NASH develop cirrhosis, and it is predicted that NASH will be the leading indication for liver transplantation by 2020.

At the present time, treatment of NASH focuses primarily on pharmacological and non-pharmacological management of those medical conditions associated with it, including hyperlipidemia, diabetes and obesity. Although not curative, pharmacological intervention of NASH itself includes treatment with vitamin E, pioglitazone, metformin, statins, omega-3 fatty acids, and ursodeoxycholic acid (UDCA (ursodiol)). Other agents being evaluated, currently approved for different indications, include losartan and telisartan, exenatide, GLP-1 agonists, DPP IV inhibitors, and carbamazepine.

In view of the deficiencies of the aforementioned current therapies, therapy with agents having distinct mechanisms of action offers a promising new avenue for the treatment and prevention of NASH and NAFLD. Addressing such deficiencies is contemplated, for example, by using the variants of FGF19 peptide sequences, fusions of FGF19 and/or FGF21 peptide sequences and variants of fusions (chimeras) of FGF19 and/or FGF21 peptide sequences as taught herein. In certain embodiments, the peptides are used in combination with other therapeutic agents and/or treatment modalities. Also provided herein is the prophylactic and/or therapeutic use of these variants of FGF19 peptide sequences, fusions of FGF19 and/or FGF21 peptide sequences and variants of fusions (chimeras) of FGF19 and/or FGF21 peptide sequences, either alone or in combination with therapies developed in the future, for the treatment or prevention of NASH and NAFLD.

4.5.1.3 Therapy for the Treatment or Prevention of Other Bile Acid-Related Disorders and Associated Diseases, Disorders and Conditions Also provided herein is the use of variants of FGF19 peptide sequences, fusions of FGF19 and/or FGF21 peptide sequences and variants of fusions (chimeras) of FGF19 and/or FGF21 peptide sequences having one or more activities associated with the treatment and/or prevention of other bile acid-related disorders and associated diseases, disorders and conditions besides PBC. In certain embodiments, the peptides are used in combination with other therapeutic agents and/or treatment modalities.

By way of example, patients with bile acid diarrhea secondary to Crohn's ileitis will be helped with glucocorticoid treatment. Microscopic colitis is also helped by steroids. In patients with a short-bowel syndrome (a bile acid deficiency occurs in the proximal intestine that leads to impaired micellar solubilization), cholylsarcosine (cholyl-N-methylglycine), a synthetic bile acid analogue, has been shown to increase lipid absorption.

Administration of the primary bile acid chenodeoxycholic Acid (CDCA) has been shown to decrease biliary cholesterol secretion and gradual dissolution of gallstones. Because CDCA is slightly hepatotoxic, it was gradually replaced by UDCA. Despite the efficacy and safety of UDCA administration for cholesterol gallstone dissolution, it is not frequently used today because of the success of laparoscopic cholecystectomy, which provides a rapid cure for symptomatic disease. Medical therapy, in contrast, requires months of therapy, does not always dissolve stones, and is followed by gradual recurrence in some patients.

Bile acid replacement is used in inborn errors of bile acid biosynthesis, usually with a mixture of CDCA or UDCA and cholic acid, to suppress the synthesis of cytotoxic bile acid precursors and restore the input of primary bile acids into the enterohepatic circulation.

In addition to the agents and therapeutic modalities set forth above, combination therapy with numerous additional agents (and classes thereof) is also contemplated, including, but not limited to, 1) insulin e.g., bolus and basal analogs), insulin mimetics and agents that entail stimulation of insulin secretion, including sulfonylureas (e.g., chlorpropamide, tolazamide, acetohexamide, tolbutamide, glyburide, glimepiride, glipizide) and meglitinides (e.g., repaglinide (PRANDIN) and nateglinide (STARLIX)); 2) biguanides (e.g., metformin (GLUCOPHAGE)) and other agents that act by promoting glucose utilization, reducing hepatic glucose production and/or diminishing intestinal glucose output; 3) alpha-glucosidase inhibitors (e.g., acarbose and miglitol) and other agents that slow down carbohydrate digestion and consequently absorption from the gut and reduce postprandial hyperglycemia; 4) thiazolidinediones (e.g., rosiglitazone (AVANDIA), troglitazone (REZULIN), pioglitazone (ACTOS), glipizide, balaglitazone, rivoglitazone, netoglitazone, troglitazone, englitazone, ciglitazone, adaglitazone, darglitazone that enhance insulin action (e.g., by insulin sensitization), thus promoting glucose utilization in peripheral tissues; 5) glucagon-like-peptides including DPP-IV inhibitors (e.g., vildagliptin (GALVUS) and sitagliptin (JANUVIA)) and Glucagon-Like Peptide-1 (GLP-1) and GLP-1 agonists and analogs (e.g., exenatide (BYETTA and ITCA 650 (an osmotic pump inserted subcutaneously that delivers an exenatide analog over a 12-month period; Intarcia, Boston, Mass.)); 6) and DPP-IV-resistant analogues (incretin mimetics), PPAR gamma agonists, dual-acting PPAR agonists, pan-acting PPAR agonists, PTP1B inhibitors, SGLT inhibitors, insulin secretagogues, RXR agonists, glycogen synthase kinase-3 inhibitors, immune modulators, beta-3 adrenergic receptor agonists, 11beta-HSD1 inhibitors, and amylin analogues.

Other exemplary agents that can be used, in certain embodiments, in combination with the peptides and methods provided herein include dipeptidyl peptidase-4 (DPP-4) inhibitors, bromocriptine formulations (e.g. and bile acid sequestrants (e.g., colesevelam), and SGLT-2 inhibitors. Appetite suppression drugs are also well known and can be used in combination with the compositions and methods provided herein. Supplementary therapies can be administered prior to, contemporaneously with or following methods and uses provided herein.

In one aspect, provided herein is a method for preventing or treating a bile acid related disorder (BARD), or a symptom thereof, in a subject comprising administering to the subject an effective amount of a peptide, wherein the peptide has an amino acid sequence comprising or consisting of:

(SEQ ID NO: 70)
MRDSSPLVHYGWGDPIRLRHLYTSGPHGLSSCFLRIRADGVVDCARGQSA

HSLLEIKAVALRTVAIKGVHSVRYLCMGADGKMQGLLQYSEEDCAFEEEI

RPDGYNVYRSEKHRLPVSLSSAKQRQLYKNRGFLPLSHFLPMLPMVPEEP

EDLRGHLESDMFSSPLETDSMDPFGLVTGLEAVRSPSFEK (M70).

In one aspect, provided herein is a method for preventing or treating a bile acid related disorder (BARD), or a symptom thereof, in a subject comprising administering to the subject an effective amount of a peptide, wherein the peptide has an amino acid sequence comprising or consisting of:

(SEQ ID NO: 69)
RDSSPLVHYGWGDPIRLRHLYTSGPHGLSSCFLRIRADGVVDCARGQSAH

SLLEIKAVALRTVAIKGVHSVRYLCMGADGKMQGLLQYSEEDCAFEEEIR

PDGYNVYRSEKHRLPVSLSSAKQRQLYKNRGFLPLSHFLPMLPMVPEEPE

DLRGHLESDMFSSPLETDSMDPFGLVTGLEAVRSPSFEK (M69).

In another aspect, provided herein is a method for preventing or treating a BARD, or a symptom thereof, in a subject comprising administering to the subject an effective amount of a peptide, wherein the peptide comprises: a) an N-terminal region comprising at least seven amino acid residues, the N-terminal region having a first amino acid position and a last amino acid position, wherein the N-terminal region comprises DSSPL (SEQ ID NO:121) or DASPH (SEQ ID NO:122); and b) a C-terminal region comprising a portion of SEQ ID NO:99 (FGF19), the C-terminal region having a first amino acid position and a last amino acid position, wherein the C-terminal region comprises amino acid residues 16-29 of SEQ ID NO:99 (FGF19), WGDPIRLRHLYTSG (SEQ ID NO:169), wherein the W residue corresponds to the first amino acid position of the C-terminal region.

Other peptides provided herein are also contemplated in the methods provided herein.

In certain embodiments, the BARD, or symptom thereof, is improved as compared to baseline. In some embodiments, baseline is a pre-dose baseline.

In some embodiments, the BARD is non-alcoholic fatty liver disease (NAFLD). In one embodiment, provided herein is a method of preventing or treating NAFLD, or a symptom thereof, in a subject, comprising administering a peptide (e.g., M70, or M69) provided herein.

In some embodiments, the method results in an improvement of the NAFLD activity score (NAS).

In some embodiments, the BARD is hepatic fibrosis. In one embodiment, provided herein is a method of preventing or treating hepatic fibrosis, or a symptom thereof, in a subject, comprising administering a peptide (e.g., M70, or M69) provided herein.

In some embodiments, the BARD is nonalcoholic steatohepatitis (NASH). In one embodiment, provided herein is a method of preventing or treating NASH or a symptom thereof, in a subject, comprising administering a peptide (e.g., M70, or M69) provided herein. In some embodiments, the subject has biopsy-confirmed NASH.

In some embodiments, the BARD is cholestatic liver disease. In one embodiment, provided herein is a method of preventing or treating cholestatic liver disease, or a symptom thereof, in a subject, comprising administering a peptide (e.g., M70, or M69) provided herein.

In some embodiments, the cholestatic liver disease is primary sclerosing cholangitis (PSC). In some embodiments, the cholestatic liver disease is primary biliary cirrhosis (PBC). In some embodiments, the cholestatic liver disease is intrahepatic cholestatis of pregnancy. In some embodiments, the cholestatic liver disease is alcoholic hepatitis. In some embodiments, the cholestatic liver disease is drug-induced cholestatis.

In some embodiments, the methods provided herein result in a decrease in liver steatosis. In one embodiment, provided herein is a method of preventing or treating liver steatosis in a subject, comprising administering a peptide (e.g., M70, or M69) provided herein.

In some embodiments, the methods provided herein result in a decrease in liver inflammation. In one embodiment, provided herein is a method of preventing or treating liver inflammation in a subject, comprising administering a peptide (e.g., M70, or M69) provided herein. In certain embodiments, the liver inflammation is lobular inflammation.

In some embodiments, the methods provided herein result in a decrease in hepatocyte ballooning. In one embodiment, provided herein is a method of decreasing hepatocyte ballooning in a subject, comprising administering a peptide (e.g., M70, or M69) provided herein.

In some embodiments, the methods provided herein result in a reduction of CYP7a1 levels in the subject. In one embodiment, provided herein is a method of reducing CYP7a1 levels in a subject, comprising administering a peptide (e.g., M70, or M69) provided herein.

In some embodiments, the methods provided herein result in a reduction of serum bile acid levels in the subject. In one embodiment, provided herein is a method of reducing serum bile acid levels in a subject, comprising administering a peptide (e.g., M70, or M69) provided herein.

In some embodiments, the methods provided herein result in a reduction of triglycerides in the subject. In one embodiment, provided herein is a method of reducing triglycerides in a subject, comprising administering a peptide (e.g., M70, or M69) provided herein.

In some embodiments, the methods provided herein result in a reduction in alkaline phosphatase (ALP) levels in the subject. In one embodiment, provided herein is a method of reducing ALP levels in a subject, comprising administering a peptide (e.g., M70, or M69) provided herein. In some embodiments, the ALP levels are reduced at least 10% in the subject. In some embodiments, the ALP levels are reduced at least 15% in the subject.

In some embodiments, the methods provided herein result in a reduction in alkaline aminotransferase (ALT) levels in the subject. In one embodiment, provided herein is a method of reducing ALT in a subject, comprising administering a peptide (e.g., M70, or M69) provided herein. In one embodiment, provided herein is a method of reducing ALT levels in a subject, comprising administering a peptide (e.g., M70, or M69) provided herein.

In some embodiments, the methods provided herein result in a reduction in aspartate aminotransfease (AST) levels in the subject. In one embodiment, provided herein is a method of reducing AST levels in a subject, comprising administering a peptide (e.g., M70, or M69) provided herein.

In some embodiments, the methods provided herein result in a reduction in gamma-glutamyltransferase (GGT) levels in the subject. In one embodiment, provided herein is a method of reducing GGT levels in a subject, comprising administering a peptide (e.g., M70, or M69) provided herein.

In some embodiments, the methods provided herein result in an improvement in a biochemical marker of liver function. In one embodiment, provided herein is a method of improving a biochemical marker of liver function in a subject, comprising administering a peptide (e.g., M70, or M69) provided herein. In some embodiments, the biochemical marker of liver function is an enzyme. In some embodiments, the enzyme is ALP. In some embodiments, the enzyme is ALT. In some embodiments, the enzyme is AST. In some embodiments, the enzyme is GGT.

In some embodiments, the methods provided herein result in a reduction in cholesterol levels in the subject. In one embodiment, provided herein is a method of reducing cholesterol levels in a subject, comprising administering a peptide (e.g., M70, or M69) provided herein.

In some embodiments, the methods provided herein result in a reduction in glucose levels in the subject. In one embodiment, provided herein is a method of reducing glucose levels in a subject, comprising administering a peptide (e.g., M70, or M69) provided herein.

In some embodiments, the methods provided herein result in an improvement in insulin resistance in the subject. In one embodiment, provided herein is a method of improving insulin resistance in a subject, comprising administering a peptide (e.g., M70, or M69) provided herein.

In some embodiments, the methods provided herein result in an improvement in insulin sensitivity in the subject. In one embodiment, provided herein is a method of improving insulin sensitivity in a subject, comprising administering a peptide (e.g., M70, or M69) provided herein. In some embodiments, the insulin sensitivity is as measured by HOMA-IR.

In some embodiments, the methods provided herein result in a reduction in body weight in the subject. In one embodiment, provided herein is a method of reducing body weight in a subject, comprising administering a peptide (e.g., M70, or M69) provided herein.

In some embodiments, the methods provided herein result in a reduction in liver weight in the subject. In one embodiment, provided herein is a method of reducing liver weight in a subject, comprising administering a peptide (e.g., M70, or M69) provided herein.

In some embodiments, the methods provided herein result in a decrease in bilirubin levels in the subject. In one embodiment, provided herein is a method of reducing bilirubin levels in a subject, comprising administering a peptide (e.g., M70, or M69) provided herein.

In some embodiments, the methods provided herein result in a decrease in a serum biomarker of early fibrosis in the subject. In one embodiment, provided herein is a method of reducing the level of a serum biomarker of early fibrosis in a subject, comprising administering a peptide (e.g., M70, or M69) provided herein.

In some embodiments, the methods provided herein result in the reduction of serum C4 levels in the subject. In one embodiment, provided herein is a method of reducing serum C4 levels in a subject, comprising administering a peptide (e.g., M70, or M69) provided herein. In some embodiments, the serum C4 levels are decreased by at least 50%, at least 60%, at least 70%, at least 80%, or at least 90% in the subject. In some embodiments, the reduction in serum C4 levels is a mean reduction in C4 levels. In some embodiments, the mean reduction in serum C4 levels is at least 90%. In some embodiments, the serum C4 levels are decreased as compared to the serum C4 levels in the subject prior to administration of the peptide.

In some embodiments, the methods provided herein result in an improvement in liver function in the subject. In one embodiment, provided herein is a method of improving liver function in a subject, comprising administering a peptide (e.g., M70, or M69) provided herein.

In some embodiments, the methods provided herein result in improving pruritus, or a symptom thereof, in the subject. In one embodiment, provided herein is a method of preventing or treating pruritus, or a symptom thereof, in a subject, comprising administering a peptide (e.g., M70, or M69) provided herein. In one embodiment, the method is a method of preventing pruritus, or a symptom thereof, in a subject. In one embodiment, the method is a method of treating pruritus, or a symptom thereof, in a subject. In some embodiments, the pruritus symptom is itching. In some embodiments, the pruritus symptom is impaired sleep. In some embodiments, the pruritus symptom is depression.

In some embodiments, the peptide is administered at a dose of 0.3 mg. In some embodiments, the peptide is administered at a dose of 1 mg. In some embodiments, the peptide is administered at a dose of 2 mg. In some embodiments, the peptide is administered at a dose of 3 mg. In some embodiments, the peptide is administered at a dose of 5 mg. In some embodiments, the peptide is administered at a dose of 10 mg.

In some embodiments, the peptide is administered once a day. In some embodiments, the peptide is administered twice a day.

In some embodiments, the peptide is administered subcutaneously.

In some embodiments, the peptide is administered for 7 days or longer. In some embodiments, the peptide is administered for 14 days or longer. In some embodiments, the peptide is administered for 21 days or longer. In some embodiments, the peptide is administered for 28 days or longer. In some embodiments, the peptide is administered for 1 to 12 months. In some embodiments, the peptide is administered for 12 months. In some embodiments, the peptide is administered for more than 12 months.

In some embodiments, the peptide is administered in combination with ursodeoxycholic acid (UDCA).

In some embodiments, the subject is overweight. In some embodiments, the subject is obese. In some embodiments, the subject has diabetes. In some embodiments, the subject does not have diabetes. In some embodiments, the diabetes is type 2 diabetes.

4.5.2 Methods of Preventing, Treating and Managing Metabolic Disorders

Also provided herein are in vitro, ex vivo and in vivo (e.g., on or in a subject) methods and uses. Such methods and uses can be practiced with any of the peptide sequences set forth herein. In various embodiments, the methods include administering a peptide sequence, such as a FGF19 or FGF21 variant, fusion or chimera disclosed herein (e.g., in the Sequence Listing or Tables 1-11), or a subsequence, a variant or modified form of a FGF19 or FGF21 variant, fusion or chimera disclosed herein (e.g., the Sequence Listing or Tables 1-11), to a subject in an amount effective for treating a metabolic or associated disorder.

In certain embodiments, the peptide is administered in combination with an additional therapeutic agent(s) and/or treatment modalities (e.g., an agent useful in the treatment and/or prevention of PBC). The additional therapeutic agent(s) can be administered before, with, or following administration of the peptides described herein.

Also provided herein are methods of preventing (e.g., in subjects predisposed to having a particular disorder(s)), delaying, slowing or inhibiting progression of, the onset of, or treating (e.g., ameliorating) a metabolic or associated disorder relative to an appropriate matched subject of comparable age, gender, race, etc.). Thus, in various embodiments, a method provided herein for, for example, modulating bile acid homeostasis or treating a metabolic or associated disorder includes contacting or administering one or more peptides provided herein (e.g., a variant or fusion of FGF19 and/or FGF21 as set forth in the Sequence Listing or Tables 1-11) in an amount effective to modulate bile acid homeostasis or treat a metabolic or associated disorder. In certain embodiments the method further comprises contacting or administering at least one additional therapeutic agent or treatment modality that is useful in the treatment or prevention of a metabolic or associated disorder (e.g., PBC).

The term "subject" refers to an animal. Typically, the animal is a mammal that would benefit from treatment with a peptide sequence provided herein. Particular examples include primates (e.g., humans), dogs, cats, horses, cows, pigs, and sheep.

Subjects include those having a disorder, e.g., a metabolic or associated disorder, or subjects that do not have a disorder but may be at risk of developing the disorder.

Non-limiting exemplary disorders or conditions preventable, treatable or manageable with the peptide formulations, methods and uses thereof provided herein, include metabolic diseases and disorders. Non limiting examples of diseases and disorders include: metabolic syndrome; a lipid- or glucose-related disorder; cholesterol or triglyceride metabolism; type 2 diabetes; cholastasis, including, for example diseases of intrahepatic cholestasis (e.g., PBC, PFIC, PSC, PIC, neonatal cholestasis, and drug induced cholestasis (e.g., estrogen)), and diseases of extrahepatic cholestasis (e.g., bile cut compression from tumor, bile duct blockade by gall stones); bile acid malabsorption and other disorders involving the distal small intestine, including ileal resection, inflammatory bowel diseases (e.g., Crohn's disease and ulcerative colitis), disorders impairing absorption of bile acids not otherwise characterized (idiopathic)) leading to diarrhea (e.g., BAD) and GI symptoms, and GI, liver, and/or biliary cancers (e.g., colon cancer and hepatocellular cancer); and/or bile acid synthesis abnormalities, such as those contributing to NASH, cirrhosis and portal hypertension. For treatment, peptide sequences provided herein can be administered to subjects in need of modulation of bile acid homeostasis or having a bile-acid related or associated disorder. Peptide sequences provided herein may also be useful in other hyperglycemic-related disorders, including kidney damage (e.g., tubule damage or nephropathy), liver degeneration, eye damage (e.g., diabetic retinopathy or cataracts), and diabetic foot disorders; dyslipidemias and their sequelae such as, for example, atherosclerosis, coronary artery disease, cerebrovascular disorders and the like.

Other conditions which may be associated with metabolic syndrome, such as obesity and elevated body mass (including the co-morbid conditions thereof such as, but not limited to, nonalcoholic fatty liver disease (NAFLD), nonalcoholic steatohepatitis (NASH), and polycystic ovarian syndrome (PCOS)), and also include thromboses, hypercoagulable and prothrombotic states (arterial and venous), hypertension (including portal hypertension (defined as a hepatic venous pressure gradient (HVPG) greater than 5 mm Hg), cardiovascular disease, stroke and heart failure; Disorders or conditions in which inflammatory reactions are involved, including atherosclerosis, chronic inflammatory bowel diseases (e.g., Crohn's disease and ulcerative colitis), asthma, lupus erythematosus, arthritis, or other inflammatory rheumatic disorders; Disorders of cell cycle or cell differentiation processes such as adipose cell tumors, lipomatous carcinomas including, for example, liposarcomas, solid tumors, and neoplasms; Neurodegenerative diseases and/or demyelinating disorders of the central and peripheral nervous systems and/or neurological diseases involving neuroinflammatory processes and/or other peripheral neuropathies, including Alzheimer's disease, multiple sclerosis, Parkinson's disease, progressive multifocal leukoencephalopathy and Guillian-Barre syndrome; Skin and dermatological disorders and/or disorders of wound healing processes, including erythemato-squamous dermatoses; and other disorders such as syndrome X, osteoarthritis, and acute respiratory distress syndrome.

In one embodiment, a subject has a hyperglycemic condition (e.g., diabetes, such as insulin-dependent (type I) diabetes, type II diabetes, or gestational diabetes), insulin resistance, hyperinsulinemia, glucose intolerance or metabolic syndrome, is obese and/or has an undesirable body mass.

In particular aspects of the methods and uses, a peptide sequence or chimeric peptide sequence provided herein is administered to a subject in an amount effective to improve glucose metabolism in the subject. In more particular aspects, a subject has a fasting plasma glucose level greater than 100 mg/dl or has a hemoglobin A1c (HbA1c) level above 6%, prior to administration.

In further embodiments, a use or method of treatment of a subject is intended to or results in reduced glucose levels, increased insulin sensitivity, reduced insulin resistance, reduced glucagon, an improvement in glucose tolerance, or glucose metabolism or homeostasis, improved pancreatic function, or reduced triglyceride, cholesterol, IDL, LDL or VLDL levels, or a decrease in blood pressure, a decrease in intimal thickening of the blood vessel, or a decrease in body mass or weight gain.

Treatment of a metabolic or associated disorder (e.g., hyperglycemia) may have the benefit of alleviating or abolishing a disorder secondary thereto. By way of example, a subject suffering from hyperglycemia may also have depression or anxiety due to the hyperglycemia; thus, treating the subject's hyperglycemia may also indirectly treat the depression or anxiety. The use of the therapies disclosed herein to target such secondary disorders is also contemplated in certain embodiments.

In particular embodiments, the subject has or is at risk of having hyperglycemia. In other particular embodiments, the subject has or is at risk of having diabetes, such as Type 2 diabetes.

Subjects at risk of developing a metabolic or associated disorder (such as the disorders described above) include, for example, those who may have a family history or genetic predisposition toward such disorder, as well those whose diet may contribute to development of such disorders.

As disclosed herein, treatment methods include contacting or administering a peptide as set forth herein (e.g., a variant or fusion of FGF19 and/or FGF21 as set forth in the Sequence Listing or Tables 1-11) in an amount effective to achieve a desired outcome or result in a subject. A treatment that results in a desired outcome or result includes decreasing, reducing or preventing the severity or frequency of one or more symptoms of the condition in the subject, e.g., an improvement in the subject's condition or a "beneficial effect" or "therapeutic effect." Therefore, treatment can decrease or reduce or prevent the severity or frequency of one or more symptoms of the disorder, stabilize or inhibit progression or worsening of the disorder, and in some instances, reverse the disorder, transiently (e.g., for 1-6, 6-12, or 12-24 hours), for medium term (e.g., 1-6, 6-12, 12-24 or 24-48 days) or long term (e.g., for 1-6, 6-12, 12-24, 24-48 weeks, or greater than 24-48 weeks). Thus, in the case of a metabolic or associated disorder, treatment can lower or reduce one or more symptoms or effects of the metabolic or associated disorders described above.

In certain embodiments, the various methods provided herein further include contacting or administering one or more additional agents or therapeutic modalities useful in the treatment or prevention of a metabolic or associated disorder, such as those agents or therapeutic modalities described herein, in an amount effective to achieve a desired outcome or result in a subject.

An "effective amount" or a "sufficient amount" for use and/or for treating a subject refers to an amount that provides, in single or multiple doses, alone, or in combination with one or more other agents, treatments, protocols, or therapeutic regimens, a detectable response of any duration of time (transient, medium or long term), a desired outcome in or an objective or subjective benefit to a subject of any measurable or detectable degree or for any duration of time (e.g., for hours, days, months, years, in remission or cured). Such amounts typically are effective to ameliorate a disorder, or one, multiple or all adverse symptoms, consequences or complications of the disorder, to a measurable extent, although reducing or inhibiting a progression or worsening of the disorder, is considered a satisfactory outcome.

As used herein, the term "ameliorate" means an improvement in the subject's disorder, a reduction in the severity of the disorder, or an inhibition of progression or worsening of the disorder (e.g., stabilizing the disorder). In the case of a metabolic or associated disorder such as those described above, an improvement can be a lowering or a reduction in one or more symptoms or effects of the disorder.

A therapeutic benefit or improvement therefore need not be complete ablation of any one, most or all symptoms, complications, consequences or underlying causes associated with the disorder or disease. Thus, a satisfactory endpoint is achieved when there is a transient, medium or long term, incremental improvement in a subject's condition, or a partial reduction in the occurrence, frequency, severity, progression, or duration, or inhibition or reversal, of one or more associated adverse symptoms or complications or consequences or underlying causes, worsening or progression (e.g., stabilizing one or more symptoms or complications of the condition, disorder or disease), of the disorder or disease, over a duration of time (hours, days, weeks, months, etc.).

Thus, in the case of a disorder treatable by a peptide sequence provided herein, either alone or in combination with an additional agent, the amount of the peptide (and optionally the additional agent) sufficient to ameliorate a disorder will depend on the type, severity and extent, or duration of the disorder, the therapeutic effect or outcome desired, and can be readily ascertained by the skilled artisan. Appropriate amounts will also depend upon the individual subject (e.g., the bioavailability within the subject, gender, age, etc.). For example, a transient, or partial, restoration of normal bile acid homeostasis in a subject can reduce the dosage amount or frequency of the peptides and agents described herein in order to treat the metabolic or associated disorders described previously even though complete freedom from treatment has not resulted. An effective amount can be ascertained, for example, by measuring one or more relevant physiological effects.

Methods and uses provided herein for treating a subject are applicable for prophylaxis to prevent or reduce the likelihood of a disorder in a subject, such as a metabolic or associated disorder. Accordingly, methods and uses provided herein for treating a subject having, or at risk of developing, a metabolic or associated disorder can be practiced prior to, substantially contemporaneously with, or following administration or application of another agent useful for the treatment or prevention of a metabolic or associated disorder, and/or can be supplemented with other forms of therapy. Supplementary therapies include other glucose lowering treatments, such as insulin, an insulin sensitivity enhancer and other drug treatments, a change in diet (low sugar, fats, etc.), weight loss surgery-(reducing stomach volume by gastric bypass, gastrectomy), gastric banding, gastric balloon, gastric sleeve, etc. For example, a method or use provided herein for treating a hyperglycemic or insulin resistance disorder can be used in combination with drugs or other pharmaceutical compositions that lower glucose or increase insulin sensitivity in a subject.

In one embodiment, a method or use includes contacting or administering to a subject one or more variant or fusion FGF19 and/or FGF21 peptide sequences in an amount effective for preventing a metabolic or associated disorder. In one embodiment, a method or use includes contacting or administering to a subject one or more variant or fusion FGF19 and/or FGF21 peptide sequences in an amount effective for treating a metabolic or associated disorder. In one embodiment, a method or use includes contacting or administering to a subject one or more variant or fusion FGF19 and/or FGF21 peptide sequences in an amount effective for managing a metabolic or associated disorder.

4.6 Nucleic Acid Molecules

Also provided are nucleic acid molecules encoding peptide sequences provided herein, including subsequences, sequence variants and modified forms of the sequences listed in the Sequence Listing (and in PCT Pub. No. WO 2013/006486 and US Pub. No. 2013/0023474, as well as PCT Publ. No. WO 2014/085365) or Tables 1-11, and vectors that include nucleic acid encoding the peptides used in the methods described herein. Accordingly, "nucleic acids" include those that encode the exemplified peptide sequences disclosed herein, as well as those encoding functional subsequences, sequence variants and modified forms of the exemplified peptide sequences, so long as the foregoing retain at least detectable or measurable activity or function useful in the treatment or prevention of a bile acid-related or associated disorder (e.g., PBC).

Nucleic acid, which can also be referred to herein as a gene, polynucleotide, nucleotide sequence, primer, oligonucleotide or probe, refers to natural or modified purine- and pyrimidine-containing polymers of any length, either polyribonucleotides or polydeoxyribonucleotides or mixed polyribo-polydeoxyribo nucleotides and α-anomeric forms thereof. The two or more purine- and pyrimidine-containing polymers are typically linked by a phosphoester bond or analog thereof. The terms can be used interchangeably to refer to all forms of nucleic acid, including deoxyribonucleic acid (DNA) and ribonucleic acid (RNA). The nucleic acids can be single strand, double, or triplex, linear or circular. Nucleic acids include genomic DNA and cDNA. RNA nucleic acid can be spliced or unspliced mRNA, rRNA, tRNA or antisense. Nucleic acids include naturally occurring, synthetic, as well as nucleotide analogs and derivatives.

As a result of the degeneracy of the genetic code, the nucleic acid molecules provided herein include sequences degenerate with respect to nucleic acid molecules encoding the peptide sequences useful in the methods provided herein. Thus, degenerate nucleic acid sequences encoding peptide sequences, including subsequences, variants and modified forms of the peptide sequences exemplified herein (e.g., in the Sequence Listing or Tables 1-11), are provided. The term "complementary," when used in reference to a nucleic acid sequence, means the referenced regions are 100% complementary, i.e., exhibit 100% base pairing with no mismatches.

Nucleic acid can be produced using any of a variety of known standard cloning and chemical synthesis methods, and can be altered intentionally by site-directed mutagenesis or other recombinant techniques known to one skilled in the art. Purity of polynucleotides can be determined through, for example, sequencing, gel electrophoresis, and UV spectrometry.

Nucleic acids may be inserted into a nucleic acid construct in which expression of the nucleic acid is influenced or regulated by an "expression control element," referred to herein as an "expression cassette." The term "expression control element" refers to one or more nucleic acid sequence elements that regulate or influence expression of a nucleic acid sequence to which it is operatively linked. An expression control element can include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. The term "operatively linked" refers to a juxtaposition wherein the referenced components are in a relationship permitting them to function in their intended manner. Typically, expression control elements are juxtaposed at the 5' or the 3' ends of the genes but can also be intronic.

Expression control elements include elements that activate transcription constitutively, that are inducible (i.e., require an external signal or stimuli for activation), or derepressible (i.e., require a signal to turn transcription off; when the signal is no longer present, transcription is activated or "derepressed"). Also included in the expression cassettes provided herein are control elements sufficient to render gene expression controllable for specific cell types or tissues (i.e., tissue-specific control elements). Typically, such elements are located upstream or downstream (i.e., 5' or 3') of the coding sequence. Promoters are generally positioned 5' of the coding sequence. Promoters, produced by recombinant DNA or synthetic techniques, can be used to provide for transcription of the polynucleotides provided herein. A "promoter" typically means a minimal sequence element sufficient to direct transcription.

Nucleic acids may be inserted into a plasmid for transformation into a host cell and for subsequent expression and/or genetic manipulation. A plasmid is a nucleic acid that can be stably propagated in a host cell; plasmids may optionally contain expression control elements in order to drive expression of the nucleic acid. As used herein, a vector is synonymous with a plasmid. Plasmids and vectors generally contain at least an origin of replication for propagation in a cell and a promoter. Plasmids and vectors may also include an expression control element for expression in a host cell, and are therefore useful for expression and/or genetic manipulation of nucleic acids encoding peptide sequences, expressing peptide sequences in host cells and organisms, or producing peptide sequences, for example.

As used herein, the term "transgene" means a polynucleotide that has been introduced into a cell or organism by artifice. For example, in a cell having a transgene, the transgene has been introduced by genetic manipulation or "transformation" of the cell. A cell or progeny thereof into which the transgene has been introduced is referred to as a "transformed cell" or "transformant." Typically, the transgene is included in progeny of the transformant or becomes a part of the organism that develops from the cell. Transgenes may be inserted into the chromosomal DNA or maintained as a self-replicating plasmid, YAC, minichromosome, or the like.

Bacterial system promoters include T7 and inducible promoters such as pL of bacteriophage λ, plac, ptrp, ptac (ptrp-lac hybrid promoter) and tetracycline-responsive promoters. Insect cell system promoters include constitutive or inducible promoters (e.g., ecdysone). Mammalian cell constitutive promoters include SV40, RSV, bovine papilloma virus (BPV) and other virus promoters, or inducible promoters derived from the genome of mammalian cells (e.g., metallothionein IIA promoter; heat shock promoter) or from mammalian viruses (e.g., the adenovirus late promoter; the inducible mouse mammary tumor virus long terminal repeat). Alternatively, a retroviral genome can be genetically modified for introducing and directing expression of a peptide sequence in appropriate host cells.

As methods and uses provided herein include in vivo delivery, expression systems further include vectors designed for in vivo use. Particular non-limiting examples include adenoviral vectors (U.S. Pat. Nos. 5,700,470 and 5,731,172), adeno-associated vectors (U.S. Pat. No. 5,604, 090), herpes simplex virus vectors (U.S. Pat. No. 5,501, 979), retroviral vectors (U.S. Pat. Nos. 5,624,820, 5,693,508 and 5,674,703), BPV vectors (U.S. Pat. No. 5,719,054), CMV vectors (U.S. Pat. No. 5,561,063) and parvovirus, rotavirus, Norwalk virus and lentiviral vectors (see, e.g., U.S. Pat. No. 6,013,516). Vectors include those that deliver genes to cells of the intestinal tract, including the stem cells (Croyle et al., Gene Ther. 5:645 (1998); S. J. Henning, Adv. Drug Deliv. Rev. 17:341 (1997), U.S. Pat. Nos. 5,821,235 and 6,110,456). Many of these vectors have been approved for human studies.

Yeast vectors include constitutive and inducible promoters (see, e.g., Ausubel et al., In: *Current Protocols in Molecular Biology*, Vol. 2, Ch. 13, ed., Greene Publish. Assoc. & Wiley Interscience, 1988; Grant et al. Methods in Enzymology, 153:516 (1987), eds. Wu & Grossman; Bitter Methods in Enzymology, 152:673 (1987), eds. Berger & Kimmel, Acad. Press, N.Y.; and, Strathern et al., *The Molecular Biology of the Yeast Saccharomyces* (1982) eds. Cold Spring Harbor Press, Vols. I and II). A constitutive yeast promoter such as ADH or LEU2 or an inducible promoter such as GAL may be used (R. Rothstein In: *DNA Cloning, A Practical Approach*, Vol. 11, Ch. 3, ed. D. M. Glover, IRL Press, Wash., D.C., 1986). Vectors that facilitate integration of foreign nucleic acid sequences into a yeast chromosome, via homologous recombination for example, are known in the art. Yeast artificial chromosomes (YAC) are typically used when the inserted polynucleotides are too large for more conventional vectors (e.g., greater than about 12 Kb).

Expression vectors also can contain a selectable marker conferring resistance to a selective pressure or identifiable marker (e.g., beta-galactosidase), thereby allowing cells having the vector to be selected for, grown and expanded. Alternatively, a selectable marker can be on a second vector that is co-transfected into a host cell with a first vector containing a nucleic acid encoding a peptide sequence. Selection systems include, but are not limited to, herpes simplex virus thymidine kinase gene (Wigler et al., Cell 11:223 (1977)), hypoxanthine-guanine phosphoribosyltransferase gene (Szybalska et al., Proc. Natl. Acad. Sci. USA 48:2026 (1962)), and adenine phosphoribosyltransferase (Lowy et al., Cell 22:817 (1980)) genes that can be employed in tk-, hgprt- or aprt-cells, respectively. Additionally, antimetabolite resistance can be used as the basis of selection for dhfr, which confers resistance to methotrexate (O'Hare et al., Proc. Natl. Acad. Sci. USA 78:1527 (1981)); the gpt gene, which confers resistance to mycophenolic acid (Mulligan et al., Proc. Natl. Acad. Sci. USA 78:2072 (1981)); neomycin gene, which confers resistance to aminoglycoside G-418 (Colberre-Garapin et al., J. Mol. Biol. 150:1(1981)); puromycin; and hygromycin gene, which confers resistance to hygromycin (Santerre et al., Gene 30:147 (1984)). Additional selectable genes include trpB, which allows cells to utilize indole in place of tryptophan; hisD, which allows cells to utilize histinol in place of histidine (Hartman et al., Proc. Natl. Acad. Sci. USA 85:8047 (1988)); and ODC (ornithine decarboxylase), which confers resistance to the ornithine decarboxylase inhibitor, 2-(difluoromethyl)-DL-ornithine, DFMO (McConlogue (1987) In: *Current Communications in Molecular Biology*, Cold Spring Harbor Laboratory).

4.7 Cell Lines and Animal Models

In certain embodiments, also provided is a transformed cell(s) (in vitro, ex vivo and in vivo) and host cells that produce a variant or fusion of FGF19 and/or FGF21 as set forth herein, where expression of the variant or fusion of FGF19 and/or FGF21 is conferred by a nucleic acid encoding the variant or fusion of FGF19 and/or FGF21. As used herein, a "transformed" or "host" cell is a cell into which a nucleic acid is introduced that can be propagated and/or transcribed for expression of an encoded peptide sequence. The term also includes any progeny or subclones of the host cell. Transformed and host cells that express peptide sequences provided herein typically include a nucleic acid that encodes the peptide sequence. In one embodiment, a transformed or host cell is a prokaryotic cell. In another embodiment, a transformed or host cell is a eukaryotic cell. In various aspects, the eukaryotic cell is a yeast or mammalian (e.g., human, primate, etc.) cell.

Transformed and host cells include but are not limited to microorganisms such as bacteria and yeast; and plant, insect and mammalian cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for transient or stable propagation or expression.

For gene therapy uses and methods, a transformed cell can be in a subject. A cell in a subject can be transformed with a nucleic acid that encodes a peptide sequence as set forth herein in vivo. Alternatively, a cell can be transformed in vitro with a transgene or polynucleotide, and then transplanted into a tissue of subject in order to effect treatment. Alternatively, a primary cell isolate or an established cell line can be transformed with a transgene or polynucleotide that encodes a variant of FGF19 and/or FGF21 or a fusion/chimeric sequence (or variant) thereof, such as a chimeric peptide sequence including all or a portion of FGF19, or including all or a portion of FGF21, and then optionally transplanted into a tissue of a subject.

Non-limiting target cells for expression of peptide sequences, particularly for expression in vivo, include pancreas cells (islet cells), muscle cells, mucosal cells and endocrine cells. Such endocrine cells can provide inducible production (secretion) of a variant of FGF19 and/or FGF21, or a fusion/chimeric sequence (or variant) thereof, such as a chimeric peptide sequence including all or a portion of FGF19, or including all or a portion of FGF21. Additional cells to transform include stem cells or other multipotent or pluripotent cells, for example, progenitor cells that differentiate into the various pancreas cells (islet cells), muscle cells, mucosal cells and endocrine cells. Targeting stem cells provides longer term expression of peptide sequences provided herein.

As used herein, the term "cultured," when used in reference to a cell, means that the cell is grown in vitro. A particular example of such a cell is a cell isolated from a subject, and grown or adapted for growth in tissue culture. Another example is a cell genetically manipulated in vitro, and transplanted back into the same or a different subject.

The term "isolated," when used in reference to a cell, means a cell that is separated from its naturally occurring in vivo environment. "Cultured" and "isolated" cells may be manipulated by the hand of man, such as genetically transformed. These terms include any progeny of the cells, including progeny cells that may not be identical to the parental cell due to mutations that occur during cell division. The terms do not include an entire human being.

Nucleic acids encoding peptide sequences provided herein can be introduced for stable expression into cells of a whole organism. Such organisms, including non-human transgenic animals, are useful for studying the effect of peptide expression in a whole animal and therapeutic benefit. For example, nucleic acids for production of a variant of FGF19 and/or FGF21 or a fusion/chimeric sequence (or variant) thereof, such as a chimeric peptide sequence including all or a portion of FGF19, or including all or a portion of FGF21 as set forth herein, can be introduced for stable expression in mice.

Mice strains that develop or are susceptible to developing a particular disease (e.g., diabetes, degenerative disorders, cancer, etc.) are also useful for introducing therapeutic proteins as described herein in order to study the effect of therapeutic protein expression in the disease-susceptible mouse. Transgenic and genetic animal models that are susceptible to particular disease or physiological conditions, such as streptozotocin (STZ)-induced diabetic (STZ) mice, are appropriate targets for expressing variants of FGF19 and/or FGF21, fusions/chimeric sequences (or variant) thereof, such as a chimeric peptide sequence including all or a portion of FGF19, or including all or a portion of FGF21, as set forth herein. Thus, in certain embodiments, there are provided non-human transgenic animals that produce a variant of FGF19 and/or FGF21, or a fusion/chimeric sequence (or variant) thereof, such as a chimeric peptide sequence including all or a portion of FGF19, or including all or a portion of FGF21, the production of which is not naturally occurring in the animal which is conferred by a transgene present in somatic or germ cells of the animal.

The term "transgenic animal" refers to an animal whose somatic or germ line cells bear genetic information received, directly or indirectly, by deliberate genetic manipulation at the subcellular level, such as by microinjection or infection with recombinant virus. The term "transgenic" further includes cells or tissues (i.e., "transgenic cell," "transgenic tissue") obtained from a transgenic animal genetically manipulated as described herein. In the present context, a "transgenic animal" does not encompass animals produced by classical crossbreeding or in vitro fertilization, but rather denotes animals in which one or more cells receive a nucleic acid molecule. Transgenic animals provided herein can be either heterozygous or homozygous with respect to the transgene. Methods for producing transgenic animals, including mice, sheep, pigs and frogs, are well known in the art (see, e.g., U.S. Pat. Nos. 5,721,367, 5,695,977, 5,650,298, and 5,614,396) and, as such, are additionally included.

Peptide sequences, nucleic acids encoding peptide sequences, vectors and transformed host cells expressing peptide sequences include isolated and purified forms. The term "isolated," when used as a modifier of a composition provided herein, means that the composition is separated, substantially, completely, or at least in part, from one or more components in an environment. Generally, compositions that exist in nature, when isolated, are substantially free of one or more materials with which they normally associate with in nature, for example, one or more protein, nucleic acid, lipid, carbohydrate or cell membrane. The term "isolated" does not exclude alternative physical forms of the composition, such as variants, modifications or derivatized forms, fusions and chimeras, multimers/oligomers, etc., or forms expressed in host cells. The term "isolated" also does not exclude forms (e.g., pharmaceutical compositions, combination compositions, etc.) in which there are combinations therein, any one of which is produced by the hand of man. An "isolated" composition can also be "purified" when free of some, a substantial number of, or most or all of one or more other materials, such as a contaminant or an undesired substance or material.

As used herein, the term "recombinant," when used as a modifier of peptide sequences, nucleic acids encoding peptide sequences, etc., means that the compositions have been manipulated (i.e., engineered) in a fashion that generally does not occur in nature (e.g., in vitro). A particular example of a recombinant peptide would be where a peptide sequence provided herein is expressed by a cell transfected with a nucleic acid encoding the peptide sequence. A particular example of a recombinant nucleic acid would be a nucleic acid (e.g., genomic or cDNA) encoding a peptide sequence cloned into a plasmid, with or without 5', 3' or intron regions that the gene is normally contiguous within the genome of the organism. Another example of a recombinant peptide or nucleic acid is a hybrid or fusion sequence, such as a chimeric peptide sequence comprising a portion of FGF19 and a portion of FGF21.

In accordance with the methods provided herein, there are provided compositions and mixtures of peptide sequences provided herein, including subsequences, variants and modified forms of the exemplified peptide sequences (including the FGF19 and FGF21 variants and subsequences listed in Tables 1-11 and the Sequence Listing, and the FGF19/FGF21 fusions and chimeras listed in Tables 1-11 and the Sequence Listing). In one embodiment, a mixture includes one or more peptide sequences and a pharmaceutically acceptable carrier or excipient. In another embodiment, a mixture includes one or more peptide sequences and an adjunct drug or therapeutic agent, such as a bile acid homeostasis modulating or anti-diabetic, or glucose lowering, drug or therapeutic agent. Combinations, such as one or more peptide sequences in a pharmaceutically acceptable carrier or excipient, with one or more of a bile acid homeostasis modulating or a treatment for a bile acid-related or associated disorder, or anti-diabetic, or glucose lowering drug or therapeutic agent are also provided. Such combinations of a peptide sequence provided herein with another drug or agent, such as a bile acid homeostasis modulating or acid related disorder treating, or glucose lowering drug or therapeutic agent, for example are useful in accordance with the methods and uses provided herein, for example, for treatment of a subject.

Combinations also include incorporation of peptide sequences or nucleic acids provided herein into particles or a polymeric substances, such as polyesters, carbohydrates, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers; entrapment in microcapsules prepared by coacervation techniques or by interfacial polymerization, for example, by the use of hydroxymethylcellulose or gelatin-microcapsules, or poly (methylmethacrolate) microcapsules, respectively; incorporation in colloid drug delivery and dispersion systems such as macromolecule complexes, nano-capsules, non-encapsulated nanoparticles, microspheres, beads, and lipid-based systems (e.g., N-fatty acyl groups such as N-lauroyl, N-oleoyl, fatty amines such as dodecyl amine, oleoyl amine, etc., see U.S. Pat. No. 6,638,513), including oil-in-water emulsions, micelles, mixed micelles, and liposomes, for example. Methods of preparing liposomes are described in, for example, U.S. Pat. Nos. 4,235,871, 4,501,728, and 4,837,028. Methods of encapsulated-free controlled release using nanoparticles are described, for example, in Pakulska et al., *Science Advances* 2(5): e1600519 (2016). Methods for preparation of the above-mentioned formulations will be apparent to those skilled in the art.

The peptides provided herein including subsequences, variants and modified forms of the exemplified peptide sequences (including the FGF19 and FGF21 variants and subsequences listed in Tables 1-11 and the Sequence Listing, and the FGF19/FGF21 fusions and chimeras listed in Tables 1-11 and the Sequence Listing) as set forth herein can be used to modulate glucose metabolism and facilitate transport of glucose from the blood to key metabolic organs such as muscle, liver and fat. Such peptide sequences can be produced in amounts sufficient or effective to restore glucose tolerance and/or to improve or provide normal glucose homeostasis.

In case of conflict, the specification, including definitions, will control. As used herein and in the appended claims, the singular forms "a," "an," and "the" include plural referents unless the context clearly dictates otherwise. Thus, for example, reference to "a peptide sequence" or "a treatment," includes a plurality of such sequences, treatments, and so forth. It is further noted that the claims can be drafted to exclude any optional element. As such, this statement is intended to serve as antecedent basis for use of such exclusive terminology such as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges, and are also encompassed within the invention, subject to any specifically excluded limit in the stated range. Where the stated range includes one or both of the limits, ranges excluding either or both of those included limits are also included in the invention.

As used herein, numerical values are often presented in a range format throughout this document. The use of a range format is merely for convenience and brevity and should not be construed as an inflexible limitation on the scope of the invention unless the context clearly indicates otherwise. Accordingly, the use of a range expressly includes all possible subranges, all individual numerical values within that range, and all numerical values or numerical ranges including integers within such ranges and fractions of the values or the integers within ranges, unless the context clearly indicates otherwise. This construction applies regardless of the breadth of the range and in all contexts throughout this patent document. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100% also includes 91%, 92%, 93%, 94%, 95%, 96%, 97%, etc., as well as 91.1%, 91.2%, 91.3%, 91.4%, 91.5%, etc., 92.1%, 92.2%, 92.3%, 92.4%, 92.5%, etc., and so forth. In addition, reference to a range of 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250 includes 1, 2, 3, 4, 5, 6, 7, 8, 9, 10, 11, 12, 13, 14, 15, 16, 17, 18, 19, 20, etc.

In a further example, reference to a range of 25-250, 250-500, 500-1000, 1000-2500, 2500-5000, 5000-25,000, or 5000-50,000 includes any numerical value or range within or encompassing such values, e.g., 25, 26, 27, 28, 29 . . . 250, 251, 252, 253, 254 . . . 500, 501, 502, 503, 504 . . . , etc. The use of a series of ranges includes combinations of the upper and lower ranges to provide another range. This construction applies regardless of the breadth of the range and in all contexts throughout this patent document. Thus, for example, reference to a series of ranges such as 5-10, 10-20, 20-30, 30-40, 40-50, 50-75, 75-100, 100-150, includes ranges such as 5-20, 5-30, 5-40, 5-50, 5-75, 5-100, 5-150, and 10-30, 10-40, 10-50, 10-75, 10-100, 10-150, and 20-40, 20-50, 20-75, 20-100, 20-150, and so forth.

For the sake of conciseness, certain abbreviations are used herein. One example is the single letter abbreviation to represent amino acid residues. The amino acids and their corresponding three letter and single letter abbreviations are as follows:

| | | |
|---|---|---|
| alanine | Ala | (A) |
| arginine | Arg | (R) |
| asparagine | Asn | (N) |
| aspartic acid | Asp | (D) |
| cysteine | Cys | (C) |
| glutamic acid | Glu | (E) |
| glutamine | Gln | (Q) |
| glycine | Gly | (G) |
| histidine | His | (H) |
| isoleucine | Ile | (I) |
| leucine | Leu | (L) |
| lysine | Lys | (K) |
| methionine | Met | (M) |
| phenylalanine | Phe | (F) |
| proline | Pro | (P) |
| serine | Ser | (S) |
| threonine | Thr | (T) |
| tryptophan | Trp | (W) |
| tyrosine | Tyr | (Y) |
| valine | Val | (V) |

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

Particular embodiments of this invention are described herein, including the best mode known to the inventors for carrying out the invention. Upon reading the foregoing description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference in its entirety as if each individual publication or patent application were specifically and individually indicated to be incorporated by reference. The publications discussed herein are provided solely for their disclosure prior to the filing date of the present application. Nothing herein is to be construed as an admission that the present invention is not entitled to antedate such publication by virtue of prior invention. Further, the dates of publication provided can be different from the actual publication dates which can need to be independently confirmed.

A number of embodiments of the invention have been described. Nevertheless, it will be understood that various modifications may be made without departing from the spirit and scope of the invention. Accordingly, the descriptions in the Experimental section are intended to illustrate but not limit the scope of invention described in the claims.

5. EXPERIMENTAL

5.1 Example 1

The following is a description of various methods and materials used in the studies herein.

Animals.

db/db mice were purchased from The Jackson Laboratory (Bar Harbor, Me.), Mice were kept in accordance with welfare guidelines under controlled light (12 hr light and 12 hr dark cycle, dark 6:30 pm-6:30 am), temperature (22±4° C.) and humidity (50%±20%) conditions. Mice had free access to water (autoclaved distilled water) and were fed ad libitum on a commercial diet (Harlan Laboratories, Indianapolis, Ind., Irradiated 2018 Teklad Global 18% Protein Rodent Diet) containing 17 kcal % fat, 23 kcal % protein and 60 kcal % carbohydrate. All animal studies were approved by the NGM Institutional Animal Care and Use Committee.

DNA and Amino Acid Sequences.

cDNA of ORF encoding human FGF19 (*Homo sapiens* FGF19, GenBank Accession No. NM_005117.2) variants. Protein sequence encoded by the cDNA (GenBank Accession No. NP_005108.1).

PCR.

FGF19 ORF was amplified with polymerase chain reaction (PCR) using recombinant DNA (cDNA) prepared from human small intestinal tissue. PCR reagents kits with Phusion® high-fidelity DNA polymerase were purchased from New England BioLabs (F-530L, Ipswich, Mass.). The following primers were used: forward PCR primer: 5' CCGACTAGTCACCatgcggagcgggtgtgtgg (SEQ ID NO:136) and reverse PCR primer: 5' ATAAGAATGCGGC-CGCTTACTTCTCAAAGCTGGGACTCCTC (SEQ ID NO:137). Amplified DNA fragment was digested with restriction enzymes Spe I and Not I (the restriction sites were included in the 5' or 3' PCR primers, respectively) and was then ligated with AAV transgene vectors that had been digested with the same restriction enzymes. The vector used for expression contained a selectable marker and an expression cassette composed of a strong eukaryotic promoter 5' of a site for insertion of the cloned coding sequence, followed by a 3' untranslated region and bovine growth hormone polyadenylation tail. The expression construct is also flanked by internal terminal repeats at the 5' and 3' ends.

Cyp7a1 Repression Assay in Primary Human Hepatocytes.

Primary human hepatocytes were plated on collagen coated plates (Becton Dickinson Biosciences) in Williams E media (Invitrogen) supplemented with 100 nM dexamethasone (Sigma) and 0.25 mg/ml MatriGel™ (Becton Dickinson Biosciences). Cells were treated with FGF19 or variants at 37° C. for 6 hours. Cyp7a1 expression was evaluated in triplicate by quantitative RT-PCR (TaqMane ABI PRISM 7700, Applied Biosystems) and normalized to GAPDH expression.

Cyp7a1 In Vivo Repression Assay.

Nine-week-old male db/db mice (Jackson Laboratories) were injected intraperitoneally with recombinant proteins FGF19 or FGF21 at 0.1 mg/kg, 1 mg/kg, and 10 mg/kg. Animals were euthanized 5 hours post-injection. Liver was harvested and homogenized in TRIzol® reagent (Invitrogen). Total RNA was extracted and treated with DNase (Ambion) followed by quantitative RT-PCR analysis and normalized to GAPDH expression.

Production and Purification of AAV.

AAV293 cells (obtained from Agilent Technologies, Santa Clara, Calif.) were cultured in Dulbeco's Modification of Eagle's Medium (DMEM, Mediatech, Inc. Manassas, Va.) supplemented with 10% fetal bovine serum and 1× antibiotic-antimycotic solution (Mediatech, Inc. Manassas, Va.). The cells were plated at 50% density on day 1 in 150 mm cell culture plates and transfected on day 2, using calcium phosphate precipitation method with the following 3 plasmids (20 µg/plate of each): AAV transgene plasmid, pHelper™ plasmids (Agilent Technologies) and AAV2/9 plasmid (Gao et al., *J. Virol.* 78:6381 (2004)). Forty-eight (48) hours after transfection, the cells were scraped off the plates, pelleted by centrifugation at 3000×g and resuspended in buffer containing 20 mM Tris pH 8.5, 100 mM NaCl and 1 mM $MgCl_2$. The suspension was frozen in an alcohol dry ice bath and was then thawed in 37° C. water bath. The freeze and thaw cycles were repeated three times; Benzonase® (Sigma-aldrich, St. Louis, Mo.) was added to 50 units/ml; deoxycholate was added to a final concentration of 0.25%. After an incubation at 37° C. for 30 min, cell debris was pelleted by centrifugation at 5000×g for 20 min. Viral particles in the supernatant were purified using a discontinued iodixanal (Sigma-aldrich, St. Louis, Mo.) gradient as previously described (Zolotukhin S. et al (1999) Gene Ther. 6:973). The viral stock was concentrated using Vivaspin® 20 (MW cutoff 100,000 Dalton, Sartorius Stedim Biotech, Aubagne, France) and re-suspended in phosphate-buffered saline (PBS) with 10% glycerol and stored at −80° C. To determine the viral genome copy number, 2 µl of viral stock were incubated in 6 µl of solution containing 50 units/ml Benzonase®, 50 mM Tris-HCl pH 7.5, 10 mM $MgCl_2$ and 10 mM $CaCl_2$ at 37° C. for 30 minutes.

Afterwards, 15 µl of the solution containing 2 mg/ml of Proteinase K, 0.5% SDS and 25 mM EDTA were added and the mixture was incubated for additional 20 min at 55° C. to release viral DNA. Viral DNA was cleaned with mini DNeasy® Kit (Qiagen, Valencia, Calif.) and eluted with 40 µl of water. Viral genome copy (GC) was determined by using quantitative PCR.

Viral stock was diluted with PBS to desirable GC/ml. Viral working solution (200 µl) was delivered into mice via tail vein injection.

Hepatocellular Carcinoma (HCC) Assay.

Liver specimens were harvested from db/db mice 24 weeks after AAV injection. HCC scores were recorded as the number of HCC nodules on the surface of the entire liver from variants-injected mice divided by the number of HCC nodules from wild-type FGF19-injected mice.

Serum FGF19/FGF21/Variants Exposure Level Assay.

Whole blood (about 50 µl/mouse) from mouse tail snips was collected into plain capillary tubes (BD Clay Adams SurePrep™, Becton Dickenson and Co. Sparks, Md.). Serum and blood cells were separated by spinning the tubes in an Autocrit™ Ultra 3 (Becton Dickinson and Co. Sparks, Md.). FGF19, FGF21, and variant exposure levels in serum was determined using EIA kits (Biovendor) by following the manufacturer's instructions.

FGFR4 Binding and Activity Assays.

Solid phase ELISA (binding) and ERK phosphorylation assay can be performed using purified recombinant proteins. FGFR binding assay can be conducted using solid phase ELISA. Briefly, a 96-well plate can be coated with 2 µg/ml anti-hFc antibody and can be incubated with 1 µg/ml FGFR1-hFc or FGFR4-hFc. Binding to FGF19 variants in the presence of 1 µg/ml soluble β-klotho and 20 µg/ml heparin can be detected by biotinylated anti-FGF19 antibodies (0.2 µg/mL), followed by streptavidin-HRP incubation (100 ng/mL). For FGFR4 activation assay, Hep3B cells can be stimulated with FGF19 variants for 10 minutes at 37° C., then can be immediately lysed and assayed for ERK phosphorylation using a commercially available kit from Cis-Bio.

5.2 Example 2

In order to confirm that FGF19 variants such as those set forth herein repress cyp7a1 expression, inhibition of cyp7a1 expression by wild-type FGF19 was determined following administration of various concentrations. The effects of FGF21 were assessed in a comparable manner.

Briefly, at time 0, db/db mice were dosed intraperitoneally with either recombinant FGF19 (0.1 mg/kg; 1 mg/kg; 10 mg/kg) or recombinant FGF21 (0.1 mg/kg; 1 mg/kg; 10 mg/kg). Five hours after dosing, livers were harvested, RNA was extracted, and cyp7a1 expression was determined by real-time PCR (QPCR) using GADPH as a normalization control. In each group of mice, n=3, and cyp7a1 expression values for the various FGF19 and FGF21 concentrations were compared to mice dosed with PBS vehicle control.

As set forth in FIG. 1, FGF19 dramatically decreased cyp7a1 expression in a concentration-dependent manner. Although administration of FGF21 caused a reduction of cyp7a1 expression, the effect was demonstrably less than that observed with FGF19.

Figures 2A, 2B, 2C, 2D:
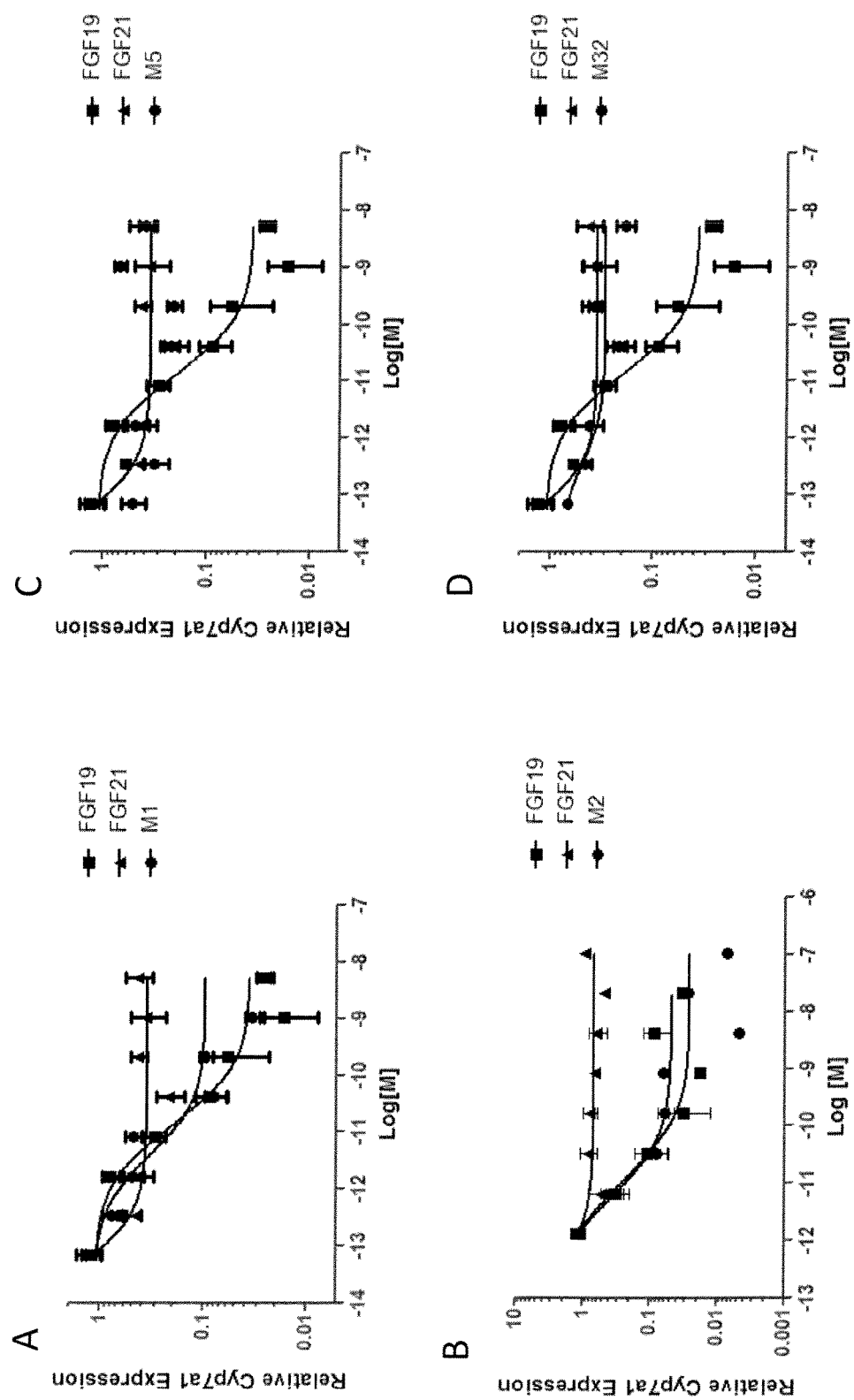

The effect of variant M70 on cyp7a1 expression in human primary hepatocytes was compared to that of FGF19. As noted in FIG. 2, variant M70 repressed cyp7a1 expression in an amount comparable to that of FGF19.

5.3 Example 3

Figures 3A, 3B, 3C, 3D:
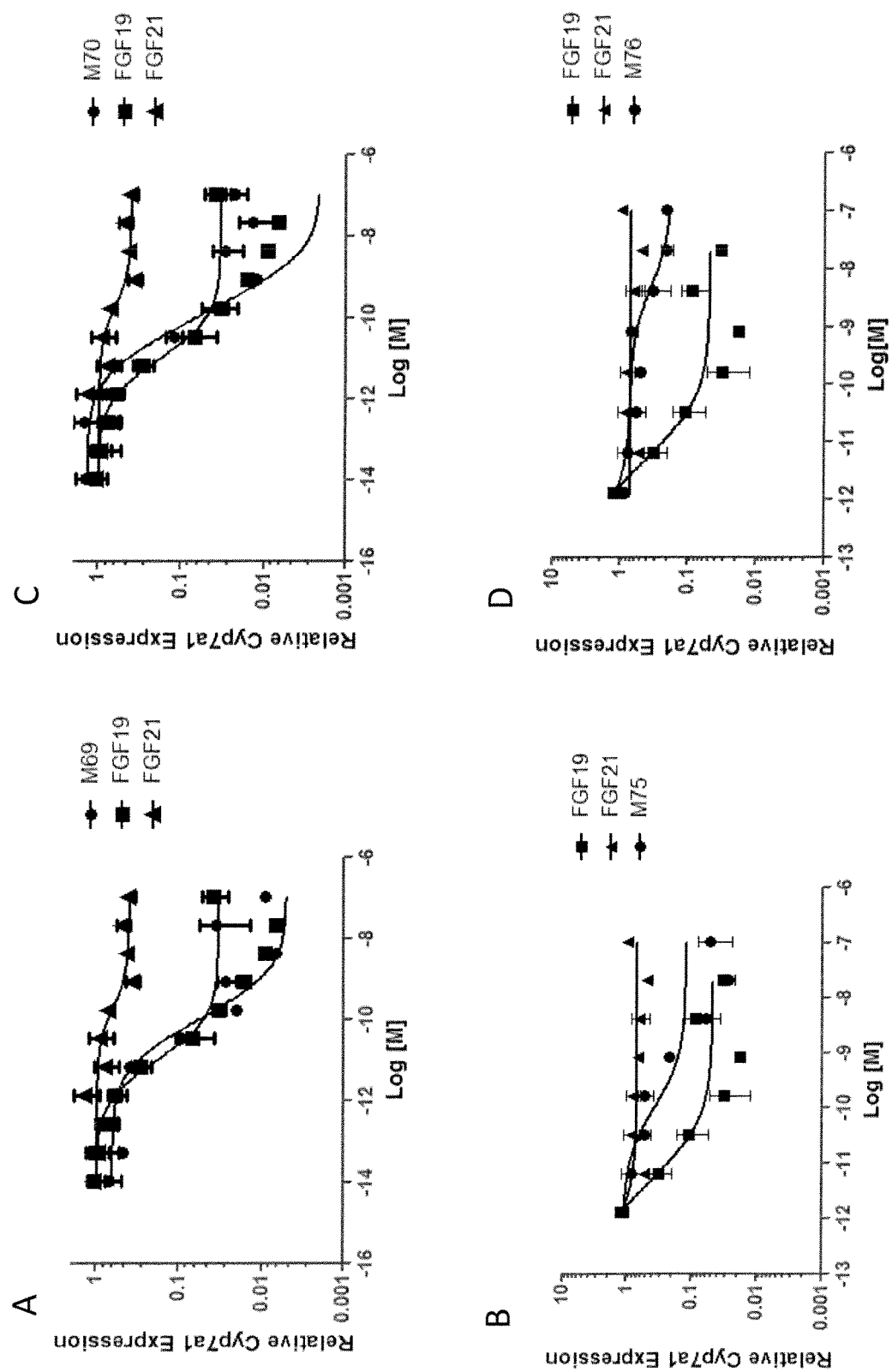
Figures 4A, 4B, 4C, 4D:
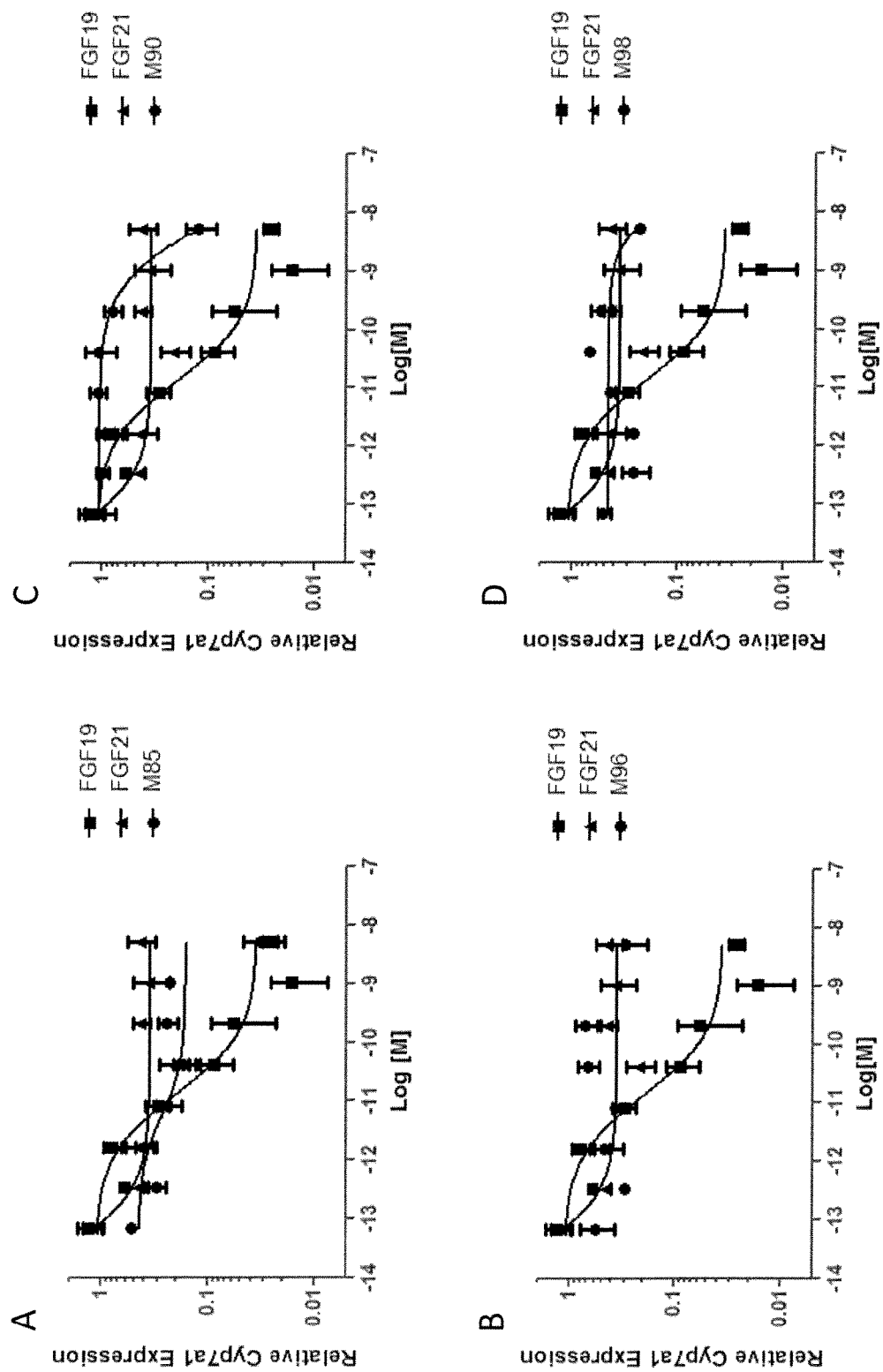

Using the assays described above, repression of cyp7a1 in primary human hepatocytes was determined for a number of FGF19 variants. As indicated in FIG. 3-FIG. 5, several variants (e.g., M1, M2, etc.) exhibited strong cyp7a1 repression.

To evaluate effects of some additional FGF19 variants on Cyp7a1 repression, the in vitro cell-based assay (primary human hepatocyte) and the in vivo assay (protein dosing in db/db mice) were utilized in which the variants were compared with saline-treated controls. FIG. 5 sets forth the results ($IC_{50}$ and Cyp7a1(%)) in tabular form. While most FGF19 variants that were evaluated exhibited Cyp7a1-inhibiting activity, a few variants (e.g., M90, M96, M98, M5 and M32) no longer repressed Cyp7a1.

FGF19 variants that retain Cyp7a1 repression activity can be further evaluated in the HCC assay (or other relevant assay or model) described above to identify variants that might be useful for modulating bile acid metabolism and/or for treating bile acid-related diseases (e.g., bile acid diarrhea and primary biliary cirrhosis) without causing induction of HCC. The figures set forth data for variants that were evaluated in the HCC assay.

5.4 Example 4

The following is a data summary of 25 additional variant peptides analyzed for lipid elevating activity and tumorigenesis. The data clearly show a positive correlation between lipid elevation and tumorigenesis, as determined by HCC formation in db/db mice.

The Tables summarize different variant peptides. Such exemplified variant peptides have FGF19 C-terminal sequence: PHGLSSCFLRIRADGVVDCARGQSAHSL-LEIKAVALRTVAIKGVHSVRYLCMGADGKMQGL LQYSEEDCAFEEEIRPDGYNVYRSEKHRLPVSLS-SAKQRQLYKNRGFLPLSHFLPMLPMVPE EPEDL-RGHLESDMFSSPLETDSMDPFGLVTGLEAVRSPSFEK (SEQ ID NO:188) at the C-terminal portion, e.g., following the "TSG" amino acid residues. Notably, variant peptides (7 total, including M5) that did not cause a statistically significant elevation of lipids did not induce HCC formation. In contrast, all variant peptides (17 total) that caused a statistically significant elevation of lipids also caused HCC formation in mice. This data indicates that there is a strong positive correlation between lipid elevating activity and HCC formation. Accordingly, lipid elevating activity can be used as an indicator and/or predictor of HCC formation in animals.

TABLE 2

Elevated Triglyceride and Cholesterol in db/db Mice Appears to Positively Correlate With HCC Formation (see SEQ ID NOs: 99, 5 and 74 to 81).

|  | N-terminal Domain | SEQ ID NO. | Core | SEQ ID NO. | Lipid Elevation | HCC Formation |
|---|---|---|---|---|---|---|
| FGF19 | RPLAFSDAGPHVHYGWGDPI | 99 (aa 1-20) | RLRHLYTSG | 185 | + | + |
| FGF21 | HPIPDSSPLLQ--FGGQV | 100 (aa 1-16) | RQRYLYTDD | 186 | - | - |
| M5 | R-HPIPDSSPLLQ--FGGQV | 5 (aa 1-17) | RLRHLYTSG | 185 | - | - |
| M74 | R----------DAGPHVHYGWGDPI | 74 (aa 1-15) | RLRHLYTSG | 185 | + | + |
| M75 | R--------------VHYGWGDPI | 75 (aa 1-10) | RLRHLYTSG | 185 | - | - |
| M76 | R-------------------GDPI | 76 (aa 1-5) | RLRHLYTSG | 185 | - | - |
| M77 | R--------------------- | 77 (a 1) | RLRHLYTSG | 185 | - | - |
| M78 | R----------AGPHVHYGWGDPI | 78 (aa 1-14) | RLRHLYTSG | 185 | + | + |
| M79 | R-----------GPHVHYGWGDPI | 79 (aa 1-13) | RLRHLYTSG | 185 | + | + |
| M80 | R------------PHVHYGWGDPI | 80 (aa 1-12) | RLRHLYTSG | 185 | - | - |
| M81 | R-------------HVHYGWGDPI | 81 (aa 1-11) | RLRHLYTSG | 185 | - | - |

TABLE 3

Elevated Triglyceride and Cholesterol in db/db Mice Appears to Positively Correlate with HCC Formation (see SEQ ID NOs: 99, 100 and 82 to 98).

| | N-terminal Domain | SEQ ID NO. | Core | SEQ ID NO. | Lipid Elevation | HCC Formation |
|---|---|---|---|---|---|---|
| FGF19 | RPLAFSDAGPHVHYGWGDPI | 99 (aa 1-20) | RLRHLYTSG | 185 | + | + |
| FGF21 | HPIPDSSPLLQ--FGGQV | 100 (aa 1-16) | RQRYLYTDD | 186 | − | − |
| M82 | RPLAFSAAGPHVHYGWGDPI | 82 (aa 1-20) | RLRHLYTSG | 185 | + | + |
| M83 | RPLAFSDAAPHVHYGWGDPI | 83 (aa 1-20) | RLRHLYTSG | 185 | +/− | +/ |
| M84 | RPLAFSDAGAHVHYGWGDPI | 84 (aa 1-20) | RLRHLYTSG | 185 | +/− | +/ |
| M85 | RPLAFSDAGPHVHYGAGDPI | 85 (aa 1-20) | RLRHLYTSG | 185 | − | − |
| M86 | RPLAFSDAGPHVHYGWGAPI | 86 (aa 1-20) | RLRHLYTSG | 185 | + | + |
| M87 | RPLAFSDAGPHVHYGWGDAI | 87 (aa 1-20) | RLRHLYTSG | 185 | + | + |

TABLE 4

Elevated Triglyceride and Cholesterol in db/db Mice Appears to Positively Correlate with HCC Formation (see SEQ ID Nos: 99, 100 and 88 to 98)

| | N-terminal Domain | Core | SEQ ID NO | Lipid Elevation | HCC Formation |
|---|---|---|---|---|---|
| FGF19 | RPLAFSDAGPHVHYGWGDPI | RLRHLYTSG | 99 (aa 1-29) | + | + |
| FGF21 | HPIPDSSPLLQ--FGGQV | RQRYLYTDD | 100 (aa 1-25) | − | − |
| H31A/S141A(M88) | | FGF19 | | + | + |
| H31A/H142A(M89) | | FGF19 | | + | + |
| K127A/R129A(M90) | | FGF19 | | + | + |
| K127A/S141A(M91) | | FGF19 | | + | + |
| K127A/H142A(M92) | | FGF19 | | + | + |
| R129A/S141A(M93) | | FGF19 | | + | + |
| S141A/H142A(M94) | | FGF19 | | + | + |
| K127A/H142A(M95) | | FGF19 | | + | + |
| K127A/R129A/S141A(M96) | | FGF19 | | + | + |
| K127A/R129A/H142A(M97) | | FGF19 | | + | + |
| K127A/R129A/H142A(M98) | | FGF19 | | + | + |

M88 (H31A/S141A):
(SEQ ID NO: 88)
RPLAFSDAGPHVHYGWGDPIRLRHLYTSGPAGLSSCFLRIRADGVVDCAR
GQSAHSLLEIKAVALRTVAIKGVHSVRYLCMGADGKMQGLLQYSEEDCAF
EEEIRPDGYNVYRSEKHRLPVSLSSAKQRQLYKNRGFLPLAHFLPMLPMV
PEEPEDLRGHLESDMFSSPLETDSMDPFGLVTGLEAVRSPSFEK

M89 (H31A/H142A):
(SEQ ID NO: 89)
RPLAFSDAGPHVHYGWGDPIRLRHLYTSGPAGLSSCFLRIRADGVVDCAR
GQSAHSLLEIKAVALRTVAIKGVHSVRYLCMGADGKMQGLLQYSEEDCAF
EEEIRPDGYNVYRSEKHRLPVSLSSAKQRQLYKNRGFLPLSAFLPMLPMV
PEEPEDLRGHLESDMFSSPLETDSMDPFGLVTGLEAVRSPSFEK

M90 (K127A/R129A):
(SEQ ID NO: 90)
RPLAFSDAGPHVHYGWGDPIRLRHLYTSGPHGLSSCFLRIRADGVVDCAR
GQSAHSLLEIKAVALRTVAIKGVHSVRYLCMGADGKMQGLLQYSEEDCAF
EEEIRPDGYNVYRSEKHRLPVSLSSAAQAQLYKNRGFLPLSHFLPMLPMV
PEEPEDLRGHLESDMFSSPLETDSMDPFGLVTGLEAVRSPSFEK

M91 (K127A/S141A):
(SEQ ID NO: 91)
RPLAFSDAGPHVHYGWGDPIRLRHLYTSGPHGLSSCFLRIRADGVVDCAR
GQSAHSLLEIKAVALRTVAIKGVHSVRYLCMGADGKMQGLLQYSEEDCAF
EEEIRPDGYNVYRSEKHRLPVSLSSAAQRQLYKNRGFLPLAHFLPMLPMV
PEEPEDLRGHLESDMFSSPLETDSMDPFGLVTGLEAVRSPSFEK

M92 (K127A/H142A):
(SEQ ID NO: 92)
RPLAFSDAGPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEIRPDGYNVYRSEKHRLPVSLSSAAQRQLYKNRGFLPLSAFLPMLPMV

PEEPEDLRGHLESDMFSSPLETDSMDPFGLVTGLEAVRSPSFEK

M93 (R129A/S141A):
(SEQ ID NO: 93)
RPLAFSDAGPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEIRPDGYNVYRSEKHRLPVSLSSAKQAQLYKNRGFLPLAHFLPMLPMV

PEEPEDLRGHLESDMFSSPLETDSMDPFGLVTGLEAVRSPSFEK

M94 (S141A/H142A):
(SEQ ID NO: 94)
RPLAFSDAGPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEIRPDGYNVYRSEKHRLPVSLSSAKQRQLYKNRGFLPLAAFLPMLPMV

PEEPEDLRGHLESDMFSSPLETDSMDPFGLVTGLEAVRSPSFEK

M95 (K127A/H142A):
(SEQ ID NO: 95)
RPLAFSDAGPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEIRPDGYNVYRSEKHRLPVSLSSAAQRQLYKNRGFLPLSAFLPMLPMV

PEEPEDLRGHLESDMFSSPLETDSMDPFGLVTGLEAVRSPSFEK

M96 (K127A/R129A/S141A):
(SEQ ID NO: 96)
RPLAFSDAGPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEIRPDGYNVYRSEKHRLPVSLSSAAQAQLYKNRGFLPLAHFLPMLPMV

PEEPEDLRGHLESDMFSSPLETDSMDPFGLVTGLEAVRSPSFEK

M97 (K127A/R129A/H142A):
(SEQ ID NO: 97)
RPLAFSDAGPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEIRPDGYNVYRSEKHRLPVSLSSAAQAQLYKNRGFLPLSAFLPMLPMV

PEEPEDLRGHLESDMFSSPLETDSMDPFGLVTGLEAVRSPSFEK

M98 (K127A/R129A/S141A/H142A):
(SEQ ID NO: 98)
RPLAFSDAGPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEIRPDGYNVYRSEKHRLPVSLSSAAQAQLYKNRGFLPLAAFLPMLPMV

PEEPEDLRGHLESDMFSSPLETDSMDPFGLVTGLEAVRSPSFEK.

5.5 Example 5

The following is a data summary of additional FGF19 variant peptides analyzed for glucose lowering activity and lipid elevating activity.

Table 5 illustrates the peptide "core sequences" of 35 additional FGF19 variants, denoted M5 to M40. Such exemplified variant peptides have FGF19 C-terminal sequence, PHGLSSCFLRIRADGVVDCARGQSAHSLLEIKAVALRTVAIKGVHSVRYLCMGADGKMQGL LQYSEEDCAFEEEIRPDGYNVYRSEKHRLPVSLSSAKQRQLYKNRGFLPLSHFLPMLPMVPE EPEDLRGHLESDMFSSPLETDSMDPFGLVTGLEAVRSPSFEK (SEQ ID NO: 188) at the C-terminal portion, e.g., following the "TSG" amino acid residues of the core sequence. The data clearly show that variants M6, M7, M8, mM38 and M39 have the desired characteristics of glucose lowering activity and not statistically significant lipid elevating activity in db/db mice.

TABLE 5

Additional Variants and Fine Mapping of the N-terminal Domain (see SEQ ID NOs: 99, 100, and 5 to 40)

|  | N-terminal Domain | SEQ ID NO of N-term-Domain | Core | SEQ ID NO. | Glucose Lowering | Lipid Elevation |
|---|---|---|---|---|---|---|
| FGF19 | RPLAFSDAGPHVHYGWGDPI | 99 (aa 1-20) | RLRHLYTSG | 185 | + | + |
| FGF21 | -HPIPDSSPLLQ--FGGQV | 100 (aa 1-16) | RQRYLYTDD | 186 | + | - |
| M5 | RHPIPDSSPLLQ--FGGQV | 5 (aa 1-17) | RLRHLYTSG | 185 | + | - |
| M6 | R----DSSPLLQ--FGGQV | 6 (aa 1-18) | RLRHLYTSG | 185 | + | - |
| M7 | RPLAFSDSSPLLQ--FGGQV | 7 (aa 1-18) | RLRHLYTSG | 185 | + | - |
| M8 | R-HPIPDSSPLLQ--WGDPI | 8 (aa 1-17) | RLRHLYTSG | 185 | + | - |
| M9 | R-HPIPDSSPLLQFGWGDPI | 9 (aa 1-19) | RLRHLYTSG | 185 | + | + |
| M10 | R-HPIPDSSPHVHYGWGDPI | 10 (aa 1-19) | RLRHLYTSG | 185 | - | + |
| M11 | RPLAFSDAGPLLQ--WGDPI | 11 (aa 1-18) | RLRHLYTSG | 185 | N/D | N/D |
| M12 | RPLAFSDAGPLLQFGWGDPI | 12 (aa 1-20) | RLRHLYTSG | 185 | - | + |
| M13 | RPLAFSDAGPLLQ--FGGQV | 13 (aa 1-18) | RLRHLYTSG | 185 | - | - |
| M14 | R-HPIPDSSPHVHYG--GQV | 14 (aa 1-17) | RLRHLYTSG | 185 | - | - |

TABLE 5-continued

Additional Variants and Fine Mapping of the N-terminal Domain (see SEQ ID NOs: 99, 100, and 5 to 40)

| | N-terminal Domain | SEQ ID NO of N-term-Domain | Core | SEQ ID NO. | Glucose Lowering | Lipid Elevation |
|---|---|---|---|---|---|---|
| M15 | RPLAFSDAGPHVHYG--GQV | 15 (aa 1-18) | RLRHLYTSG | 185 | + | + |
| M16 | RPLAFSDAGPHVH--WGDPI | 16 (aa 1-18) | RLRHLYTSG | 185 | N/D | N/D |
| M17 | RPLAFSDAGPHV--GWGDPI | 17 (aa 1-18) | RLRHLYTSG | 185 | N/D | N/D |
| M18 | RPLAFSDAGPH--YGWGDPI | 18 (aa 1-18) | RLRHLYTSG | 185 | N/D | N/D |
| M19 | RPLAFSDAGP-V-YGWGDPI | 19 (aa 1-18) | RLRHLYTSG | 185 | N/D | N/D |
| M20 | RPLAFSDAGP-VH-GWGDPI | 20 (aa 1-18) | RLRHLYTSG | 185 | N/D | N/D |
| M21 | RPLAFSDAGP-VHY-WGDPI | 21 (aa 1-18) | RLRHLYTSG | 185 | N/D | N/D |
| M22 | RPLAFSDAGPHVH-GWGDPI | 22 (aa 1-18) | RLRHLYTSG | 185 | N/D | N/D |
| M23 | RPLAFSDAGPH-H-GWGDPI | 23 (aa 1-18) | RLRHLYTSG | 185 | N/D | N/D |
| M24 | RPLAFSDAGPH-HY-WGDPI | 24 (aa 1-18) | RLRHLYTSG | 185 | N/D | N/D |
| M25 | RPLAFSDAGPHV-Y-WGDPI | 25 (aa 1-18) | RLRHLYTSG | 185 | N/D | N/D |
| M26 | RPLAFSDSSPLVH--WGDPI | 26 (aa 1-18) | RLRHLYTSG | 185 | N/D | N/D |
| M27 | RPLAFSDSSPHVH--WGDPI | 27 (aa 1-18) | RLRHLYTSG | 185 | N/D | N/D |
| M28 | RPLAFSDAPHV----WGDPI | 28 (aa 1-16) | RLRHLYTSG | 185 | N/D | N/D |
| M29 | RPLAFSDAGPHVHY-WGDPI | 29 (aa 1-19) | RLRHLYTSG | 185 | N/D | N/D |
| M30 | RPLAFSDAGPHVHYAWGDPI | 30 (aa 1-20) | RLRHLYTSG | 185 | N/D | N/D |
| M31 | R-HPIPDSSPLLQ--FGAQV | 31 (aa 1-17) | RLRHLYTSG | 185 | +/− | − |
| M32 | R-HPIPDSSPLLQ--FGIYQV | 32 (aa 1-18) | RLRHLYTSG | 185 | − | − |
| M33 | R-HPIPDSSPLLQ--FGGQV | 33 (aa 1-17) | RLRHLYTSG | 185 | − | − |
| M34 | R-HPIPDSSPLLQ--FGGAV | 34 (aa 1-17) | RLRHLYTSG | 185 | +/− | − |
| M35 | R-HPIPDSSPLLQ--FGGEV | 35 (aa 1-17) | RLRHLYTSG | 185 | +/− | +/ |
| M36 | R-HPIPDSSPLLQ--FGGQV | 36 (aa 1-17) | RLRHLYTSG | 185 | +/− | − |
| M37 | R-HPIPDSSPLLQ--FGGUA | 37 (aa 1-17) | RLRHLYTSG | 185 | − | − |
| M38 | R-HPIPDSSPLLQ--FGGQT | 38 (aa 1-17) | RLRHLYTSG | 185 | + | − |
| M39 | R-HPIPDSSPLLQ--FGGQT | 39 (aa 1-17) | RLRHLYTSG | 185 | + | − |
| M40 | R-HPIPDSSPLLQFGWGQP | 40 (aa 1-16) | RLRHLYTSG | 185 | − | + |

TABLE 5a (see SEQ ID NOs: 99, 100, 5, 9, 8, 12, 10, 13, 15, 14, 43, 6 and 7)

| | N-terminal Domain | Core | SEQ ID NO. | Glucose Lowering | Lipid Elevation | HCC Formation |
|---|---|---|---|---|---|---|
| FGF19 | RPLAFSDAGPHVHYGWGDPI | RLRHLYTSG | 99 (aa 1-29) | + | + | + |
| FGF21 | HPIPDSSPLLQ--FGGQV | RQRYLYTDD | 100 (aa 1-25) | + | - | - |
| M5 | R-HPIPDSSPLLQ--FGGQV | RLRHLYTSG | 5 (aa 1-26) | + | - | - |
| M9 | R-HPIPDSSPLLQFGWGDPI | RLRHLYTSG | 9 (aa 1-28) | + | + | + |
| M8 | R-HPIPDSSPLLQ--WGDPI | RLRHLYTSG | 8 (aa 1-26) | + | + | + |
| M12 | RPLAFSDAGPLLQFGWGDPI | RLRHLYTSG | 12 (aa 1-29) | - | + | + |
| M10 | R-HPIPDSSPHVHYGWGDPI | RLRHLYTSG | 10 (aa 1-28) | - | + | + |
| M13 | RPLAFSDAGPLLQ--FGGQV | RLRHLYTSG | 13 (aa 1-27) | - | + | + |
| M15 | RPLAFSDAGPHVHYG--GQV | RLRHLYTSG | 15 (aa 1-27) | - | - | +/- |
| M14 | R-HPIPDSSPHVHYG--GQV | RLRHLYTSG | 14 (aa 1-26) | - | - | +/- |
| M43 | RPLAFSDAGPHVHYG-GD-I | RLRHLYTSG | 43 (aa 1-27) | + | - | +/- |
| M6 | R-----DSSPLLQ--FGGQV | RLRHLYTSG | 6 (aa 1-22) | + | - | - |
| M7 | RPLAFSDSSPLLQ--FGGQV | RLRHLYTSG | 7 (aa 1-27) | - | - | - |

TABLE 5b (see SEQ ID NOs: 99, 5 and 31 to 40)

| | N-terminal Domain | Core | SEQ ID NO. | Glucose Lowering | Lipid Elevation | HCC Formation |
|---|---|---|---|---|---|---|
| FGF19 | RPLAFSDAGPHVHYGWGDPI | RLRHLYTSG | 99 (aa 1-29) | + | + | + |
| FGF21 | HPIPDSSPLLQ--FGGQV | RQRYLYTDD | 100 (aa 1-25) | + | - | - |
| M5 | R-HPIPDSSPLLQ--FGGQV | RLRHLYTSG | 5 (aa 1-26) | + | - | - |
| M31 | R-HPIPDSSPLLQ--FGAQV | RLRHLYTSG | 31 (aa 1-26) | + | - | + |
| M32 | R-HPIPDSSPLLQ--FGDQV | RLRHLYTSG | 32 (aa 1-26) | + | - | - |
| M33 | R-HPIPDSSPLLQ--FGPQV | RLRHLYTSG | 33 (aa 1-26) | - | - | + |
| M34 | R-HPIPDSSPLLQ--FGGAV | RLRHLYTSG | 34 (aa 1-26) | - | - | + |
| M35 | R-HPIPDSSPLLQ--FGGEV | RLRHLYTSG | 35 (aa 1-26) | - | - | + |
| M36 | R-HPIPDSSPLLQ--FGGNV | RLRHLYTSG | 36 (aa 1-26) | + | - | +/- |
| M37 | R-HPIPDSSPLLQ--FGGQA | RLRHLYTSG | 37 (aa 1-26) | - | - | + |
| M38 | R-HPIPDSSPLLQ--FGGQI | RLRHLYTSG | 38 (aa 1-26) | - | - | + |
| M39 | R-HPIPDSSPLLQ--FGGQT | RLRHLYTSG | 39 (aa 1-26) | - | - | + |
| M40 | R-HPIPDSSPLLQFGWGQPV | RLRHLYTSG | 40 (aa 1-28) | - | + | + |

TABLE 5c (see SEQ ID NOs: 99, 100, 5, 52, 54, to 68, 4, 69, 70 and 53)

| | N-terminal Domain | Core | SEQ ID NO. | | Glucose Lowering | Lipid Elevation | HCC Formation |
|---|---|---|---|---|---|---|---|
| FGF19 | RPLAFSDAGPHVHYGWGDPI | RLRHLYTSG | 99 | (aa 1-29) | + | + | + |
| FGF21 | HPIPDSSPLLQ--FGGQV | RQRYLYTDD | 100 | (aa 1-25) | + | - | - |
| M5 | R-HPIPDSSPLLQ--FGGQV | RLRHLYTSG | 5 | (aa 1-26) | + | - | - |
| M52 | R-----DSSPLLQ--WGDPI | RLRHLYTSG | 52 | (aa 1-22) | + | + | - |
| M54 | RPLAFSDAGPLLQ--WGDPI | RLRHLYTSG | 54 | (aa 1-27) | - | + | + |
| M55 | RPLAFSDAGPH--YGWGDPI | RLRHLYTSG | 55 | (aa 1-27) | - | + | + |
| M56 | RPLAFSDAGP-V-YGWGDPI | RLRHLYTSG | 56 | (aa 1-27) | - | + | + |
| M57 | RPLAFSDAGP-VT-GWGDPI | RLRHLYTSG | 57 | (aa 1-27) | - | + | + |
| M58 | RPLAFSDAGP-VHY-WGDPI | RLRHLYTSG | 58 | (aa 1-27) | - | + | + |
| M59 | RPLAFSDAGPH-H-GWGDPI | RLRHLYTSG | 59 | (aa 1-27) | - | + | + |
| M60 | RPLAFSDAGPH-HY-WGDPI | RLRHYLYSG | 60 | (aa 1-27) | - | + | + |
| M61 | RPLAFSDAGPHV--GWGDPI | RLRHLYTSG | 61 | (aa 1-27) | - | + | + |
| M62 | RPLAFSDAGPHV-Y-WGDPI | RLRHLYTSG | 62 | (aa 1-27) | - | + | + |
| M63 | RPLAFSDAGPVH--WGDPI | RLRHLYTSG | 63 | (aa 1-27) | + | + | + |
| M64 | RPLAFSDSSPLVH--WGDPI | RLRHLYTSG | 64 | (aa 1-27) | + | + | + |
| M65 | RPLAFSDSSPHVH--WGDPI | RLRHLYTSG | 65 | (aa 1-27) | - | + | + |
| M66 | RPLAFSDAGPHLQ--WGDPI | RLRHLYTSG | 66 | (aa 1-27) | + | + | + |
| M67 | RPLAFSDAGPHV---WGDPI | RLRHLYTSG | 67 | (aa 1-26) | - | - | +/- |
| M68 | RPLAFSDAGPHVY-WGDPI | RLRHLYTSG | 68 | (aa 1-28) | - | + | - |
| M4 | RPLAFSDAGPHVHYAWGDPI | RLRHLYTSG | 4 | (aa 1-29) | + | + | + |
| M69 | R-----DSSPLVHYGWGDPI | RLRHLYTSG | 69 | (aa 1-24) | + | + | - |
| M70 | MR----DSSPLVHYGWGDPI | RLRHLYTSG | 70 | (aa 1-25) | + | + | - |
| M53 | M-----DSSPLLQ--WGDPI | RLRHLYTSG | 192 | (aa 1-22) | + | + | - |

Table 6 illustrates the peptide sequences of additional variants.

TABLE 6

Additional Variants (SEQ ID NOs: 41, 42 and 44-46)

M41:
RPLAFSDAGPHVHYGWGDPIRLRHLYTSGPHGLSSCFLRIRADGVVDCAR
GQSAHSLLEIKAVALRTVAIKGVHSVRYLCMGADGKMQGLLQYSEEDCAF
EEEIRPDGYNVYRSEKHRLPVSLSSAKQRQLYKNRGFLPLSHFLPMLPEP
PGILAPQPPDVGSSDPLSMVGPSQGRSPSYAS (SEQ ID NO: 41)

M42:
HPIPDSSPLLQFGGQVRLRHLYTSGPHGLSSCFLRIRADGVVDCARGQSA
HSLLEIKAVALRTVAIKGVHSVRYLCMGADGKMQGLLQYSEEDCAFEEEI
RPDGYNVYRSEKHRLPVSLSSAKQRQLYKNRGFLPLSHFLPMLPEPPGIL
APQPPDVGSSDPLSMVGPSQGRSPSYAS (SEQ ID NO: 42)

M44:
RPLAFSDAGPHVHYGWGDPIRQRYLYTDDAQQTEAHLEIREDGTVGGAAD
QSPESLLQLKALKPGVIQILGVKTSRFLCQRPDGALYGSLHFDPEACSFR
ELLLEDGYNVYQSEAHGLPLHLPGNKSPHRDPAPRGPARFLPLPGLPPAL
PEPPGILAPQPPDVGSSDPLSMVGPSQGRSPSYAS (SEQ ID NO: 44)

M45:
HPIPDSSPLLQFGGQVRQRYLYTDDAQQTEAHLEIREDGTVGGAADQSPE
SLLQLKALKPGVIQILGVKTSRFLCQRPDGALYGSLHFDPEACSFRELLL
EDGYNVYQSEAHGLPLHLPGNKSPHRDPAPRGPARFLPLPGLPPALPMVP
EEPEDLRGHLESDMFSSPLETDSMDPFGLVTGLEAVRSPSFEK (SEQ ID NO: 45)

M46:
RPLAFSDAGPHVHYGWGDPIRQRYLYTDDAQQTEAHLEIREDGTVGGAAD
QSPESLLQLKALKPGVIQILGVKTSRFLCQRPDGALYGSLHFDPEACSFR
ELLLEDGYNVYQSEAHGLPLHLPGNKSPHRDPAPRGPARFLPLPGLPPAL
PEPPGILAPQPPDVGSSDPLSMVGPSQGRSPSYASPMVPEEPEDLRGHLE
SDMFSSPLETDSMDPFGLVTGLEAVRSPSFEK (SEQ ID NO: 46)

Table 7 illustrates the peptide sequences of 3 FGF19 variants, denoted M1, M2 and M69. The data clearly show that these three variants have the desired characteristics of glucose lowering activity in db/db mice. These three variants appear to elevate lipids in db/db mice.

TABLE 7

Additional Variants (SEQ ID NOs: 1, 2 and 69)

M1:
RPLAFSDASPHVHYGWGDPIRLRHLYTSGPHGLSSCFLRIRADGVVDCAR
GQSAHSLLEIKAVALRTVAIKGVHSVRYLCMGADGKMQGLLQYSEEDCAF
EEEIRPDGYNVYRSEKHRLPVSLSSAKQRQLYKNRGFLPLSHFLPMLPMV
PEEPEDLRGHLESDMFSSPLETDSMDPFGLVTGLEAVRSPSFEK (SEQ ID NO: 1 or 139)

M2:
RPLAFSDSSPLVHYGWGDPIRLRHLYTSGPHGLSSCFLRIRADGVVDCAR
GQSAHSLLEIKAVALRTVAIKGVHSVRYLCMGADGKMQGLLQYSEEDCAF
EEEIRPDGYNVYRSEKHRLPVSLSSAKQRQLYKNRGFLPLSHFLPMLPMV
PEEPEDLRGHLESDMFSSPLETDSMDPFGLVTGLEAVRSPSFEK (SEQ ID NO: 2 or 140)

M69:
RDSSPLVHYGWGDPIRLRHLYTSGPHGLSSCFLRIRADGVVDCARGQSAH
SLLEIKAVALRTVAIKGVHSVRYLCMGADGKMQGLLQYSEEDCAFEEEIR
PDGYNVYRSEKHRLPVSLSSAKQRQLYKNRGFLPLSHFLPMLPMVPEEPE
DLRGHLESDMFSSPLETDSMDPFGLVTGLEAVRSPSFEK (SEQ ID NO: 69).

5.6 Example 6

The following is a data summary showing that FGF19 reduces body weight in diet-induced obese mice and in ob/ob mice, and liver tumor formation activity and body weight in db/db mice.

Mice were injected with FGF19 or FGF21 in AAV vector. Body weight was recorded 4 weeks after injection.

TABLE 8

FGF19 reduces body weight in diet-induced obese mice and in ob/ob mice (sequences correspond to aa 1-29 of SEQ ID NO: 99 and aa 1-25 of SEQ ID NO: 100, respectively)

| | N-terminal Domain | Core | Body Weight-Lowering in DIO | Body Weight-Lowering in Ob/ob |
|---|---|---|---|---|
| FGF19 | RPLAFSDAGPHVHYGWGDPI | RLRHLYTSG | + | + |
| FGF21 | HPIPDSSPLLQ--FGGQV | RQRYLYTDD | + | − |

TABLE 9

Correlation of body weight and liver tumor formation of FGF19, FGF21 and selected variants in db/db mice (see, e.g., SEQ ID NOs: 99, 100, 5, 6, 32, 52 and 69)

| | N-terminal Domain | core | SEQ ID NO | | Liver Tumor Nodule | Body Weight |
|---|---|---|---|---|---|---|
| FGF19 | RPLAFSDAGPHVHYGWGDPI | RLRHLYTSG | 99 | (aa 1-29) | + | Increased |
| FGF21 | HPIPDSSPLLQ--FGGQV | RQRYLYTDD | 100 | (aa 1-25) | − | Decreased |
| M5 | R-HPIPDSSPLLQ--FGGQV | RLRHLYTSG | 5 | (aa 1-26) | − | Increased |
| M6 | R-----DSSPLLQ--FGGQV | RLRHLYTSG | 6 | (aa 1-22) | − | Decreased |
| M32 | R-HPIPDSSPLLQ--FGDQV | RLRHLYTSG | 32 | (aa 1-26) | − | Decreased |
| M52 | R-----DSSPLLQ--WGDPI | RLRHLYTSG | 52 | (aa 1-22) | − | Decreased |
| M69 | R-----DSSPLVHYGWGDPI | RLRHLYTSG | 69 | (aa 1-24) | − | Increased |

5.7 Example 7

The following is a study showing that variant M5 and variant M69 peptides reduce blood glucose.

Mice (ob/ob) were injected (subcutaneously) with M5 (0.1 and 1 mg/kg, s.c.) or FGF19 (1 mg/kg, s.c.), or variant M69 (0.1 and 1 mg/kg, s.c.) or FGF19 (1 mg/kg, s.c.). Plasma glucose levels were measured at 2, 4, 7, and 24 hours after injection. The results of variant M5 and variant M69 showed similar glucose lowering effects as wild type FGF19 (data not shown).

5.8 Example 8

This example sets forth several variant polypeptides and particular characteristics thereof, including the variants' effect on glucose lowering, lipid profile parameters, and HCC formation.

In particular, Table 10 compares data generated for variants M5 (SEQ ID NO:5), M6 (SEQ ID NO:6) and M50 (SEQ ID NO:50) with data generated for corresponding variant polypeptides (denoted as M144, M145, and M146, respectively) having N-terminal Arg (R) deletions. Only certain sequence domains for each variant are listed: N-terminal domain, Core, and Sheet-8/Loop-8/Sheet-9 region.

TABLE 10

| | N-terminal Domain | Core | Sheet-8/Loop8/Sheet-9 region | Glucose Lowering | Body Weight Reduction | HDL Elevation | Triglyceride Elevation | HCC Formation |
|---|---|---|---|---|---|---|---|---|
| FGF19 | RPLAFSDAGPHVHYGWGDPI (aa 1-20 of SEQ ID NO: 99) | RLRHLYTSG (aa 21-29 of SEQ ID NO: 99) | //EEIRPDGYNVY// (aa 102-112 of SEQ ID NO: 99) | + | − | + | + | + |
| FGF21 | HPIPDSSPLLQ--FGGQV (aa 1-20 of SEQ ID NO: 100) | RQRYLYTDD (aa 21-29 of SEQ ID NO: 100) | //ELLLEDGYNVY// (aa 97-107 of SEQ ID NO: 100) | + | + | − | − | − |
| M5 | R-HPIPDSSPLLQ-FGGQV (aa 1-17 of SEQ ID NO: 5) | RLRHLYTSG (aa 18-26 of SEQ ID NO: 5) | //EEIRPDGYNVY// (aa 99-109 of SEQ ID NO: 5) | + | − | − | − | − |
| M6 | R-----DSSPLLQ-FGGQV (aa 1-14 of SEQ ID NO: 6) | RLRHLYTSG (aa 15-23 of SEQ ID NO: 6) | //EEIRPDGYNVY// (aa 95-105 of SEQ ID NO: 6) | + | − | − | − | − |
| M50 | R-HPIPDSSPLLQ-FGDQV (aa 1-17 of SEQ ID NO: 50) | RLRHLYTSG (aa 18-26 of SEQ ID NO: 50) | //EEIRPDGYNVY// (aa 99-109 of SEQ ID NO: 50) | + | + | − | − | − |
| M144 | --HPIPDSSPLLQ--FGGQV (aa 2-17 of SEQ ID NO: 5) | RLRHLYTSG (aa 18-26 of SEQ ID NO: 5) | //EEIRPDGYNVY// (aa 99-109 of SEQ ID NO: 5) | + | − | − | − | − |
| M145 | ------DSSPLLQ--FGGQV (aa 2-14 of SEQ ID NO: 6) | RLRHLYTSG (aa 15-23 of SEQ ID NO: 6) | //EEIRPDGYNVY// (aa 95-105 of SEQ ID NO: 6) | + | − | − | − | − |
| M146 | --HPIPDSSPLLQ--FGDQV (aa 2-17 of SEQ ID NO: 50) | RLRHLYTSG (aa 18-26 of SEQ ID NO: 50) | //EEIRPDGYNVY// (aa 99-109 of SEQ ID NO: 50) | + | + | − | − | − |

As the data in Table 10 indicate, the deletion of the N-terminal Arg (R) did not significantly impact glucose lowering, body weight reduction, HDL and triglyceride elevation, and HCC formation.

5.9 Example 9

This example sets forth several variant peptides having amino acid substitutions in the Loop 8 region of FGF19, along with the variants' effect on body weight, certain metabolic parameters, and HCC formation.

The data in Table 10 are associated with variant polypeptides denoted as M3, M139, M140, M141 and M160. The amino acid sequence for M3 is set forth elsewhere herein, and the amino acid sequences for M139, M140, M141 and M160 are as follows:

```
                                          (SEQ ID NO: 193)
RPLAFSDAGPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEILPDGYNVYRSEKHRLPVSLSSAKQRQLYKNRGFLPLSHFLPMLPMV

PEEPEDLRGHLESDMFSSPLETDSMDPFGLVTGLEAVRSPSFEK (M139);

(SEQ ID NO: 194)
RPLAFSDAGPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEIREDGYNVYRSEKHRLPVSLSSAKQRQLYKNRGFLPLSHFLPMLPMV

PEEPEDLRGHLESDMFSSPLETDSMDPFGLVTGLEAVRSPSFEK (M140);

(SEQ ID NO: 195)
RPLAFSDAGPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEILCDGYNVYRSEKHRLPVSLSSAKQRQLYKNRGFLPLSHFLPMLPMV

PEEPEDLRGHLESDMFSSPLETDSMDPFGLVTGLEAVRSPSFEK (M141);

and
                                          (SEQ ID NO: 196)
RPLAFSDAGPHVHYGWGDPIRQRHLYTSGPHGLSSCFLRIRADGVVDCAR

GQSAHSLLEIKAVALRTVAIKGVHSVRYLCMGADGKMQGLLQYSEEDCAF

EEEILEDGYNVYRSEKHRLPVSLSSAKQRQLYKNRGFLPLSHFLPMLPMV

PEEPEDLRGHLESDMFSSPLETDSMDPFGLVTGLEAVRSPSFEK (M160).
```

Only the following sequence domains for each of the aforementioned variants are listed in Table 10: N-terminal domain, Core, and Sheet-8/Loop-8/Sheet-9 region. While the particular amino acid residues making up the Loop 8 region are not universally accepted in the literature, FGF19 residues 127-129 are defined herein as constituting the Loop-8 region.

TABLE 11

| | N-terminal Domain | Core | | Glucose Lowering | Body Weight Reduction | HDL Elevation | Triglyceride Elevation | HCC Formation |
|---|---|---|---|---|---|---|---|---|
| FGF19 | RPLAFSDAGPHVHYGWGDPI (aa 1-20 of SEQ ID NO: 99) | RLRHLYTSG (aa 21-29 of SEQ ID NO: 99) | //EEIRPDGYNVY// (aa 102-112 of SEQ ID NO: 99) | + | − | + | + | + |
| FGF21 | HPIPDSSPLLQ--FGGQV (aa 1-20 of SEQ ID NO: 100) | RQRYLYTDD (aa 21-29 of SEQ ID NO: 100) | //ELLLEDGYNVY// (aa 97-107 of SEQ ID NO: 100) | + | + | − | − | − |
| M3 | RPLAFSDAGPHVHYGWGDPI (aa 1-20 of SEQ ID NO: 3) | RLRHLYTSG (aa 21-29 of SEQ ID NO: 3) | //EEILEDGYNVY// ((aa 102-112 of SEQ ID NO: 3) | + | + | + | + | +/− |
| M139 | RPLAFSDAGPHVHYGWGDPI (aa 1-20 of SEQ ID NO: 193) | RLRHLYTSG (aa 21-29 of SEQ ID NO: 193) | //EEILPDGYNVY// (aa 102-112 of SEQ ID NO: 193) | + | − | + | + | + |
| M140 | RPLAFSDAGPHVHYGWGDPI (aa 1-20 of SEQ ID NO: 194) | RLRHLYTSG (aa 21-29 of SEQ ID NO: 194) | //EEIREDGYNVY// (aa 102-112 of SEQ ID NO: 194) | + | + | + | + | +/− |
| M141 | RPLAFSDAGPHVHYGWGDPI (aa 1-20 of SEQ ID NO: 195) | RLRHLYTSG (aa 21-29 of SEQ ID NO: 195) | //EEILCDGYNVY// (aa 102-112 of SEQ ID NO: 195) | + | − | + | + | + |
| M160 | RPLAFSDAGPHVHYGWGDPI (aa 1-20 of SEQ ID NO: 196) | RQRHLYTSG (aa 21-29 of SEQ ID NO: 196) | //EEILEDGYNVY// (aa 102-112 of SEQ ID NO: 196) | + | + | + | + | − |

Referring to Table 11, the P128E substitution appears necessary to significantly prevent HCC formation, but is insufficient by itself to prevent HCC formation. In particular, an improvement in preventing HCC formation is observed with the P128E substitution in M140. Conversely, by itself the R127L substitution does not prevent HCC formation (see M139). As indicated in comparison to M3, a combination of the R127L and P128E substitutions decreases HCC formation but does not eliminate HCC formation. Surprisingly, however, a combination of the R127L and P128E substitutions along with a substitution of Gln (Q) for Leu (L) in the FGF19 core region does significantly prevent HCC formation (see M160).

These data indicate that the FGF19 Loop 8 region plays a role in HCC formation. Amino acid residues outside of the Loop 8 region (e.g., substitutions in the core region) may enhance the prevention of HCC formation.

M1
(SEQ ID NO: 1)
RPLAFSDASPHVHYGWGDPIRLRHLYTSGPHGLSSCFLRIRADGVVDCAR
GQSAHSLLEIKAVALRTVAIKGVHSVRYLCMGADGKMQGLLQYSEEDCAF
EEEIRPDGYNVYRSEKHRLPVSLSSAKQRQLYKNRGFLPLSHFLPMLPMV
PEEPEDLRGHLESDMFSSPLETDSMDPFGLVTGLEAVRSPSFEK

M2
(SEQ ID NO: 2)
RPLAFSDSSPLVHYGWGDPIRLRHLYTSGPHGLSSCFLRIRADGVVDCAR
GQSAHSLLEIKAVALRTVAIKGVHSVRYLCMGADGKMQGLLQYSEEDCAF
EEEIRPDGYNVYRSEKHRLPVSLSSAKQRQLYKNRGFLPLSHFLPMLPMV
PEEPEDLRGHLESDMFSSPLETDSMDPFGLVTGLEAVRSPSFEK

M3
(SEQ ID NO: 3)
RPLAFSDAGPHVHYGWGDPIRLRHLYTSGPHGLSSCFLRIRADGVVDCAR
GQSAHSLLEIKAVALRTVAIKGVHSVRYLCMGADGKMQGLLQYSEEDCAF
EEEILEDGYNVYRSEKHRLPVSLSSAKQRQLYKNRGFLPLSHFLPMLPMV
PEEPEDLRGHLESDMFSSPLETDSMDPFGLVTGLEAVRSPSFEK

M5
(SEQ ID NO: 5)
RHPIPDSSPLLQFGGQVRLRHLYTSGPHGLSSCFLRIRADGVVDCARGQS
AHSLLEIKAVALRTVAIKGVHSVRYLCMGADGKMQGLLQYSEEDCAFEEE
IRPDGYNVYRSEKHRLPVSLSSAKQRQLYKNRGFLPLSHFLPMLPMVPEE
PEDLRGHLESDMFSSPLETDSMDPFGLVTGLEAVRSPSFEK

M5-R
(SEQ ID NO: 160)
HPIPDSSPLLQFGGQVRLRHLYTSGPHGLSSCFLRIRADGVVDCARGQSA
HSLLEIKAVALRTVAIKGVHSVRYLCMGADGKMQGLLQYSEEDCAFEEEI
RPDGYNVYRSEKHRLPVSLSSAKQRQLYKNRGFLPLSHFLPMLPMVPEEP
EDLRGHLESDMFSSPLETDSMDPFGLVTGLEAVRSPSFEK

M48
(SEQ ID NO: 48)
RDSSPLLQFGGQVRLRHLYTSGPHGLSSCFLRIRADGVVDCARGQSAHSL
LEIKAVALRTVAIKGVHSVRYLCMGADGKMQGLLQYSEEDCAFEEEIRPD
GYNVYRSEKHRLPVSLSSAKQRQLYKNRGFLPLSHFLPMLPMVPEEPEDL
RGHLESDMFSSPLETDSMDPFGLVTGLEAVRSPSFEK

M49
(SEQ ID NO: 49)
RPLAFSDSSPLLQFGGQVRLRHLYTSGPHGLSSCFLRIRADGVVDCARGQ
SAHSLLEIKAVALRTVAIKGVHSVRYLCMGADGKMQGLLQYSEEDCAFEE
EIRPDGYNVYRSEKHRLPVSLSSAKQRQLYKNRGFLPLSHFLPMLPMVPE
EPEDLRGHLESDMFSSPLETDSMDPFGLVTGLEAVRSPSFEK

M50
(SEQ ID NO: 50)
RHPIPDSSPLLQFGDQVRLRHLYTSGPHGLSSCFLRIRADGVVDCARGQS
AHSLLEIKAVALRTVAIKGVHSVRYLCMGADGKMQGLLQYSEEDCAFEEE
ILEDGYNVYRSEKHRLPVSLSSAKQRQLYKNRGFLPLSHFLPMLPMVPEE
PEDLRGHLESDMFSSPLETDSMDPFGLVTGLEAVRSPSFEK

M51
(SEQ ID NO: 51)
RHPIPDSSPLLQFGGNVRLRHLYTSGPHGLSSCFLRIRADGVVDCARGQS
AHSLLEIKAVALRTVAIKGVHSVRYLCMGADGKMQGLLQYSEEDCAFEEE
IRPDGYNVYRSEKHRLPVSLSSAKQRQLYKNRGFLPLSHFLPMLPMVPEE
PEDLRGHLESDMFSSPLETDSMDPFGLVTGLEAVRSPSFEK

M52
(SEQ ID NO: 52)
RDSSPLLQWGDPIRLRHLYTSGPHGLSSCFLRIRADGVVDCARGQSAHSL
LEIKAVALRTVAIKGVHSVRYLCMGADGKMQGLLQYSEEDCAFEEEIRPD
GYNVYRSEKHRLPVSLSSAKQRQLYKNRGFLPLSHFLPMLPMVPEEPEDL
RGHLESDMFSSPLETDSMDPFGLVTGLEAVRSPSFEK

M53
(SEQ ID NO: 192)
MDSSPLLQWGDPIRLRHLYTSGPHGLSSCFLRIRADGVVDCARGQSAHSL
LEIKAVALRTVAIKGVHSVRYLCMGADGKMQGLLQYSEEDCAFEEEIRPD
GYNVYRSEKHRLPVSLSSAKQRQLYKNRGFLPLSHFLPMLPMVPEEPEDL
RGHLESDMFSSPLETDSMDPFGLVTGLEAVRSPSFEK

M69
(SEQ ID NO: 69)
RDSSPLVHYGWGDPIRLRHLYTSGPHGLSSCFLRIRADGVVDCARGQSAH
SLLEIKAVALRTVAIKGVHSVRYLCMGADGKMQGLLQYSEEDCAFEEEIR
PDGYNVYRSEKHRLPVSLSSAKQRQLYKNRGFLPLSHFLPMLPMVPEEPE
DLRGHLESDMFSSPLETDSMDPFGLVTGLEAVRSPSFEK

M70
(SEQ ID NO: 70)
MRDSSPLVHYGWGDPIRLRHLYTSGPHGLSSCFLRIRADGVVDCARGQSA
HSLLEIKAVALRTVAIKGVHSVRYLCMGADGKMQGLLQYSEEDCAFEEEI
RPDGYNVYRSEKHRLPVSLSSAKQRQLYKNRGFLPLSHFLPMLPMVPEEP
EDLRGHLESDMFSSPLETDSMDPFGLVTGLEAVRSPSFEK

M71
(SEQ ID NO: 71)
HPIPDSSPLLQFGGQVRQRYLYTDDAQQTEAHLEIREDGTVGGAADQSPE
SLLQLKALKPGVIQILGVKTSRFLCQRPDGALYGSLHFDPEACSFRELLL
EDGYNVYQSEAHSLPLHLPGNKSPHRDPAPRGPARFLPLPGLPPALPEPP
GILAPQPPDVGSSDPLSMVGPSQGRSPSYAS

M72
(SEQ ID NO: 72)
HPIPDSSPLLQFGGQVRQRYLYTDDAQQTEAHLEIREDGTVGGAADQSPE
SLLQLKALKPGVIQILGVKTSRFLCQRPDGALYGSLHFDPEACSFRELLL
EDGYNVYQSEAHGLPLHLPGNKSPHRDPAPRGPARFLPLPGLPPAPPEPP
GILAPQPPDVGSSDPLSMVGPSQGRSPSYAS

M73
(SEQ ID NO: 73)
HPIPDSSPLLQFGGQVRQRYLYTDDAQQTEAHLEIREDGTVGGAADQSPE
SLLQLKALKPGVIQILGVKTSRFLCQRPDGALYGSLHFDPEACSFRELLL
EDGYNVYQSEAHGLPLHLPGNKSPHRDPAPRGPARFLPLPGLPPALPEPP

-continued

GILAPQPPDVGSSDPLSMVVQDELQGVGGEGCHMHPENCKTLLTDIDRTH

TEKPVWDGITGE

M75
(SEQ ID NO: 75)
RVHYGWGDPIRLRHLYTSGPHGLSSCFLRIRADGVVDCARGQSAHSLLEI

KAVALRTVAIKGVHSVRYLCMGADGKMQGLLQYSEEDCAFEEEIRPDGYN

VYRSEKHRLPVSLSSAKQRQLYKNRGFLPLSHFLPMLPMVPEEPEDLRGH

LESDMFSSPLETDSMDPFGLVTGLEAVRSPSFEK

M76
(SEQ ID NO: 76)
RGDPIRLRHLYTSGPHGLSSCFLRIRADGVVDCARGQSAHSLLEIKAVAL

RTVAIKGVHSVRYLCMGADGKMQGLLQYSEEDCAFEEEIRPDGYNVYRSE

KHRLPVSLSSAKQRQLYKNRGFLPLSHFLPMLPMVPEEPEDLRGHLESDM

FSSPLETDSMDPFGLVTGLEAVRSPSFEK

FGF19
(SEQ ID NO: 99)
RPLAFSDAGPHVHYGWGDPIRLRHLYTSGPHGLSSCFLRIRADGVVDCAR

GQSAHSLLEIKAVALRTVAIKGVHSVRYLCMGADGKMQGLLQYSEEDCAF

EEEIRPDGYNVYRSEKHRLPVSLSSAKQRQLYKNRGFLPLSHFLPMLPMV

PEEPEDLRGHLESDMFSSPLETDSMDPFGLVTGLEAVRSPSFEK.

5.10 Example 10

This example shows that administration of M70 in human patients results in suppression of 7a-hydroxy-4-cholsten-3-one (C4), a marker of bile acid synthesis.

Study Subjects:

Healthy adults in the age range 18-65 years and with normal body weight (body mass index, BMI 20-35) were enrolled in the study. The study protocol was approved by the Human Research Ethics Committee in Australia, and written informed consent was obtained from each subject. For inclusion in the study each subject had to be in good health determined by no clinically significant findings from medical history, physical exam, 12 lead ECG, clinical laboratory findings, and vital signs at screening. Subjects with history or clinical manifestation of any significant metabolic, allergic, dermatological, hepatic, renal, hematological, pulmonary, cardiovascular, GI, neurological, or psychiatric disorder were excluded from enrollment.

Study Design:

The study was a randomized, double-blind, placebo-controlled design. Prescreening of subjects was performed 7-30 days prior to entry, and baseline evaluations were performed before treatment. Each subject was given subcutaneous injection of M70 at doses 3 mg/day in a single bolus dose daily for 7 days. Blood samples were collected into heparinized tubes through an indwelling catheter. Blood samples taken on Day 1 and Day 7 at 4.5 hrs or 24 hrs after administration of M70 or placebo were analyzed. Serum levels of 7a-hydroxy-4-cholesten-3-one (C4) were used to monitor CYP7A1 enzymatic activity (bile acid synthesis). They were analyzed from individual serum samples after sample extraction followed by high-pressure liquid chromatography (HPLC) as described previously (Galman et al. (2003) J Lipid Res. 2003; 44(4):859-66).

Figure 6:
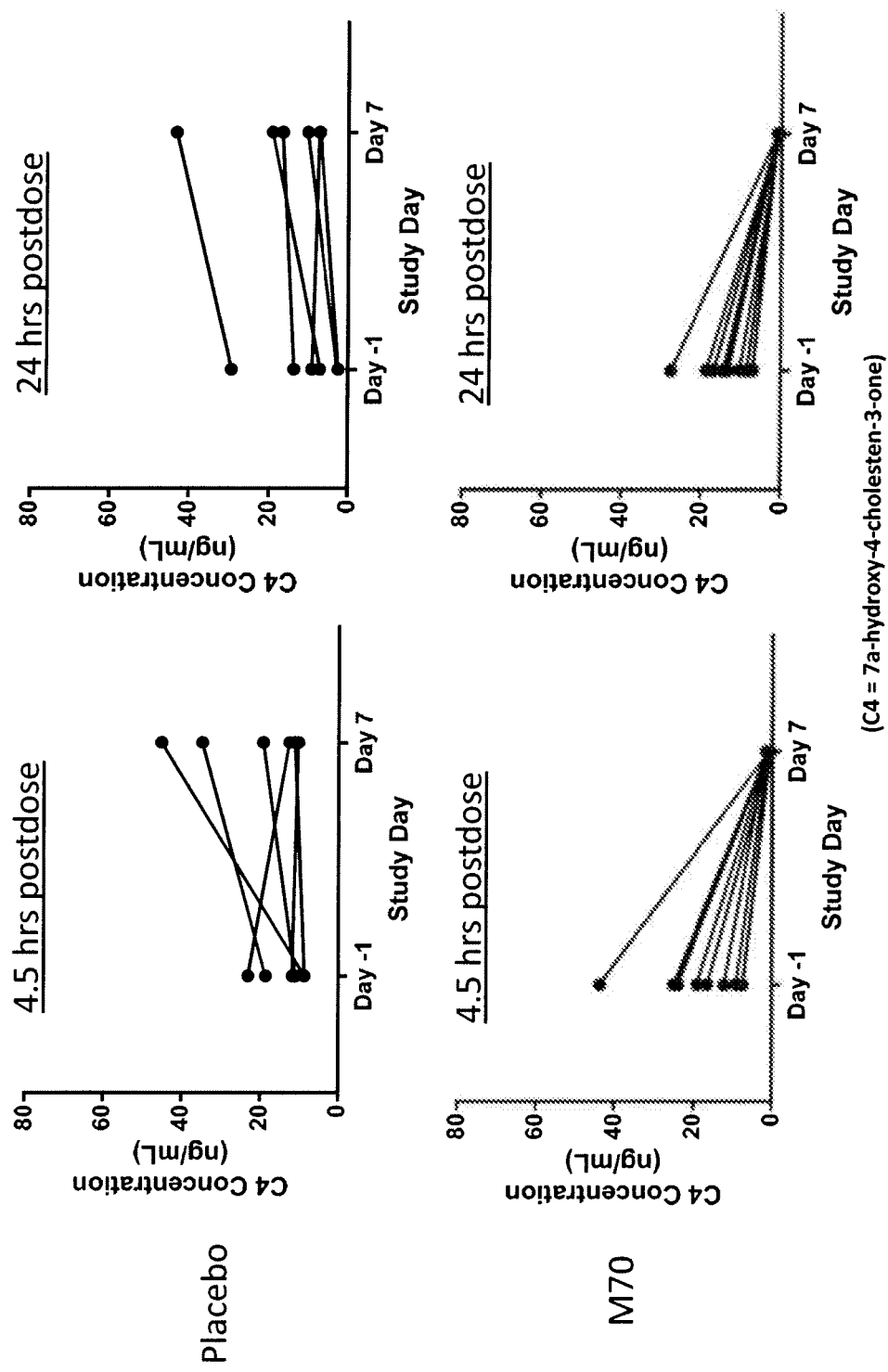
FIG. 6 depicts the results of a human clinical trial, showing administration of M70 is able to suppress 7a-hydroxy-4-cholsten-3-one (C4), a marker of bile acid synthesis, as compared to a placebo.

Results:

The data provided in FIG. 6 show that on days 1 and 7, at both 4.5 hours and 24 hours post-dose, serum levels of C4 were significantly suppressed in the patients, as compared to patients receiving a placebo.

5.11 Example 11

This example shows activation of mouse FGFR4-β-klotho signaling by FGF19, M3, and M70 in a rat myoblast cell line Methods:

An ELK luciferase assay was performed in L6 cells transiently transfected with mouse FGFR4, b-klotho, and reporter constructs containing 5×UAS luciferase and GAL4-DNA-binding domain (DBD) fused to ELK1. In this system, luciferase activity is regulated by the endogenous phosphorylated extracellular signal-regulated kinase (ERK). Cells were incubated with ligands for 6 hours before lysed for luciferase activity measurements.

A cell-based receptor activation assay was used to evaluate the ability of mouse FGFR4 to mediate ligand-dependent signaling in the presence of β-klotho. To this end, a rat L6 myoblast cell line, which lacks endogenous expression of these proteins, was transfected with DNAs encoding FGFR4 and β-klotho from mouse, as well as plasmids containing an Elk1-dependent chimeric transcription factor-based reporter system.

Following transfection, concentration response of ligand-dependent luciferase expression was analyzed in whole-cell lysates in the presence of luciferin substrate.

Figure 7:
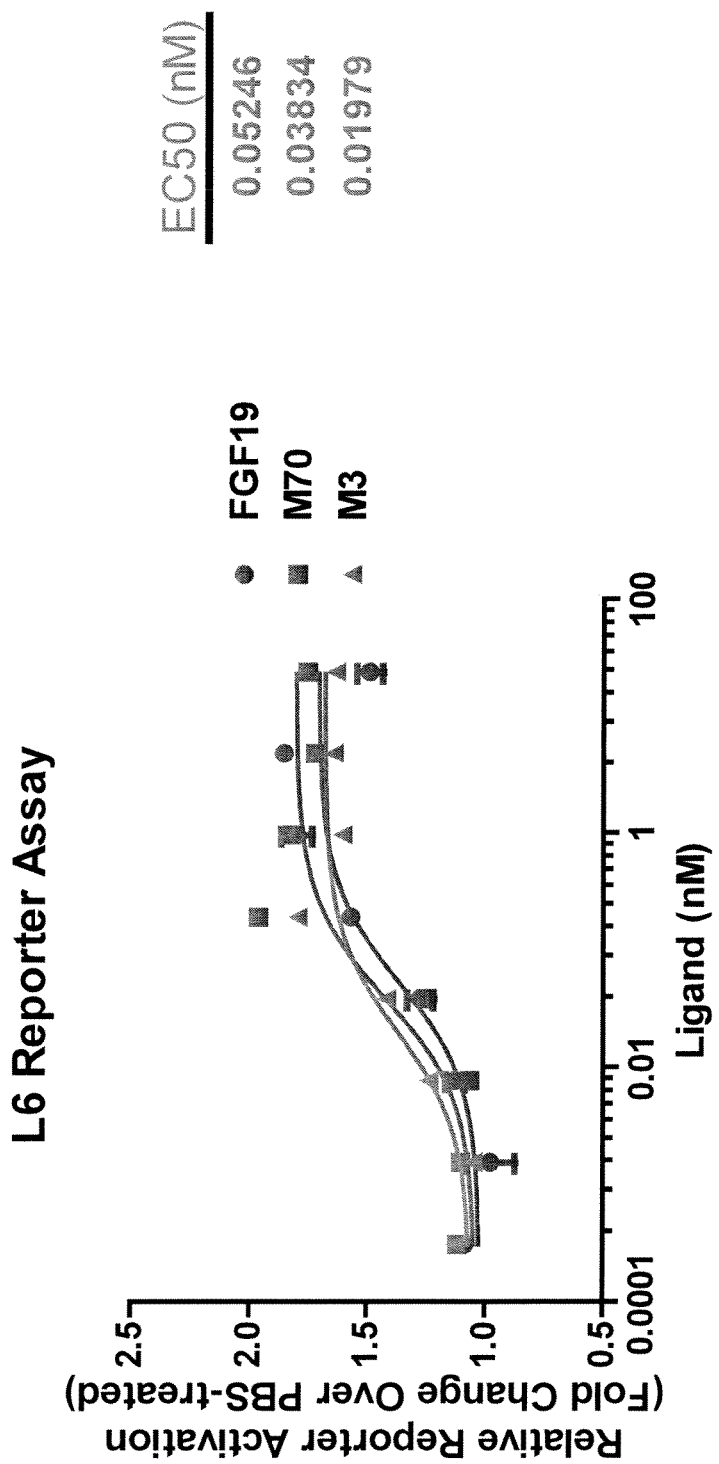
FIG. 7 depicts that the expression of FGFR4/β-klotho complex in L6 cells potentiates activation of intracellular signaling pathways by FGF19, M3 and M70.

Results:

Co-expression of FGFR4 and β-klotho in L6 cells was found to potentiate activation of intracellular signaling pathways by both M3, M70 and FGF19 ($EC_{50}$=20, 38 and 53 pM, respectively (see Table 12 and FIG. 7).

TABLE 12

Co-expression of Mouse FGFR4/β-klotho complex in L6 Cells Potentiates Activation of Intracellular Signaling Pathways by FGF19, M3 and M70.

| | FGFR4/βklotho | |
|---|---|---|
| Ligand | $EC_{50}$ (pM) | $E_{max}$ (fold potentiation) |
| FGF19 | 52.5 ± 0.01 | 1.82 ± 0.09 |
| M3 | 19.8 + 0.04 | 1.68 + 0.04 |
| M70 | 38.3 ± 0.12 | 1.85 ± 0.14 |

$EC_{50}$ = half-maximal effective concentration;
$E_{max}$ = maximum efficacy.
Data are expressed as mean ± SD These data suggest that the formation of a ternary complex between the FGFR4-β-klotho co-receptors and cognate ligands is important for potent activation of intracellular signaling.

5.12 Example 12

This example shows that M70 selectively activates signaling through the KLB/FGFR4 receptor complex in a manner that beneficially does not cause HCC in mice, as shown in two different models of oncogenic potential.

Study Subjects:

An FDA-accepted model of accelerated tumorigenesis, known as the rasH2 transgenic model, as well as the db/db animal model.

Study Design and Results:

M70 expressed at exposures roughly 1,000 times greater than normal levels of FGF19 in human blood did not cause HCC after exposure for one year. By contrast, human FGF19, utilized as a positive control in the mouse experiment, did cause HCC.

Co-administration of M70 and FGF19 via gene delivery in the db/db animal model obviated the expected FGF19-driven HCC, suggesting that M70 blocked the ability of FGF19 to occupy the relevant receptor and signal in such a way as to cause HCC.

5.13 Example 13

This example discusses the results of a Phase 1 randomized, double blind, placebo controlled, single ascending dose (SAD) and multiple ascending dose (MAD) study to evaluate the safety, tolerability and pharmacokinetics of M70 in healthy adult participants. An overview of the study is provided in Table 13.

TABLE 13

Phase 1 Study Design to Evaluate the Safety, Tolerability and Pharmacokinetics of M70 in Healthy Adult Participants.

| Study Population | Primary Outcome Measure | Primary Outcome Results | Selected Secondary Outcomes |
|---|---|---|---|
| Healthy subjects | Safety and tolerability | No safety or tolerability signals identified<br>No serious adverse events reported<br>Majority of adverse events were mild | PK supports qd dosing<br>Statistically significant reduction in C4 at all doses tested (0.3, 1 and 3 mg) vs. pre-dose levels (MAD); $p < 0.001$<br>Statistically significant reduction in triglycerides with doses >1 mg (MAD); $p < 0.05$<br>Statistically significant increase in total cholesterol (MAD); $p < 0.05$ |

Figure 8:
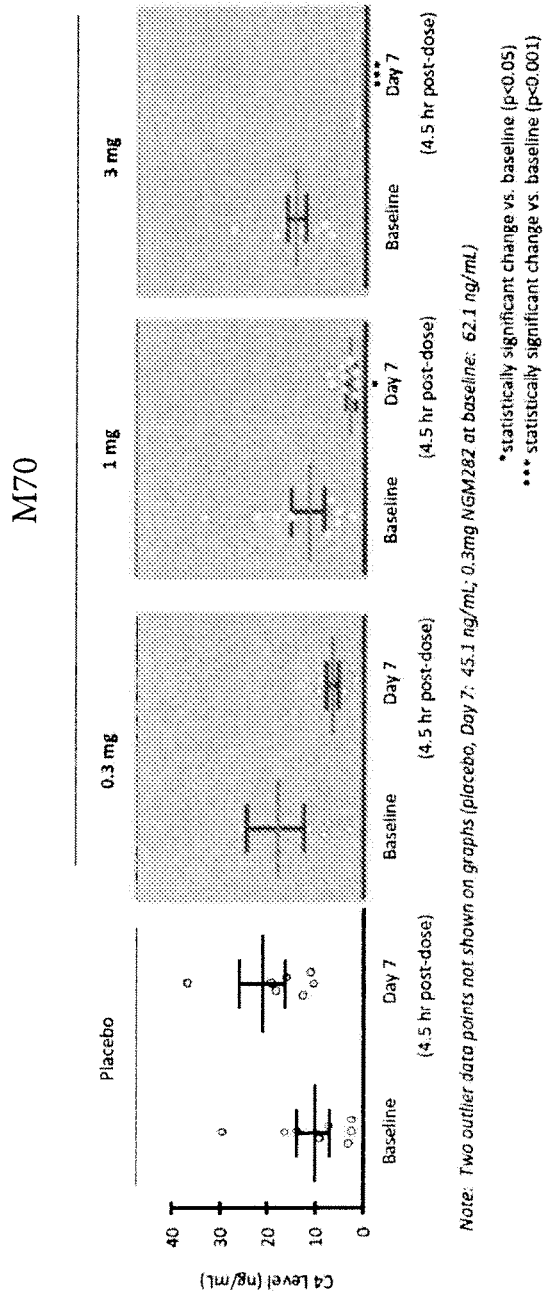
FIG. 8 depicts that administration of M70 is able to suppress C4 as compared to a placebo.

As shown in FIG. 8, the Phase 1 trial with M70 demonstrated a favorable safety profile with signs of biological activity consistent with FGF19-like activity related to FGFR1c and FGFR4 signaling, supports its application in NASH and bile acid related disorders (BARDs).

Study Design:

In this blinded, placebo-controlled, Phase 1 trial, overweight or obese but otherwise healthy adults were randomized to receive M70 or placebo as a daily subcutaneous injection in escalating doses.

Results:

As shown in FIG. 8, a rapid and dose-proportional reduction of serum C4 concentrations indicated that M70 has a statistically significant effect on bile acid synthesis at the 0.3 mg, 1 mg and 3 mg doses. A mean reduction of approximately 94% in serum C4 concentrations was noted after the sixth dose at 3 mg when compared with pre-dose levels. This rapid reduction in C4 supports the potential biological activity of M70 as an inhibitor of bile acid synthesis through CYP7a1. Two outlier data points are not shown in FIG. 8, but were included in the statistic analysis (placebo, Day 7: 45.1 ng/ml; 0.3 mg NGM282 at baseline: 62.1 ng/ml).

Laboratory analysis of blood samples collected from subjects receiving M70 in the Phase 1 MAD trial showed administration of the drug was associated with statistically significant reductions in triglycerides at doses of 1 mg and greater ($p<0.05$) and a statistically significant decrease in total cholesterol ($p<0.05$) (data not shown).

In both the SAD and MAD trials, M70 was well tolerated and exhibited linear pharmacokinetics with no immunogenicity. There were no serious adverse events. The most frequently observed adverse events were diarrhea, vomiting and injection site reactions. Also, there were no clinically significant laboratory abnormalities documented in M70-treated subjects, as determined by the Safety Data Monitoring Committee for the study, and there were no anti-drug antibodies, or ADAs, observed.

5.14 Example 14

This example discusses the results of preclinical testing, which supports the role of M70 for the treatment of NASH.

Normally the liver contains some fat. However, if more than 5-10% of the liver's weight is fat, it is referred to as a fatty liver, or steatosis. The spectrum of NAFLD ranges from simple steatosis to NASH, which can ultimately progress to end-stage liver disease.

Bile acid synthesis and serum bile acid levels are correlated with NAFLD and progression of disease to NASH, as evidenced by elevations of CYP7a1 and increased serum bile acid levels observed in NAFLD and NASH patients, respectively. Accordingly, by reducing triglycerides and blocking bile acid synthesis through the CYP7a1 pathway, M70 can disrupt the cascade that leads from NAFLD to NASH, and through fibrosis and cirrhosis to either transplant or death.

Study Design:

A mouse model of NASH, known as STAM™ was used to study the beneficial effect of M70 in treatment of NASH. This model is characterized by steatosis, lobular inflammation and hepatocyte ballooning consistent with NASH pathology in humans. Mice in which M70 was continuously expressed had statistically significant decreases in total body weight, liver weight and liver-to-body weight ratio reflective of a decrease in total liver fat content ($p<0.001$ relative to control).

Results:

M70 expression demonstrated statistically significant improvements in all components of the NAFLD Activity Score (NAS), resulting in a total NAS score of 1.5 compared to 5.33 for control, as shown in the chart below. The NAS is a histological feature scoring system that is widely used to grade the activity of fatty liver disease and the total score represents the sum of the scores for steatosis, lobular inflammation and ballooning. Generally, a score of 5 or greater is considered to be diagnostic of NASH. These results are summarized below.

TABLE 14

Treatment Effect on NAS by M70
Treatment Effect on NAS

| NAS Component | NAS Score | M70 (n = 6) | Control (n = 6) | M70 vs. Control |
|---|---|---|---|---|
| Steatosis | 0 | 6 | 1 | P = 0.0117 |
|  | 1 | 0 | 4 |  |
|  | 2 | 0 | 1 |  |
|  | 3 | 0 | 0 |  |
| Lobular Inflammation | 0 | 3 | 0 | P = 0.0041 |
|  | 1 | 2 | 0 |  |
|  | 2 | 1 | 4 |  |
|  | 3 | 0 | 2 |  |
| Hepatocyte Ballooning | 0 | 1 | 0 | P = 0.0009 |
|  | 1 | 5 | 0 |  |
|  | 2 | 0 | 6 |  |
| Total NAS (mean ± SD) |  | 1.5 ± 1.0 | 5.33 ± 1.5 | P = 0.0005 |

Additional preclinical work in a mouse bile duct ligation model of liver fibrosis has demonstrated that expression of M70 effectively prevents mice from developing hepatic fibrosis, as indicated by histology as well as gene expression analysis of several markers of fibrosis and inflammation. These preclinical data, combined with the Phase 1 MAD study data, further supports the role for M70 providing benefits in patients with NASH.

5.15 Example 15

This example shows the role of M70 in the treatment of cholestatic liver disease and other BARDs.

Cholestatic liver disease is a form of BARD defined as an impairment of bile flow from the liver and is often characterized by fatigue, pruritus and, in its more advanced form, jaundice. Elevated serum bile acids are a hallmark of many cholestatic liver diseases including PSC, PBC, intrahepatic cholestasis of pregnancy, alcoholic hepatitis and drug-induced cholestasis. Impairment of bile acid flow from the liver leads to cholestasis, hepatocellular injury and progressive liver disease that may ultimately result in liver failure.

Bile acids are believed to play a role in causing pruritus, and elevated serum levels of certain forms of bile acid have been correlated to higher rates of pruritus. Severe pruritus, which patients often describe as intense, constant, unrelievable itching under the skin at any place on the body, may present at all stages of cholestatic liver disease and is the most debilitating symptom afflicting cholestatic disease patients. Patients often resort to destructive scratching behaviors that can cause bleeding and scarring, and the condition can lead to a marked decrease in quality of life, impaired sleep, depression and, potentially, suicidal thoughts or actions. Caregivers also suffer from impaired sleep and anxiety as they struggle to help manage this debilitating symptom. In some patients, the emotional and physical effects of pruritus alone can justify liver transplantation.

The potent bile acid regulation effect of M70, and the fact that it is not a derivative of a bile acid, support its role as a treatment for certain cholestatic liver diseases such as PSC, PBC and other BARDs. A large body of in vivo preclinical data testing the efficacy of M70 in a bile duct ligation (BDL) model, an alpha-naphthylisothiocyanate (ANIT) model, and an Mdr2 knockout model showed statistically significant reduction of serum bile acid (p<0.001) and improvements in biochemical markers of liver damage. In addition, as described above in Example 13, the Phase 1 data demonstrated that M70 administration statistically significant reductions in serum C4 levels (p<0.001), indicating biological activity consistent with FGF19 suppression of CYP7a1 in the liver and reduction in serum bile acid levels. In a Phase 2a trial in PBC, subjects demonstrated statistically significant reductions in ALP, GGT, ALT and AST (p<0.05) without generally exacerbating pruritus. All these observations support the view that M70 offers a safe and effective, non-invasive pharmacological approach to reduce serum bile acid and decrease the damaging effects of high bile acid levels in the liver and the debilitating pruritus often associated with cholestatic liver diseases. Accordingly, these results support that M70 can be effective in treating liver cholestatic diseases, such as PSC and other orphan BARDs.

5.16 Example 16

This example shows that M70 improved liver function in preclinical studies.

M70 potently represses in vitro CYP7a1 expression in primary human hepatocytes, or liver cells, and in vivo CYP7a1 expression in mice. In addition, an average reduction of 81% in serum C4 concentrations was observed in cynomolgus monkeys treated for six days with FGF19 (1 mg/kg subcutaneous daily injection) relative to control. Furthermore, preclinical studies using two in vivo models of cholestasis showed that inhibiting de novo bile acid synthesis through the CYP7a1 pathway with M70 showed statistically significant improvements in biochemical markers of liver function in mice.

Study Design and Results:

The first model, bile duct ligation (BDL), uses a surgical method to transect the common bile duct and prevent bile flow out of the liver and induce a state of cholestasis. Mice that were subjected to BDL and received M70 showed a statistically significant reduction of serum bile acids (p<0.001) and improvements in biochemical markers of liver damage, such as alkaline phosphatase (ALP), alkaline aminotransferase (ALT), aspartate aminotransfease (AST) and gamma-glutamyltransferase (GGT), following BDL surgery.

Figure 9:
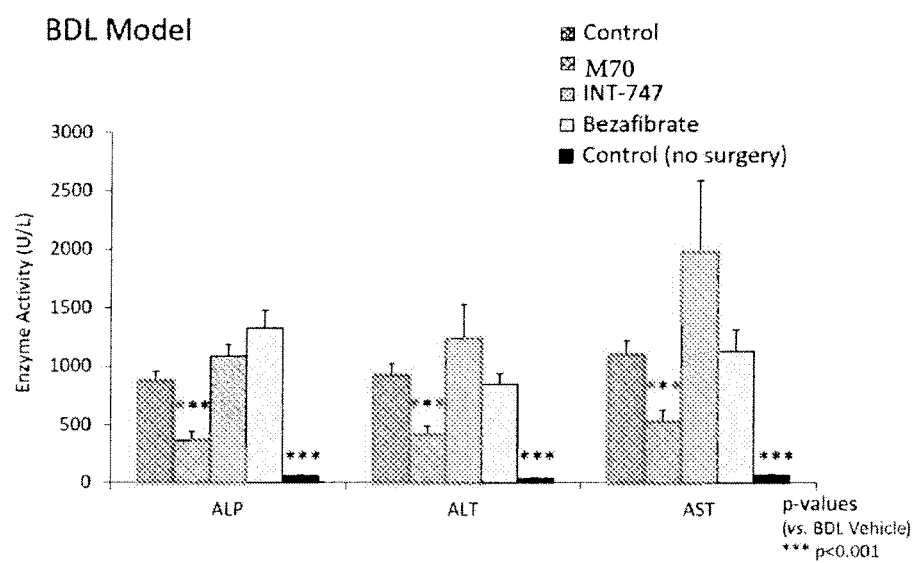
FIG. 9 depicts that mice treated with M70 showed a statistically significant improvement in biochemical markers of liver damage, such as alkaline phosphatase (ALP), alkaline aminotransferase (ALT), aspartate aminotransfease (AST) and gamma-glutamyltransferase (GGT), following bile duct ligation (BDL) surgery.

The results shown in FIG. 9 compare the results from the control group (the mice were subjected to BDL, but did not receive any treatment), a group receiving M70, a group receiving INT-747 (Intercept Pharmaceuticals, Inc.; an FXR agonist ligand and novel bile acid analogue shown to be efficacious in treating humans with PBC in Phase 3 studies), and a group receiving bezafibrate (a drug that is not approved for the treatment of PBC but is nevertheless sometimes prescribed off-label by some physicians).

Notably, as shown in FIG. 9, M70 reduced circulating bile acid levels and improved liver function in the BDL animal model.

Mice treated with ANIT, represent an animal model in which the cholestatic state is pharmacologically induced by chemical treatment that leads to damage of the cells that line the bile ducts.

Figure 10:
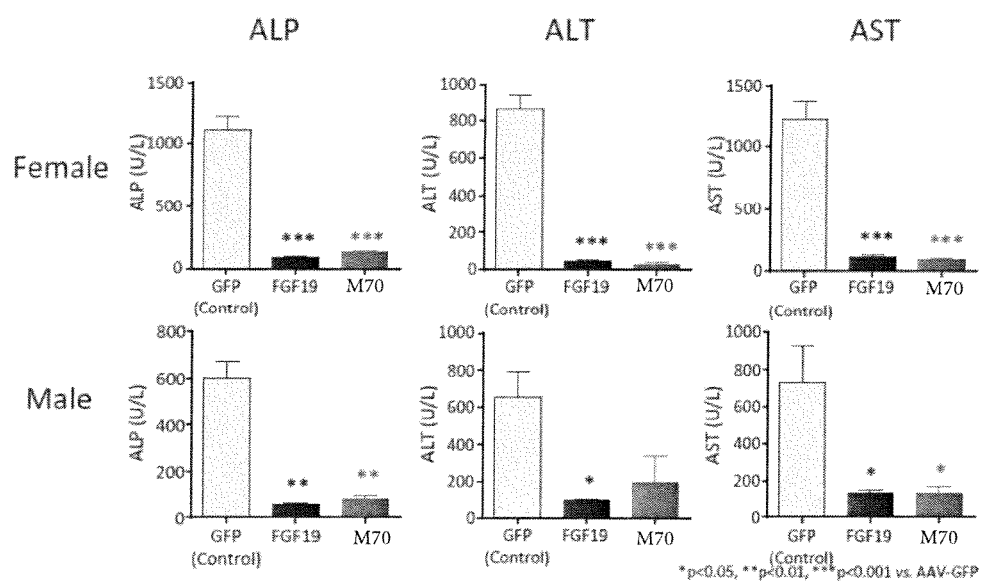
FIG. 10 depicts that continuous expression of M70 in Mdr2 knockout mouse normalized liver enzymes such as ALP, ALT, and AST.
Figure 11:
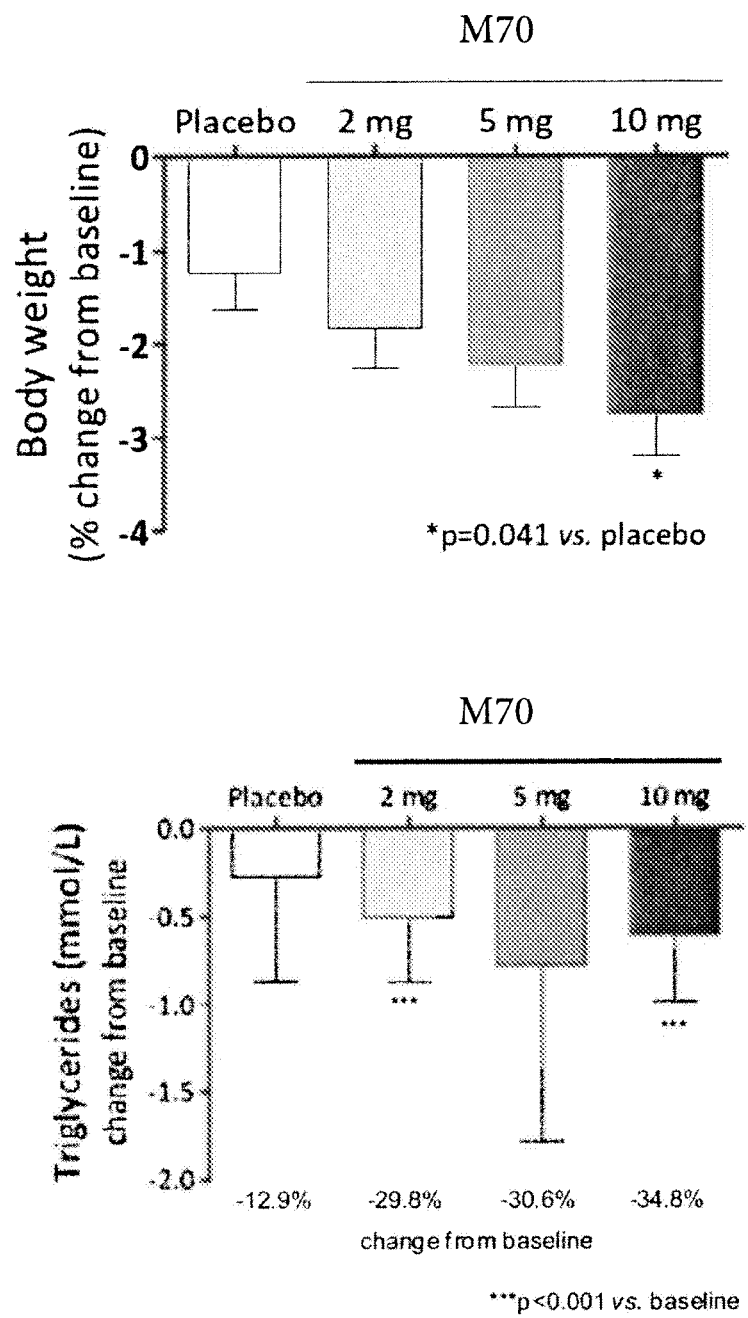
FIG. 11 depicts the results of a human clinical trial, showing administration of M70 was able to promote body weight loss and to reduce serum triglycerides in type 2 diabetes patients.

As shown in FIG. 10, ANIT-treated mice showed a statistically significant elevation in serum bile acids (p<0.01) and an impaired liver function, similar to profiles of human patients suffering from cholestatic disease. As with the BDL model, inhibiting de novo bile acid synthesis through the classical pathway with M70 resulted in statistically significant improvements in biochemical markers of liver function (p<0.001) in the ANIT model.

The Mdr2 knockout mouse model of chronic cholestasis and liver inflammation resembles many aspects of human PSC. In a study in which M70 was continuously expressed in Mdr2 knockout mice for 24 weeks, reduced serum levels of total bile acid, normalized liver enzymes such as ALP, ALT and AST, and reduced liver weight was observed.

Overall, these data further confirmed that M70 is a non-tumorigenic FGF19 variant that can effectively treat PSC and PBC and other manifestations of BARDs. Results from a range of nonclinical safety studies indicated that M70 is safe and well-tolerated and support the dosing range and duration of treatment in clinical trials. Thus, M70 can be a safe and effective pharmacological approach to reducing serum bile acids and decreasing the damaging effects of high bile acid levels in the liver and, potentially, the debilitating pruritus often associated with cholestatic liver diseases.

5.17 Example 17

This example describes a Phase 2, randomized, double blind, placebo controlled, parallel group, multiple center study to evaluate the safety, tolerability and pharmacodynamic activity of M70 in combination with ursodeoxycholic acid (UDCA) administered for 28 days in patients with PBC, and shows the role of M70 in treating human patients.

PBC is a chronic cholestatic liver disease in which the bile ducts become inflamed and are slowly destroyed by an apparent autoimmune reaction, driving bile acid build-up in the liver and, eventually, leading to irreversible scarring. Although a large proportion of patients are asymptomatic at diagnosis, common symptoms of pruritus and fatigue can develop as the disease progresses. The one approved treatment in the United States, UDCA has been shown to slow disease progression in some patients, but only approximately one-third of patients with PBC fully respond to treatment.

Study Design and Results:

A Phase 2a PBC trial was designed to investigate the effects of M70 in combination with UDCA after 28 days of treatment, compared to control. Eligible subjects were randomized to control or one of two treatment groups, including a high dose (3.0 mg) or a low dose (0.3 mg) of M70.

All subjects completed the 28-day treatment phase of the study and were eligible to participate in a 52-week extension trial, also referred to as the Phase 2b trial in PBC subjects. The Phase 2a trial achieved statistical significance in the primary endpoint (change in ALP from baseline, as noted below) at both doses. There were improvements in a number of secondary endpoints (change in the biochemical markers, ALT, AST, GGT, C4, fasting serum bile levels and pruritus and fatigue), including: (1) statistically significant percentage reduction in ALP from baseline to Day 28 with both M70 doses (0.3 mg=−15.8%, p-value=0.009; 3.0 mg=−19.2%, p-value=0.003); (2) marked reductions in other markers of liver injury, including ALT (0.3 mg=−17.5 IU/L; 3.0 mg=−26.7 IU/L), AST (0.3 mg=−10.9 IU/L; 3.0 mg=−15.3 IU/L) and GGT (0.3 mg=−28.2 IU/L; 3.0 mg=−50.9 IU/L); (3) no statistically significant change in pruritus in either M70 treatment arm; and (4) acceptable safety and tolerability profile with no drug-related safety signals. Most adverse events were mild, with a single serious adverse event that was deemed not related to treatment. The most frequent adverse events were mild headache and mild lower GI symptoms. The lower GI symptoms were observed in 21% of the 0.3 mg and 43% of the 3 mg cohorts, compared to 13% of the control group. Mild injection site reactions were also observed more frequently with M70.

The Phase 2b trial was designed as a 52-week extension to enable subjects from the Phase 2a 28-day PBC study to get access to M70 for an extended period and thus allow collection of data on the longer term safety profile and disease impact of M70. An analysis of available data was performed for those subjects that transitioned from the Phase 2a study and reached 12 weeks of treatment. A reduction of ALP from baseline was observed in all groups at that time point, with the lowest dose (0.3 mg) cohort achieving a statistically significant reduction (p=0.004). In the Phase 2b PBC trial, M70 has thus far exhibited a safety and tolerability profile consistent with that seen in the Phase 2a PBC trial.

While UDCA is the only treatment approved for PBC in the United States, there are several treatments in development. INT-747, an FXR agonist ligand and novel bile acid analogue, is one such treatment. FXR is a nuclear receptor involved in regulating the expression of numerous genes, including the gene that produces the FGF19 hormone. Although INT-747's Phase 3 trial demonstrated a statistically significant effect on ALP reduction (p<0.0001), the drug nearly doubled the rate of pruritus in PBC subjects as compared to control (68% and 38% at the 10 mg and placebo doses, respectively), perhaps as a consequence of introduc-

TABLE 15

Clinical Trial Design on PBC treatment by M70)

| Study Population | Primary Outcome Measure | Primary Outcome Results | Selected Secondary Outcomes | Safety and Tolerability |
|---|---|---|---|---|
| PBC subjects on UDCA for at least 12 months with an incomplete response | Change in ALP (absolute international units per liter, or IU/L, %) from baseline at Day 28 | Statistically significant ALP reductions with both doses 0.3 mg: −49 IU/L (−15.8%) 3 mg: −69 IU/L (−19.2%) | Liver enzymes: statistically significant reduction in ALT, AST and GGT at both dose levels vs. placebo (p < 0.05) Serum C4: reduction observed with 3 mg dose Cholesterol: no statistically significant change | No statistically significant evidence of drug-induced pruritus Majority of adverse events were mild or moderate One serious adverse event reported (not drug related) | ing a bile acid analog into the livers of subjects suffering from excessive bile acid accumulation.

5.18 Example 18

This example discussed the role of M70 for the treatment of primary sclerosing cholangitis (PSC). PSC is a chronic cholestatic liver disease, characterized by progressive inflammation, fibrosis and obstruction of the bile ducts leading to cholestasis and, in most cases, liver failure and an increased risk of liver cancer. Though cholestatic symptoms will eventually present, patients can remain asymptomatic and undiagnosed for several years. The median life expectancy after diagnosis with PSC is 12 to 18 years without liver transplantation and, even in the case of liver transplanted patients, PSC returns in 30% to 50% of patients within ten years. PSC is often associated with ulcerative colitis and also appears to have overlap with other forms of autoimmune disease, including autoimmune hepatitis and autoimmune pancreatitis. The patient population is estimated to be between 50,000 and 132,000 in the United States and Europe, with a 2:1 incidence in men versus women and a particularly high incidence in northern Europe. There are no approved therapeutics for the treatment of PSC, but liver transplantation is the most frequent treatment approach in end-stage PSC, making it the fifth leading indication for liver transplant in the United States. Many PSC patients suffer from the same pruritus symptoms of PBC and for which there are currently no drug treatments available.

The bile acid synthesis-inhibiting properties of M70 can help slow the progression of PSC by reducing the pool of bile acid in the obstructed bile ducts and thereby lessening the impact on liver fibrosis.

Study Design:

The study of M70 in PSC subjects will explore the activity of the compound in approximately 60 subjects in a 12-week, randomized, placebo-controlled, double-blind, multi-center trial. The subjects will be confirmed PSC patients as assessed by elevated ALP and cholangiography or liver biopsy with no evidence of cirrhosis or advanced liver disease. The primary endpoint will be change in ALP from baseline at 12 weeks of treatment. The study is designed to investigate the effects of M70 on changes from baseline in other biochemical markers associated with PSC, such as ALT, GGT and bilirubin, serum bile acid, C4, pruritus and inflammatory bowel disease symptoms, following daily dosing over 12 weeks.

5.19 Example 19

This example describes a Phase 2 randomized, double blind, placebo controlled, parallel group, multiple center study to evaluate the safety, tolerability and activity of M70 administered for 28 days to participants with type 2 diabetes Study Design:

A four-week, randomized, double-blind, multi-center trial was conducted to evaluate M70 in subjects with type 2 diabetes. As a consequence of the contribution of obesity and insulin resistance to both conditions, there is a substantial overlap in the prevalence of type 2 diabetes and NASH patients.

The type 2 diabetes trial was also designed to measure several of the metabolic parameters that are believed to play a role in the disease progression of NAFLD and NASH, including indicators of insulin sensitivity, triglyceride levels and liver enzyme levels. Three doses of M70 were tested in subjects with type 2 diabetes inadequately controlled by metformin to assess changes from baseline in biochemical markers associated with type 2 diabetes, such as fasting plasma glucose and stimulated glucose/insulin.

The primary endpoint measured by this trial was the change in fasting plasma glucose after 28 days of treatment. Although this endpoint was not different in the M70 subjects as compared to the control arm, there were trends towards improvement in insulin sensitivity, as measured by HOMA-IR and a statistically significant weight loss observed in the 10 mg group, which lost an average of 2.6 kilograms over the 28 days of treatment (p<0.041). Moreover, there was a statistically significant reduction in triglycerides with the 2 mg (p=0.009) and 10 mg (p=0.007) doses and dose-dependent reductions in ALT, or alanine transaminase, and AST, or aspartate transaminase, consistent with improvements in liver health. The trial further established that M70 improves both metabolic and liver health in a patient population that closely resembles NASH patients.

TABLE 16

Clinical Trial Design on Type 2 Diabetes treatment by M70

| Study Population | Primary Outcome Measure | Primary Outcome Results | Selected Secondary Outcomes | Safety and Tolerability |
| --- | --- | --- | --- | --- |
| Type 2 diabetes subjects inadequately controlled by metformin | Change in fasting plasma glucose (FPG) from baseline at Day 28 | No statistically significant reduction in FPG | HOMA-IR: statistically significant reduction at 10 mg dose (p = 0.001) Body weight: statistically significant reduction at 10 mg dose (p = 0.019) Serum triglycerides: statistically significant reduction at 2 and 10 mg doses (p = 0.009 and p = 0.007, respectively) | No serious adverse events reported Majority of adverse events were mild or moderate |

TABLE 16-continued

Clinical Trial Design on Type 2 Diabetes treatment by M70

| Study Population | Primary Outcome Measure | Primary Outcome Results | Selected Secondary Outcomes | Safety and Tolerability |
|---|---|---|---|---|
| | | | Liver enzymes: reduction in ALT and AST Cholesterol: statistically significant increase ($p < 0.05$) | |

Overall, M70 was well tolerated at each dose. There were no serious adverse events reported. These preclinical and clinical data suggest that M70 offers a potentially novel approach in the treatment of NASH by reducing body weight and triglyceride levels and improving insulin sensitivity to combat the metabolic drivers of the disease, while also reducing bile acid synthesis to combat the liver damage caused by pooling of toxic bile acid.

6. SEQUENCE LISTING

The present specification is being filed with a computer readable form (CRF) copy of the Sequence Listing. The CRF entitled 13370-038-228_SEQLIST.txt, which was created on Nov. 6, 2016 and is 262,144 bytes in size, is identical to the paper copy of the Sequence Listing and is incorporated herein by reference in its entirety.

What is claimed is:

1. A method of treating pruritus associated with a cholestatic liver disease in a subject in need thereof, comprising administering to the subject an effective amount of a peptide, wherein the peptide has an amino acid sequence comprising:

(SEQ ID NO: 70)
MRDSSPLVHYGWGDPIRLRHLYTSGPHGLSSCFLRIRADGVVDCARGQSA
HSLLEIKAVALRTVAIKGVHSVRYLCMGADGKMQGLLQYSEEDCAFEEEI
RPDGYNVYRSEKHRLPVSLSSAKQRQLYKNRGFLPLSHFLPMLPMVPEEP
EDLRGHLESDMFSSPLETDSMDPFGLVTGLEAVRSPSFEK.

2. The method of claim 1, wherein the effective amount of the peptide is 0.3 mg.

3. The method of claim 1, wherein the effective amount of the peptide is 1 mg.

4. The method of claim 1, wherein the effective amount of the peptide is 2 mg.

5. The method of claim 1, wherein the effective amount of the peptide is 3 mg.

6. The method of claim 1, wherein the effective amount of the peptide is 5 mg.

7. The method of claim 1, wherein the effective amount of the peptide is 10 mg.

8. The method of claim 1, wherein the peptide is administered once a day.

9. The method of claim 1, wherein the peptide is administered twice a day.

10. The method of claim 1, wherein the peptide is administrated subcutaneously.

11. The method of claim 1, wherein the peptide is administered for 7 days or longer.

12. The method of claim 1, wherein the peptide is administered for 14 days or longer.

13. The method of claim 1, wherein the peptide is administered for 21 days or longer.

14. The method of claim 1, wherein the peptide is administered for 28 days or longer.

15. The method of claim 1, wherein the peptide is administered for 1 to 12 months.

16. The method of claim 1, wherein the peptide is administered for 12 months.

17. The method of claim 1, wherein the peptide is administered for more than 12 months.

18. The method of claim 1, wherein the peptide is administered in combination with ursodeoxycholic acid (UDCA).

19. The method of claim 1, wherein the subject has a cholestatic liver disease.

20. The method of claim 19, wherein the cholestatic liver disease is primary sclerosing cholangitis (PSC).

21. The method of claim 19, wherein the cholestatic liver disease is primary biliary cirrhosis (PBC).

22. The method of claim 19, wherein the cholestatic liver disease is intrahepatic cholestasis of pregnancy.

23. The method of claim 19, wherein the cholestatic liver disease is alcoholic hepatitis.

24. The method of claim 19, wherein the cholestatic liver disease is drug-induced cholestasis.

25. The method of claim 1, wherein the subject is human.

26. A method of treating pruritus associated with a cholestatic liver disease in a subject in need thereof, comprising administering to the subject an effective amount of a peptide, wherein the peptide has an amino acid sequence consisting of:

```
                                            (SEQ ID NO: 70)
MRDSSPLVHYGWGDPIRLRHLYTSGPHGLSSCFLRIRADGVVDCARGQSA

HSLLEIKAVALRTVAIKGVHSVRYLCMGADGKMQGLLQYSEEDCAFEEEI

RPDGYNVYRSEKHRLPVSLSSAKQRQLYKNRGFLPLSHFLPMLPMVPEEP

EDLRGHLESDMFSSPLETDSMDPFGLVTGLEAVRSPSFEK.
```

27. The method of claim 26, wherein the effective amount of the peptide is 0.3 mg.

28. The method of claim 26, wherein the effective amount of the peptide is 1 mg.

29. The method of claim 26, wherein the effective amount of the peptide is 2 mg.

30. The method of claim 26, wherein the effective amount of the peptide is 3 mg.

31. The method of claim 26, wherein the effective amount of the peptide is 5 mg.

32. The method of claim 26, wherein the effective amount of the peptide is 10 mg.

33. The method of claim 26, wherein the peptide is administered once a day.

34. The method of claim 26, wherein the peptide is administered twice a day.

35. The method of claim 26, wherein the peptide is administrated subcutaneously.

36. The method of claim 26, wherein the peptide is administered for 7 days or longer.

37. The method of claim 26, wherein the peptide is administered for 14 days or longer.

38. The method of claim 26, wherein the peptide is administered for 21 days or longer.

39. The method of claim 26, wherein the peptide is administered for 28 days or longer.

40. The method of claim 26, wherein the peptide is administered for 1 to 12 months.

41. The method of claim 26, wherein the peptide is administered for 12 months.

42. The method of claim 26, wherein the peptide is administered for more than 12 months.

43. The method of claim 26, wherein the peptide is administered in combination with UDCA.

44. The method of claim 26, wherein the subject has a cholestatic liver disease.

45. The method of claim 44, wherein the cholestatic liver disease is PSC.

46. The method of claim 44, wherein the cholestatic liver disease is PBC.

47. The method of claim 44, wherein the cholestatic liver disease is intrahepatic cholestasis of pregnancy.

48. The method of claim 44, wherein the cholestatic liver disease is alcoholic hepatitis.

49. The method of claim 44, wherein the cholestatic liver disease is drug-induced cholestasis.

50. The method of claim 26, wherein the subject is human.

51. A method of preventing the induction or exacerbation of pruritus associated with a cholestatic liver disease in a subject being treated for the cholestatic liver disease, comprising administering to the subject an effective amount of a peptide, wherein the peptide has an amino acid sequence comprising:

```
                                            (SEQ ID NO: 70)
MRDSSPLVHYGWGDPIRLRHLYTSGPHGLSSCFLRIRADGVVDCARGQSA

HSLLEIKAVALRTVAIKGVHSVRYLCMGADGKMQGLLQYSEEDCAFEEEI

RPDGYNVYRSEKHRLPVSLSSAKQRQLYKNRGFLPLSHFLPMLPMVPEEP

EDLRGHLESDMFSSPLETDSMDPFGLVTGLEAVRSPSFEK.
```

52. The method of claim 51, wherein the peptide has an amino acid sequence consisting of SEQ ID NO:70.

* * * * *

```
                         SEQUENCE LISTING

<160> NUMBER OF SEQ ID NOS: 205

<210> SEQ ID NO 1
<211> LENGTH: 194
<212> TYPE: PRT
<213> ORGANISM: Homo sapiens

<400> SEQUENCE: 1

Arg Pro Leu Ala Phe Ser Asp Ala Ser Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 2
<211> LENGTH: 194
```

```
<212> TYPE: PRT
<213> ORGANISM: Homo sapiens

<400> SEQUENCE: 2

Arg Pro Leu Ala Phe Ser Asp Ser Ser Pro Leu Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
        50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 3
<211> LENGTH: 194
<212> TYPE: PRT
<213> ORGANISM: Homo sapiens

<400> SEQUENCE: 3

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
        50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Leu Glu Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
```

```
145                 150                 155                 160
Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 4
<211> LENGTH: 194
<212> TYPE: PRT
<213> ORGANISM: Homo sapiens

<400> SEQUENCE: 4

Arg Pro Leu Ala Phe Ser Asp Ala Gly Pro His Val His Tyr Ala Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 5
<211> LENGTH: 191
<212> TYPE: PRT
<213> ORGANISM: Homo sapiens

<400> SEQUENCE: 5

Arg His Pro Ile Pro Asp Ser Ser Pro Leu Leu Gln Phe Gly Gly Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80
```

```
Asp Gly Lys Met Gln Gly Leu Leu Gln Tyr Ser Glu Glu Asp Cys Ala
            85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
            130                 135             140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 6
<211> LENGTH: 187
<212> TYPE: PRT
<213> ORGANISM: Homo sapiens

<400> SEQUENCE: 6

Arg Asp Ser Ser Pro Leu Leu Gln Phe Gly Gly Gln Val Arg Leu Arg
1               5                   10                  15

His Leu Tyr Thr Ser Gly Pro His Gly Leu Ser Ser Cys Phe Leu Arg
            20                  25                  30

Ile Arg Ala Asp Gly Val Val Asp Cys Ala Arg Gly Gln Ser Ala His
            35                  40                  45

Ser Leu Leu Glu Ile Lys Ala Val Ala Leu Arg Thr Val Ala Ile Lys
50                  55                  60

Gly Val His Ser Val Arg Tyr Leu Cys Met Gly Ala Asp Gly Lys Met
65                  70                  75                  80

Gln Gly Leu Leu Gln Tyr Ser Glu Glu Asp Cys Ala Phe Glu Glu Glu
            85                  90                  95

Ile Arg Pro Asp Gly Tyr Asn Val Tyr Arg Ser Glu Lys His Arg Leu
            100                 105                 110

Pro Val Ser Leu Ser Ser Ala Lys Gln Arg Gln Leu Tyr Lys Asn Arg
            115                 120                 125

Gly Phe Leu Pro Leu Ser His Phe Leu Pro Met Leu Pro Met Val Pro
            130                 135             140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 7
<211> LENGTH: 192
<212> TYPE: PRT
<213> ORGANISM: Homo sapiens

<400> SEQUENCE: 7

Arg Pro Leu Ala Phe Ser Asp Ser Ser Pro Leu Leu Gln Phe Gly Gly
1               5                   10                  15

Gln Val Arg Leu Arg His Leu Tyr Thr Ser Gly Pro His Gly Leu Ser
            20                  25                  30
```

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
 50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 8
<211> LENGTH: 191
<212> TYPE: PRT
<213> ORGANISM: Homo sapiens

<400> SEQUENCE: 8

Arg His Pro Ile Pro Asp Ser Ser Pro Leu Leu Gln Trp Gly Asp Pro
 1               5                  10                  15

Ile Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
 50                  55                  60

Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 9
<211> LENGTH: 193
<212> TYPE: PRT
<213> ORGANISM: Homo sapiens

```
<400> SEQUENCE: 9

Arg His Pro Ile Pro Asp Ser Ser Pro Leu Leu Gln Phe Gly Trp Gly
1               5                   10                  15

Asp Pro Ile Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Asp
                85                  90                  95

Cys Ala Phe Glu Glu Glu Ile Arg Pro Asp Gly Tyr Asn Val Tyr Arg
                100                 105                 110

Ser Glu Lys His Arg Leu Pro Val Ser Leu Ser Ser Ala Lys Gln Arg
            115                 120                 125

Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
            180                 185                 190

Lys

<210> SEQ ID NO 10
<211> LENGTH: 193
<212> TYPE: PRT
<213> ORGANISM: Homo sapiens

<400> SEQUENCE: 10

Arg His Pro Ile Pro Asp Ser Ser Pro His Val His Tyr Gly Trp Gly
1               5                   10                  15

Asp Pro Ile Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Asp
                85                  90                  95

Cys Ala Phe Glu Glu Glu Ile Arg Pro Asp Gly Tyr Asn Val Tyr Arg
                100                 105                 110

Ser Glu Lys His Arg Leu Pro Val Ser Leu Ser Ser Ala Lys Gln Arg
            115                 120                 125

Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160
```

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
            180                 185                 190

Lys

<210> SEQ ID NO 11
<211> LENGTH: 192
<212> TYPE: PRT
<213> ORGANISM: Homo sapiens

<400> SEQUENCE: 11

Arg Pro Leu Ala Phe Ser Asp Ala Gly Pro Leu Leu Gln Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 12
<211> LENGTH: 194
<212> TYPE: PRT
<213> ORGANISM: Homo sapiens

<400> SEQUENCE: 12

Arg Pro Leu Ala Phe Ser Asp Ala Gly Pro Leu Leu Gln Phe Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr

Arg Ser Glu Lys His Arg Leu Pro Val Ser Leu Ser Ala Lys Gln
            115                 120                 125

Arg Gln Leu Tyr Lys Asn Arg Gly Phe Leu Pro Leu Ser His Phe Leu
        130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 13
<211> LENGTH: 192
<212> TYPE: PRT
<213> ORGANISM: Homo sapiens

<400> SEQUENCE: 13

Arg Pro Leu Ala Phe Ser Asp Ala Gly Pro Leu Leu Gln Phe Gly Gly
1               5                   10                  15

Gln Val Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
                180                 185                 190

<210> SEQ ID NO 14
<211> LENGTH: 191
<212> TYPE: PRT
<213> ORGANISM: Homo sapiens

<400> SEQUENCE: 14

Arg His Pro Ile Pro Asp Ser Ser Pro His Val His Tyr Gly Gly Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

-continued

```
Gln Ser Ala His Ser Leu Leu Glu Ile Lys Ala Val Ala Leu Arg Thr
     50                  55                  60

Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 15
<211> LENGTH: 192
<212> TYPE: PRT
<213> ORGANISM: Homo sapiens

<400> SEQUENCE: 15

Arg Pro Leu Ala Phe Ser Asp Ala Gly Pro His Val His Tyr Gly Gly
 1               5                  10                  15

Gln Val Arg Leu Arg His Leu Tyr Thr Ser Gly Pro His Gly Leu Ser
             20                  25                  30

Ser Cys Phe Leu Arg Ile Arg Ala Asp Gly Val Val Asp Cys Ala Arg
         35                  40                  45

Gly Gln Ser Ala His Ser Leu Leu Glu Ile Lys Ala Val Ala Leu Arg
     50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 16
<211> LENGTH: 192
<212> TYPE: PRT
<213> ORGANISM: Homo sapiens

<400> SEQUENCE: 16
```

```
Arg Pro Leu Ala Phe Ser Asp Ala Gly Pro His Val His Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 17
<211> LENGTH: 192
<212> TYPE: PRT
<213> ORGANISM: Homo sapiens

<400> SEQUENCE: 17

Arg Pro Leu Ala Phe Ser Asp Ala Gly Pro His Val Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
```

```
                     180                 185                 190

<210> SEQ ID NO 18
<211> LENGTH: 192
<212> TYPE: PRT
<213> ORGANISM: Homo sapiens

<400> SEQUENCE: 18

Arg Pro Leu Ala Phe Ser Asp Ala Gly Pro His Tyr Gly Trp Gly Asp
1               5                   10                  15

Pro Ile Arg Leu Arg His Leu Tyr Thr Ser Gly Pro His Gly Leu Ser
                20                  25                  30

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
        50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 19
<211> LENGTH: 192
<212> TYPE: PRT
<213> ORGANISM: Homo sapiens

<400> SEQUENCE: 19

Arg Pro Leu Ala Phe Ser Asp Ala Gly Pro Val Tyr Gly Trp Gly Asp
1               5                   10                  15

Pro Ile Arg Leu Arg His Leu Tyr Thr Ser Gly Pro His Gly Leu Ser
                20                  25                  30

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
        50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
```

```
                130               135                140
Leu Pro Met Val Pro Glu Glu Pro Glu Asp Leu Arg Gly His Leu Glu
145                 150                155                160

Ser Asp Met Phe Ser Ser Pro Leu Glu Thr Asp Ser Met Asp Pro Phe
                165                 170                175

Gly Leu Val Thr Gly Leu Glu Ala Val Arg Ser Pro Ser Phe Glu Lys
            180                 185                190

<210> SEQ ID NO 20
<211> LENGTH: 192
<212> TYPE: PRT
<213> ORGANISM: Homo sapiens

<400> SEQUENCE: 20

Arg Pro Leu Ala Phe Ser Asp Ala Gly Pro Val His Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 21
<211> LENGTH: 192
<212> TYPE: PRT
<213> ORGANISM: Homo sapiens

<400> SEQUENCE: 21

Arg Pro Leu Ala Phe Ser Asp Ala Gly Pro Val His Tyr Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
```

```
            85                  90                  95
Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
            130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
                180                 185                 190

<210> SEQ ID NO 22
<211> LENGTH: 193
<212> TYPE: PRT
<213> ORGANISM: Homo sapiens

<400> SEQUENCE: 22

Arg Pro Leu Ala Phe Ser Asp Ala Gly Pro His Val His Gly Trp Gly
1               5                   10                  15

Asp Pro Ile Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
            35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
            115                 120                 125

Gln Leu Tyr Lys Asn Arg Gly Phe Leu Pro Leu Ser His Phe Leu Pro
            130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
                180                 185                 190

Lys

<210> SEQ ID NO 23
<211> LENGTH: 192
<212> TYPE: PRT
<213> ORGANISM: Homo sapiens

<400> SEQUENCE: 23

Arg Pro Leu Ala Phe Ser Asp Ala Gly Pro His His Gly Trp Gly Asp
1               5                   10                  15

Pro Ile Arg Leu Arg His Leu Tyr Thr Ser Gly Pro His Gly Leu Ser
            20                  25                  30
```

```
Ser Cys Phe Leu Arg Ile Arg Ala Asp Gly Val Val Asp Cys Ala Arg
         35                  40                  45

Gly Gln Ser Ala His Ser Leu Leu Glu Ile Lys Ala Val Ala Leu Arg
 50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
             100                 105                 110

Glu Lys His Arg Leu Pro Val Ser Leu Ser Ser Ala Lys Gln Arg Gln
         115                 120                 125

Leu Tyr Lys Asn Arg Gly Phe Leu Pro Leu Ser His Phe Leu Pro Met
 130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 24
<211> LENGTH: 192
<212> TYPE: PRT
<213> ORGANISM: Homo sapiens

<400> SEQUENCE: 24

Arg Pro Leu Ala Phe Ser Asp Ala Gly Pro His His Tyr Trp Gly Asp
 1               5                  10                  15

Pro Ile Arg Leu Arg His Leu Tyr Thr Ser Gly Pro His Gly Leu Ser
             20                  25                  30

Ser Cys Phe Leu Arg Ile Arg Ala Asp Gly Val Val Asp Cys Ala Arg
         35                  40                  45

Gly Gln Ser Ala His Ser Leu Leu Glu Ile Lys Ala Val Ala Leu Arg
 50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
             100                 105                 110

Glu Lys His Arg Leu Pro Val Ser Leu Ser Ser Ala Lys Gln Arg Gln
         115                 120                 125

Leu Tyr Lys Asn Arg Gly Phe Leu Pro Leu Ser His Phe Leu Pro Met
 130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 25
<211> LENGTH: 192
<212> TYPE: PRT
```

<213> ORGANISM: Homo sapiens

<400> SEQUENCE: 25

```
Arg Pro Leu Ala Phe Ser Asp Ala Gly Pro His Val Tyr Trp Gly Asp
1               5                   10                  15

Pro Ile Arg Leu Arg His Leu Tyr Thr Ser Gly Pro His Gly Leu Ser
                20                  25                  30

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
        50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190
```

<210> SEQ ID NO 26
<211> LENGTH: 192
<212> TYPE: PRT
<213> ORGANISM: Homo sapiens

<400> SEQUENCE: 26

```
Arg Pro Leu Ala Phe Ser Asp Ser Ser Pro Leu Val His Trp Gly Asp
1               5                   10                  15

Pro Ile Arg Leu Arg His Leu Tyr Thr Ser Gly Pro His Gly Leu Ser
                20                  25                  30

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
        50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
```

```
                165                 170                 175
Gly Leu Val Thr Gly Leu Glu Ala Val Arg Ser Pro Ser Phe Glu Lys
            180                 185                 190

<210> SEQ ID NO 27
<211> LENGTH: 192
<212> TYPE: PRT
<213> ORGANISM: Homo sapiens

<400> SEQUENCE: 27

Arg Pro Leu Ala Phe Ser Asp Ser Ser Pro His Val His Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 28
<211> LENGTH: 191
<212> TYPE: PRT
<213> ORGANISM: Homo sapiens

<400> SEQUENCE: 28

Arg Pro Leu Ala Phe Ser Asp Ala Gly Pro His Val Trp Gly Asp Pro
1               5                   10                  15

Ile Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
```

```
            115                 120                 125
Tyr Lys Asn Arg Gly Phe Leu Pro Leu Ser His Phe Leu Pro Met Leu
        130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190
```

<210> SEQ ID NO 29
<211> LENGTH: 193
<212> TYPE: PRT
<213> ORGANISM: Homo sapiens

<400> SEQUENCE: 29

```
Arg Pro Leu Ala Phe Ser Asp Ala Gly Pro His Val His Tyr Trp Gly
1               5                   10                  15

Asp Pro Ile Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
        115                 120                 125

Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
            180                 185                 190

Lys
```

<210> SEQ ID NO 30
<211> LENGTH: 194
<212> TYPE: PRT
<213> ORGANISM: Homo sapiens

<400> SEQUENCE: 30

```
Arg Pro Leu Ala Phe Ser Asp Ala Gly Pro His Val His Tyr Ala Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60
```

```
Leu Arg Thr Val Ala Ile Lys Gly Val His Ser Val Arg Tyr Leu Cys
 65                  70                  75                  80

Met Gly Ala Asp Gly Lys Met Gln Gly Leu Gln Tyr Ser Glu Glu
                 85                  90                  95

Asp Cys Ala Phe Glu Glu Glu Ile Arg Pro Asp Gly Tyr Asn Val Tyr
                100                 105                 110

Arg Ser Glu Lys His Arg Leu Pro Val Ser Leu Ser Ser Ala Lys Gln
                115                 120                 125

Arg Gln Leu Tyr Lys Asn Arg Gly Phe Leu Pro Leu Ser His Phe Leu
                130                 135                 140

Pro Met Leu Pro Met Val Pro Glu Glu Pro Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 31
<211> LENGTH: 191
<212> TYPE: PRT
<213> ORGANISM: Homo sapiens

<400> SEQUENCE: 31

Arg His Pro Ile Pro Asp Ser Ser Pro Leu Leu Gln Phe Gly Ala Gln
  1               5                  10                  15

Val Arg Leu Arg His Leu Tyr Thr Ser Gly Pro His Gly Leu Ser Ser
                 20                  25                  30

Cys Phe Leu Arg Ile Arg Ala Asp Gly Val Val Asp Cys Ala Arg Gly
                 35                  40                  45

Gln Ser Ala His Ser Leu Leu Glu Ile Lys Ala Val Ala Leu Arg Thr
     50                  55                  60

Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
                115                 120                 125

Tyr Lys Asn Arg Gly Phe Leu Pro Leu Ser His Phe Leu Pro Met Leu
                130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 32
<211> LENGTH: 191
<212> TYPE: PRT
<213> ORGANISM: Homo sapiens

<400> SEQUENCE: 32
```

Arg His Pro Ile Pro Asp Ser Ser Pro Leu Gln Phe Gly Asp Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
                35                  40                  45

Gln Ser Ala His Ser Leu Leu Glu Ile Lys Ala Val Ala Leu Arg Thr
50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
                115                 120                 125

Tyr Lys Asn Arg Gly Phe Leu Pro Leu Ser His Phe Leu Pro Met Leu
130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 33
<211> LENGTH: 191
<212> TYPE: PRT
<213> ORGANISM: Homo sapiens

<400> SEQUENCE: 33

Arg His Pro Ile Pro Asp Ser Ser Pro Leu Leu Gln Phe Gly Pro Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
                35                  40                  45

Gln Ser Ala His Ser Leu Leu Glu Ile Lys Ala Val Ala Leu Arg Thr
50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
                115                 120                 125

Tyr Lys Asn Arg Gly Phe Leu Pro Leu Ser His Phe Leu Pro Met Leu
130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

```
<210> SEQ ID NO 34
<211> LENGTH: 191
<212> TYPE: PRT
<213> ORGANISM: Homo sapiens

<400> SEQUENCE: 34

Arg His Pro Ile Pro Asp Ser Ser Pro Leu Leu Gln Phe Gly Gly Ala
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 35
<211> LENGTH: 191
<212> TYPE: PRT
<213> ORGANISM: Homo sapiens

<400> SEQUENCE: 35

Arg His Pro Ile Pro Asp Ser Ser Pro Leu Leu Gln Phe Gly Gly Glu
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140
```

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 36
<211> LENGTH: 191
<212> TYPE: PRT
<213> ORGANISM: Homo sapiens

<400> SEQUENCE: 36

Arg His Pro Ile Pro Asp Ser Ser Pro Leu Leu Gln Phe Gly Gly Asn
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 37
<211> LENGTH: 191
<212> TYPE: PRT
<213> ORGANISM: Homo sapiens

<400> SEQUENCE: 37

Arg His Pro Ile Pro Asp Ser Ser Pro Leu Leu Gln Phe Gly Gly Gln
1               5                   10                  15

Ala Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 38
<211> LENGTH: 191
<212> TYPE: PRT
<213> ORGANISM: Homo sapiens

<400> SEQUENCE: 38

Arg His Pro Ile Pro Asp Ser Ser Pro Leu Leu Gln Phe Gly Gly Gln
1               5                   10                  15

Ile Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 39
<211> LENGTH: 191
<212> TYPE: PRT
<213> ORGANISM: Homo sapiens

<400> SEQUENCE: 39

Arg His Pro Ile Pro Asp Ser Ser Pro Leu Leu Gln Phe Gly Gly Gln
1               5                   10                  15

Thr Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

```
Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
 65                 70                  75                  80

Asp Gly Lys Met Gln Gly Leu Leu Gln Tyr Ser Glu Glu Asp Cys Ala
                85                  90                  95

Phe Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
        130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 40
<211> LENGTH: 193
<212> TYPE: PRT
<213> ORGANISM: Homo sapiens

<400> SEQUENCE: 40

Arg His Pro Ile Pro Asp Ser Ser Pro Leu Leu Gln Phe Gly Trp Gly
  1               5                  10                  15

Gln Pro Val Arg Leu Arg His Leu Tyr Thr Ser Gly Pro His Gly Leu
                20                  25                  30

Ser Ser Cys Phe Leu Arg Ile Arg Ala Asp Gly Val Val Asp Cys Ala
            35                  40                  45

Arg Gly Gln Ser Ala His Ser Leu Leu Glu Ile Lys Ala Val Ala Leu
        50                  55                  60

Arg Thr Val Ala Ile Lys Gly Val His Ser Val Arg Tyr Leu Cys Met
 65                 70                  75                  80

Gly Ala Asp Gly Lys Met Gln Gly Leu Leu Gln Tyr Ser Glu Glu Asp
                85                  90                  95

Cys Ala Phe Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
            115                 120                 125

Gln Leu Tyr Lys Asn Arg Gly Phe Leu Pro Leu Ser His Phe Leu Pro
        130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
                180                 185                 190

Lys

<210> SEQ ID NO 41
<211> LENGTH: 182
<212> TYPE: PRT
<213> ORGANISM: Homo sapiens
```

<400> SEQUENCE: 41

```
Arg Pro Leu Ala Phe Ser Asp Ala Gly Pro His Val His Tyr Gly Trp
1               5                   10                  15
Gly Asp Pro Ile Arg Leu Arg His Leu Tyr Thr Ser Gly Pro His Gly
            20                  25                  30
Leu Ser Ser Cys Phe Leu Arg Ile Arg Ala Asp Gly Val Val Asp Cys
        35                  40                  45
Ala Arg Gly Gln Ser Ala His Ser Leu Leu Glu Ile Lys Ala Val Ala
    50                  55                  60
Leu Arg Thr Val Ala Ile Lys Gly Val His Ser Val Arg Tyr Leu Cys
65                  70                  75                  80
Met Gly Ala Asp Gly Lys Met Gln Gly Leu Leu Gln Tyr Ser Glu Glu
                85                  90                  95
Asp Cys Ala Phe Glu Glu Ile Arg Pro Asp Gly Tyr Asn Val Tyr
            100                 105                 110
Arg Ser Glu Lys His Arg Leu Pro Val Ser Leu Ser Ala Lys Gln
        115                 120                 125
Arg Gln Leu Tyr Lys Asn Arg Gly Phe Leu Pro Leu Ser His Phe Leu
    130                 135                 140
Pro Met Leu Pro Glu Pro Pro Gly Ile Leu Ala Pro Gln Pro Pro Asp
145                 150                 155                 160
Val Gly Ser Ser Asp Pro Leu Ser Met Val Gly Pro Ser Gln Gly Arg
                165                 170                 175
Ser Pro Ser Tyr Ala Ser
            180
```

<210> SEQ ID NO 42
<211> LENGTH: 178
<212> TYPE: PRT
<213> ORGANISM: Homo sapiens

<400> SEQUENCE: 42

```
His Pro Ile Pro Asp Ser Ser Pro Leu Leu Gln Phe Gly Gly Gln Val
1               5                   10                  15
Arg Leu Arg His Leu Tyr Thr Ser Gly Pro His Gly Leu Ser Ser Cys
            20                  25                  30
Phe Leu Arg Ile Arg Ala Asp Gly Val Val Asp Cys Ala Arg Gly Gln
        35                  40                  45
Ser Ala His Ser Leu Leu Glu Ile Lys Ala Val Ala Leu Arg Thr Val
    50                  55                  60
Ala Ile Lys Gly Val His Ser Val Arg Tyr Leu Cys Met Gly Ala Asp
65                  70                  75                  80
Gly Lys Met Gln Gly Leu Leu Gln Tyr Ser Glu Glu Asp Cys Ala Phe
                85                  90                  95
Glu Glu Glu Ile Arg Pro Asp Gly Tyr Asn Val Tyr Arg Ser Glu Lys
            100                 105                 110
His Arg Leu Pro Val Ser Leu Ser Ala Lys Gln Arg Gln Leu Tyr
        115                 120                 125
Lys Asn Arg Gly Phe Leu Pro Leu Ser His Phe Leu Pro Met Leu Pro
    130                 135                 140
Glu Pro Pro Gly Ile Leu Ala Pro Gln Pro Pro Asp Val Gly Ser Ser
145                 150                 155                 160
Asp Pro Leu Ser Met Val Gly Pro Ser Gln Gly Arg Ser Pro Ser Tyr
                165                 170                 175
```

Ala Ser

<210> SEQ ID NO 43
<211> LENGTH: 192
<212> TYPE: PRT
<213> ORGANISM: Homo sapiens

<400> SEQUENCE: 43

Arg Pro Leu Ala Phe Ser Asp Ala Gly Pro His Val His Tyr Gly Gly
1               5                   10                  15

Asp Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 44
<211> LENGTH: 185
<212> TYPE: PRT
<213> ORGANISM: Homo sapiens

<400> SEQUENCE: 44

Arg Pro Leu Ala Phe Ser Asp Ala Gly Pro His Val His Tyr Gly Trp
1               5                   10                  15

Gly Asp Pro Ile Arg Gln Arg Tyr Leu Tyr Thr Asp Ala Gln Gln
            20                  25                  30

Thr Glu Ala His Leu Glu Ile Arg Glu Asp Gly Thr Val Gly Gly Ala
        35                  40                  45

Ala Asp Gln Ser Pro Glu Ser Leu Leu Gln Leu Lys Ala Leu Lys Pro
    50                  55                  60

Gly Val Ile Gln Ile Leu Gly Val Lys Thr Ser Arg Phe Leu Cys Gln
65                  70                  75                  80

Arg Pro Asp Gly Ala Leu Tyr Gly Ser Leu His Phe Asp Pro Glu Ala
                85                  90                  95

Cys Ser Phe Arg Glu Leu Leu Leu Glu Asp Gly Tyr Asn Val Tyr Gln
            100                 105                 110

Ser Glu Ala His Gly Leu Pro Leu His Leu Pro Gly Asn Lys Ser Pro
        115                 120                 125

His Arg Asp Pro Ala Pro Arg Gly Pro Ala Arg Phe Leu Pro Leu Pro
130                 135                 140

Gly Leu Pro Pro Ala Leu Pro Glu Pro Pro Gly Ile Leu Ala Pro Gln
145                 150                 155                 160

Pro Pro Asp Val Gly Ser Ser Asp Pro Leu Ser Met Val Gly Pro Ser
            165                 170                 175

Gln Gly Arg Ser Pro Ser Tyr Ala Ser
            180                 185

<210> SEQ ID NO 45
<211> LENGTH: 193
<212> TYPE: PRT
<213> ORGANISM: Homo sapiens

<400> SEQUENCE: 45

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
            180                 185                 190

Lys

<210> SEQ ID NO 46
<211> LENGTH: 232
<212> TYPE: PRT
<213> ORGANISM: Homo sapiens

<400> SEQUENCE: 46

Arg Pro Leu Ala Phe Ser Asp Ala Gly Pro His Val His Tyr Gly Trp
1               5                   10                  15

Gly Asp Pro Ile Arg Gln Arg Tyr Leu Tyr Thr Asp Asp Ala Gln Gln
            20                  25                  30

Thr Glu Ala His Leu Glu Ile Arg Glu Asp Gly Thr Val Gly Gly Ala
        35                  40                  45

Ala Asp Gln Ser Pro Glu Ser Leu Leu Gln Leu Lys Ala Leu Lys Pro
50                  55                  60

Gly Val Ile Gln Ile Leu Gly Val Lys Thr Ser Arg Phe Leu Cys Gln

```
            65                  70                  75                  80
    Arg Pro Asp Gly Ala Leu Tyr Gly Ser Leu His Phe Asp Pro Glu Ala
                    85                  90                  95

Cys Ser Phe Arg Glu Leu Leu Leu Glu Asp Gly Tyr Asn Val Tyr Gln
                    100                 105                 110

Ser Glu Ala His Gly Leu Pro Leu His Leu Pro Gly Asn Lys Ser Pro
                    115                 120                 125

His Arg Asp Pro Ala Pro Arg Gly Pro Ala Arg Phe Leu Pro Leu Pro
            130                 135                 140

Gly Leu Pro Pro Ala Leu Pro Glu Pro Gly Ile Leu Ala Pro Gln
    145                 150                 155                 160

Pro Pro Asp Val Gly Ser Ser Asp Pro Leu Ser Met Val Gly Pro Ser
                        165                 170                 175

Gln Gly Arg Ser Pro Ser Tyr Ala Ser Pro Met Val Pro Glu Glu Pro
                    180                 185                 190

Glu Asp Leu Arg Gly His Leu Glu Ser Asp Met Phe Ser Ser Pro Leu
                    195                 200                 205

Glu Thr Asp Ser Met Asp Pro Phe Gly Leu Val Thr Gly Leu Glu Ala
                    210                 215                 220

Val Arg Ser Pro Ser Phe Glu Lys
    225                 230

<210> SEQ ID NO 47
<211> LENGTH: 190
<212> TYPE: PRT
<213> ORGANISM: Homo sapiens

<400> SEQUENCE: 47

His Pro Ile Pro Asp Ser Ser Pro Leu Leu Gln Trp Gly Asp Pro Ile
    1               5                   10                  15

Arg Leu Arg His Leu Tyr Thr Ser Gly Pro His Gly Leu Ser Ser Cys
                    20                  25                  30

Phe Leu Arg Ile Arg Ala Asp Gly Val Val Asp Cys Ala Arg Gly Gln
                35                  40                  45

Ser Ala His Ser Leu Leu Glu Ile Lys Ala Val Ala Leu Arg Thr Val
        50                  55                  60

Ala Ile Lys Gly Val His Ser Val Arg Tyr Leu Cys Met Gly Ala Asp
    65                  70                  75                  80

Gly Lys Met Gln Gly Leu Leu Gln Tyr Ser Glu Glu Asp Cys Ala Phe
                    85                  90                  95

Glu Glu Glu Ile Arg Pro Asp Gly Tyr Asn Val Tyr Arg Ser Glu Lys
                    100                 105                 110

His Arg Leu Pro Val Ser Leu Ser Ala Lys Gln Arg Gln Leu Tyr
                    115                 120                 125

Lys Asn Arg Gly Phe Leu Pro Leu Ser His Phe Leu Pro Met Leu Pro
            130                 135                 140

Met Val Pro Glu Glu Pro Glu Asp Leu Arg Gly His Leu Glu Ser Asp
    145                 150                 155                 160

Met Phe Ser Ser Pro Leu Glu Thr Asp Ser Met Asp Pro Phe Gly Leu
                    165                 170                 175

Val Thr Gly Leu Glu Ala Val Arg Ser Pro Ser Phe Glu Lys
                    180                 185                 190

<210> SEQ ID NO 48
<211> LENGTH: 187
```

```
<212> TYPE: PRT
<213> ORGANISM: Homo sapiens

<400> SEQUENCE: 48

Arg Asp Ser Ser Pro Leu Leu Gln Phe Gly Gly Gln Val Arg Leu Arg
1               5                   10                  15

His Leu Tyr Thr Ser Gly Pro His Gly Leu Ser Ser Cys Phe Leu Arg
            20                  25                  30

Ile Arg Ala Asp Gly Val Val Asp Cys Ala Arg Gly Gln Ser Ala His
        35                  40                  45

Ser Leu Leu Glu Ile Lys Ala Val Ala Leu Arg Thr Val Ala Ile Lys
    50                  55                  60

Gly Val His Ser Val Arg Tyr Leu Cys Met Gly Ala Asp Gly Lys Met
65                  70                  75                  80

Gln Gly Leu Leu Gln Tyr Ser Glu Glu Asp Cys Ala Phe Glu Glu Glu
                85                  90                  95

Ile Arg Pro Asp Gly Tyr Asn Val Tyr Arg Ser Glu Lys His Arg Leu
            100                 105                 110

Pro Val Ser Leu Ser Ser Ala Lys Gln Arg Gln Leu Tyr Lys Asn Arg
        115                 120                 125

Gly Phe Leu Pro Leu Ser His Phe Leu Pro Met Leu Pro Met Val Pro
    130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 49
<211> LENGTH: 192
<212> TYPE: PRT
<213> ORGANISM: Homo sapiens

<400> SEQUENCE: 49

Arg Pro Leu Ala Phe Ser Asp Ser Ser Pro Leu Leu Gln Phe Gly Gly
1               5                   10                  15

Gln Val Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160
```

```
Ser Asp Met Phe Ser Ser Pro Leu Glu Thr Asp Ser Met Asp Pro Phe
            165                 170                 175

Gly Leu Val Thr Gly Leu Glu Ala Val Arg Ser Pro Ser Phe Glu Lys
            180                 185                 190

<210> SEQ ID NO 50
<211> LENGTH: 191
<212> TYPE: PRT
<213> ORGANISM: Homo sapiens

<400> SEQUENCE: 50

Arg His Pro Ile Pro Asp Ser Ser Pro Leu Leu Gln Phe Gly Asp Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
        50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
            85                  90                  95

Phe Glu Glu Glu Ile Leu Glu Asp Gly Tyr Asn Val Tyr Arg Ser Glu
            100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
        130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
            165                 170                 175

Leu Val Thr Gly Leu Glu Ala Val Arg Ser Pro Ser Phe Glu Lys
            180                 185                 190

<210> SEQ ID NO 51
<211> LENGTH: 191
<212> TYPE: PRT
<213> ORGANISM: Homo sapiens

<400> SEQUENCE: 51

Arg His Pro Ile Pro Asp Ser Ser Pro Leu Leu Gln Phe Gly Gly Asn
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
        50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
            85                  90                  95

Phe Glu Glu Glu Ile Arg Pro Asp Gly Tyr Asn Val Tyr Arg Ser Glu
            100                 105                 110
```

```
Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190
```

<210> SEQ ID NO 52
<211> LENGTH: 187
<212> TYPE: PRT
<213> ORGANISM: Homo sapiens

<400> SEQUENCE: 52

```
Arg Asp Ser Ser Pro Leu Leu Gln Trp Gly Asp Pro Ile Arg Leu Arg
1               5                   10                  15

His Leu Tyr Thr Ser Gly Pro His Gly Leu Ser Ser Cys Phe Leu Arg
            20                  25                  30

Ile Arg Ala Asp Gly Val Val Asp Cys Ala Arg Gly Gln Ser Ala His
        35                  40                  45

Ser Leu Leu Glu Ile Lys Ala Val Ala Leu Arg Thr Val Ala Ile Lys
50                  55                  60

Gly Val His Ser Val Arg Tyr Leu Cys Met Gly Ala Asp Gly Lys Met
65                  70                  75                  80

Gln Gly Leu Leu Gln Tyr Ser Glu Glu Asp Cys Ala Phe Glu Glu Glu
                85                  90                  95

Ile Arg Pro Asp Gly Tyr Asn Val Tyr Arg Ser Glu Lys His Arg Leu
            100                 105                 110

Pro Val Ser Leu Ser Ser Ala Lys Gln Arg Gln Leu Tyr Lys Asn Arg
        115                 120                 125

Gly Phe Leu Pro Leu Ser His Phe Leu Pro Met Leu Pro Met Val Pro
130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185
```

<210> SEQ ID NO 53
<211> LENGTH: 189
<212> TYPE: PRT
<213> ORGANISM: Homo sapiens

<400> SEQUENCE: 53

```
Met Asp Ser Ser Pro Leu Val His Tyr Gly Trp Gly Asp Pro Ile Arg
1               5                   10                  15

Leu Arg His Leu Tyr Thr Ser Gly Pro His Gly Leu Ser Ser Cys Phe
            20                  25                  30

Leu Arg Ile Arg Ala Asp Gly Val Val Asp Cys Ala Arg Gly Gln Ser
        35                  40                  45

Ala His Ser Leu Leu Glu Ile Lys Ala Val Ala Leu Arg Thr Val Ala
50                  55                  60
```

```
Ile Lys Gly Val His Ser Val Arg Tyr Leu Cys Met Gly Ala Asp Gly
 65                  70                  75                  80

Lys Met Gln Gly Leu Leu Gln Tyr Ser Glu Glu Asp Cys Ala Phe Glu
                 85                  90                  95

Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185

<210> SEQ ID NO 54
<211> LENGTH: 192
<212> TYPE: PRT
<213> ORGANISM: Homo sapiens

<400> SEQUENCE: 54

Arg Pro Leu Ala Phe Ser Asp Ala Gly Pro Leu Leu Gln Trp Gly Asp
 1               5                  10                  15

Pro Ile Arg Leu Arg His Leu Tyr Thr Ser Gly Pro His Gly Leu Ser
                20                  25                  30

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
        50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 55
<211> LENGTH: 192
<212> TYPE: PRT
<213> ORGANISM: Homo sapiens

<400> SEQUENCE: 55

Arg Pro Leu Ala Phe Ser Asp Ala Gly Pro His Tyr Gly Trp Gly Asp
 1               5                  10                  15
```

-continued

```
Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190
```

<210> SEQ ID NO 56
<211> LENGTH: 192
<212> TYPE: PRT
<213> ORGANISM: Homo sapiens

<400> SEQUENCE: 56

```
Arg Pro Leu Ala Phe Ser Asp Ala Gly Pro Val Tyr Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190
```

<210> SEQ ID NO 57

<211> LENGTH: 192
<212> TYPE: PRT
<213> ORGANISM: Homo sapiens

<400> SEQUENCE: 57

Arg Pro Leu Ala Phe Ser Asp Ala Gly Pro Val His Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 58
<211> LENGTH: 192
<212> TYPE: PRT
<213> ORGANISM: Homo sapiens

<400> SEQUENCE: 58

Arg Pro Leu Ala Phe Ser Asp Ala Gly Pro Val His Tyr Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
            165                 170                 175

Gly Leu Val Thr Gly Leu Glu Ala Val Arg Ser Pro Ser Phe Glu Lys
            180                 185                 190

<210> SEQ ID NO 59
<211> LENGTH: 192
<212> TYPE: PRT
<213> ORGANISM: Homo sapiens

<400> SEQUENCE: 59

Arg Pro Leu Ala Phe Ser Asp Ala Gly Pro His His Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
            165                 170                 175

Gly Leu Val Thr Gly Leu Glu Ala Val Arg Ser Pro Ser Phe Glu Lys
            180                 185                 190

<210> SEQ ID NO 60
<211> LENGTH: 192
<212> TYPE: PRT
<213> ORGANISM: Homo sapiens

<400> SEQUENCE: 60

Arg Pro Leu Ala Phe Ser Asp Ala Gly Pro His His Tyr Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

```
Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 61
<211> LENGTH: 192
<212> TYPE: PRT
<213> ORGANISM: Homo sapiens

<400> SEQUENCE: 61

Arg Pro Leu Ala Phe Ser Asp Ala Gly Pro His Val Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 62
<211> LENGTH: 192
<212> TYPE: PRT
<213> ORGANISM: Homo sapiens

<400> SEQUENCE: 62

Arg Pro Leu Ala Phe Ser Asp Ala Gly Pro His Val Tyr Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60
```

```
Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
                180                 185                 190
```

<210> SEQ ID NO 63
<211> LENGTH: 192
<212> TYPE: PRT
<213> ORGANISM: Homo sapiens

<400> SEQUENCE: 63

```
Arg Pro Leu Ala Phe Ser Asp Ala Gly Pro His Val His Trp Gly Asp
  1               5                  10                  15

Pro Ile Arg Leu Arg His Leu Tyr Thr Ser Gly Pro His Gly Leu Ser
             20                  25                  30

Ser Cys Phe Leu Arg Ile Arg Ala Asp Gly Val Val Asp Cys Ala Arg
         35                  40                  45

Gly Gln Ser Ala His Ser Leu Leu Glu Ile Lys Ala Val Ala Leu Arg
     50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
                180                 185                 190
```

<210> SEQ ID NO 64
<211> LENGTH: 192
<212> TYPE: PRT
<213> ORGANISM: Homo sapiens

<400> SEQUENCE: 64

```
Arg Pro Leu Ala Phe Ser Asp Ser Ser Pro Leu Val His Trp Gly Asp
  1               5                  10                  15
```

```
Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 65
<211> LENGTH: 192
<212> TYPE: PRT
<213> ORGANISM: Homo sapiens

<400> SEQUENCE: 65

Arg Pro Leu Ala Phe Ser Asp Ser Ser Pro His Val His Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190
```

```
<210> SEQ ID NO 66
<211> LENGTH: 192
<212> TYPE: PRT
<213> ORGANISM: Homo sapiens

<400> SEQUENCE: 66

Arg Pro Leu Ala Phe Ser Asp Ala Gly Pro His Leu Gln Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 67
<211> LENGTH: 191
<212> TYPE: PRT
<213> ORGANISM: Homo sapiens

<400> SEQUENCE: 67

Arg Pro Leu Ala Phe Ser Asp Ala Gly Pro His Val Trp Gly Asp Pro
1               5                   10                  15

Ile Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
```

```
145                 150                 155                 160
Asp Met Phe Ser Ser Pro Leu Glu Thr Asp Ser Met Asp Pro Phe Gly
                165                 170                 175
Leu Val Thr Gly Leu Glu Ala Val Arg Ser Pro Ser Phe Glu Lys
            180                 185                 190
```

<210> SEQ ID NO 68
<211> LENGTH: 193
<212> TYPE: PRT
<213> ORGANISM: Homo sapiens

<400> SEQUENCE: 68

```
Arg Pro Leu Ala Phe Ser Asp Ala Gly Pro His Val His Tyr Trp Gly
1               5                   10                  15
Asp Pro Ile Arg Leu Arg His Leu Tyr Thr Ser Gly Pro His Gly Leu
            20                  25                  30
Ser Ser Cys Phe Leu Arg Ile Arg Ala Asp Gly Val Val Asp Cys Ala
        35                  40                  45
Arg Gly Gln Ser Ala His Ser Leu Leu Glu Ile Lys Ala Val Ala Leu
50                  55                  60
Arg Thr Val Ala Ile Lys Gly Val His Ser Val Arg Tyr Leu Cys Met
65                  70                  75                  80
Gly Ala Asp Gly Lys Met Gln Gly Leu Leu Gln Tyr Ser Glu Glu Asp
                85                  90                  95
Cys Ala Phe Glu Glu Glu Ile Arg Pro Asp Gly Tyr Asn Val Tyr Arg
            100                 105                 110
Ser Glu Lys His Arg Leu Pro Val Ser Leu Ser Ser Ala Lys Gln Arg
        115                 120                 125
Gln Leu Tyr Lys Asn Arg Gly Phe Leu Pro Leu Ser His Phe Leu Pro
130                 135                 140
Met Leu Pro Met Val Pro Glu Glu Pro Glu Asp Leu Arg Gly His Leu
145                 150                 155                 160
Glu Ser Asp Met Phe Ser Ser Pro Leu Glu Thr Asp Ser Met Asp Pro
                165                 170                 175
Phe Gly Leu Val Thr Gly Leu Glu Ala Val Arg Ser Pro Ser Phe Glu
            180                 185                 190
Lys
```

<210> SEQ ID NO 69
<211> LENGTH: 189
<212> TYPE: PRT
<213> ORGANISM: Homo sapiens

<400> SEQUENCE: 69

```
Arg Asp Ser Ser Pro Leu Val His Tyr Gly Trp Gly Asp Pro Ile Arg
1               5                   10                  15
Leu Arg His Leu Tyr Thr Ser Gly Pro His Gly Leu Ser Ser Cys Phe
            20                  25                  30
Leu Arg Ile Arg Ala Asp Gly Val Val Asp Cys Ala Arg Gly Gln Ser
        35                  40                  45
Ala His Ser Leu Leu Glu Ile Lys Ala Val Ala Leu Arg Thr Val Ala
50                  55                  60
Ile Lys Gly Val His Ser Val Arg Tyr Leu Cys Met Gly Ala Asp Gly
65                  70                  75                  80
Lys Met Gln Gly Leu Leu Gln Tyr Ser Glu Glu Asp Cys Ala Phe Glu
                85                  90                  95
```

```
Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185

<210> SEQ ID NO 70
<211> LENGTH: 190
<212> TYPE: PRT
<213> ORGANISM: Homo sapiens

<400> SEQUENCE: 70

Met Arg Asp Ser Ser Pro Leu Val His Tyr Gly Trp Gly Asp Pro Ile
1               5                   10                  15

Arg Leu Arg His Leu Tyr Thr Ser Gly Pro His Gly Leu Ser Ser Cys
            20                  25                  30

Phe Leu Arg Ile Arg Ala Asp Gly Val Val Asp Cys Ala Arg Gly Gln
        35                  40                  45

Ser Ala His Ser Leu Leu Glu Ile Lys Ala Val Ala Leu Arg Thr Val
    50                  55                  60

Ala Ile Lys Gly Val His Ser Val Arg Tyr Leu Cys Met Gly Ala Asp
65                  70                  75                  80

Gly Lys Met Gln Gly Leu Leu Gln Tyr Ser Glu Glu Asp Cys Ala Phe
                85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ser Ala Lys Gln Arg Gln Leu Tyr
        115                 120                 125

Lys Asn Arg Gly Phe Leu Pro Leu Ser His Phe Leu Pro Met Leu Pro
    130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys
            180                 185                 190

<210> SEQ ID NO 71
<211> LENGTH: 181
<212> TYPE: PRT
<213> ORGANISM: Homo sapiens

<400> SEQUENCE: 71

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45
```

```
Pro Glu Ser Leu Leu Gln Leu Lys Ala Leu Lys Pro Gly Val Ile Gln
     50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Glu Asp Gly Tyr Asn Val Tyr Gln Ser Glu Ala His
            100                 105                 110

Ser Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 72
<211> LENGTH: 181
<212> TYPE: PRT
<213> ORGANISM: Homo sapiens

<400> SEQUENCE: 72

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
             35                  40                  45

Pro Glu Ser Leu Leu Gln Leu Lys Ala Leu Lys Pro Gly Val Ile Gln
     50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 73
<211> LENGTH: 212
<212> TYPE: PRT
<213> ORGANISM: Homo sapiens

<400> SEQUENCE: 73
```

His Pro Ile Pro Asp Ser Ser Pro Leu Leu Gln Phe Gly Gly Gln Val
1               5                   10                  15

Arg Gln Arg Tyr Leu Tyr Thr Asp Ala Gln Gln Thr Glu Ala His
            20                  25                  30

Leu Glu Ile Arg Glu Asp Gly Thr Val Gly Ala Ala Asp Gln Ser
            35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Val Gln Asp Glu Leu Gln Gly
                165                 170                 175

Val Gly Gly Glu Gly Cys His Met His Pro Glu Asn Cys Lys Thr Leu
                180                 185                 190

Leu Thr Asp Ile Asp Arg Thr His Thr Glu Lys Pro Val Trp Asp Gly
                195                 200                 205

Ile Thr Gly Glu
        210

<210> SEQ ID NO 74
<211> LENGTH: 189
<212> TYPE: PRT
<213> ORGANISM: Homo sapiens

<400> SEQUENCE: 74

Arg Asp Ala Gly Pro His Val His Tyr Gly Trp Gly Asp Pro Ile Arg
1               5                   10                  15

Leu Arg His Leu Tyr Thr Ser Gly Pro His Gly Leu Ser Ser Cys Phe
            20                  25                  30

Leu Arg Ile Arg Ala Asp Gly Val Val Asp Cys Ala Arg Gly Gln Ser
            35                  40                  45

Ala His Ser Leu Leu Glu Ile Lys Ala Val Ala Leu Arg Thr Val Ala
50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
                100                 105                 110

Arg Leu Pro Val Ser Leu Ser Ser Ala Lys Gln Arg Gln Leu Tyr Lys
            115                 120                 125

Asn Arg Gly Phe Leu Pro Leu Ser His Phe Leu Pro Met Leu Pro Met
130                 135                 140

Val Pro Glu Glu Pro Glu Asp Leu Arg Gly His Leu Glu Ser Asp Met

```
                 145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185

<210> SEQ ID NO 75
<211> LENGTH: 184
<212> TYPE: PRT
<213> ORGANISM: Homo sapiens

<400> SEQUENCE: 75

Arg Val His Tyr Gly Trp Gly Asp Pro Ile Arg Leu Arg His Leu Tyr
1               5                   10                  15

Thr Ser Gly Pro His Gly Leu Ser Ser Cys Phe Leu Arg Ile Arg Ala
            20                  25                  30

Asp Gly Val Val Asp Cys Ala Arg Gly Gln Ser Ala His Ser Leu Leu
        35                  40                  45

Glu Ile Lys Ala Val Ala Leu Arg Thr Val Ala Ile Lys Gly Val His
    50                  55                  60

Ser Val Arg Tyr Leu Cys Met Gly Ala Asp Gly Lys Met Gln Gly Leu
65                  70                  75                  80

Leu Gln Tyr Ser Glu Glu Asp Cys Ala Phe Glu Glu Ile Arg Pro
                85                  90                  95

Asp Gly Tyr Asn Val Tyr Arg Ser Glu Lys His Arg Leu Pro Val Ser
            100                 105                 110

Leu Ser Ser Ala Lys Gln Arg Gln Leu Tyr Lys Asn Arg Gly Phe Leu
        115                 120                 125

Pro Leu Ser His Phe Leu Pro Met Leu Pro Met Val Pro Glu Glu Pro
    130                 135                 140

Glu Asp Leu Arg Gly His Leu Glu Ser Asp Met Phe Ser Ser Pro Leu
145                 150                 155                 160

Glu Thr Asp Ser Met Asp Pro Phe Gly Leu Val Thr Gly Leu Glu Ala
                165                 170                 175

Val Arg Ser Pro Ser Phe Glu Lys
            180

<210> SEQ ID NO 76
<211> LENGTH: 179
<212> TYPE: PRT
<213> ORGANISM: Homo sapiens

<400> SEQUENCE: 76

Arg Gly Asp Pro Ile Arg Leu Arg His Leu Tyr Thr Ser Gly Pro His
1               5                   10                  15

Gly Leu Ser Ser Cys Phe Leu Arg Ile Arg Ala Asp Gly Val Val Asp
            20                  25                  30

Cys Ala Arg Gly Gln Ser Ala His Ser Leu Leu Glu Ile Lys Ala Val
        35                  40                  45

Ala Leu Arg Thr Val Ala Ile Lys Gly Val His Ser Val Arg Tyr Leu
    50                  55                  60

Cys Met Gly Ala Asp Gly Lys Met Gln Gly Leu Leu Gln Tyr Ser Glu
65                  70                  75                  80

Glu Asp Cys Ala Phe Glu Glu Ile Arg Pro Asp Gly Tyr Asn Val
                85                  90                  95

Tyr Arg Ser Glu Lys His Arg Leu Pro Val Ser Leu Ser Ser Ala Lys
```

```
            100                 105                 110
Gln Arg Gln Leu Tyr Lys Asn Arg Gly Phe Leu Pro Leu Ser His Phe
        115                 120                 125

Leu Pro Met Leu Pro Met Val Pro Glu Glu Pro Glu Asp Leu Arg Gly
130                 135                 140

His Leu Glu Ser Asp Met Phe Ser Ser Pro Leu Glu Thr Asp Ser Met
145                 150                 155                 160

Asp Pro Phe Gly Leu Val Thr Gly Leu Glu Ala Val Arg Ser Pro Ser
                165                 170                 175

Phe Glu Lys

<210> SEQ ID NO 77
<211> LENGTH: 175
<212> TYPE: PRT
<213> ORGANISM: Homo sapiens

<400> SEQUENCE: 77

Arg Arg Leu Arg His Leu Tyr Thr Ser Gly Pro His Gly Leu Ser Ser
1               5                   10                  15

Cys Phe Leu Arg Ile Arg Ala Asp Gly Val Val Asp Cys Ala Arg Gly
                20                  25                  30

Gln Ser Ala His Ser Leu Leu Glu Ile Lys Ala Val Ala Leu Arg Thr
            35                  40                  45

Val Ala Ile Lys Gly Val His Ser Val Arg Tyr Leu Cys Met Gly Ala
        50                  55                  60

Asp Gly Lys Met Gln Gly Leu Leu Gln Tyr Ser Glu Glu Asp Cys Ala
65                  70                  75                  80

Phe Glu Glu Glu Ile Arg Pro Asp Gly Tyr Asn Val Tyr Arg Ser Glu
                85                  90                  95

Lys His Arg Leu Pro Val Ser Leu Ser Ser Ala Lys Gln Arg Gln Leu
            100                 105                 110

Tyr Lys Asn Arg Gly Phe Leu Pro Leu Ser His Phe Leu Pro Met Leu
        115                 120                 125

Pro Met Val Pro Glu Glu Pro Glu Asp Leu Arg Gly His Leu Glu Ser
130                 135                 140

Asp Met Phe Ser Ser Pro Leu Glu Thr Asp Ser Met Asp Pro Phe Gly
145                 150                 155                 160

Leu Val Thr Gly Leu Glu Ala Val Arg Ser Pro Ser Phe Glu Lys
                165                 170                 175

<210> SEQ ID NO 78
<211> LENGTH: 188
<212> TYPE: PRT
<213> ORGANISM: Homo sapiens

<400> SEQUENCE: 78

Arg Ala Gly Pro His Val His Tyr Gly Trp Gly Asp Pro Ile Arg Leu
1               5                   10                  15

Arg His Leu Tyr Thr Ser Gly Pro His Gly Leu Ser Ser Cys Phe Leu
                20                  25                  30

Arg Ile Arg Ala Asp Gly Val Val Asp Cys Ala Arg Gly Gln Ser Ala
            35                  40                  45

His Ser Leu Leu Glu Ile Lys Ala Val Ala Leu Arg Thr Val Ala Ile
        50                  55                  60

Lys Gly Val His Ser Val Arg Tyr Leu Cys Met Gly Ala Asp Gly Lys
65                  70                  75                  80
```

```
Met Gln Gly Leu Leu Gln Tyr Ser Glu Glu Asp Cys Ala Phe Glu Glu
                85                  90                  95

Glu Ile Arg Pro Asp Gly Tyr Asn Val Tyr Arg Ser Glu Lys His Arg
            100                 105                 110

Leu Pro Val Ser Leu Ser Ser Ala Lys Gln Arg Gln Leu Tyr Lys Asn
        115                 120                 125

Arg Gly Phe Leu Pro Leu Ser His Phe Leu Pro Met Leu Pro Met Val
    130                 135                 140

Pro Glu Glu Pro Glu Asp Leu Arg Gly His Leu Glu Ser Asp Met Phe
145                 150                 155                 160

Ser Ser Pro Leu Glu Thr Asp Ser Met Asp Pro Phe Gly Leu Val Thr
                165                 170                 175

Gly Leu Glu Ala Val Arg Ser Pro Ser Phe Glu Lys
            180                 185

<210> SEQ ID NO 79
<211> LENGTH: 187
<212> TYPE: PRT
<213> ORGANISM: Homo sapiens

<400> SEQUENCE: 79

Arg Gly Pro His Val His Tyr Gly Trp Gly Asp Pro Ile Arg Leu Arg
1               5                   10                  15

His Leu Tyr Thr Ser Gly Pro His Gly Leu Ser Ser Cys Phe Leu Arg
            20                  25                  30

Ile Arg Ala Asp Gly Val Val Asp Cys Ala Arg Gly Gln Ser Ala His
        35                  40                  45

Ser Leu Leu Glu Ile Lys Ala Val Ala Leu Arg Thr Val Ala Ile Lys
    50                  55                  60

Gly Val His Ser Val Arg Tyr Leu Cys Met Gly Ala Asp Gly Lys Met
65                  70                  75                  80

Gln Gly Leu Leu Gln Tyr Ser Glu Glu Asp Cys Ala Phe Glu Glu Glu
                85                  90                  95

Ile Arg Pro Asp Gly Tyr Asn Val Tyr Arg Ser Glu Lys His Arg Leu
            100                 105                 110

Pro Val Ser Leu Ser Ser Ala Lys Gln Arg Gln Leu Tyr Lys Asn Arg
        115                 120                 125

Gly Phe Leu Pro Leu Ser His Phe Leu Pro Met Leu Pro Met Val Pro
    130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 80
<211> LENGTH: 186
<212> TYPE: PRT
<213> ORGANISM: Homo sapiens

<400> SEQUENCE: 80

Arg Pro His Val His Tyr Gly Trp Gly Asp Pro Ile Arg Leu Arg His
1               5                   10                  15

Leu Tyr Thr Ser Gly Pro His Gly Leu Ser Ser Cys Phe Leu Arg Ile
            20                  25                  30
```

Arg Ala Asp Gly Val Val Asp Cys Ala Arg Gly Gln Ser Ala His Ser
        35                  40                  45

Leu Leu Glu Ile Lys Ala Val Ala Leu Arg Thr Val Ala Ile Lys Gly
 50                  55                  60

Val His Ser Val Arg Tyr Leu Cys Met Gly Ala Asp Gly Lys Met Gln
 65                  70                  75                  80

Gly Leu Leu Gln Tyr Ser Glu Glu Asp Cys Ala Phe Glu Glu Glu Ile
                 85                  90                  95

Arg Pro Asp Gly Tyr Asn Val Tyr Arg Ser Glu Lys His Arg Leu Pro
                100                 105                 110

Val Ser Leu Ser Ser Ala Lys Gln Arg Gln Leu Tyr Lys Asn Arg Gly
            115                 120                 125

Phe Leu Pro Leu Ser His Phe Leu Pro Met Leu Pro Met Val Pro Glu
130                 135                 140

Glu Pro Glu Asp Leu Arg Gly His Leu Glu Ser Asp Met Phe Ser Ser
145                 150                 155                 160

Pro Leu Glu Thr Asp Ser Met Asp Pro Phe Gly Leu Val Thr Gly Leu
                165                 170                 175

Glu Ala Val Arg Ser Pro Ser Phe Glu Lys
                180                 185

<210> SEQ ID NO 81
<211> LENGTH: 185
<212> TYPE: PRT
<213> ORGANISM: Homo sapiens

<400> SEQUENCE: 81

Arg His Val His Tyr Gly Trp Gly Asp Pro Ile Arg Leu Arg His Leu
1               5                   10                  15

Tyr Thr Ser Gly Pro His Gly Leu Ser Ser Cys Phe Leu Arg Ile Arg
            20                  25                  30

Ala Asp Gly Val Val Asp Cys Ala Arg Gly Gln Ser Ala His Ser Leu
        35                  40                  45

Leu Glu Ile Lys Ala Val Ala Leu Arg Thr Val Ala Ile Lys Gly Val
 50                  55                  60

His Ser Val Arg Tyr Leu Cys Met Gly Ala Asp Gly Lys Met Gln Gly
 65                  70                  75                  80

Leu Leu Gln Tyr Ser Glu Glu Asp Cys Ala Phe Glu Glu Glu Ile Arg
                 85                  90                  95

Pro Asp Gly Tyr Asn Val Tyr Arg Ser Glu Lys His Arg Leu Pro Val
                100                 105                 110

Ser Leu Ser Ser Ala Lys Gln Arg Gln Leu Tyr Lys Asn Arg Gly Phe
            115                 120                 125

Leu Pro Leu Ser His Phe Leu Pro Met Leu Pro Met Val Pro Glu Glu
130                 135                 140

Pro Glu Asp Leu Arg Gly His Leu Glu Ser Asp Met Phe Ser Ser Pro
145                 150                 155                 160

Leu Glu Thr Asp Ser Met Asp Pro Phe Gly Leu Val Thr Gly Leu Glu
                165                 170                 175

Ala Val Arg Ser Pro Ser Phe Glu Lys
                180                 185

<210> SEQ ID NO 82
<211> LENGTH: 194
<212> TYPE: PRT

<213> ORGANISM: Homo sapiens

<400> SEQUENCE: 82

```
Arg Pro Leu Ala Phe Ser Ala Ala Gly Pro His Val His Tyr Gly Trp
1               5                   10                  15
Gly Asp Pro Ile Arg Leu Arg His Leu Tyr Thr Ser Gly Pro His Gly
                20                  25                  30
Leu Ser Ser Cys Phe Leu Arg Ile Arg Ala Asp Gly Val Val Asp Cys
            35                  40                  45
Ala Arg Gly Gln Ser Ala His Ser Leu Leu Glu Ile Lys Ala Val Ala
    50                  55                  60
Leu Arg Thr Val Ala Ile Lys Gly Val His Ser Val Arg Tyr Leu Cys
65                  70                  75                  80
Met Gly Ala Asp Gly Lys Met Gln Gly Leu Leu Gln Tyr Ser Glu Glu
                85                  90                  95
Asp Cys Ala Phe Glu Glu Glu Ile Arg Pro Asp Gly Tyr Asn Val Tyr
            100                 105                 110
Arg Ser Glu Lys His Arg Leu Pro Val Ser Leu Ser Ser Ala Lys Gln
        115                 120                 125
Arg Gln Leu Tyr Lys Asn Arg Gly Phe Leu Pro Leu Ser His Phe Leu
    130                 135                 140
Pro Met Leu Pro Met Val Pro Glu Glu Pro Glu Asp Leu Arg Gly His
145                 150                 155                 160
Leu Glu Ser Asp Met Phe Ser Ser Pro Leu Glu Thr Asp Ser Met Asp
                165                 170                 175
Pro Phe Gly Leu Val Thr Gly Leu Glu Ala Val Arg Ser Pro Ser Phe
            180                 185                 190
Glu Lys
```

<210> SEQ ID NO 83
<211> LENGTH: 194
<212> TYPE: PRT
<213> ORGANISM: Homo sapiens

<400> SEQUENCE: 83

```
Arg Pro Leu Ala Phe Ser Asp Ala Ala Pro His Val His Tyr Gly Trp
1               5                   10                  15
Gly Asp Pro Ile Arg Leu Arg His Leu Tyr Thr Ser Gly Pro His Gly
                20                  25                  30
Leu Ser Ser Cys Phe Leu Arg Ile Arg Ala Asp Gly Val Val Asp Cys
            35                  40                  45
Ala Arg Gly Gln Ser Ala His Ser Leu Leu Glu Ile Lys Ala Val Ala
    50                  55                  60
Leu Arg Thr Val Ala Ile Lys Gly Val His Ser Val Arg Tyr Leu Cys
65                  70                  75                  80
Met Gly Ala Asp Gly Lys Met Gln Gly Leu Leu Gln Tyr Ser Glu Glu
                85                  90                  95
Asp Cys Ala Phe Glu Glu Glu Ile Arg Pro Asp Gly Tyr Asn Val Tyr
            100                 105                 110
Arg Ser Glu Lys His Arg Leu Pro Val Ser Leu Ser Ser Ala Lys Gln
        115                 120                 125
Arg Gln Leu Tyr Lys Asn Arg Gly Phe Leu Pro Leu Ser His Phe Leu
    130                 135                 140
Pro Met Leu Pro Met Val Pro Glu Glu Pro Glu Asp Leu Arg Gly His
145                 150                 155                 160
```

```
Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 84
<211> LENGTH: 194
<212> TYPE: PRT
<213> ORGANISM: Homo sapiens

<400> SEQUENCE: 84

Arg Pro Leu Ala Phe Ser Asp Ala Gly Ala His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 85
<211> LENGTH: 194
<212> TYPE: PRT
<213> ORGANISM: Homo sapiens

<400> SEQUENCE: 85

Arg Pro Leu Ala Phe Ser Asp Ala Gly Pro His Val His Tyr Gly Ala
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
```

```
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 86
<211> LENGTH: 194
<212> TYPE: PRT
<213> ORGANISM: Homo sapiens

<400> SEQUENCE: 86

Arg Pro Leu Ala Phe Ser Asp Ala Gly Pro His Val His Tyr Gly Trp
1               5                   10                  15

Gly Ala Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 87
<211> LENGTH: 167
<212> TYPE: PRT
<213> ORGANISM: Homo sapiens

<400> SEQUENCE: 87

Arg Pro Leu Ala Phe Ser Asp Ala Gly Pro His Val His Tyr Gly Trp
1               5                   10                  15
```

```
Gly Asp Ala Ile Cys Ala Arg Gly Gln Ser Ala His Ser Leu Leu Glu
             20                  25                  30

Ile Lys Ala Val Ala Leu Arg Thr Val Ala Ile Lys Gly Val His Ser
         35                  40                  45

Val Arg Tyr Leu Cys Met Gly Ala Asp Gly Lys Met Gln Gly Leu Leu
 50                  55                  60

Gln Tyr Ser Glu Glu Asp Cys Ala Phe Glu Glu Ile Arg Pro Asp
 65                  70                  75                  80

Gly Tyr Asn Val Tyr Arg Ser Glu Lys His Arg Leu Pro Val Ser Leu
                 85                  90                  95

Ser Ser Ala Lys Gln Arg Gln Leu Tyr Lys Asn Arg Gly Phe Leu Pro
             100                 105                 110

Leu Ser His Phe Leu Pro Met Leu Pro Met Val Pro Glu Glu Pro Glu
         115                 120                 125

Asp Leu Arg Gly His Leu Glu Ser Asp Met Phe Ser Ser Pro Leu Glu
     130                 135                 140

Thr Asp Ser Met Asp Pro Phe Gly Leu Val Thr Gly Leu Glu Ala Val
145                 150                 155                 160

Arg Ser Pro Ser Phe Glu Lys
             165

<210> SEQ ID NO 88
<211> LENGTH: 194
<212> TYPE: PRT
<213> ORGANISM: Homo sapiens

<400> SEQUENCE: 88

Arg Pro Leu Ala Phe Ser Asp Ala Gly Pro His Val His Tyr Gly Trp
  1               5                  10                  15

Gly Asp Pro Ile Arg Leu Arg His Leu Tyr Thr Ser Gly Pro Ala Gly
             20                  25                  30

Leu Ser Ser Cys Phe Leu Arg Ile Arg Ala Asp Gly Val Val Asp Cys
         35                  40                  45

Ala Arg Gly Gln Ser Ala His Ser Leu Leu Glu Ile Lys Ala Val Ala
 50                  55                  60

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Ile Arg Pro Asp Gly Tyr Asn Val Tyr
             100                 105                 110

Arg Ser Glu Lys His Arg Leu Pro Val Ser Leu Ser Ser Ala Lys Gln
         115                 120                 125

Arg Gln Leu Tyr Lys Asn Arg Gly Phe Leu Pro Leu Ala His Phe Leu
     130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                 165                 170                 175

Pro Phe Gly Leu Val Thr Gly Leu Glu Ala Val Arg Ser Pro Ser Phe
             180                 185                 190

Glu Lys

<210> SEQ ID NO 89
<211> LENGTH: 194
```

```
<212> TYPE: PRT
<213> ORGANISM: Homo sapiens

<400> SEQUENCE: 89

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro Ala Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
        50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser Ala Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 90
<211> LENGTH: 194
<212> TYPE: PRT
<213> ORGANISM: Homo sapiens

<400> SEQUENCE: 90

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
        50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Ala Gln
        115                 120                 125

Ala Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
```

```
                145                 150                 155                 160
Leu Glu Ser Asp Met Phe Ser Ser Pro Leu Glu Thr Asp Ser Met Asp
                165                 170                 175
Pro Phe Gly Leu Val Thr Gly Leu Glu Ala Val Arg Ser Pro Ser Phe
                180                 185                 190
Glu Lys

<210> SEQ ID NO 91
<211> LENGTH: 194
<212> TYPE: PRT
<213> ORGANISM: Homo sapiens

<400> SEQUENCE: 91

Arg Pro Leu Ala Phe Ser Asp Ala Gly Pro His Val His Tyr Gly Trp
1               5                   10                  15
Gly Asp Pro Ile Arg Leu Arg His Leu Tyr Thr Ser Gly Pro His Gly
                20                  25                  30
Leu Ser Ser Cys Phe Leu Arg Ile Arg Ala Asp Gly Val Val Asp Cys
            35                  40                  45
Ala Arg Gly Gln Ser Ala His Ser Leu Leu Glu Ile Lys Ala Val Ala
        50                  55                  60
Leu Arg Thr Val Ala Ile Lys Gly Val His Ser Val Arg Tyr Leu Cys
65                  70                  75                  80
Met Gly Ala Asp Gly Lys Met Gln Gly Leu Leu Gln Tyr Ser Glu Glu
                85                  90                  95
Asp Cys Ala Phe Glu Glu Glu Ile Arg Pro Asp Gly Tyr Asn Val Tyr
                100                 105                 110
Arg Ser Glu Lys His Arg Leu Pro Val Ser Leu Ser Ser Ala Ala Gln
            115                 120                 125
Arg Gln Leu Tyr Lys Asn Arg Gly Phe Leu Pro Leu Ala His Phe Leu
        130                 135                 140
Pro Met Leu Pro Met Val Pro Glu Glu Pro Glu Asp Leu Arg Gly His
145                 150                 155                 160
Leu Glu Ser Asp Met Phe Ser Ser Pro Leu Glu Thr Asp Ser Met Asp
                165                 170                 175
Pro Phe Gly Leu Val Thr Gly Leu Glu Ala Val Arg Ser Pro Ser Phe
                180                 185                 190
Glu Lys

<210> SEQ ID NO 92
<211> LENGTH: 194
<212> TYPE: PRT
<213> ORGANISM: Homo sapiens

<400> SEQUENCE: 92

Arg Pro Leu Ala Phe Ser Asp Ala Gly Pro His Val His Tyr Gly Trp
1               5                   10                  15
Gly Asp Pro Ile Arg Leu Arg His Leu Tyr Thr Ser Gly Pro His Gly
                20                  25                  30
Leu Ser Ser Cys Phe Leu Arg Ile Arg Ala Asp Gly Val Val Asp Cys
            35                  40                  45
Ala Arg Gly Gln Ser Ala His Ser Leu Leu Glu Ile Lys Ala Val Ala
        50                  55                  60
Leu Arg Thr Val Ala Ile Lys Gly Val His Ser Val Arg Tyr Leu Cys
65                  70                  75                  80
```

-continued

Met Gly Ala Asp Gly Lys Met Gln Gly Leu Gln Tyr Ser Glu Glu
            85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Ala Gln
            115                 120                 125

Arg Gln Leu Tyr Lys Asn Arg Gly Phe Leu Pro Leu Ser Ala Phe Leu
            130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
            165                 170                 175

Pro Phe Gly Leu Val Thr Gly Leu Glu Ala Val Arg Ser Pro Ser Phe
            180                 185                 190

Glu Lys

<210> SEQ ID NO 93
<211> LENGTH: 194
<212> TYPE: PRT
<213> ORGANISM: Homo sapiens

<400> SEQUENCE: 93

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
            50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
            85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
            115                 120                 125

Ala Gln Leu Tyr Lys Asn Arg Gly Phe Leu Pro Leu Ala His Phe Leu
            130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
            165                 170                 175

Pro Phe Gly Leu Val Thr Gly Leu Glu Ala Val Arg Ser Pro Ser Phe
            180                 185                 190

Glu Lys

<210> SEQ ID NO 94
<211> LENGTH: 194
<212> TYPE: PRT
<213> ORGANISM: Homo sapiens

<400> SEQUENCE: 94

Arg Pro Leu Ala Phe Ser Asp Ala Gly Pro His Val His Tyr Gly Trp
1               5                   10                  15

```
Gly Asp Pro Ile Arg Leu Arg His Leu Tyr Thr Ser Gly Pro His Gly
             20                  25                  30

Leu Ser Ser Cys Phe Leu Arg Ile Arg Ala Asp Gly Val Val Asp Cys
         35                  40                  45

Ala Arg Gly Gln Ser Ala His Ser Leu Leu Glu Ile Lys Ala Val Ala
     50                  55                  60

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ala Ala Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 95
<211> LENGTH: 194
<212> TYPE: PRT
<213> ORGANISM: Homo sapiens

<400> SEQUENCE: 95

Arg Pro Leu Ala Phe Ser Asp Ala Gly Pro His Val His Tyr Gly Trp
 1               5                  10                  15

Gly Asp Pro Ile Arg Leu Arg His Leu Tyr Thr Ser Gly Pro His Gly
             20                  25                  30

Leu Ser Ser Cys Phe Leu Arg Ile Arg Ala Asp Gly Val Val Asp Cys
         35                  40                  45

Ala Arg Gly Gln Ser Ala His Ser Leu Leu Glu Ile Lys Ala Val Ala
     50                  55                  60

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Ala Gln
        115                 120                 125

Arg Gln Leu Tyr Lys Asn Arg Gly Phe Leu Pro Leu Ser Ala Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190
```

Glu Lys

<210> SEQ ID NO 96
<211> LENGTH: 194
<212> TYPE: PRT
<213> ORGANISM: Homo sapiens

<400> SEQUENCE: 96

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Ala Gln
        115                 120                 125

Ala Gln Leu Tyr Lys Asn Arg Gly Phe Leu Pro Leu Ala His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 97
<211> LENGTH: 194
<212> TYPE: PRT
<213> ORGANISM: Homo sapiens

<400> SEQUENCE: 97

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Ala Gln

```
              115                 120                 125
Ala Gln Leu Tyr Lys Asn Arg Gly Phe Leu Pro Leu Ser Ala Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Pro Leu Glu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 98
<211> LENGTH: 194
<212> TYPE: PRT
<213> ORGANISM: Homo sapiens

<400> SEQUENCE: 98

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
        50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
                100                 105                 110

Arg Ser Glu Lys His Arg Leu Pro Val Ser Leu Ser Ser Ala Ala Gln
            115                 120                 125

Ala Gln Leu Tyr Lys Asn Arg Gly Phe Leu Pro Leu Ala Ala Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Pro Leu Glu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 99
<211> LENGTH: 194
<212> TYPE: PRT
<213> ORGANISM: Homo sapiens

<400> SEQUENCE: 99

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45
```

-continued

Ala Arg Gly Gln Ser Ala His Ser Leu Leu Glu Ile Lys Ala Val Ala
 50                  55                  60

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
            115                 120                 125

Arg Gln Leu Tyr Lys Asn Arg Gly Phe Leu Pro Leu Ser His Phe Leu
130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 100
<211> LENGTH: 181
<212> TYPE: PRT
<213> ORGANISM: Homo sapiens

<400> SEQUENCE: 100

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
                 20                  25                  30

Leu Glu Ile Arg Glu Asp Gly Thr Val Gly Gly Ala Ala Asp Gln Ser
             35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 101
<211> LENGTH: 4
<212> TYPE: PRT
<213> ORGANISM: Homo sapiens

```
<400> SEQUENCE: 101

Val His Tyr Gly
1

<210> SEQ ID NO 102
<211> LENGTH: 9
<212> TYPE: PRT
<213> ORGANISM: Homo sapiens

<400> SEQUENCE: 102

Asp Ala Ser Pro His Val His Tyr Gly
1               5

<210> SEQ ID NO 103
<211> LENGTH: 9
<212> TYPE: PRT
<213> ORGANISM: Homo sapiens

<400> SEQUENCE: 103

Asp Ser Ser Pro Leu Val His Tyr Gly
1               5

<210> SEQ ID NO 104
<211> LENGTH: 7
<212> TYPE: PRT
<213> ORGANISM: Homo sapiens

<400> SEQUENCE: 104

Asp Ser Ser Pro Leu Leu Gln
1               5

<210> SEQ ID NO 105
<211> LENGTH: 12
<212> TYPE: PRT
<213> ORGANISM: Homo sapiens

<400> SEQUENCE: 105

Asp Ser Ser Pro Leu Leu Gln Phe Gly Gly Gln Val
1               5                   10

<210> SEQ ID NO 106
<211> LENGTH: 5
<212> TYPE: PRT
<213> ORGANISM: Homo sapiens

<400> SEQUENCE: 106

Arg His Pro Ile Pro
1               5

<210> SEQ ID NO 107
<211> LENGTH: 4
<212> TYPE: PRT
<213> ORGANISM: Homo sapiens

<400> SEQUENCE: 107

His Pro Ile Pro
1

<210> SEQ ID NO 108
<211> LENGTH: 5
<212> TYPE: PRT
<213> ORGANISM: Homo sapiens

<400> SEQUENCE: 108
```

Arg Pro Leu Ala Phe
1               5

<210> SEQ ID NO 109
<211> LENGTH: 4
<212> TYPE: PRT
<213> ORGANISM: Homo sapiens

<400> SEQUENCE: 109

Pro Leu Ala Phe
1

<210> SEQ ID NO 110
<211> LENGTH: 6
<212> TYPE: PRT
<213> ORGANISM: Homo sapiens

<400> SEQUENCE: 110

Met Asp Ser Ser Pro Leu
1               5

<210> SEQ ID NO 111
<211> LENGTH: 7
<212> TYPE: PRT
<213> ORGANISM: Homo sapiens

<400> SEQUENCE: 111

Met Ser Asp Ser Ser Pro Leu
1               5

<210> SEQ ID NO 112
<211> LENGTH: 6
<212> TYPE: PRT
<213> ORGANISM: Homo sapiens

<400> SEQUENCE: 112

Ser Asp Ser Ser Pro Leu
1               5

<210> SEQ ID NO 113
<211> LENGTH: 5
<212> TYPE: PRT
<213> ORGANISM: Homo sapiens

<400> SEQUENCE: 113

Met Ser Ser Pro Leu
1               5

<210> SEQ ID NO 114
<211> LENGTH: 4
<212> TYPE: PRT
<213> ORGANISM: Homo sapiens

<400> SEQUENCE: 114

Ser Ser Pro Leu
1

<210> SEQ ID NO 115
<211> LENGTH: 4
<212> TYPE: PRT
<213> ORGANISM: Homo sapiens

<400> SEQUENCE: 115

Arg Asp Ser Ser
1

```
<210> SEQ ID NO 116
<211> LENGTH: 4
<212> TYPE: PRT
<213> ORGANISM: Homo sapiens

<400> SEQUENCE: 116

Met Asp Ser Ser
1

<210> SEQ ID NO 117
<211> LENGTH: 5
<212> TYPE: PRT
<213> ORGANISM: Homo sapiens

<400> SEQUENCE: 117

Met Arg Asp Ser Ser
1               5

<210> SEQ ID NO 118
<211> LENGTH: 5
<212> TYPE: PRT
<213> ORGANISM: Homo sapiens

<400> SEQUENCE: 118

Met Ser Ser Pro Leu
1               5

<210> SEQ ID NO 119
<211> LENGTH: 6
<212> TYPE: PRT
<213> ORGANISM: Homo sapiens

<400> SEQUENCE: 119

Met Asp Ser Ser Pro Leu
1               5

<210> SEQ ID NO 120
<211> LENGTH: 7
<212> TYPE: PRT
<213> ORGANISM: Homo sapiens

<400> SEQUENCE: 120

Met Ser Asp Ser Ser Pro Leu
1               5

<210> SEQ ID NO 121
<211> LENGTH: 5
<212> TYPE: PRT
<213> ORGANISM: Homo sapiens

<400> SEQUENCE: 121

Asp Ser Ser Pro Leu
1               5

<210> SEQ ID NO 122
<211> LENGTH: 5
<212> TYPE: PRT
<213> ORGANISM: Homo sapiens

<400> SEQUENCE: 122

Asp Ala Ser Pro His
1               5
```

```
<210> SEQ ID NO 123
<211> LENGTH: 4
<212> TYPE: PRT
<213> ORGANISM: Homo sapiens

<400> SEQUENCE: 123

Arg Asp Ser Ser
1

<210> SEQ ID NO 124
<211> LENGTH: 4
<212> TYPE: PRT
<213> ORGANISM: Homo sapiens

<400> SEQUENCE: 124

Met Asp Ser Ser
1

<210> SEQ ID NO 125
<211> LENGTH: 5
<212> TYPE: PRT
<213> ORGANISM: Homo sapiens

<400> SEQUENCE: 125

Met Arg Asp Ser Ser
1               5

<210> SEQ ID NO 126
<211> LENGTH: 6
<212> TYPE: PRT
<213> ORGANISM: Homo sapiens

<400> SEQUENCE: 126

Met Asp Ser Ser Pro Leu
1               5

<210> SEQ ID NO 127
<211> LENGTH: 7
<212> TYPE: PRT
<213> ORGANISM: Homo sapiens

<400> SEQUENCE: 127

Met Ser Asp Ser Ser Pro Leu
1               5

<210> SEQ ID NO 128
<211> LENGTH: 5
<212> TYPE: PRT
<213> ORGANISM: Homo sapiens

<400> SEQUENCE: 128

Met Ser Ser Pro Leu
1               5

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Linker
      sequence

<400> SEQUENCE: 129

Gly Ser Gly Gly Ser
1               5
```

<210> SEQ ID NO 130
<211> LENGTH: 4
<212> TYPE: PRT
<213> ORGANISM: Artificial Sequence
<220> FEATURE:
<223> OTHER INFORMATION: Description of Artificial Sequence: Linker
      sequence

<400> SEQUENCE: 130

Gly Gly Gly Ser
1

<210> SEQ ID NO 131
<211> LENGTH: 4
<212> TYPE: PRT
<213> ORGANISM: Artificial Sequence
<220> FEATURE:
<223> OTHER INFORMATION: Description of Artificial Sequence: Linker
      sequence

<400> SEQUENCE: 131

Gly Gly Ser Gly
1

<210> SEQ ID NO 132
<211> LENGTH: 5
<212> TYPE: PRT
<213> ORGANISM: Artificial Sequence
<220> FEATURE:
<223> OTHER INFORMATION: Description of Artificial Sequence: Linker
      sequence

<400> SEQUENCE: 132

Gly Gly Ser Gly Gly
1               5

<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence: Linker
      sequence

<400> SEQUENCE: 133

Gly Ser Gly Ser Gly
1               5

<210> SEQ ID NO 134
<211> LENGTH: 5
<212> TYPE: PRT
<213> ORGANISM: Artificial Sequence
<220> FEATURE:
<223> OTHER INFORMATION: Description of Artificial Sequence: Linker
      sequence

<400> SEQUENCE: 134

Gly Ser Gly Gly Gly
1               5

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Linker
      sequence

<400> SEQUENCE: 135

Gly Ser Ser Ser Gly
1               5

<210> SEQ ID NO 136
<211> LENGTH: 32
<212> TYPE: DNA
<213> ORGANISM: Artificial Sequence
<220> FEATURE:
<223> OTHER INFORMATION: Description of Artificial Sequence: Forward
      primer

<400> SEQUENCE: 136
ccgactagtc accatgcgga gcgggtgtgt gg                                   32

<210> SEQ ID NO 137
<211> LENGTH: 41
<212> TYPE: DNA
<213> ORGANISM: Artificial Sequence
<220> FEATURE:
<223> OTHER INFORMATION: Description of Artificial Sequence: Reverse
      primer

<400> SEQUENCE: 137
ataagaatgc ggccgcttac ttctcaaagc tgggactcct c                         41

<210> SEQ ID NO 138
<211> LENGTH: 186
<212> TYPE: PRT
<213> ORGANISM: Homo sapiens

<400> SEQUENCE: 138

Asp Ser Ser Pro Leu Leu Gln Phe Gly Gly Gln Val Arg Leu Arg His
1               5                   10                  15

Leu Tyr Thr Ser Gly Pro His Gly Leu Ser Ser Cys Phe Leu Arg Ile
                20                  25                  30

Arg Ala Asp Gly Val Val Asp Cys Ala Arg Gly Gln Ser Ala His Ser
            35                  40                  45

Leu Leu Glu Ile Lys Ala Val Ala Leu Arg Thr Val Ala Ile Lys Gly
        50                  55                  60

Val His Ser Val Arg Tyr Leu Cys Met Gly Ala Asp Gly Lys Met Gln
65                  70                  75                  80

Gly Leu Leu Gln Tyr Ser Glu Glu Asp Cys Ala Phe Glu Glu Glu Ile
                85                  90                  95

Arg Pro Asp Gly Tyr Asn Val Tyr Arg Ser Glu Lys His Arg Leu Pro
            100                 105                 110

Val Ser Leu Ser Ser Ala Lys Gln Arg Gln Leu Tyr Lys Asn Arg Gly
        115                 120                 125

Phe Leu Pro Leu Ser His Phe Leu Pro Met Leu Pro Met Val Pro Glu
    130                 135                 140

Glu Pro Glu Asp Leu Arg Gly His Leu Glu Ser Asp Met Phe Ser Ser
145                 150                 155                 160

Pro Leu Glu Thr Asp Ser Met Asp Pro Phe Gly Leu Val Thr Gly Leu
                165                 170                 175

Glu Ala Val Arg Ser Pro Ser Phe Glu Lys
            180                 185

<210> SEQ ID NO 139
<211> LENGTH: 194
<212> TYPE: PRT

<213> ORGANISM: Homo sapiens

<400> SEQUENCE: 139

```
Arg Pro Leu Ala Phe Ser Asp Ala Ser Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys
```

<210> SEQ ID NO 140
<211> LENGTH: 194
<212> TYPE: PRT
<213> ORGANISM: Homo sapiens

<400> SEQUENCE: 140

```
Arg Pro Leu Ala Phe Ser Asp Ser Pro Leu Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160
```

```
Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 141
<211> LENGTH: 188
<212> TYPE: PRT
<213> ORGANISM: Homo sapiens

<400> SEQUENCE: 141

Asp Ser Ser Pro Leu Val His Tyr Gly Trp Gly Asp Pro Ile Arg Leu
1               5                   10                  15

Arg His Leu Tyr Thr Ser Gly Pro His Gly Leu Ser Ser Cys Phe Leu
            20                  25                  30

Arg Ile Arg Ala Asp Gly Val Val Asp Cys Ala Arg Gly Gln Ser Ala
        35                  40                  45

His Ser Leu Leu Glu Ile Lys Ala Val Ala Leu Arg Thr Val Ala Ile
50                  55                  60

Lys Gly Val His Ser Val Arg Tyr Leu Cys Met Gly Ala Asp Gly Lys
65                  70                  75                  80

Met Gln Gly Leu Leu Gln Tyr Ser Glu Glu Asp Cys Ala Phe Glu Glu
                85                  90                  95

Glu Ile Arg Pro Asp Gly Tyr Asn Val Tyr Arg Ser Glu Lys His Arg
            100                 105                 110

Leu Pro Val Ser Leu Ser Ser Ala Lys Gln Arg Gln Leu Tyr Lys Asn
        115                 120                 125

Arg Gly Phe Leu Pro Leu Ser His Phe Leu Pro Met Leu Pro Met Val
    130                 135                 140

Pro Glu Glu Pro Glu Asp Leu Arg Gly His Leu Glu Ser Asp Met Phe
145                 150                 155                 160

Ser Ser Pro Leu Glu Thr Asp Ser Met Asp Pro Phe Gly Leu Val Thr
                165                 170                 175

Gly Leu Glu Ala Val Arg Ser Pro Ser Phe Glu Lys
            180                 185

<210> SEQ ID NO 142
<211> LENGTH: 193
<212> TYPE: PRT
<213> ORGANISM: Homo sapiens

<400> SEQUENCE: 142

Arg His Pro Ile Pro Asp Ser Ser Pro Leu Leu Gln Phe Gly Trp Gly
1               5                   10                  15

Asp Pro Ile Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95
```

Cys Ala Phe Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
115                 120                 125

Gln Leu Tyr Lys Asn Arg Gly Phe Leu Pro Leu Ser His Phe Leu Pro
        130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
            180                 185                 190

Lys

<210> SEQ ID NO 143
<211> LENGTH: 191
<212> TYPE: PRT
<213> ORGANISM: Homo sapiens

<400> SEQUENCE: 143

Arg His Pro Ile Pro Asp Ser Ser Pro Leu Leu Gln Trp Gly Asp Pro
1               5                   10                  15

Ile Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 144
<211> LENGTH: 194
<212> TYPE: PRT
<213> ORGANISM: Homo sapiens

<400> SEQUENCE: 144

Arg Pro Leu Ala Phe Ser Asp Ala Gly Pro Leu Leu Gln Phe Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys

```
                35                  40                  45
Ala Arg Gly Gln Ser Ala His Ser Leu Leu Glu Ile Lys Ala Val Ala
 50                  55                  60
Leu Arg Thr Val Ala Ile Lys Gly Val His Ser Val Arg Tyr Leu Cys
 65                  70                  75                  80
Met Gly Ala Asp Gly Lys Met Gln Gly Leu Leu Gln Tyr Ser Glu Glu
                 85                  90                  95
Asp Cys Ala Phe Glu Glu Glu Ile Arg Pro Asp Gly Tyr Asn Val Tyr
                100                 105                 110
Arg Ser Glu Lys His Arg Leu Pro Val Ser Leu Ser Ser Ala Lys Gln
                115                 120                 125
Arg Gln Leu Tyr Lys Asn Arg Gly Phe Leu Pro Leu Ser His Phe Leu
130                 135                 140
Pro Met Leu Pro Met Val Pro Glu Glu Pro Asp Leu Arg Gly His
145                 150                 155                 160
Leu Glu Ser Asp Met Phe Ser Ser Pro Leu Glu Thr Asp Ser Met Asp
                165                 170                 175
Pro Phe Gly Leu Val Thr Gly Leu Glu Ala Val Arg Ser Pro Ser Phe
                180                 185                 190
Glu Lys
```

<210> SEQ ID NO 145
<211> LENGTH: 193
<212> TYPE: PRT
<213> ORGANISM: Homo sapiens

<400> SEQUENCE: 145

```
Arg His Pro Ile Pro Asp Ser Ser Pro His Val His Tyr Gly Trp Gly
  1               5                  10                  15
Asp Pro Ile Arg Leu Arg His Leu Tyr Thr Ser Gly Pro His Gly Leu
                 20                  25                  30
Ser Ser Cys Phe Leu Arg Ile Arg Ala Asp Gly Val Val Asp Cys Ala
                 35                  40                  45
Arg Gly Gln Ser Ala His Ser Leu Leu Glu Ile Lys Ala Val Ala Leu
 50                  55                  60
Arg Thr Val Ala Ile Lys Gly Val His Ser Val Arg Tyr Leu Cys Met
 65                  70                  75                  80
Gly Ala Asp Gly Lys Met Gln Gly Leu Leu Gln Tyr Ser Glu Glu Asp
                 85                  90                  95
Cys Ala Phe Glu Glu Glu Ile Arg Pro Asp Gly Tyr Asn Val Tyr Arg
                100                 105                 110
Ser Glu Lys His Arg Leu Pro Val Ser Leu Ser Ser Ala Lys Gln Arg
                115                 120                 125
Gln Leu Tyr Lys Asn Arg Gly Phe Leu Pro Leu Ser His Phe Leu Pro
130                 135                 140
Met Leu Pro Met Val Pro Glu Glu Pro Asp Leu Arg Gly His Leu
145                 150                 155                 160
Glu Ser Asp Met Phe Ser Ser Pro Leu Glu Thr Asp Ser Met Asp Pro
                165                 170                 175
Phe Gly Leu Val Thr Gly Leu Glu Ala Val Arg Ser Pro Ser Phe Glu
                180                 185                 190
Lys
```

<210> SEQ ID NO 146

<211> LENGTH: 192
<212> TYPE: PRT
<213> ORGANISM: Homo sapiens

<400> SEQUENCE: 146

```
Arg Pro Leu Ala Phe Ser Asp Ala Gly Pro Leu Leu Gln Phe Gly Gly
1               5                   10                  15

Gln Val Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190
```

<210> SEQ ID NO 147
<211> LENGTH: 191
<212> TYPE: PRT
<213> ORGANISM: Homo sapiens

<400> SEQUENCE: 147

```
Arg His Pro Ile Pro Asp Ser Ser Pro His Val His Tyr Gly Gly Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160
```

-continued

```
Asp Met Phe Ser Ser Pro Leu Glu Thr Asp Ser Met Asp Pro Phe Gly
            165                 170                 175

Leu Val Thr Gly Leu Glu Ala Val Arg Ser Pro Ser Phe Glu Lys
        180                 185                 190

<210> SEQ ID NO 148
<211> LENGTH: 187
<212> TYPE: PRT
<213> ORGANISM: Homo sapiens

<400> SEQUENCE: 148

Arg Asp Ser Ser Pro Leu Leu Gln Phe Gly Gly Gln Val Arg Leu Arg
1               5                   10                  15

His Leu Tyr Thr Ser Gly Pro His Gly Leu Ser Ser Cys Phe Leu Arg
            20                  25                  30

Ile Arg Ala Asp Gly Val Val Asp Cys Ala Arg Gly Gln Ser Ala His
        35                  40                  45

Ser Leu Leu Glu Ile Lys Ala Val Ala Leu Arg Thr Val Ala Ile Lys
    50                  55                  60

Gly Val His Ser Val Arg Tyr Leu Cys Met Gly Ala Asp Gly Lys Met
65                  70                  75                  80

Gln Gly Leu Leu Gln Tyr Ser Glu Glu Asp Cys Ala Phe Glu Glu Glu
                85                  90                  95

Ile Arg Pro Asp Gly Tyr Asn Val Tyr Arg Ser Glu Lys His Arg Leu
            100                 105                 110

Pro Val Ser Leu Ser Ser Ala Lys Gln Arg Gln Leu Tyr Lys Asn Arg
        115                 120                 125

Gly Phe Leu Pro Leu Ser His Phe Leu Pro Met Leu Pro Met Val Pro
    130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 149
<211> LENGTH: 192
<212> TYPE: PRT
<213> ORGANISM: Homo sapiens

<400> SEQUENCE: 149

Arg Pro Leu Ala Phe Ser Asp Ser Ser Pro Leu Leu Gln Phe Gly Gly
1               5                   10                  15

Gln Val Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110
```

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 150
<211> LENGTH: 191
<212> TYPE: PRT
<213> ORGANISM: Homo sapiens

<400> SEQUENCE: 150

Arg His Pro Ile Pro Asp Ser Ser Pro Leu Leu Gln Phe Gly Ala Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 151
<211> LENGTH: 191
<212> TYPE: PRT
<213> ORGANISM: Homo sapiens

<400> SEQUENCE: 151

Arg His Pro Ile Pro Asp Ser Ser Pro Leu Leu Gln Phe Gly Asp Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

```
Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 152
<211> LENGTH: 191
<212> TYPE: PRT
<213> ORGANISM: Homo sapiens

<400> SEQUENCE: 152

Arg His Pro Ile Pro Asp Ser Ser Pro Leu Leu Gln Phe Gly Pro Gln
  1               5                  10                  15

Val Arg Leu Arg His Leu Tyr Thr Ser Gly Pro His Gly Leu Ser Ser
                 20                  25                  30

Cys Phe Leu Arg Ile Arg Ala Asp Gly Val Val Asp Cys Ala Arg Gly
             35                  40                  45

Gln Ser Ala His Ser Leu Leu Glu Ile Lys Ala Val Ala Leu Arg Thr
         50                  55                  60

Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 153
<211> LENGTH: 191
<212> TYPE: PRT
<213> ORGANISM: Homo sapiens

<400> SEQUENCE: 153

Arg His Pro Ile Pro Asp Ser Ser Pro Leu Leu Gln Phe Gly Gly Ala
  1               5                  10                  15
```

```
Val Arg Leu Arg His Leu Tyr Thr Ser Gly Pro His Gly Leu Ser Ser
        20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
        50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
                115                 120                 125

Tyr Lys Asn Arg Gly Phe Leu Pro Leu Ser His Phe Leu Pro Met Leu
        130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 154
<211> LENGTH: 191
<212> TYPE: PRT
<213> ORGANISM: Homo sapiens

<400> SEQUENCE: 154

Arg His Pro Ile Pro Asp Ser Ser Pro Leu Leu Gln Phe Gly Gly Glu
1               5                   10                  15

Val Arg Leu Arg His Leu Tyr Thr Ser Gly Pro His Gly Leu Ser Ser
        20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
        50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
                115                 120                 125

Tyr Lys Asn Arg Gly Phe Leu Pro Leu Ser His Phe Leu Pro Met Leu
        130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190
```

```
<210> SEQ ID NO 155
<211> LENGTH: 191
<212> TYPE: PRT
<213> ORGANISM: Homo sapiens

<400> SEQUENCE: 155

Arg His Pro Ile Pro Asp Ser Ser Pro Leu Leu Gln Phe Gly Gly Asn
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 156
<211> LENGTH: 191
<212> TYPE: PRT
<213> ORGANISM: Homo sapiens

<400> SEQUENCE: 156

Arg His Pro Ile Pro Asp Ser Ser Pro Leu Leu Gln Phe Gly Gly Gln
1               5                   10                  15

Ala Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
```

```
                145                 150                 155                 160
Asp Met Phe Ser Ser Pro Leu Glu Thr Asp Ser Met Asp Pro Phe Gly
                    165                 170                 175

Leu Val Thr Gly Leu Glu Ala Val Arg Ser Pro Ser Phe Glu Lys
                180                 185                 190

<210> SEQ ID NO 157
<211> LENGTH: 191
<212> TYPE: PRT
<213> ORGANISM: Homo sapiens

<400> SEQUENCE: 157

Arg His Pro Ile Pro Asp Ser Ser Pro Leu Leu Gln Phe Gly Gly Gln
1               5                   10                  15

Ile Arg Leu Arg His Leu Tyr Thr Ser Gly Pro His Gly Leu Ser Ser
                20                  25                  30

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
        50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                    165                 170                 175

Leu Val Thr Gly Leu Glu Ala Val Arg Ser Pro Ser Phe Glu Lys
                180                 185                 190

<210> SEQ ID NO 158
<211> LENGTH: 191
<212> TYPE: PRT
<213> ORGANISM: Homo sapiens

<400> SEQUENCE: 158

Arg His Pro Ile Pro Asp Ser Ser Pro Leu Leu Gln Phe Gly Gly Gln
1               5                   10                  15

Thr Arg Leu Arg His Leu Tyr Thr Ser Gly Pro His Gly Leu Ser Ser
                20                  25                  30

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
        50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
```

```
            100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
            130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 159
<211> LENGTH: 193
<212> TYPE: PRT
<213> ORGANISM: Homo sapiens

<400> SEQUENCE: 159

Arg His Pro Ile Pro Asp Ser Ser Pro Leu Leu Gln Phe Gly Trp Gly
1               5                   10                  15

Gln Pro Val Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
            115                 120                 125

Gln Leu Tyr Lys Asn Arg Gly Phe Leu Pro Leu Ser His Phe Leu Pro
        130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
            180                 185                 190

Lys

<210> SEQ ID NO 160
<211> LENGTH: 190
<212> TYPE: PRT
<213> ORGANISM: Homo sapiens

<400> SEQUENCE: 160

His Pro Ile Pro Asp Ser Ser Pro Leu Leu Gln Phe Gly Gly Gln Val
1               5                   10                  15

Arg Leu Arg His Leu Tyr Thr Ser Gly Pro His Gly Leu Ser Ser Cys
            20                  25                  30

Phe Leu Arg Ile Arg Ala Asp Gly Val Val Asp Cys Ala Arg Gly Gln
        35                  40                  45
```

Ser Ala His Ser Leu Leu Glu Ile Lys Ala Val Ala Leu Arg Thr Val
            50                  55                  60

Ala Ile Lys Gly Val His Ser Val Arg Tyr Leu Cys Met Gly Ala Asp
65                  70                  75                  80

Gly Lys Met Gln Gly Leu Leu Gln Tyr Ser Glu Glu Asp Cys Ala Phe
                85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ser Ala Lys Gln Arg Gln Leu Tyr
        115                 120                 125

Lys Asn Arg Gly Phe Leu Pro Leu Ser His Phe Leu Pro Met Leu Pro
130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys
            180                 185                 190

<210> SEQ ID NO 161
<211> LENGTH: 186
<212> TYPE: PRT
<213> ORGANISM: Homo sapiens

<400> SEQUENCE: 161

Asp Ser Ser Pro Leu Leu Gln Phe Gly Gly Gln Val Arg Leu Arg His
1               5                   10                  15

Leu Tyr Thr Ser Gly Pro His Gly Leu Ser Ser Cys Phe Leu Arg Ile
            20                  25                  30

Arg Ala Asp Gly Val Val Asp Cys Ala Arg Gly Gln Ser Ala His Ser
        35                  40                  45

Leu Leu Glu Ile Lys Ala Val Ala Leu Arg Thr Val Ala Ile Lys Gly
    50                  55                  60

Val His Ser Val Arg Tyr Leu Cys Met Gly Ala Asp Gly Lys Met Gln
65                  70                  75                  80

Gly Leu Leu Gln Tyr Ser Glu Glu Asp Cys Ala Phe Glu Glu Glu Ile
                85                  90                  95

Arg Pro Asp Gly Tyr Asn Val Tyr Arg Ser Glu Lys His Arg Leu Pro
            100                 105                 110

Val Ser Leu Ser Ser Ala Lys Gln Arg Gln Leu Tyr Lys Asn Arg Gly
        115                 120                 125

Phe Leu Pro Leu Ser His Phe Leu Pro Met Leu Pro Met Val Pro Glu
    130                 135                 140

Glu Pro Glu Asp Leu Arg Gly His Leu Glu Ser Asp Met Phe Ser Ser
145                 150                 155                 160

Pro Leu Glu Thr Asp Ser Met Asp Pro Phe Gly Leu Val Thr Gly Leu
                165                 170                 175

Glu Ala Val Arg Ser Pro Ser Phe Glu Lys
            180                 185

<210> SEQ ID NO 162
<211> LENGTH: 190
<212> TYPE: PRT
<213> ORGANISM: Homo sapiens

<400> SEQUENCE: 162

```
His Pro Ile Pro Asp Ser Ser Pro Leu Leu Gln Trp Gly Asp Pro Ile
1               5                   10                  15

Arg Leu Arg His Leu Tyr Thr Ser Gly Pro His Gly Leu Ser Ser Cys
            20                  25                  30

Phe Leu Arg Ile Arg Ala Asp Gly Val Val Asp Cys Ala Arg Gly Gln
        35                  40                  45

Ser Ala His Ser Leu Leu Glu Ile Lys Ala Val Ala Leu Arg Thr Val
50                  55                  60

Ala Ile Lys Gly Val His Ser Val Arg Tyr Leu Cys Met Gly Ala Asp
65                  70                  75                  80

Gly Lys Met Gln Gly Leu Leu Gln Tyr Ser Glu Glu Asp Cys Ala Phe
                85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ser Ala Lys Gln Arg Gln Leu Tyr
        115                 120                 125

Lys Asn Arg Gly Phe Leu Pro Leu Ser His Phe Leu Pro Met Leu Pro
130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys
            180                 185                 190

<210> SEQ ID NO 163
<211> LENGTH: 192
<212> TYPE: PRT
<213> ORGANISM: Homo sapiens

<400> SEQUENCE: 163

His Pro Ile Pro Asp Ser Ser Pro Leu Leu Gln Phe Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
```

```
                      180                 185                 190

<210> SEQ ID NO 164
<211> LENGTH: 192
<212> TYPE: PRT
<213> ORGANISM: Homo sapiens

<400> SEQUENCE: 164

His Pro Ile Pro Asp Ser Ser Pro His Val His Tyr Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 165
<211> LENGTH: 190
<212> TYPE: PRT
<213> ORGANISM: Homo sapiens

<400> SEQUENCE: 165

His Pro Ile Pro Asp Ser Ser Pro His Val His Tyr Gly Gly Gln Val
1               5                   10                  15

Arg Leu Arg His Leu Tyr Thr Ser Gly Pro His Gly Leu Ser Ser Cys
            20                  25                  30

Phe Leu Arg Ile Arg Ala Asp Gly Val Val Asp Cys Ala Arg Gly Gln
        35                  40                  45

Ser Ala His Ser Leu Leu Glu Ile Lys Ala Val Ala Leu Arg Thr Val
    50                  55                  60

Ala Ile Lys Gly Val His Ser Val Arg Tyr Leu Cys Met Gly Ala Asp
65                  70                  75                  80

Gly Lys Met Gln Gly Leu Leu Gln Tyr Ser Glu Glu Asp Cys Ala Phe
                85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ser Ala Lys Gln Arg Gln Leu Tyr
        115                 120                 125

Lys Asn Arg Gly Phe Leu Pro Leu Ser His Phe Leu Pro Met Leu Pro
```

```
                130               135               140
Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys
            180                 185                 190

<210> SEQ ID NO 166
<211> LENGTH: 188
<212> TYPE: PRT
<213> ORGANISM: Homo sapiens

<400> SEQUENCE: 166

Asp Ala Gly Pro His Val His Tyr Gly Trp Gly Asp Pro Ile Arg Leu
1               5                   10                  15

Arg His Leu Tyr Thr Ser Gly Pro His Gly Leu Ser Ser Cys Phe Leu
            20                  25                  30

Arg Ile Arg Ala Asp Gly Val Val Asp Cys Ala Arg Gly Gln Ser Ala
        35                  40                  45

His Ser Leu Leu Glu Ile Lys Ala Val Ala Leu Arg Thr Val Ala Ile
    50                  55                  60

Lys Gly Val His Ser Val Arg Tyr Leu Cys Met Gly Ala Asp Gly Lys
65                  70                  75                  80

Met Gln Gly Leu Leu Gln Tyr Ser Glu Glu Asp Cys Ala Phe Glu Glu
                85                  90                  95

Glu Ile Arg Pro Asp Gly Tyr Asn Val Tyr Arg Ser Glu Lys His Arg
            100                 105                 110

Leu Pro Val Ser Leu Ser Ser Ala Lys Gln Arg Gln Leu Tyr Lys Asn
        115                 120                 125

Arg Gly Phe Leu Pro Leu Ser His Phe Leu Pro Met Leu Pro Met Val
    130                 135                 140

Pro Glu Glu Pro Glu Asp Leu Arg Gly His Leu Glu Ser Asp Met Phe
145                 150                 155                 160

Ser Ser Pro Leu Glu Thr Asp Ser Met Asp Pro Phe Gly Leu Val Thr
                165                 170                 175

Gly Leu Glu Ala Val Arg Ser Pro Ser Phe Glu Lys
            180                 185

<210> SEQ ID NO 167
<211> LENGTH: 183
<212> TYPE: PRT
<213> ORGANISM: Homo sapiens

<400> SEQUENCE: 167

Val His Tyr Gly Trp Gly Asp Pro Ile Arg Leu Arg His Leu Tyr Thr
1               5                   10                  15

Ser Gly Pro His Gly Leu Ser Ser Cys Phe Leu Arg Ile Arg Ala Asp
            20                  25                  30

Gly Val Val Asp Cys Ala Arg Gly Gln Ser Ala His Ser Leu Leu Glu
        35                  40                  45

Ile Lys Ala Val Ala Leu Arg Thr Val Ala Ile Lys Gly Val His Ser
    50                  55                  60

Val Arg Tyr Leu Cys Met Gly Ala Asp Gly Lys Met Gln Gly Leu Leu
65                  70                  75                  80

Gln Tyr Ser Glu Glu Asp Cys Ala Phe Glu Glu Glu Ile Arg Pro Asp
```

```
                 85                  90                  95
Gly Tyr Asn Val Tyr Arg Ser Glu Lys His Arg Leu Pro Val Ser Leu
                100                 105                 110

Ser Ser Ala Lys Gln Arg Gln Leu Tyr Lys Asn Arg Gly Phe Leu Pro
            115                 120                 125

Leu Ser His Phe Leu Pro Met Leu Pro Met Val Pro Glu Glu Pro Glu
        130                 135                 140

Asp Leu Arg Gly His Leu Glu Ser Asp Met Phe Ser Ser Pro Leu Glu
145                 150                 155                 160

Thr Asp Ser Met Asp Pro Phe Gly Leu Val Thr Gly Leu Glu Ala Val
                165                 170                 175

Arg Ser Pro Ser Phe Glu Lys
            180

<210> SEQ ID NO 168
<211> LENGTH: 174
<212> TYPE: PRT
<213> ORGANISM: Homo sapiens

<400> SEQUENCE: 168

Arg Leu Arg His Leu Tyr Thr Ser Gly Pro His Gly Leu Ser Ser Cys
1               5                   10                  15

Phe Leu Arg Ile Arg Ala Asp Gly Val Val Asp Cys Ala Arg Gly Gln
            20                  25                  30

Ser Ala His Ser Leu Leu Glu Ile Lys Ala Val Ala Leu Arg Thr Val
        35                  40                  45

Ala Ile Lys Gly Val His Ser Val Arg Tyr Leu Cys Met Gly Ala Asp
    50                  55                  60

Gly Lys Met Gln Gly Leu Leu Gln Tyr Ser Glu Glu Asp Cys Ala Phe
65                  70                  75                  80

Glu Glu Glu Ile Arg Pro Asp Gly Tyr Asn Val Tyr Arg Ser Glu Lys
                85                  90                  95

His Arg Leu Pro Val Ser Leu Ser Ser Ala Lys Gln Arg Gln Leu Tyr
            100                 105                 110

Lys Asn Arg Gly Phe Leu Pro Leu Ser His Phe Leu Pro Met Leu Pro
        115                 120                 125

Met Val Pro Glu Glu Pro Glu Asp Leu Arg Gly His Leu Glu Ser Asp
    130                 135                 140

Met Phe Ser Ser Pro Leu Glu Thr Asp Ser Met Asp Pro Phe Gly Leu
145                 150                 155                 160

Val Thr Gly Leu Glu Ala Val Arg Ser Pro Ser Phe Glu Lys
                165                 170

<210> SEQ ID NO 169
<211> LENGTH: 14
<212> TYPE: PRT
<213> ORGANISM: Artificial Sequence
<220> FEATURE:
<223> OTHER INFORMATION: Synthetic peptide

<400> SEQUENCE: 169

Trp Gly Asp Pro Ile Arg Leu Arg His Leu Tyr Thr Ser Gly
1               5                   10

<210> SEQ ID NO 170
<211> LENGTH: 5
<212> TYPE: PRT
<213> ORGANISM: Artificial Sequence
```

```
<220> FEATURE:
<223> OTHER INFORMATION: Synthetic peptide

<400> SEQUENCE: 170

Trp Gly Asp Pro Ile
1               5

<210> SEQ ID NO 171
<211> LENGTH: 4
<212> TYPE: PRT
<213> ORGANISM: Artificial Sequence
<220> FEATURE:
<223> OTHER INFORMATION: Synthetic peptide

<400> SEQUENCE: 171

Trp Gly Pro Ile
1

<210> SEQ ID NO 172
<211> LENGTH: 5
<212> TYPE: PRT
<213> ORGANISM: Artificial Sequence
<220> FEATURE:
<223> OTHER INFORMATION: Synthetic peptide

<400> SEQUENCE: 172

Trp Gly Asp Pro Val
1               5

<210> SEQ ID NO 173
<211> LENGTH: 4
<212> TYPE: PRT
<213> ORGANISM: Artificial Sequence
<220> FEATURE:
<223> OTHER INFORMATION: Synthetic peptide

<400> SEQUENCE: 173

Trp Gly Asp Ile
1

<210> SEQ ID NO 174
<211> LENGTH: 4
<212> TYPE: PRT
<213> ORGANISM: Artificial Sequence
<220> FEATURE:
<223> OTHER INFORMATION: Synthetic peptide

<400> SEQUENCE: 174

Gly Asp Pro Ile
1

<210> SEQ ID NO 175
<211> LENGTH: 5
<212> TYPE: PRT
<213> ORGANISM: Artificial Sequence
<220> FEATURE:
<223> OTHER INFORMATION: Synthetic peptide

<400> SEQUENCE: 175

Trp Gly Gln Pro Ile
1               5

<210> SEQ ID NO 176
<211> LENGTH: 5
<212> TYPE: PRT
<213> ORGANISM: Artificial Sequence
<220> FEATURE:
```

```
<223> OTHER INFORMATION: Synthetic peptide

<400> SEQUENCE: 176

Trp Gly Ala Pro Ile
1               5

<210> SEQ ID NO 177
<211> LENGTH: 5
<212> TYPE: PRT
<213> ORGANISM: Artificial Sequence
<220> FEATURE:
<223> OTHER INFORMATION: Synthetic peptide

<400> SEQUENCE: 177

Ala Gly Asp Pro Ile
1               5

<210> SEQ ID NO 178
<211> LENGTH: 5
<212> TYPE: PRT
<213> ORGANISM: Artificial Sequence
<220> FEATURE:
<223> OTHER INFORMATION: Synthetic peptide

<400> SEQUENCE: 178

Trp Ala Asp Pro Ile
1               5

<210> SEQ ID NO 179
<211> LENGTH: 5
<212> TYPE: PRT
<213> ORGANISM: Artificial Sequence
<220> FEATURE:
<223> OTHER INFORMATION: Synthetic peptide

<400> SEQUENCE: 179

Trp Gly Asp Ala Ile
1               5

<210> SEQ ID NO 180
<211> LENGTH: 5
<212> TYPE: PRT
<213> ORGANISM: Artificial Sequence
<220> FEATURE:
<223> OTHER INFORMATION: Synthetic peptide

<400> SEQUENCE: 180

Trp Gly Asp Pro Ala
1               5

<210> SEQ ID NO 181
<211> LENGTH: 4
<212> TYPE: PRT
<213> ORGANISM: Artificial Sequence
<220> FEATURE:
<223> OTHER INFORMATION: Synthetic peptide

<400> SEQUENCE: 181

Trp Asp Pro Ile
1

<210> SEQ ID NO 182
<211> LENGTH: 4
<212> TYPE: PRT
<213> ORGANISM: Artificial Sequence
<220> FEATURE:
<223> OTHER INFORMATION: Synthetic peptide
```

-continued

<400> SEQUENCE: 182

Trp Gly Asp Ile
1

<210> SEQ ID NO 183
<211> LENGTH: 4
<212> TYPE: PRT
<213> ORGANISM: Artificial Sequence
<220> FEATURE:
<223> OTHER INFORMATION: Synthetic peptide

<400> SEQUENCE: 183

Trp Gly Asp Pro
1

<210> SEQ ID NO 184
<211> LENGTH: 5
<212> TYPE: PRT
<213> ORGANISM: Artificial Sequence
<220> FEATURE:
<223> OTHER INFORMATION: Synthetic peptide

<400> SEQUENCE: 184

Phe Gly Asp Pro Ile
1               5

<210> SEQ ID NO 185
<211> LENGTH: 9
<212> TYPE: PRT
<213> ORGANISM: Artificial Sequence
<220> FEATURE:
<223> OTHER INFORMATION: Synthetic peptide

<400> SEQUENCE: 185

Arg Leu Arg His Leu Tyr Thr Ser Gly
1               5

<210> SEQ ID NO 186
<211> LENGTH: 9
<212> TYPE: PRT
<213> ORGANISM: Artificial Sequence
<220> FEATURE:
<223> OTHER INFORMATION: core sequence

<400> SEQUENCE: 186

Arg Gln Arg Tyr Leu Tyr Thr Asp Asp
1               5

<210> SEQ ID NO 187
<211> LENGTH: 13
<212> TYPE: PRT
<213> ORGANISM: Artificial Sequence
<220> FEATURE:
<223> OTHER INFORMATION: Synthetic peptide

<400> SEQUENCE: 187

Ala Gly Pro His Val His Tyr Gly Trp Gly Asp Pro Ile
1               5                   10

<210> SEQ ID NO 188
<211> LENGTH: 165
<212> TYPE: PRT
<213> ORGANISM: Homo sapiens
<220> FEATURE:
<223> OTHER INFORMATION: FGF19 C-terminal sequence

<400> SEQUENCE: 188

Pro His Gly Leu Ser Ser Cys Phe Leu Arg Ile Arg Ala Asp Gly Val
1               5                   10                  15

Val Asp Cys Ala Arg Gly Gln Ser Ala His Ser Leu Leu Glu Ile Lys
            20                  25                  30

Ala Val Ala Leu Arg Thr Val Ala Ile Lys Gly Val His Ser Val Arg
        35                  40                  45

Tyr Leu Cys Met Gly Ala Asp Gly Lys Met Gln Gly Leu Leu Gln Tyr
    50                  55                  60

Ser Glu Glu Asp Cys Ala Phe Glu Glu Ile Arg Pro Asp Gly Tyr
65                  70                  75                  80

Asn Val Tyr Arg Ser Glu Lys His Arg Leu Pro Val Ser Leu Ser Ser
                85                  90                  95

Ala Lys Gln Arg Gln Leu Tyr Lys Asn Arg Gly Phe Leu Pro Leu Ser
            100                 105                 110

His Phe Leu Pro Met Leu Pro Met Val Pro Glu Glu Pro Glu Asp Leu
        115                 120                 125

Arg Gly His Leu Glu Ser Asp Met Phe Ser Ser Pro Leu Glu Thr Asp
    130                 135                 140

Ser Met Asp Pro Phe Gly Leu Val Thr Gly Leu Glu Ala Val Arg Ser
145                 150                 155                 160

Pro Ser Phe Glu Lys
                165

<210> SEQ ID NO 189
<211> LENGTH: 5
<212> TYPE: PRT
<213> ORGANISM: Artificial Sequence
<220> FEATURE:
<223> OTHER INFORMATION: Linker sequence

<400> SEQUENCE: 189

Gly Gly Gly Ser Gly
1               5

<210> SEQ ID NO 190
<211> LENGTH: 11
<212> TYPE: PRT
<213> ORGANISM: Homo sapiens
<220> FEATURE:
<223> OTHER INFORMATION: Sheet-8/Loop-8/Sheet-9 region of FGF19

<400> SEQUENCE: 190

Glu Glu Ile Arg Pro Asp Gly Tyr Asn Val Tyr
1               5                   10

<210> SEQ ID NO 191
<211> LENGTH: 11
<212> TYPE: PRT
<213> ORGANISM: Homo sapiens
<220> FEATURE:
<223> OTHER INFORMATION: Sheet-8/Loop-8/Sheet-9 region of FGF21

<400> SEQUENCE: 191

Glu Leu Leu Leu Glu Asp Gly Tyr Asn Val Tyr
1               5                   10

<210> SEQ ID NO 192
<211> LENGTH: 187
<212> TYPE: PRT
<213> ORGANISM: Artificial Sequence
<220> FEATURE:
<223> OTHER INFORMATION: M53 sequence

<400> SEQUENCE: 192

Met Asp Ser Ser Pro Leu Leu Gln Trp Gly Asp Pro Ile Arg Leu Arg
1               5                   10                  15

His Leu Tyr Thr Ser Gly Pro His Gly Leu Ser Ser Cys Phe Leu Arg
            20                  25                  30

Ile Arg Ala Asp Gly Val Val Asp Cys Ala Arg Gly Gln Ser Ala His
        35                  40                  45

Ser Leu Leu Glu Ile Lys Ala Val Ala Leu Arg Thr Val Ala Ile Lys
    50                  55                  60

Gly Val His Ser Val Arg Tyr Leu Cys Met Gly Ala Asp Gly Lys Met
65                  70                  75                  80

Gln Gly Leu Leu Gln Tyr Ser Glu Glu Asp Cys Ala Phe Glu Glu Glu
                85                  90                  95

Ile Arg Pro Asp Gly Tyr Asn Val Tyr Arg Ser Glu Lys His Arg Leu
            100                 105                 110

Pro Val Ser Leu Ser Ser Ala Lys Gln Arg Gln Leu Tyr Lys Asn Arg
        115                 120                 125

Gly Phe Leu Pro Leu Ser His Phe Leu Pro Met Leu Pro Met Val Pro
    130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 193
<211> LENGTH: 194
<212> TYPE: PRT
<213> ORGANISM: Artificial Sequence
<220> FEATURE:
<223> OTHER INFORMATION: M139 sequence

<400> SEQUENCE: 193

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Leu Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His

```
                      145                 150                 155                 160
Leu Glu Ser Asp Met Phe Ser Ser Pro Leu Glu Thr Asp Ser Met Asp
                  165                 170                 175

Pro Phe Gly Leu Val Thr Gly Leu Glu Ala Val Arg Ser Pro Ser Phe
              180                 185                 190

Glu Lys

<210> SEQ ID NO 194
<211> LENGTH: 194
<212> TYPE: PRT
<213> ORGANISM: Artificial Sequence
<220> FEATURE:
<223> OTHER INFORMATION: M140 sequence

<400> SEQUENCE: 194

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Ile Arg Glu Asp Gly Tyr Asn Val Tyr
                100                 105                 110

Arg Ser Glu Lys His Arg Leu Pro Val Ser Leu Ser Ser Ala Lys Gln
            115                 120                 125

Arg Gln Leu Tyr Lys Asn Arg Gly Phe Leu Pro Leu Ser His Phe Leu
    130                 135                 140

Pro Met Leu Pro Met Val Pro Glu Gly Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 195
<211> LENGTH: 194
<212> TYPE: PRT
<213> ORGANISM: Artificial Sequence
<220> FEATURE:
<223> OTHER INFORMATION: M141 sequence

<400> SEQUENCE: 195

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
    50                  55                  60
```

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Glu Ile Leu Cys Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 196
<211> LENGTH: 194
<212> TYPE: PRT
<213> ORGANISM: Artificial Sequence
<220> FEATURE:
<223> OTHER INFORMATION: M160 sequence

<400> SEQUENCE: 196

Arg Pro Leu Ala Phe Ser Asp Ala Gly Pro His Val His Tyr Gly Trp
1               5                   10                  15

Gly Asp Pro Ile Arg Gln Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
 50                  55                  60

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Glu Ile Leu Glu Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 197
<211> LENGTH: 189
<212> TYPE: PRT

<213> ORGANISM: Artificial Sequence
<220> FEATURE:
<223> OTHER INFORMATION: M200 Sequence

<400> SEQUENCE: 197

```
Arg Asp Ser Ser Pro Leu Val His Tyr Gly Trp Gly Asp Pro Ile Arg
1               5                   10                  15

Leu Arg His Leu Tyr Thr Ser Gly Pro His Gly Leu Ser Ser Cys Phe
            20                  25                  30

Leu Arg Ile Arg Ala Asp Gly Val Asp Cys Ala Arg Gly Gln Ser
        35                  40                  45

Ala His Ser Leu Leu Glu Ile Lys Ala Val Ala Leu Arg Thr Val Ala
    50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Leu Glu Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185
```

<210> SEQ ID NO 198
<211> LENGTH: 194
<212> TYPE: PRT
<213> ORGANISM: Artificial Sequence
<220> FEATURE:
<223> OTHER INFORMATION: M201 Sequence

<400> SEQUENCE: 198

```
Arg Pro Leu Ala Phe Ser Asp Ser Ser Pro Leu Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Leu Glu Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140
```

```
Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 199
<211> LENGTH: 194
<212> TYPE: PRT
<213> ORGANISM: Artificial Sequence
<220> FEATURE:
<223> OTHER INFORMATION: M202 Sequence

<400> SEQUENCE: 199

Arg Pro Leu Ala Phe Ser Asp Ala Ser Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Leu Glu Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 200
<211> LENGTH: 187
<212> TYPE: PRT
<213> ORGANISM: Artificial Sequence
<220> FEATURE:
<223> OTHER INFORMATION: M203 Sequence

<400> SEQUENCE: 200

Arg Asp Ser Ser Pro Leu Leu Gln Trp Gly Asp Pro Ile Arg Leu Arg
1               5                   10                  15

His Leu Tyr Thr Ser Gly Pro His Gly Leu Ser Ser Cys Phe Leu Arg
                20                  25                  30

Ile Arg Ala Asp Gly Val Val Asp Cys Ala Arg Gly Gln Ser Ala His
            35                  40                  45

Ser Leu Leu Glu Ile Lys Ala Val Ala Leu Arg Thr Val Ala Ile Lys
```

```
                    50                  55                  60

Gly Val His Ser Val Arg Tyr Leu Cys Met Gly Ala Asp Gly Lys Met
 65                  70                  75                  80

Gln Gly Leu Leu Gln Tyr Ser Glu Glu Asp Cys Ala Phe Glu Glu Glu
                     85                  90                  95

Ile Leu Glu Asp Gly Tyr Asn Val Tyr Arg Ser Glu Lys His Arg Leu
                    100                 105                 110

Pro Val Ser Leu Ser Ser Ala Lys Gln Arg Gln Leu Tyr Lys Asn Arg
                    115                 120                 125

Gly Phe Leu Pro Leu Ser His Phe Leu Pro Met Leu Pro Met Val Pro
                    130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                    165                 170                 175

Leu Glu Ala Val Arg Ser Pro Ser Phe Glu Lys
                    180                 185
```

<210> SEQ ID NO 201
<211> LENGTH: 191
<212> TYPE: PRT
<213> ORGANISM: Artificial Sequence
<220> FEATURE:
<223> OTHER INFORMATION: M204 Sequence

<400> SEQUENCE: 201

```
Arg His Pro Ile Pro Asp Ser Ser Pro Leu Leu Gln Phe Gly Asp Gln
  1               5                  10                  15

Val Arg Leu Arg His Leu Tyr Thr Ser Gly Pro His Gly Leu Ser Ser
                 20                  25                  30

Cys Phe Leu Arg Ile Arg Ala Asp Gly Val Val Asp Cys Ala Arg Gly
                 35                  40                  45

Gln Ser Ala His Ser Leu Leu Glu Ile Lys Ala Val Ala Leu Arg Thr
 50                  55                  60

Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Leu Glu Asp Gly Tyr Asn Val Tyr Arg Ser Glu
                100                 105                 110

Lys His Arg Leu Pro Val Ser Leu Ser Ser Ala Lys Gln Arg Gln Leu
                115                 120                 125

Tyr Lys Asn Arg Gly Phe Leu Pro Leu Ser His Phe Leu Pro Met Leu
130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190
```

<210> SEQ ID NO 202
<211> LENGTH: 187
<212> TYPE: PRT
<213> ORGANISM: Artificial Sequence
<220> FEATURE:
<223> OTHER INFORMATION: M205 Sequence

<400> SEQUENCE: 202

Arg Asp Ser Ser Pro Leu Leu Gln Phe Gly Gly Gln Val Arg Leu Arg
1               5                   10                  15

His Leu Tyr Thr Ser Gly Pro His Gly Leu Ser Ser Cys Phe Leu Arg
            20                  25                  30

Ile Arg Ala Asp Gly Val Val Asp Cys Ala Arg Gly Gln Ser Ala His
        35                  40                  45

Ser Leu Leu Glu Ile Lys Ala Val Ala Leu Arg Thr Val Ala Ile Lys
    50                  55                  60

Gly Val His Ser Val Arg Tyr Leu Cys Met Gly Ala Asp Gly Lys Met
65                  70                  75                  80

Gln Gly Leu Leu Gln Tyr Ser Glu Glu Asp Cys Ala Phe Glu Glu Glu
                85                  90                  95

Ile Leu Glu Asp Gly Tyr Asn Val Tyr Arg Ser Glu Lys His Arg Leu
            100                 105                 110

Pro Val Ser Leu Ser Ser Ala Lys Gln Arg Gln Leu Tyr Lys Asn Arg
        115                 120                 125

Gly Phe Leu Pro Leu Ser His Phe Leu Pro Met Leu Pro Met Val Pro
    130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 203
<211> LENGTH: 191
<212> TYPE: PRT
<213> ORGANISM: Artificial Sequence
<220> FEATURE:
<223> OTHER INFORMATION: M206 Sequence

<400> SEQUENCE: 203

Arg His Pro Ile Pro Asp Ser Ser Pro Leu Leu Gln Phe Gly Gly Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Leu Glu Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

-continued

```
Asp Met Phe Ser Ser Pro Leu Glu Thr Asp Ser Met Asp Pro Phe Gly
            165                 170                 175

Leu Val Thr Gly Leu Glu Ala Val Arg Ser Pro Ser Phe Glu Lys
        180                 185                 190

<210> SEQ ID NO 204
<211> LENGTH: 190
<212> TYPE: PRT
<213> ORGANISM: Artificial Sequence
<220> FEATURE:
<223> OTHER INFORMATION: M207 Sequence

<400> SEQUENCE: 204

Met Arg Asp Ser Ser Pro Leu Val His Tyr Gly Trp Gly Asp Pro Ile
1               5                   10                  15

Arg Leu Arg His Leu Tyr Thr Ser Gly Pro His Gly Leu Ser Ser Cys
            20                  25                  30

Phe Leu Arg Ile Arg Ala Asp Gly Val Val Asp Cys Ala Arg Gly Gln
        35                  40                  45

Ser Ala His Ser Leu Leu Glu Ile Lys Ala Val Ala Leu Arg Thr Val
    50                  55                  60

Ala Ile Lys Gly Val His Ser Val Arg Tyr Leu Cys Met Gly Ala Asp
65                  70                  75                  80

Gly Lys Met Gln Gly Leu Leu Gln Tyr Ser Glu Glu Asp Cys Ala Phe
            85                  90                  95

Glu Glu Glu Ile Leu Glu Asp Gly Tyr Asn Val Tyr Arg Ser Glu Lys
            100                 105                 110

His Arg Leu Pro Val Ser Leu Ser Ser Ala Lys Gln Arg Gln Leu Tyr
            115                 120                 125

Lys Asn Arg Gly Phe Leu Pro Leu Ser His Phe Leu Pro Met Leu Pro
        130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
            165                 170                 175

Val Thr Gly Leu Glu Ala Val Arg Ser Pro Ser Phe Glu Lys
        180                 185                 190

<210> SEQ ID NO 205
<211> LENGTH: 11
<212> TYPE: PRT
<213> ORGANISM: Artificial Sequence
<220> FEATURE:
<223> OTHER INFORMATION: Modified Sheet-8/Loop-8/Sheet-9 region of FGF19

<400> SEQUENCE: 205

Glu Glu Ile Leu Glu Asp Gly Tyr Asn Val Tyr
1               5                   10
```